US008945900B2

(12) United States Patent
Juntunen et al.

(10) Patent No.: US 8,945,900 B2
(45) Date of Patent: Feb. 3, 2015

(54) VARIANTS OF FUNGAL SERINE PROTEASE

(75) Inventors: Kari Juntunen, Espoo (FI); Leena Valtakari, Rajamäki (FI); Nina Hakulinen, Niittylahti (FI); Marja Paloheimo, Vantaa (FI)

(73) Assignee: AB Enzymes Oy, Rajamäki (FI)

( * ) Notice: Subject to any disclaimer, the term of this patent is extended or adjusted under 35 U.S.C. 154(b) by 149 days.

(21) Appl. No.: 13/283,891

(22) Filed: Oct. 28, 2011

(65) Prior Publication Data

US 2012/0107905 A1  May 3, 2012

Related U.S. Application Data

(60) Provisional application No. 61/456,055, filed on Oct. 29, 2010.

(30) Foreign Application Priority Data

Oct. 29, 2010  (FI) ...................................... 20106135

(51) Int. Cl.
  C12N 9/02  (2006.01)
  C11D 3/02  (2006.01)
  (Continued)

(52) U.S. Cl.
  CPC .............. *C12N 9/58* (2013.01); *C11D 3/38609* (2013.01); *C11D 3/38618* (2013.01)
  USPC ............................ 435/189; 510/108; 510/114

(58) Field of Classification Search
  None
  See application file for complete search history.

(56) References Cited

U.S. PATENT DOCUMENTS

| 3,652,399 A | 3/1972 | Isono et al. |
| 5,288,627 A | 2/1994 | Nielsen et al. |
| 5,770,418 A | 6/1998 | Yaver et al. |

(Continued)

FOREIGN PATENT DOCUMENTS

| EP | 0244234 | 11/1987 |
| EP | 0352244 A2 | 1/1990 |

(Continued)

OTHER PUBLICATIONS

Guo et al., Protein tolerance to random amino acid change, 2004, Proc. Natl. Acad. Sci. USA 101: 9205-9210.*

(Continued)

*Primary Examiner* — Alexander Kim
(74) *Attorney, Agent, or Firm* — Fish & Richardson P.C.

(57) ABSTRACT

The present invention relates to fungal serine protease variants, which comprise an amino acid substitution of valine at position 208 of the parent *Fusarium equiseti* Fe_RF6318 serine protease, wherein the position of the substitution corresponds to the amino acid sequence of the mature Fe_RF6318 enzyme defined in SEQ ID NO:2. The variants have improved thermal stability and/or detergent stability compared to the parent Fe_RF6318 enzyme. Preferably the substitution is V208I and more preferably the variants comprise additional amino acid changes which further increase the stability. Also disclosed are nucleic acid sequences encoding said protease variants as well as recombinant vectors and host cells for the production of the variants. The serine protease variants are applicable in laundry and dish-washing detergent compositions, in treating fibers, in treating wool, in treating hair, in treating leather, in treating food or feed, or in any application involving modification, degradation or removal of proteinaceous material.

31 Claims, 23 Drawing Sheets

(51) Int. Cl.
C11D 3/386 (2006.01)
C12N 9/58 (2006.01)

(56) References Cited

U.S. PATENT DOCUMENTS

| | | | |
|---|---|---|---|
| 5,843,745 A | 12/1998 | Berka et al. | |
| 5,846,802 A * | 12/1998 | Buxton et al. | 435/225 |
| 5,962,765 A | 10/1999 | St.Leger et al. | |
| 6,300,116 B1 | 10/2001 | Von der Osten et al. | |
| 6,573,086 B1 | 6/2003 | Emalfrab et al. | |
| 6,682,924 B1 | 1/2004 | Sierkstra et al. | |
| 2004/0023355 A1 | 2/2004 | Sierkstra et al. | |
| 2010/0120649 A1 | 5/2010 | Andersen | |
| 2011/0003729 A1 | 1/2011 | Juntunen et al. | |
| 2011/0008870 A1 | 1/2011 | Makinen et al. | |
| 2011/0028375 A1 | 2/2011 | Juntunen et al. | |

FOREIGN PATENT DOCUMENTS

| | | |
|---|---|---|
| EP | 0290567 | 6/1992 |
| EP | 0290569 | 6/1992 |
| EP | 0519229 | 12/1992 |
| EP | 0 479 870 | 10/2000 |
| EP | 1347045 | 9/2003 |
| EP | 1464626 A2 | 10/2004 |
| EP | 1870453 A1 | 12/2007 |
| EP | 1 009 815 | 1/2008 |
| EP | 1464626 B1 | 11/2009 |
| WO | 88/03946 | 6/1988 |
| WO | 88/07581 | 10/1988 |
| WO | 89/04361 | 5/1989 |
| WO | 89/06270 | 7/1989 |
| WO | 92/03529 | 3/1992 |
| WO | 92/05239 | 4/1992 |
| WO | 92/18599 | 10/1992 |
| WO | 94/25583 | 11/1994 |
| WO | 96/18722 | 6/1996 |
| WO | 97/02753 | 1/1997 |
| WO | 97/08325 | 3/1997 |
| WO | 97/28243 | 8/1997 |
| WO | 98/20116 | 5/1998 |
| WO | 02/08398 | 1/2002 |
| WO | 2006/073839 | 7/2006 |
| WO | 2007/145963 | 12/2007 |
| WO | 2008/045148 | 4/2008 |
| WO | 2009/096916 | 8/2009 |
| WO | 2010/039840 | 4/2010 |
| WO | WO 2010/039840 | 4/2010 |
| WO | 2010/125174 | 11/2010 |
| WO | 2010/125175 | 11/2010 |
| WO | 2011/003968 | 1/2011 |

OTHER PUBLICATIONS

Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Branden and Tooze, Introduction to Protein Structure (1999), 2nd edition, Garland Science Publisher, pp. 3-12.*
Alkaline protease *Aspergillus fumigatus* CAA75806.1 created Sep. 3, 1998.*
Katz et al., Extreme DNA sequence variation in isolates of *Aspergillus fumigatus*., FEMS Immunology & Medical Microbiology (1998), vol. 20, Issue 4, pp. 283-288.*
Guo, H.H. et al., "Protein tolerance to random amino acid change", PNAS, vol. 101, No. 25, (2004), pp. 9205-9210.
Search Report issued in the corresponding Finnish Patent Application No. 20106135 dated May 13, 2011, 1 page.

Altschul S.F. et al. 1990 Basic Local Alignment Search Tool. J. Mol. Biol. 215:403-410.
AMFEP list of commercial enzymes. www.amfep.org updated Nov. 30, 2007.
Antal, ZS. et al. 2000. Colony growth, in vitro antagonism and secretion of extracellular enzymes in cold-tolerant strains of *Trichoderma* species Mycol. Res. (5):545-549.
Anwar, A. and Saleemuddin, M. 1998 Alkaline proteases: a review. Bioresource Technology 64:175-183.
Bolton, E.T. and McCarthy B.J. 1962. A general method for the isolation of RNA. Proc Natl. Acad. Sci. USA 48:1390-1397.
Chen, Y-J and Inoye, M. 2008. The intramolecular chaperone mediated protein folding. Curr. Opinion in Structural Biology. 18:765-770.
Cherry, J.R. and Fidantsef, A.L. 2003. Directed evolution of industrial enzymes: an update. Curr. Opin. Biotechnol.,14:438-443.
Database EMBL (online) Sep. 27, 2001 Accession No. BI750343.
Database EMBL (online) Apr. 20, 2007 "*Hypocrea lixii* mRNA for serine endopeptidase (p10261 gene)" CP002594316 EMBL:AM294980.
Database EMBL (online), Jul. 14, 2005. "EST 10474749 FvN *Gibberella amoniliformis* cDNA clone FVNC210, mRNA sequences:\". Database accession No. DR657362.
Database EMBL (online), Jun. 15, 2004. Fg02__08b01__R Fg02__AAFC__ECORC__Fusarium__graminearum-mycelium *Gibberella zeae* cDNA clone Fg02__08b01, mRNA sequence: Expressed sequence tags from *Fusarium gramineum* mycelium. Database accession No. BI750343.
Database EPO Proteins (online) May 10, 2010 Accession No. HC687299.
Database UniProt (online) Feb. 10, 2009. Subname: Full Extracellular serine protease. Accession No. Q874K4.
Database UniProt (online) May 29, 2007. "Sub-name: Full-Serine endopeptidase." Accession No. A4V8W7.
Database UniProt (online) Jun. 1, 2003. Subname: Full-alkaline proteinase. Accession No. Q86ZV3.
Database UniProt (online) Jun. 16, 2009. RecName: Full-Alkaline proteinase. Accession No. Q03420.
Database UniProt (online) May 29, 2007, "SubName: Full=serine endopeptidase;" XP00259425 EB1 accession No. UNIPROT: A4V8W7.
Database Uniprot (online), Oct. 2, 2009. "Full=Serine endopeptidase" *Trichoderma harzianum* (*Hypocrea lixii*). IDS A4V8W7_TRIHA. Database accession No. A4V8W7.
Dienes et al. 2007. Identification of a trypsin-like serine protease from *Trichoderma reesei* QM9414,Enzyme and Microb.Techn., 40(5):1087-1094.
Edman P. and Begg, G. 1967. A protein sequenator, Eur. J. Biochem., 1:80-91.
European Patent Office Database (online) Nov. 2, 2008. Sequence 313 from Patent WO2008045148. *Hypocrea lixii*. ID GM007507.
European Patent Office Database (online), Nov. 20, 2008. Sequence 313 from patent WO2008045148, *Hypoxrea lixii* protein, IDS GM007507, Database accession No. GM007507.
Galye et al., Identification of regions in interleukin-1 alpha important for activity. J Biol Chem. Oct. 15, 1993; 268(29):22105-11.
Gasteiger, E. et al. 2003 ExPASy: the proteomics server for in-depth protein knowledge and analysis. Nucleic Acids Res., 31(13):3784-3788.
GenBank Acc#AAA34209 from Geremia et al., Mol Microbiol May 1993; 8(3):603-613. Alignment with SEQ ID No. 10.
Geremia, R.A. et al 1993. Molecular characterization of the proteinase-encoding gene, *prb1*, related to mycoparasitism by *Trichoderma harzianum*. Molec. Microbiol., 8(3):603-613.
Gupta, R. et al. 2002. An overview on fermentation, downstream processing and properties of microbial alkaline proteases. Appl. Microbiol Biotechnol. 60(4):381-395.
Gun, S.J. et al. 1987 The structure and organization of nuclear genes of filamentous fungi pp. 93-139. In (JR Kinghorn, ed.) Gene Structure in Eukaryotic Microbes.

(56) References Cited

OTHER PUBLICATIONS

Joutsjoki, V.V. et al. 1993. Transformation of *Trichoderma reesei* with the *Hormoconis resinae* glucoamylase P (gamP) gene: production of a heterologous glucoamylase by *Trichoderma reesei*. Curr. Genet., 24(3):223-228.
Kalisz, H.M. 1988. Microbial proteinases. Advances in Biochemical engineering/Biotechnology. 36:1-65.
Karhunen, T. et al. 1993. High frequency one-step gene replacement in *Trichoderma reesei* I. Endoglucanase I overproduction. Mol Gen Genet., 241(5-6):515-522.
Kredics, L. et al. 2005. Extracellular proteases of *Trichoderma* species. Acta Microbiologica et Immunologica Hungarica, 52(2):169-184.
Laemmli, U.K. 1970 Cleavage of structural proteins during the assembly of the head of bacteriophage T4. Nature 227(5259):680-685.
Malardier L. et al. 1989 Cloning of the nitrate reductase gene (niaD) of *Aspergillus nidulans* and its use for transformation of *Fusarium oxysporum*. Gene 78(1):147-156.
Manonmani, H.K. and Joseph, R. 1993. Purification and properties of an extracellular proteinase of *Trichoderma koningii*. Enzyme Microb. Technol. 15:624-628.
Martinez et al. 2008. Genome sequencing and analysis of the biomass-degrading fungus *Trichoderma reesei* (syn. *Hypocrea jecornia*). Nature Biotech 26:553-560.
Mauer K-H. 2004. Detergent proteases. Current opinion in Biotechnology. 15(4):330-334.
NCBI REFSEQ Database (online Nov. 3, 2009) Hypothetical protein FG03325.2 (*Gibberella zeae* PH1). Accession XP_383491.
NCBI REFSEQ Database, Sep. 4, 2008 "Hypothetical protein FG03315.1 (*Gibberella zease* PH-1)", version XP_383491.1, Database accession No. XP-383491.
Nielsen, H. et al. 1997. Identification of procaryotic and eucaryotic signal peptides and prediction of their cleavage sites. Protein Engineering, 10(1):1-6.
Nielsen, H. et al. 1998. Prediction of signal peptides and signal anchors by a hidden Markov model. Proc. 6th Intl. Conf. of Intelligent systems. pp. 122-130.
Paloheimo, M. et al. 2003. High-Yield Production of a Bacterial Xylanase in the Filamentous Fungus*Trichoderma reesei* Requires a Carrier Polypeptide with an Intact Domain Structure. Appl. Env. Microbiol. 69(12):7073-3082.
Penttila, M. et al. 1987 A versatile transformation system for the celluloytic filamentous fungus *Trichoderma reesei*. Gene 61(2):155-164.
Poutanen, P. et al. 2001. Use of matrix-assisted laser desorption/ionization time-of-flight mass mapping and nanospray liquid chromatography/electrospray ionization tandem mass spectrometry sequence tag analysis for high sensitivity identification of yeast proteins separated by two-dimensional gel electrophoresis. Rapid Comm. Mass Spectrom., 15(18):1685-1962.
Pozo, M.J. 2004 Functional analysis of tvsp1, a serine protease-encoding gene in the biocontrol agent *Trichoderma virens*. Fungal Genetics and Biology 41:334-348.
Raeder, U. et al. 1985. Rapid Preparation of DNA from filamentous fungi. Lett. Appl. Microbiol., 1:17-20.
Rao, M.B et al. 1998. Molecular and Biotechnological aspects of microbial proteases. Microbiol. and Mol. Biol. Rev., 62(3):597-635.
Shevchenko, A. et al. 1996. Mass spectrometric sequencing of proteins from silver-stained polyacrylamide gels. Anal. Chem., 68(5):850-858.
Shimogaki, H. 1991. Purification and properties of a novel Surface-active agent and Alkaline-resistant Protease from *Bacillus* sp. Y. Agric. Biol. Chem., 55(9):2251-2258.
Steyaert, J.M. et al. 2004. Co-expression of two genes, a chitinase (chit42) and proteinase (prb1) , implicated in mycoparasitism by *Trichoderma hamatum*. Mycologia, 96(6):1245-1252.
Suarez, M.B. et al. 2007. Characterization of genes encoding novel peptidases in the biocontrol fungus *Trichoderma harzianum* CECT 2413 using the TrichoEST functional genomics approach Curr. Genet., 51(5):31-342.
UniProt database Acc#Q86ZV3_TRIHM from Steyaert et al, Mycologia 96:1245-1252 (2004). Alignment with SEQ ID No. 10.
Whisstock et al., Prediction of protein function from protein sequence and structure. Q Rev biophys. Aug. 2003; 36(3):307-40. Review.
D'Acunzo, F. et al., "Oxidation of phenols by laccase and laccase-mediator systems", Eur. J. Biochem., vol. 269, (2002), pp. 5330-5335.
Fabbrini, M. et al., "Comparing the catalytic efficiency of some mediators of lacasse", Journal of Molecular Catalysis B: Enzymatic, vol. 16, (2002), pp. 231-240.
Genbank Acc#AAA34209 from Geremia et al., Mol Microbiol May 1993;8(3):603-613. Alignment with SEQ ID No. 10 of U.S. Appl. No. 12/803,456 (3 pages).
Liao, J. et al., "Engineering proteinase K using machine learning and synthetic genes", BMC Biotechnology, vol. 7, No. 16, (2007), pp. 1-19.
Uniprot 201110 database Acc# A4V8W7_TRIHA from Suarez et al., Curr Genet. May 2007; 51(5):331-42, Epub Apr. 6, 2007, Alignment with SEQ ID No. 18 of U.S. Appl. No. 12/799,638 (2 pages).
Uniprot database Acc# Q86ZV3_TRIHM from Steyaert et al., Mycologia 96: 1245-1252 (2004). Alignment with SEQ ID No. 10 of U.S. Appl. No. 12/803,456 (2 pages).
USPTO in house alignment Q86ZV3_TRIHM from Steyaert et al. Mycologia 96:1245-1252 (2004) Alignment with SEQ ID No. 10 of U.S. Appl. No. 12/803,456 (1 page).
USPTO in house alignment AAA34209 from Geremia et al., Mol. Microbiol. May 1993;8(3):603-613. Alignment with SEQ ID No. 10 of U.S. Appl. No. 12/803,456 (2 pages).
Beg et al., "Purification and characterization of an oxidation-stable, thiol-dependent serine alkaline protease from *Bacillus mojavensis*," Enzyme and Microbial Technology, 32:394-304 (2003).
Abu-Shady, M. R. et al., "Production, Partial Purification and Some Properties of Thermostable Alkaline Protease from *Malbranchea sulfurea* and its Compatibility with Commercial Detergents", Afr. J. Mycol. and Biotech,, vol. 9, No. 3, (2001), pp. 17-26.
Banerjee, U. C. et al., "Thermostable alkaline protease from *Bacillus brevis* and its characterization as a laundry detergent additive", Process Biochemistry, vol. 35, (1999), pp. 213-219.
Gaucher, G. M. et al. "567. Thermomycolin", Handbook of Proteolytic Enzymes, (2004), pp. 1834-1835.
Kelly, J. M. et al., "Transformation of *Aspergillus niger* by the amdS gene of *Aspergillus nidulans*", The EMBO Journal, vol. 4, No. 2, (1985), pp. 475-479.
Maurer, K. H. et al. "Enzymes, Detergent", Encyclopedia of Industrial Biotechnology: Bioprocess, Bioseparation, and Cell Technology (Michael C. Flickinger, ed.), John Wiley & Sons, Inc., (2010), pp. 1-17.
Ong, P. S. et al., "Production, purification and characterization of thermomycolase, the extracellular serine protease of the thermophilic fungus *Malbranchea pulchella* var. sulfurea", Can. J. Microbiol., vol. 22, (1975), pp. 165-175.
Sambrook, J. and Russell, D. W., Molecular Cloning, a Laboratory Manual, Cold Spring Harbor Laboratory, New York, US, (2001), pp. 6.51, 6.52, 11.27.
Siezen, R. J. et al., "Subtilases: The superfamily of subtilisin-like serine proteases", Protein Science, vol. 6, (1997), pp. 501-523 (total pp. 30).
Uniprot database (online), Database Accession No. C7ZKJ9, Oct. 13, 2009, from Coleman, J.J. et al, "The genome of *Nectria haematococca*: contribution of supernumerary chromosomes to gene expansion", PLoS Genet. 5: E1000618-E1000618, (2009), (1 page).
Uniprot database (online), Database Accession No. C9SL49, Nov. 24, 2009, from Ma, L.—J.J., et al, "Annotation of *Verticillium albo-atrum* VaMs. 102.", Submitted (May 2008) to the EMBL/GenBank/DDBJ databases, (1 page).
Uniprot database (online), Database Accession No. E3Q3S5, Jan. 11, 2011, from Vaillancourt, L. et al., "The genome sequence of

(56) References Cited

OTHER PUBLICATIONS

*Glomerella graminicola* strain M1.001.", Submitted (Jun. 2009) to the EMBL/GenBank/DDBJ databases, (1 page).
Uniprot database (online), Database Accession No. C7YXB3, Oct. 13, 2009, from Coleman, J.J. et al., "The genome of *Nectria haematococca*: contribution of supernumerary chromosomes to gene expansion", PLoS Genet. 5: E1000618-E1000618, (2009), (1 page).
Uniprot database (online), Database Accession No. A5JS74, Jun. 26, 2007, from Gao, L. et al., "Gene cloning of serine protease from *Hirsutella minnesotania*", Submitted (Apr. 2007) to the EMBL/GenBank/DDBJ databases, (1 page).
Uniprot database (online), Database Accession No. Q69IF7, Sep. 13, 2004, from Hane, J.K. et al., "*Dothideomycete*-plant interactions illuminated by genome sequencing and EST analysis of the wheat pathogen *Stagonospora nodorum*.", Plant Cell, vol. 19, (2007), pp. 3347-3368, (1 page).
International Search Report from corresponding PCT Application No. PCT/EP2011/068837 dated Dec. 15, 2011, (6 pages).
McDonagh et al., "Production of caseinophosphopeptides (CPPs) from sodium caseinate using a range of commercial protease preparations," *International Dairy Journal*, 8(1): 39-45 (1998).

\* cited by examiner

FIG. 1A

```
  1  atgactagct tccgccgtat cgctcttggc cttgcagctc tgctgcccgc agtcctcgcc
  1   m  t  s  f  r  r  i  a  l  g  l  a  a  l  l  p  a  v  l  a 61  gctcccaccg agaagcgaca ggagctcact gccgcgcctg acaagtacat catcaccctc
 21   a  p  t  e  k  r  q  e  l  t  a  a  p  d  k  y  i  i  t  l 121  aagcccgagg ctgctgaggc caaggtcgag gctcacatgg cctgggttac cgacgtccac
 41   k  p  e  a  a  e  a  k  v  e  a  h  m  a  w  v  t  d  v  h 181  cgccgcagcc tcggcaagcg tgacacttcc ggtgttgaga agaagttcaa catcagcagc
 61   r  r  s  l  g  k  r  d  t  s  g  v  e  k  k  f  n  i  s  s 241  tggaacgcct actctggcga gttcgacgat gctaccattg ctgagatcaa gaagagcccc
 81   w  n  a  y  s  g  e  f  d  d  a  t  i  a  e  i  k  k  s  p 301  gaggttgcct tcgtcgagcc cgactacatt gtcaccctcg actacaaggt tgagcctctc
101   e  v  a  f  v  e  p  d  y  i  v  t  l  d  y  k  v  e  p  l 361  tctgaccgtG CTCTGACCAC TCAGAGCAAC GCTCCTTGGG GTCTTGCTGC CATCTCCCGC
121   s  d  r  A  L  T  T  Q  S  N  A  P  W  G  L  A  A  I  S  R 421  CGAACCCCCG GTGGCAGCAC CTACACCTAC GACACCACTG CCGGTGCCGG TACTTACGGT
141   R  T  P  G  G  S  T  Y  T  Y  D  T  T  A  G  A  G  T  Y  G 481  TACGTCGTTG ACTCTGGTAT CAACACCGCC CACACTGACT.TTGGCGGCCG TGCTTCTCTC
161   Y  V  V  D  S  G  I  N  T  A  H  T  D  F  G  G  R  A  S  L 541  GGTTACAACG CTGCTGGTGG CGCCCACACT GATACCCTTG GCCACGGTAC CCACGTTGCT
181   G  Y  N  A  A  G  G  A  H  T  D  T  L  G  H  G  T  H  V  A 601  GGTACCATTG CCTCCAACAC CTACGGTGTT GCCAAGCGTG CCAACGTCAT CTCTGTCAAG
201   G  T  I  A  S  N  T  Y  G  V  A  K  R  A  N  V  I  S  V  K 661  GTTTTCGTCG GTAACCAAGC TTCTACCTCT GTTATCCTTG CTGGTTTCAA CTGGGCTGTC
221   V  F  V  G  N  Q  A  S  T  S  V  I  L  A  G  F  N  W  A  V 721  AACGACATCA CCTCCAAGAA CCGTGCTAGC CGCTCTGTCA TCAACATGTC TCTCGGTGGT
241   N  D  I  T  S  K  N  R  A  S  R  S  V  I  N  M  S  L  G  G 781  CCCTCTTCTC AGACCTGGGC TACTGCCATC AACGCTGCCT ACAGCCAAGG TGTCCTCTCC
261   P  S  S  Q  T  W  A  T  A  I  N  A  A  Y  S  Q  G  V  L  S 841  GTTGTTGCTG CCGGTAACGG TGATTCCAAC GGTCGTCCTC TCCCCGCCTC TGGCCAGTCT
281   V  V  A  A  G  N  G  D  S  N  G  R  P  L  P  A  S  G  Q  S 901  CCTGCCAACG TTCCCAACGC TATCACCGTT GCTGCCGCCG ACTCCAGCTG GCGAACTGCC
301   P  A  N  V  P  N  A  I  T  V  A  A  A  D  S  S  W  R  T  A
```

FIG. 1B

```
 961   TCTTTCACCA ACTACGGTCC TGAGGTCGAT GTCTTCGGTC CTGGTGTCAA CATCCAGTCC
 321     S  F  T    N  Y  G    P  E  V  D    V  F  G    P  G  V    N  I  Q  S

1021   ACCTGGTACA CCTCCAACAG CGCTACCAAC ACCATCAGCG GTACCTCCAT GGCTTGCCCT
 341     T  W  Y    T  S  N    S  A  T  N    T  I  S    G  T  S    M  A  C  P

1081   CACGTTGCTG GTCTTGCTCT CTACCTCCAG GCTCTCGAGA ACCTCAATAC CCCTGCTGCC
 361     H  V  A    G  L  A    L  Y  L  Q    A  L  E    N  L  N    T  P  A  A

1141   GTCACCAACC GCATCAAGTC TCTTGCCACT ACCGGCCGCA TCACTGGCAG CCTCAGCGGC
 381     V  T  N    R  I  K    S  L  A  T    T  G  R    I  T  G    S  L  S  G

1201   AGCCCCAACG CCATGGCTTT CAACGGCGCT ACTGCTTAA
 401     S  P  N    A  M  A    F  N  G  A    T  A  *
```

FIG. 2A

```
        SacII
   1    ccgcggactg cgcatcatga ctagcttccg ccgtatcgct cttggccttg cagctctgct
        >>...`pcbh1....>>
                           >>..............Fe_Prt8A_cDNA..................>

61    gcccgcagtc ctcgccgctc ccaccgagaa gcgacaggag ctcactgccg cgcctgacaa
        >........................Fe_Prt8A_cDNA..........................>

121    gtacatcatc accctcaagc ccgaggctgc tgaggccaag gtcgaggctc acatggcctg
        >........................Fe_Prt8A_cDNA..........................>

181    ggttaccgac gtccaccgcc gcagcctcgg caagcgtgac acttccggtg ttgagaagaa
        >........................Fe_Prt8A_cDNA..........................>

241    gttcaacatc agcagctgga acgcctactc tggcgagttc gacgatgcta ccattgctga
        >........................Fe_Prt8A_cDNA..........................>

301    gatcaagaag agccccgagg ttgccttcgt cgagcccgac tacattgtca ccctcgacta
        >........................Fe_Prt8A_cDNA..........................>

361    caaggttgag cctctctctg accgtgctct gaccactcag agcaacgctc cttggggtct
        >........................Fe_Prt8A_cDNA..........................>

421    tgctgccatc tcccgccgaa cccccggtgg cagcacctac acctacgaca ccactgccgg
        >........................Fe_Prt8A_cDNA..........................>

481    tgccggtact tacggttacg tcgttgactc tggtatcaac accgcccaca ctgactttgg
        >........................Fe_Prt8A_cDNA..........................>

541    cggccgtgct tctctcggtt acaacgctgc tggtggcgcc cacactgata cccttggcca
        >........................Fe_Prt8A_cDNA..........................>

601    cggtacccac gttgctggta ccattgcctc caacacctac ggtgttgcca agcgtgccaa
        >........................Fe_Prt8A_cDNA..........................>

661    cgtcatctct gtcaaggttt tcgtcggtaa ccaagcttct acctctgtta tccttgctgg
        >........................Fe_Prt8A_cDNA..........................>

721    tttcaactgg gctgtcaacg acatcacctc caagaaccgt gctagccgct ctgtcatcaa
        >........................Fe_Prt8A_cDNA..........................>

781    catgtctctc ggtggtccct cttctcagac ctgggctact gccatcaacg ctgcctacag
        >........................Fe_Prt8A_cDNA..........................>

841    ccaaggtgtc ctctccgttg ttgctgccgg taacggtgat ccaacggtc gtcctctccc
        >........................Fe_Prt8A_cDNA..........................>
```

FIG. 2B

```
 901   cgcctctggc cagtctcctg ccaacgttcc caacgctatc accgttgctg ccgccgactc
       >........................Fe_Prt8A_cDNA........................>
 961   cagctggcga actgcctctt tcaccaacta cggtcctgag gtcgatgtct tcggtcctgg
       >........................Fe_Prt8A_cDNA........................>
1021   tgtcaacatc cagtccacct ggtacacctc caacagcgct accaacacca tcagcggtac
       >........................Fe_Prt8A_cDNA........................>
1081   ctccatggct tgccctcacg ttgctggtct tgctctctac ctccaggctc tcgagaacct
       >........................Fe_Prt8A_cDNA........................>
1141   caataccct gctgccgtca ccaaccgcat caagtctctt gccactaccg gccgcatcac
       >........................Fe_Prt8A_cDNA........................>
1201   tggcagcctc agcggcagcc ccaacgccat ggctttcaac ggcgctactg cttaaagctc
       >........................Fe_Prt8A_cDNA.....................>>
                                                                  tcbh1 >>..>
                       AgeI
1261   cgtggcgaaa gcctgacgca ccggt
       >.........tcbh1´.........>>
```

FIG. 8A

```
  1  atgactagct tccgccgtat cgctcttggc cttgcagctc tgctgcccgc agtcctcgcc
  1   m  t  s   f  r  r   i  a  l   g   l  a  a   l  l  p   a  v  l  a 61  gctcccaccg agaagcgaca ggagctcact gccgcgcctg acaagtacat catcaccctc
 21   a  p  t   e  k  r   q  e  l   t   a  a  p   d  k  y   i  i  t  l 121  aagcccgagg ctgctgaggc caaggtcgag gctcacatgg cctgggttac cgacgtccac
 41   k  p  e   a  a  e   a  k  v   e   a  h  m   a  w  v   t  d  v  h 181  cgccgcagcc tcggcaagcg tgacacttcc ggtgttgaga agaagttcaa catcagcagc
 61   r  r  s   l  g  k   r  d  t   s   g  v  e   k  k  f   n  i  s  s 241  tggaacgcct actctggcga gttcgacgat gctaccattg ctgagatcaa gaagagcccc
 81   w  n  a   y  s  g   e  f  d   d   a  t  i   a  e  i   k  k  s  p 301  gaggttgcct tcgtcgagcc cgactacatt gtcaccctcg actacaaggt tgagcctctc
101   e  v  a   f  v  e   p  d  y   i   v  t  l   d  y  k   v  e  p  l 361  tctgaccgtG CTCTGACCAC TCAGAGCAAC GCTCCTTGGG GTCTTGCTGC CATCTCCCGC
121   s  d  r   A  L  T   T  Q  S   N   A  P  W   G  L  A   A  I  S  R 421  CGAACCCCCG GTGGCAGCAC CTACACCTAC GACACCACTG CCGGTGCCGG TACTTACGGT
141   R  T  P   G  G  S   T  Y  T   Y   D  T  T   A  G  A   G  T  Y  G 481  TACGTCGTTG ACTCTGGTAT CAACACCGCC CACACTGACT TTGGCGGCCG TGCTTCTCTC
161   Y  V  V   D  S  G   I  N  T   A   H  T  D   F  G  G   R  A  S  L 541  GGTTACAACG CTGCTGGTGG CGCCCACACT GATACCCTTG GCCACGGTAC CCACGTTGCT
181   G  Y  N   A  A  G   G  A  H   T   D  T  L   G  H  G   T  H  V  A 601  GGTACCATTG CCTCCAACAC CTACGGTGTT GCCAAGCGTG CCAACGTCAT CTCTGTCAAG
201   G  T  I   A  S  N   T  Y  G   V   A  K  R   A  N  V   I  S  V  K 661  GTTTTCGTCG GTAACCAAGC TTCTACCTCT GTTATCCTTG AC GGTTTCAA CTGGGCTGTC
221   V  F  V   G  N  Q   A  S  T   S   V  I  L   D  G  F   N  W  A  V 721  AACGACATCA CCTCCAAGAA CCGTGCTAGC CGCTCTGTCA TCAACATGTC TCTCGGTGGT
241   N  D  I   T  S  K   N  R  A   S   R  S  V   I  N  M   S  L  G  G 781  CCCTCTTCTC AGACCTGGGC TACTGCCATC AACGCTGCCT ACAGCCAAGG TGTCCTCTCC
261   P  S  S   Q  T  W   A  T  A   I   N  A  A   Y  S  Q   G  V  L  S 841  GTTGTTGCTG CCGGTAACGG TGATTCCAAC GGTCGTCCTC TCCCCGCCTC TGGCCAGTCT
281   V  V  A   A  G  N   G  D  S   N   G  R  P   L  P  A   S  G  Q  S
```

FIG. 8B

```
 901  CCTGCCAACG TTCCCAACGC TATCACCGTT GCTGCCGCCG ACTCCAGCTG GCGAACTGCC
 301    P   A   N    V   P   N    A   I   T   V    A   A   A   D    S   S   W   R   T   A

961  TCTTTCACCA ACTACGGTCC TGAGGTCGAT ATCTTCGGTC CTGGTGTCAA CATCCAGTCC
 321    S   F   T    N   Y   G    P   E   V   D    I   F   G    P   G   V   N   I   Q   S

1021  ACCTGGTACA CCTCCAACAG CGCTACCAAC ACCATCAGCG GTACCTCCAT GGCTTGCCCT
 341    T   W   Y    T   S   N    S   A   T   N    T   I   S   G    T   S   M   A   C   P

1081  CACGTTGCTG GTCTTGCTCT CTACCTCCAG GCTCTCGAGA ACCTCAATAC CCCTGCTGCC
 361    H   V   A    G   L   A    L   Y   L   Q    A   L   E    N   L   N   T   P   A   A

1141  GTCACCAACC GCATCAAGTC TCTTGCCACT ACCGGCCGCA TCACTGGCAG CCTCAGCGGC
 381    V   T   N    R   I   K    S   L   A   T    T   G   R    I   T   G   S   L   S   G

1201  AGCCCCAACC TCATGGCTTT CAACGGCGCT ACTGCTTAA
 401    S   P   N    L   M   A    F   N   G   A    T   A   *
```

Wash performance, blood/milk/ink (Art.117, EMPA), Liquid Base Detergent at 5 g/l
(60 min, 30°C, pH approx. 7.4)

Wash performance, blood/milk/ink (Art.117, EMPA), Liquid Base Detergent at 5 g/l
(60 min, 45°C, pH approx. 7.4)

Stability in Liquid Base Detergent for colored fabrics (37°C, pH approx. 8.2)

Stability in Liquid Base Detergent for colored fabrics with 2% sodium tetraborate decahydrate and 17% propylene glycol (37°C, pH approx. 7)

Stability in Ecolabel Reference Detergent (wfk Testgewebe GmbH) (18 hrs, 37°C, pH approx. 7.2)

Stability in Commercial liquid detergent (37°C, pH approx. 8.2)

Stability in Ecolabel Reference Detergent (wfk Testgewebe GmbH) with 2% sodium tetraborate decahydrate and 17% propylene glycol (37°C, pH approx. 6.5)

Stability in Commercial liquid Detergent with 2% sodium tetraborate decahydrate and 17% propylene glycol (37°C, pH approx. 7.5)

Wash performance, blood/milk/ink (Art.117, EMPA), Commercial liquid detergent at 5 g/l (60 min, 30°C, pH approx. 7.8)

Wash performance, blood/milk/ink (Art. 117, EMPA), Commercial liquid detergent at 5 g/l (60 min, 30°C, pH approx. 7.8)

Wash performance, blood/milk/ink (Art.117, EMPA), Commercial liquid detergent at 5 g/l (60 min, 50°C, pH approx. 7.8)

Wash performance, blood/milk/ink (Art.117, EMPA), Commercial liquid detergent at 5 g/l (60 min, 50°C, pH approx. 7.8)

Wash performance, blood/milk/ink (Art.117, EMPA), Commercial liquid detergent at 5 g/l
(60 min, 30°C, pH approx. 7.8)

Wash performance, blood/milk/ink (Art.117, EMPA), Commercial liquid detergent at 5 g/l
(60 min, 50°C, pH approx. 7.8)

Stability in Commercial liquid detergent (37°C, pH approx. 8.2)

Stability in Commercial liquid detergent (37°C, pH approx. 8.2)

Stability in Commercial liquid detergent with 2% sodium tetraborate decahydrate and 17% propylene glycol (37°C, pH approx. 7.5)

Stability in Commercial liquid detergent with 2% sodium tetraborate decahydrate and 17% propylene glycol (37°C, pH approx. 7.5)

Stability in Ecolabel Reference Detergent (20 hrs, 37°C, pH approx. 7.2)

SEQUENCE LISTING

```
<160> NUMBER OF SEQ ID NOS: 55

<210> SEQ ID NO 1
<211> LENGTH: 870
<212> TYPE: DNA
<213> ORGANISM: Fusarium equiseti
<220> FEATURE:
<223> OTHER INFORMATION: The nucleotide sequence encoding the amino acid
      sequence of the mature form of Fe_RF6318 protease

<400> SEQUENCE: 1
gctctgacca ctcagagcaa cgctccttgg ggtcttgctg ccatctcccg ccgaaccccc        60
ggtggcagca cctacaccta cgacaccact gccggtgccg gtacttacgg ttacgtcgtt       120
gactctggta tcaacaccgc ccacactgac tttggcggcc gtgcttctct cggttacaac       180
gctgctggtg gcgcccacac tgatacccct ggccacggta cccacgttgc tggtaccatt       240
gcctccaaca cctacggtgt tgccaagcgt gccaacgtca tctctgtcaa ggttttcgtc       300
ggtaaccaag cttctacctc tgttatcctt gctggtttca ctgggctgt caacgacatc       360 acctccaaga accgtgctag ccgctctgtc atcaacatgt ctctcggtgg tccctcttct       420
cagacctggg ctactgccat caacgctgcc tacagccaag gtgtcctctc cgttgttgct       480
gccggtaacg gtgattccaa cggtcgtcct ctccccgcct ctggccagtc tcctgccaac       540
gttcccaacg ctatcaccgt tgctgccgcc gactccagct ggcgaactgc ctctttcacc       600
aactacggtc ctgaggtcga tgtcttcggt cctggtgtca acatccagtc cacctggtac       660
acctccaaca gcgctaccaa caccatcagc ggtacctcca tggcttgccc tcacgttgct       720
ggtcttgctc tctacctcca ggctctcgag aacctcaata ccctgctgc cgtcaccaac       780 cgcatcaagt ctcttgccac taccgccgc atcactggca gcctcagcgg cagcccaac       840 gccatggctt tcaacggcgc tactgcttaa                                        870

<210> SEQ ID NO 2
<211> LENGTH: 289
<212> TYPE: PRT
```

<213> ORGANISM: Fusarium equiseti
<220> FEATURE:
<223> OTHER INFORMATION: The amino acid sequence of the mature form of Fe_RF6318 protease

<400> SEQUENCE: 2

| | | | | | | | | | | | | | | |
|---|---|---|---|---|---|---|---|---|---|---|---|---|---|---|
| Ala | Leu | Thr | Thr | Gln | Ser | Asn | Ala | Pro | Trp | Gly | Leu | Ala | Ala | Ile | Ser |
| 1 | | | | 5 | | | | | 10 | | | | | 15 | |
| Arg | Arg | Thr | Pro | Gly | Gly | Ser | Thr | Tyr | Thr | Tyr | Asp | Thr | Thr | Ala | Gly |
| | | | 20 | | | | | 25 | | | | | 30 | | |
| Ala | Gly | Thr | Tyr | Gly | Tyr | Val | Val | Asp | Ser | Gly | Ile | Asn | Thr | Ala | His |
| | | 35 | | | | | 40 | | | | | 45 | | | |
| Thr | Asp | Phe | Gly | Gly | Arg | Ala | Ser | Leu | Gly | Tyr | Asn | Ala | Ala | Gly | Gly |
| 50 | | | | | 55 | | | | | 60 | | | | | |
| Ala | His | Thr | Asp | Thr | Leu | Gly | His | Gly | Thr | His | Val | Ala | Gly | Thr | Ile |
| 65 | | | | | 70 | | | | | 75 | | | | | 80 |
| Ala | Ser | Asn | Thr | Tyr | Gly | Val | Ala | Lys | Arg | Ala | Asn | Val | Ile | Ser | Val |
| | | | | 85 | | | | | 90 | | | | | 95 | |
| Lys | Val | Phe | Val | Gly | Asn | Gln | Ala | Ser | Thr | Ser | Val | Ile | Leu | Ala | Gly |
| | | | | 100 | | | | | 105 | | | | | 110 | |
| Phe | Asn | Trp | Ala | Val | Asn | Asp | Ile | Thr | Ser | Lys | Asn | Arg | Ala | Ser | Arg |
| | | | 115 | | | | | 120 | | | | | 125 | | |
| Ser | Val | Ile | Asn | Met | Ser | Leu | Gly | Gly | Pro | Ser | Ser | Gln | Thr | Trp | Ala |
| | 130 | | | | | 135 | | | | | 140 | | | | |
| Thr | Ala | Ile | Asn | Ala | Ala | Tyr | Ser | Gln | Gly | Val | Leu | Ser | Val | Val | Ala |
| 145 | | | | | 150 | | | | | 155 | | | | | 160 |
| Ala | Gly | Asn | Gly | Asp | Ser | Asn | Gly | Arg | Pro | Leu | Pro | Ala | Ser | Gly | Gln |
| | | | | 165 | | | | | 170 | | | | | 175 | |
| Ser | Pro | Ala | Asn | Val | Pro | Asn | Ala | Ile | Thr | Val | Ala | Ala | Ala | Asp | Ser |
| | | 180 | | | | | 185 | | | | | 190 | | | |
| Ser | Trp | Arg | Thr | Ala | Ser | Phe | Thr | Asn | Tyr | Gly | Pro | Glu | Val | Asp | Val |
| | | 195 | | | | | 200 | | | | | 205 | | | |
| Phe | Gly | Pro | Gly | Val | Asn | Ile | Gln | Ser | Thr | Trp | Tyr | Thr | Ser | Asn | Ser |
| | 210 | | | | | 215 | | | | | 220 | | | | |
| Ala | Thr | Asn | Thr | Ile | Ser | Gly | Thr | Ser | Met | Ala | Cys | Pro | His | Val | Ala |
| 225 | | | | | 230 | | | | | 235 | | | | | 240 |
| Gly | Leu | Ala | Leu | Tyr | Leu | Gln | Ala | Leu | Glu | Asn | Leu | Asn | Thr | Pro | Ala |
| | | | | 245 | | | | | 250 | | | | | 255 | |
| Ala | Val | Thr | Asn | Arg | Ile | Lys | Ser | Leu | Ala | Thr | Thr | Gly | Arg | Ile | Thr |
| | | | 260 | | | | | 265 | | | | | 270 | | |
| Gly | Ser | Leu | Ser | Gly | Ser | Pro | Asn | Ala | Met | Ala | Phe | Asn | Gly | Ala | Thr |
| | | 275 | | | | | 280 | | | | | 285 | | | |
| Ala | | | | | | | | | | | | | | | |

<210> SEQ ID NO 3
<211> LENGTH: 870
<212> TYPE: DNA
<213> ORGANISM: Fusarium acuminatum
<220> FEATURE:
<223> OTHER INFORMATION: The nucleotide sequence encoding the amino acid sequence of the mature form of Fusarium acuminatum RF7182 protease

<400> SEQUENCE: 3 gctct

```
gctgctggtg gtgctcacac cgatacccte ggccacggaa cccacgttgc tggtaccatc    240
ggtggcacca agtatggtgt ctccaagaag gccaacctca tctctgtcaa ggtcttcgcc    300
ggtaaccagg ctgctacatc tgttatcctt gatggcttta actgggccgt caacgacatc    360
acctccaagg gccgtgctgg caagtccgtt atcaacatgt ctctcggcgg accttcttct    420
gctacttgga ccactgccat caacgctgga tacaacgctg gtgtcctctc cgttgtcgct    480
gccggtaacg gtgatgtcaa tggcaaccct ctccccgtct ctagccagtc tcctgccaac    540
gcccccaacg ccctgaccgt cgctgccatt gactccaact ggcgcactgc ctctttcacc    600
aactacggtg ccgtgttga tatcttcggc cccggtgtca acattctgtc cgcctggatc    660
ggctccagca ccgctaccaa caccatcagc ggaacttcca tggcctcccc ccaccttgct    720
ggtcttgctc tctacctcca ggtccttgag ggtcttagca ctcctgctgc tgtcaccaac    780
cgcatcaagg ctcttggtac ctctggcaag gtcactggta gcctcagcgg cagccccaac    840
ctcgttgcct acaacggtaa cggtgcttag                                     870

<210> SEQ ID NO 4
<211> LENGTH: 289
<212> TYPE: PRT
<213> ORGANISM: Fusarium acuminatum
<220> FEATURE:
<223> OTHER INFORMATION: The amino acid sequence of the mature form of
      Fusarium acuminatum RF7182 protease

<400> SEQUENCE: 4

Ala Leu Thr Thr Gln Ser Gly Ala Pro Trp Gly Leu Gly Ala Ile Ser
1               5                   10                  15

His Lys Ser Ser Gly Ser Thr Ser Tyr Ile Tyr Asp Thr Thr Ala Gly
                20                  25                  30

Ser Gly Ser Tyr Gly Tyr Val Val Asp Ser Gly Ile Asn Ile Ala His
            35                  40                  45

Thr Asp Phe Gly Gly Arg Ala Thr Leu Gly Tyr Asn Ala Ala Gly Gly
    50                  55                  60

Ala His Thr Asp Thr Leu Gly His Gly Thr His Val Ala Gly Thr Ile
65                  70                  75                  80

Gly Gly Thr Lys Tyr Gly Val Ser Lys Lys Ala Asn Leu Ile Ser Val
                85                  90                  95

Lys Val Phe Ala Gly Asn Gln Ala Ala Thr Ser Val Ile Leu Asp Gly
                100                 105                 110

Phe Asn Trp Ala Val Asn Asp Ile Thr Ser Lys Gly Arg Ala Gly Lys
            115                 120                 125

Ser Val Ile Asn Met Ser Leu Gly Gly Pro Ser Ser Ala Thr Trp Thr
    130                 135                 140

Thr Ala Ile Asn Ala Gly Tyr Asn Ala Gly Val Leu Ser Val Val Ala
145                 150                 155                 160

Ala Gly Asn Gly Asp Val Asn Gly Asn Pro Leu Pro Val Ser Ser Gln
                165                 170                 175

Ser Pro Ala Asn Ala Pro Asn Ala Leu Thr Val Ala Ala Ile Asp Ser
            180                 185                 190

Asn Trp Arg Thr Ala Ser Phe Thr Asn Tyr Gly Ala Gly Val Asp Ile
    195                 200                 205

Phe Gly Pro Gly Val Asn Ile Leu Ser Ala Trp Ile Gly Ser Ser Thr
    210                 215                 220

Ala Thr Asn Thr Ile Ser Gly Thr Ser Met Ala Ser Pro His Leu Ala
```

```
225                 230                 235                 240
Gly Leu Ala Leu Tyr Leu Gln Val Leu Glu Gly Leu Ser Thr Pro Ala
                245                 250                 255

Ala Val Thr Asn Arg Ile Lys Ala Leu Gly Thr Ser Gly Lys Val Thr
                260                 265                 270

Gly Ser Leu Ser Gly Ser Pro Asn Leu Val Ala Tyr Asn Gly Asn Gly
        275                 280                 285

Ala
```

<210> SEQ ID NO 5
<211> LENGTH: 870
<212> TYPE: DNA
<213> ORGANISM: Artificial sequence
<220> FEATURE:
<223> OTHER INFORMATION: Description of Artificial Sequence: Synthetic
      polynucleotide
<220> FEATURE:
<223> OTHER INFORMATION: The nucleotide sequence encoding the amino acid
      sequence of the mature form of Fe_RF6318 serine protease variant
      comprising substitution V208I

<400> SEQUENCE: 5

```
gctctgacca ctcagagcaa cgctccttgg ggtcttgctg ccatctcccg ccgaaccccc       60
ggtggcagca cctacaccta cgacaccact gccggtgccg gtacttacgg ttacgtcgtt      120
gactctggta tcaacaccgc ccacactgac tttggcggcc gtgcttctct cggttacaac      180
gctgctggtg gcgcccacac tgataccctt ggccacggta cccacgttgc tggtaccatt      240
gcctccaaca cctacggtgt tgccaagcgt gccaacgtca tctctgtcaa ggttttcgtc      300
ggtaaccaag cttctacctc tgttatcctt gctggtttca actgggctgt caacgacatc      360
acctccaaga accgtgctag ccgctctgtc atcaacatgt ctctcggtgg tccctcttct      420
cagacctggg ctactgccat caacgctgcc tacagccaag tgtcctctc cgttgttgct       480
gccggtaacg tgattccaa cggtcgtcct ctccccgcct ctggccagtc tcctgccaac       540
gttcccaacg ctatcaccgt tgctgccgcc gactccagct ggcgaactgc ctctttcacc      600
aactacggtc tgaggtcga tatcttcggt cctggtgtca acatccagtc cacctggtac      660
acctccaaca gcgctaccaa caccatcagc ggtacctcca tggcttgccc tcacgttgct      720
ggtcttgctc tctacctcca ggctctcgag aacctcaata cccctgctgc cgtcaccaac      780
cgcatcaagt ctcttgccac taccggccgc atcactggca gcctcagcgg cagccccaac      840
gccatggctt tcaacggcgc tactgcttaa                                       870
```

<210> SEQ ID NO 6
<211> LENGTH: 289
<212> TYPE: PRT
<213> ORGANISM: Artificial sequence
<220> FEATURE:
<223> OTHER INFORMATION: Description of Artificial Sequence: Synthetic
      polypeptide
<220> FEATURE:
<223> OTHER INFORMATION: The amino acid sequence of the mature form of
      Fe_RF6318 serine protease variant comprising substitution V208I

<400> SEQUENCE: 6

```
Ala Leu Thr Thr Gln Ser Asn Ala Pro Trp Gly Leu Ala Ala Ile Ser
1               5                   10                  15

Arg Arg Thr Pro Gly Gly Ser Thr Tyr Thr Tyr Asp Thr Thr Ala Gly
                20                  25                  30

Ala Gly Thr Tyr Gly Tyr Val Val Asp Ser Gly Ile Asn Thr Ala His
```

```
                    35                  40                  45
Thr Asp Phe Gly Gly Arg Ala Ser Leu Gly Tyr Asn Ala Ala Gly Gly
 50                  55                  60
Ala His Thr Asp Thr Leu Gly His Gly Thr His Val Ala Gly Thr Ile
 65                  70                  75                  80
Ala Ser Asn Thr Tyr Gly Val Ala Lys Arg Ala Asn Val Ile Ser Val
                 85                  90                  95
Lys Val Phe Val Gly Asn Gln Ala Ser Thr Ser Val Ile Leu Ala Gly
            100                 105                 110
Phe Asn Trp Ala Val Asn Asp Ile Thr Ser Lys Asn Arg Ala Ser Arg
        115                 120                 125
Ser Val Ile Asn Met Ser Leu Gly Gly Pro Ser Ser Gln Thr Trp Ala
130                 135                 140
Thr Ala Ile Asn Ala Ala Tyr Ser Gln Gly Val Leu Ser Val Val Ala
145                 150                 155                 160
Ala Gly Asn Gly Asp Ser Asn Gly Arg Pro Leu Pro Ala Ser Gly Gln
                165                 170                 175
Ser Pro Ala Asn Val Pro Asn Ala Ile Thr Val Ala Ala Ala Asp Ser
            180                 185                 190
Ser Trp Arg Thr Ala Ser Phe Thr Asn Tyr Gly Pro Glu Val Asp Ile
        195                 200                 205
Phe Gly Pro Gly Val Asn Ile Gln Ser Thr Trp Tyr Thr Ser Asn Ser
210                 215                 220
Ala Thr Asn Thr Ile Ser Gly Thr Ser Met Ala Cys Pro His Val Ala
225                 230                 235                 240
Gly Leu Ala Leu Tyr Leu Gln Ala Leu Glu Asn Leu Asn Thr Pro Ala
                245                 250                 255
Ala Val Thr Asn Arg Ile Lys Ser Leu Ala Thr Thr Gly Arg Ile Thr
            260                 265                 270
Gly Ser Leu Ser Gly Ser Pro Asn Ala Met Ala Phe Asn Gly Ala Thr
        275                 280                 285
Ala
```

<210> SEQ ID NO 7
<211> LENGTH: 870
<212> TYPE: DNA
<213> ORGANISM: Artificial sequence
<220> FEATURE:
<223> OTHER INFORMATION: Description of Artificial Sequence: Synthetic
      polynucleotide
<220> FEATURE:
<223> OTHER INFORMATION: The nucleotide sequence encoding the amino acid
      sequence of the mature form of Fe_RF6318 serine protease variant
      comprising substitutions V208I and A111D

<400> SEQUENCE: 7
gctctgacca ctcagagcaa cgctccttgg ggtcttgctg ccatctcccg ccgaaccccc     60
ggtggcagca cctacaccta cgacaccact gccggtgccg gtacttacgg ttacgtcgtt    120
gactctggta tcaacaccgc ccacactgac tttggcggcc gtgcttctct cggttacaac    180
gctgctggtg gcgcccacac tgataccctt ggccacggta cccacgttgc tggtaccatt    240
gcctccaaca cctacggtgt tgccaagcgt gccaacgtca tctctgtcaa ggttttcgtc    300
ggtaaccaag cttctacctc tgttatcctt gacggtttca actgggctgt caacgacatc    360
acctccaaga ccgtgctag ccgctctgtc atcaacatgt ctctcggtgg tcctctcttct    420 cagacctggg ctactgccat caacgctgcc tacagccaag gtgtcctctc cgttgttgct    480

```
gccggtaacg gtgattccaa cggtcgtcct ctccccgcct ctggccagtc tcctgccaac    540
gttcccaacg ctatcaccgt tgctgccgcc gactccagct ggcgaactgc ctctttcacc    600
aactacggtc tgaggtcga tatcttcggt cctggtgtca acatccagtc cacctggtac     660
acctccaaca gcgctaccaa caccatcagc ggtacctcca tggcttgccc tcacgttgct    720
ggtcttgctc tctacctcca ggctctcgag aacctcaata cccctgctgc cgtcaccaac    780
cgcatcaagt ctcttgccac taccggccgc atcactggca gcctcagcgg cagccccaac    840
gccatggctt tcaacggcgc tactgcttaa                                      870
```

```
<210> SEQ ID NO 8
<211> LENGTH: 289
<212> TYPE: PRT
<213> ORGANISM: Artificial sequence
<220> FEATURE:
<223> OTHER INFORMATION: Description of Artificial Sequence: Synthetic
      polypeptide
<220> FEATURE:
<223> OTHER INFORMATION: The amino acid sequence of the mature form of
      Fe_RF6318 serine protease variant comprising substitutions V208I
      and A111D

<400> SEQUENCE: 8
```

```
Ala Leu Thr Thr Gln Ser Asn Ala Pro Trp Gly Leu Ala Ala Ile Ser
1               5                   10                  15

Arg Arg Thr Pro Gly Gly Ser Thr Tyr Thr Tyr Asp Thr Thr Ala Gly
                20                  25                  30

Ala Gly Thr Tyr Gly Tyr Val Val Asp Ser Gly Ile Asn Thr Ala His
            35                  40                  45

Thr Asp Phe Gly Gly Arg Ala Ser Leu Gly Tyr Asn Ala Ala Gly Gly
        50                  55                  60

Ala His Thr Asp Thr Leu Gly His Gly Thr His Val Ala Gly Thr Ile
65                  70                  75                  80

Ala Ser Asn Thr Tyr Gly Val Ala Lys Arg Ala Asn Val Ile Ser Val
                85                  90                  95

Lys Val Phe Val Gly Asn Gln Ala Ser Thr Ser Val Ile Leu Asp Gly
                100                 105                 110

Phe Asn Trp Ala Val Asn Asp Ile Thr Ser Lys Asn Arg Ala Ser Arg
            115                 120                 125

Ser Val Ile Asn Met Ser Leu Gly Gly Pro Ser Ser Gln Thr Trp Ala
        130                 135                 140

Thr Ala Ile Asn Ala Ala Tyr Ser Gln Gly Val Leu Ser Val Val Ala
145                 150                 155                 160

Ala Gly Asn Gly Asp Ser Asn Gly Arg Pro Leu Pro Ala Ser Gly Gln
                165                 170                 175

Ser Pro Ala Asn Val Pro Asn Ala Ile Thr Val Ala Ala Ala Asp Ser
            180                 185                 190

Ser Trp Arg Thr Ala Ser Phe Asn Tyr Gly Pro Glu Val Asp Ile
        195                 200                 205

Phe Gly Pro Gly Val Asn Ile Gln Ser Thr Trp Tyr Thr Ser Asn Ser
    210                 215                 220

Ala Thr Asn Thr Ile Ser Gly Thr Ser Met Ala Cys Pro His Val Ala
225                 230                 235                 240

Gly Leu Ala Leu Tyr Leu Gln Ala Leu Glu Asn Leu Asn Thr Pro Ala
                245                 250                 255

Ala Val Thr Asn Arg Ile Lys Ser Leu Ala Thr Thr Gly Arg Ile Thr
```

```
                260                 265                 270
Gly Ser Leu Ser Gly Ser Pro Asn Ala Met Ala Phe Asn Gly Ala Thr
            275                 280                 285

Ala

<210> SEQ ID NO 9
<211> LENGTH: 870
<212> TYPE: DNA
<213> ORGANISM: Artificial sequence
<220> FEATURE:
<223> OTHER INFORMATION: Description of Artificial Sequence: Synthetic
      polynucleotide
<220> FEATURE:
<223> OTHER INFORMATION: The nucleotide sequence encoding the amino acid
      sequence of the mature form of Fe_RF6318 serine protease variant
      comprising substitutions V208I and A281L

<400> SEQUENCE: 9
gctctgacca ctcagagcaa cgctccttgg ggtcttgctg ccatctcccg ccgaaccccc        60
ggtggcagca cctacaccta cgacaccact gccggtgccg gtacttacgg ttacgtcgtt       120
gactctggta tcaacaccgc ccacactgac tttggcggcc gtgcttctct cggttacaac       180
gctgctggtg gcgcccacac tgataccctt ggccacggta cccacgttgc tggtaccatt       240
gcctccaaca cctacggtgt tgccaagcgt gccaacgtca tctctgtcaa ggttttcgtc       300
ggtaaccaag cttctacctc tgttatcctt gctggtttca ctgggctgt caacgacatc        360 acctccaaga accgtgctag ccgctctgtc atcaacatgt ctctcggtgg tccctcttct       420
cagacctggg ctactgccat caacgctgcc tacagccaag gtgtcctctc cgttgttgct       480
gccggtaacg gtgattccaa cggtcgtcct ctccccgcct ctggccagtc tcctgccaac       540
gttcccaacg ctatcaccgt tgctgccgcc gactccagct ggcgaactgc ctctttcacc       600
aactacggtc tgaggtcga tatcttcggt cctggtgtca acatccagtc cacctggtac       660
acctccaaca cgctaccaa caccatcagc ggtacctcca tggcttgccc tcacgttgct        720
ggtcttgctc tctacctcca ggctctcgag aacctcaata cccctgctgc cgtcaccaac       780
cgcatcaagt ctcttgccac taccggccgc atcactggca gcctcagcgg cagccccaac       840
ctcatggctt tcaacggcgc tactgcttaa                                        870

<210> SEQ ID NO 10
<211> LENGTH: 289
<212> TYPE: PRT
<213> ORGANISM: Artificial sequence
<220> FEATURE:
<223> OTHER INFORMATION: Description of Artificial Sequence: Synthetic
      polypeptide
<220> FEATURE:
<223> OTHER INFORMATION: The amino acid sequence of the mature form of
      Fe_RF6318 serine protease variant comprising substitutions V208I
      and A281L

<400> SEQUENCE: 10

Ala Leu Thr Thr Gln Ser Asn Ala Pro Trp Gly Leu Ala Ala Ile Ser
1               5                  10                  15

Arg Arg Thr Pro Gly Gly Ser Thr Tyr Thr Tyr Asp Thr Thr Ala Gly
            20                  25                  30

Ala Gly Thr Tyr Gly Tyr Val Val Asp Ser Gly Ile Asn Thr Ala His
        35                  40                  45

Thr Asp Phe Gly Gly Arg Ala Ser Leu Gly Tyr Asn Ala Ala Gly Gly
    50                  55                  60
```

Ala His Thr Asp Thr Leu Gly His Gly Thr His Val Ala Gly Thr Ile
65                  70                  75                  80

Ala Ser Asn Thr Tyr Gly Val Ala Lys Arg Ala Asn Val Ile Ser Val
                85                  90                  95

Lys Val Phe Val Gly Asn Gln Ala Ser Thr Ser Val Ile Leu Ala Gly
            100                 105                 110

Phe Asn Trp Ala Val Asn Asp Ile Thr Ser Lys Asn Arg Ala Ser Arg
        115                 120                 125

Ser Val Ile Asn Met Ser Leu Gly Gly Pro Ser Ser Gln Thr Trp Ala
    130                 135                 140

Thr Ala Ile Asn Ala Ala Tyr Ser Gln Gly Val Leu Ser Val Val Ala
145                 150                 155                 160

Ala Gly Asn Gly Asp Ser Asn Gly Arg Pro Leu Pro Ala Ser Gly Gln
                165                 170                 175

Ser Pro Ala Asn Val Pro Asn Ala Ile Thr Val Ala Ala Ala Asp Ser
            180                 185                 190

Ser Trp Arg Thr Ala Ser Phe Thr Asn Tyr Gly Pro Glu Val Asp Ile
        195                 200                 205

Phe Gly Pro Gly Val Asn Ile Gln Ser Thr Trp Tyr Thr Ser Asn Ser
    210                 215                 220

Ala Thr Asn Thr Ile Ser Gly Thr Ser Met Ala Cys Pro His Val Ala
225                 230                 235                 240

Gly Leu Ala Leu Tyr Leu Gln Ala Leu Glu Asn Leu Asn Thr Pro Ala
                245                 250                 255

Ala Val Thr Asn Arg Ile Lys Ser Leu Ala Thr Thr Gly Arg Ile Thr
            260                 265                 270

Gly Ser Leu Ser Gly Ser Pro Asn Leu Met Ala Phe Asn Gly Ala Thr
        275                 280                 285

Ala

<210> SEQ ID NO 11
<211> LENGTH: 870
<212> TYPE: DNA
<213> ORGANISM: Artificial sequence
<220> FEATURE:
<223> OTHER INFORMATION: Description of Artificial Sequence: Synthetic
    polynucleotide
<220> FEATURE:
<223> OTHER INFORMATION: The nucleotide sequence encoding the amino acid
    sequence of the mature form of Fe_RF6318 serine protease variant
    comprising substitutions V208I, A111D and A281L

<400> SEQUENCE: 11
gctctgacca ctcagagcaa cgctccttgg ggtcttgctg ccatctcccg ccgaaccccc      60
ggtggcagca cctacaccta cgacaccact gccggtgccg gtacttacgg ttacgtcgtt     120
gactctggta tcaacaccgc ccacactgac tttggcggcc gtgcttctct cggttacaac     180
gctgctggtg cgcccacac tgataccctt ggccacggta cccacgttgc tggtaccatt     240
gcctccaaca cctacggtgt tgccaagcgt gccaacgtca tctctgtcaa ggttttcgtc     300
ggtaaccaag cttctacctc tgttatcctt gacggtttca actgggctgt caacgacatc     360
acctccaaga accgtgctag ccgctctgtc atcaacatgt ctctcggtgg tccctcttct     420
cagacctggg ctactgccat caacgctgcc tacagccaag gtgtcctctc cgttgttgct     480
gccggtaacg gtgattccaa cggtcgtcct ctccccgcct ctggccagtc tcctgccaac     540
gttcccaacg ctatcaccgt tgctgccgcc gactccagct ggcgaactgc ctctttcacc     600

```
aactacggtc ctgaggtcga tatcttcggt cctggtgtca acatccagtc cacctggtac    660
acctccaaca gcgctaccaa caccatcagc ggtacctcca tggcttgccc tcacgttgct    720
ggtcttgctc tctacctcca ggctctcgag aacctcaata ccctgctgc cgtcaccaac     780 cgcatcaagt tcttgccac taccggccgc atcactggca gcctcagcgg cagccccaac    840
ctcatggctt tcaacggcgc tactgcttaa                                     870
```

<210> SEQ ID NO 12
<211> LENGTH: 289
<212> TYPE: PRT
<213> ORGANISM: Artificial sequence
<220> FEATURE:
<223> OTHER INFORMATION: Description of Artificial Sequence: Synthetic polypeptide
<220> FEATURE:
<223> OTHER INFORMATION: The amino acid sequence of the mature form of Fe_RF6318 serine protease variant comprising substitutions V208I, A111D and A281L

<400> SEQUENCE: 12

```
Ala Leu Thr Thr Gln Ser Asn Ala Pro Trp Gly Leu Ala Ala Ile Ser
1               5                   10                  15

Arg Arg Thr Pro Gly Gly Ser Thr Tyr Thr Tyr Asp Thr Thr Ala Gly
            20                  25                  30

Ala Gly Thr Tyr Gly Tyr Val Val Asp Ser Gly Ile Asn Thr Ala His
        35                  40                  45

Thr Asp Phe Gly Gly Arg Ala Ser Leu Gly Tyr Asn Ala Ala Gly Gly
    50                  55                  60

Ala His Thr Asp Thr Leu Gly His Gly Thr His Val Ala Gly Thr Ile
65                  70                  75                  80

Ala Ser Asn Thr Tyr Gly Val Ala Lys Arg Ala Asn Val Ile Ser Val
                85                  90                  95

Lys Val Phe Val Gly Asn Gln Ala Ser Thr Ser Val Ile Leu Asp Gly
            100                 105                 110

Phe Asn Trp Ala Val Asn Asp Ile Thr Ser Lys Asn Arg Ala Ser Arg
        115                 120                 125

Ser Val Ile Asn Met Ser Leu Gly Gly Pro Ser Gln Thr Trp Ala
    130                 135                 140

Thr Ala Ile Asn Ala Ala Tyr Ser Gln Gly Val Leu Ser Val Val Ala
145                 150                 155                 160

Ala Gly Asn Gly Asp Ser Asn Gly Arg Pro Leu Pro Ala Ser Gly Gln
                165                 170                 175

Ser Pro Ala Asn Val Pro Asn Ala Ile Thr Val Ala Ala Asp Ser
            180                 185                 190

Ser Trp Arg Thr Ala Ser Phe Thr Asn Tyr Gly Pro Glu Val Asp Ile
        195                 200                 205

Phe Gly Pro Gly Val Asn Ile Gln Ser Thr Trp Tyr Thr Ser Asn Ser
    210                 215                 220

Ala Thr Asn Thr Ile Ser Gly Thr Ser Met Ala Cys Pro His Val Ala
225                 230                 235                 240

Gly Leu Ala Leu Tyr Leu Gln Ala Leu Glu Asn Leu Asn Thr Pro Ala
                245                 250                 255

Ala Val Thr Asn Arg Ile Lys Ser Leu Ala Thr Thr Gly Arg Ile Thr
            260                 265                 270

Gly Ser Leu Ser Gly Ser Pro Asn Leu Met Ala Phe Asn Gly Ala Thr
        275                 280                 285
```

Ala

<210> SEQ ID NO 13
<211> LENGTH: 870
<212> TYPE: DNA
<213> ORGANISM: Artificial sequence
<220> FEATURE:
<223> OTHER INFORMATION: Description of Artificial Sequence: Synthetic polynucleotide
<220> FEATURE:
<223> OTHER INFORMATION: The nucleotide sequence encoding the amino acid sequence of the mature form of Fe_RF6318 serine protease variant comprising substitutions V208I, A111D, A281L and A33E

<400> SEQUENCE: 13

```
gctctgacca ctcagagcaa cgctccttgg ggtcttgctg ccatctcccg ccgaaccccc    60
ggtggcagca cctacaccta cgacaccact gccggtgagg gtacttacgg ttacgtcgtt   120
gactctggta tcaacaccgc ccacactgac tttggcggcc gtgcttctct cggttacaac   180
gctgctggtg cgcccacac tgatacccttggcacggta cccacgttgc tggtaccatt    240
gcctccaaca cctacggtgt tgccaagcgt gccaacgtca tctctgtcaa ggttttcgtc   300
ggtaaccaag cttctacctc tgttatcctt gacggtttca ctgggctgt caacgacatc    360
acctccaaga accgtgctag ccgctctgtc atcaacatgt ctctcggtgg tccctcttct   420
cagacctggg ctactgccat caacgctgcc tacagccaag tgtcctctc cgttgttgct   480
gccggtaacg gtgattccaa cggtcgtcct ctccccgcct ctggccagtc tcctgccaac   540
gttcccaacg ctatcaccgt tgctgccgcc gactccagct ggcgaactgc ctctttcacc   600
aactacggtc ctgaggtcga tatcttcggt cctggtgtca catccagtc cacctggtac    660
acctccaaca gcgctaccaa caccatcagc ggtacctcca tggcttgccc tcacgttgct   720
ggtcttgctc tctacctcca ggctctcgag aacctcaata cccctgctgc cgtcaccaac   780
cgcatcaagt ctcttgccac taccggccgc atcactggca gcctcagcgg cagccccaac   840
ctcatggctt tcaacggcgc tactgcttaa                                    870
```

<210> SEQ ID NO 14
<211> LENGTH: 289
<212> TYPE: PRT
<213> ORGANISM: Artificial sequence
<220> FEATURE:
<223> OTHER INFORMATION: Description of Artificial Sequence: Synthetic polypeptide
<220> FEATURE:
<223> OTHER INFORMATION: The amino acid sequence of the mature form of Fe_RF6318 serine protease variant comprising substitutions V208I, A111D, A281L and A33E

<400> SEQUENCE: 14

```
Ala Leu Thr Thr Gln Ser Asn Ala Pro Trp Gly Leu Ala Ala Ile Ser
1               5                   10                  15

Arg Arg Thr Pro Gly Gly Ser Thr Tyr Thr Tyr Asp Thr Thr Ala Gly
            20                  25                  30

Glu Gly Thr Tyr Gly Tyr Val Val Asp Ser Gly Ile Asn Thr Ala His
        35                  40                  45

Thr Asp Phe Gly Gly Arg Ala Ser Leu Gly Tyr Asn Ala Ala Gly Gly
    50                  55                  60

Ala His Thr Asp Thr Leu Gly His Gly Thr His Val Ala Gly Thr Ile
65                  70                  75                  80

Ala Ser Asn Thr Tyr Gly Val Ala Lys Arg Ala Asn Val Ile Ser Val
                85                  90                  95
```

Lys Val Phe Val Gly Asn Gln Ala Ser Thr Ser Val Ile Leu Asp Gly
            100                 105                 110

Phe Asn Trp Ala Val Asn Asp Ile Thr Ser Lys Asn Arg Ala Ser Arg
            115                 120                 125

Ser Val Ile Asn Met Ser Leu Gly Gly Pro Ser Gln Thr Trp Ala
            130                 135                 140

Thr Ala Ile Asn Ala Ala Tyr Ser Gln Gly Val Leu Ser Val Val Ala
145                 150                 155                 160

Ala Gly Asn Gly Asp Ser Asn Gly Arg Pro Leu Pro Ala Ser Gly Gln
            165                 170                 175

Ser Pro Ala Asn Val Pro Asn Ala Ile Thr Val Ala Ala Ala Asp Ser
            180                 185                 190

Ser Trp Arg Thr Ala Ser Phe Thr Asn Tyr Gly Pro Glu Val Asp Ile
            195                 200                 205

Phe Gly Pro Gly Val Asn Ile Gln Ser Thr Trp Tyr Thr Ser Asn Ser
            210                 215                 220

Ala Thr Asn Thr Ile Ser Gly Thr Ser Met Ala Cys Pro His Val Ala
225                 230                 235                 240

Gly Leu Ala Leu Tyr Leu Gln Ala Leu Glu Asn Leu Asn Thr Pro Ala
            245                 250                 255

Ala Val Thr Asn Arg Ile Lys Ser Leu Ala Thr Thr Gly Arg Ile Thr
            260                 265                 270

Gly Ser Leu Ser Gly Ser Pro Asn Leu Met Ala Phe Asn Gly Ala Thr
            275                 280                 285

Ala

<210> SEQ ID NO 15
<211> LENGTH: 870
<212> TYPE: DNA
<213> ORGANISM: Artificial sequence
<220> FEATURE:
<223> OTHER INFORMATION: Description of Artificial Sequence: Synthetic
      polynucleotide
<220> FEATURE:
<223> OTHER INFORMATION: The nucleotide sequence encoding the amino acid
      sequence of the mature form of Fe_RF6318 serine protease variant
      comprising substitutions V208I, A111D, A281L and A47E

<400> SEQUENCE: 15
gctctgacca ctcagagcaa cgctccttgg ggtcttgctg ccatctcccg ccgaaccccc      60
ggtggcagca cctacaccta cgacaccact gccggtgccg gtacttacgg ttacgtcgtt     120
gactctggta tcaacaccga gcacactgac tttggcggcc gtgcttctct cggttacaac     180
gctgctggtg cgcccacac tgatacccctt ggccacggta cccacgttgc tggtaccatt     240
gcctccaaca cctacggtgt tgccaagcgt gccaacgtca tctctgtcaa ggttttcgtc     300
ggtaaccaag cttctacctc tgttatcctt gacggtttca ctgggctgt caacgacatc     360 acctccaaga accgtgctag ccgctctgtc atcaacatgt ctctcggtgg tccctcttct     420
cagacctggg ctactgccat caacgctgcc tacagccaag gtgtcctctc cgttgttgct     480
gccggtaacg gtgattccaa cggtcgtcct ctccccgcct ctggccagtc tcctgccaac     540
gttcccaacg ctatcaccgt gctgccgcc gactccagct ggcgaactgc ctctttcacc     600
aactacggtc ctgaggtcga tatcttcggt cctggtgtca acatccagtc cacctggtac     660
acctccaaca gcgctaccaa caccatcagc ggtacctcca tggcttgccc tcacgttgct     720
ggtcttgctc tctacctcca ggctctcgag aacctcaata cccctgctgc cgtcaccaac     780

```
cgcatcaagt ctcttgccac taccggccgc atcactggca gcctcagcgg cagccccaac    840
ctcatggctt tcaacggcgc tactgcttaa                                     870
```

<210> SEQ ID NO 16
<211> LENGTH: 289
<212> TYPE: PRT
<213> ORGANISM: Artificial sequence
<220> FEATURE:
<223> OTHER INFORMATION: Description of Artificial Sequence: Synthetic polypeptide
<220> FEATURE:
<223> OTHER INFORMATION: The amino acid sequence of the mature form of Fe_RF6318 serine protease variant comprising substitutions V208I, A111D, A281L and A47E

<400> SEQUENCE: 16

```
Ala Leu Thr Thr Gln Ser Asn Ala Pro Trp Gly Leu Ala Ala Ile Ser
 1               5                  10                  15

Arg Arg Thr Pro Gly Gly Ser Thr Tyr Thr Tyr Asp Thr Thr Ala Gly
                20                  25                  30

Ala Gly Thr Tyr Gly Tyr Val Val Asp Ser Gly Ile Asn Thr Glu His
            35                  40                  45

Thr Asp Phe Gly Gly Arg Ala Ser Leu Gly Tyr Asn Ala Ala Gly Gly
        50                  55                  60

Ala His Thr Asp Thr Leu Gly His Gly Thr His Val Ala Gly Thr Ile
65                  70                  75                  80

Ala Ser Asn Thr Tyr Gly Val Ala Lys Arg Ala Asn Val Ile Ser Val
                85                  90                  95

Lys Val Phe Val Gly Asn Gln Ala Ser Thr Ser Val Ile Leu Asp Gly
               100                 105                 110

Phe Asn Trp Ala Val Asn Asp Ile Thr Ser Lys Asn Arg Ala Ser Arg
            115                 120                 125

Ser Val Ile Asn Met Ser Leu Gly Gly Pro Ser Ser Gln Thr Trp Ala
        130                 135                 140

Thr Ala Ile Asn Ala Ala Tyr Ser Gln Gly Val Leu Ser Val Val Ala
145                 150                 155                 160

Ala Gly Asn Gly Asp Ser Asn Gly Arg Pro Leu Pro Ala Ser Gly Gln
                165                 170                 175

Ser Pro Ala Asn Val Pro Asn Ala Ile Thr Val Ala Ala Ala Asp Ser
            180                 185                 190

Ser Trp Arg Thr Ala Ser Phe Thr Asn Tyr Gly Pro Glu Val Asp Ile
        195                 200                 205

Phe Gly Pro Gly Val Asn Ile Gln Ser Thr Trp Tyr Thr Ser Asn Ser
    210                 215                 220

Ala Thr Asn Thr Ile Ser Gly Thr Ser Met Ala Cys Pro His Val Ala
225                 230                 235                 240

Gly Leu Ala Leu Tyr Leu Gln Ala Leu Glu Asn Leu Asn Thr Pro Ala
                245                 250                 255

Ala Val Thr Asn Arg Ile Lys Ser Leu Ala Thr Thr Gly Arg Ile Thr
            260                 265                 270

Gly Ser Leu Ser Gly Ser Pro Asn Leu Met Ala Phe Asn Gly Ala Thr
        275                 280                 285

Ala
```

<210> SEQ ID NO 17
<211> LENGTH: 870

<212> TYPE: DNA
<213> ORGANISM: Artificial sequence
<220> FEATURE:
<223> OTHER INFORMATION: Description of Artificial Sequence: Synthetic
      polynucleotide
<220> FEATURE:
<223> OTHER INFORMATION: The nucleotide sequence encoding the amino acid
      sequence of the mature form of Fe_RF6318 serine protease variant
      comprising substitutions V208I, A111D, A281L and G63P

<400> SEQUENCE: 17

```
gctctgacca ctcagagcaa cgctccttgg ggtcttgctg ccatctcccg ccgaacccc       60
ggtggcagca cctacaccta cgacaccact gccggtgccg gtacttacgg ttacgtcgtt     120
gactctggta tcaacaccgc ccacactgac tttggcggcc gtgcttctct cggttacaac     180
gctgctcccg cgcccacac tgataccctt ggccacggta cccacgttgc tggtaccatt      240
gcctccaaca cctacggtgt tgccaagcgt gccaacgtca tctctgtcaa ggttttcgtc     300
ggtaaccaag cttctacctc tgttatcctt gacggtttca ctgggctgt caacgacatc      360
acctccaaga accgtgctag ccgctctgtc atcaacatgt ctctcggtgg tccctcttct    420
cagacctggg ctactgccat caacgctgcc tacagccaag tgtcctctc cgttgttgct      480
gccggtaacg tgattccaa cggtcgtcct ctccccgcct ctggccagtc tcctgccaac     540
gttcccaacg ctatcaccgt tgctgccgcc gactccagct ggcgaactgc ctctttcacc    600
aactacggtc tgaggtcga tatcttcggt cctggtgtca acatccagtc cacctggtac     660
acctccaaca cgctaccaa caccatcagc ggtacctcca tggcttgccc tcacgttgct     720
ggtcttgctc tctacctcca ggctctcgag aacctcaata cccctgctgc cgtcaccaac    780
cgcatcaagt ctcttgccac taccggccgc atcactggca gcctcagcgg cagccccaac    840
ctcatggctt tcaacggcgc tactgcttaa                                     870
```

<210> SEQ ID NO 18
<211> LENGTH: 289
<212> TYPE: PRT
<213> ORGANISM: Artificial sequence
<220> FEATURE:
<223> OTHER INFORMATION: Description of Artificial Sequence: Synthetic
      polypeptide
<220> FEATURE:
<223> OTHER INFORMATION: The amino acid sequence of the mature form of
      Fe_RF6318 serine protease variant comprising substitutions V208I,
      A111D, A281L and G63P

<400> SEQUENCE: 18

```
Ala Leu Thr Thr Gln Ser Asn Ala Pro Trp Gly Leu Ala Ala Ile Ser
1               5                   10                  15

Arg Arg Thr Pro Gly Gly Ser Thr Tyr Thr Tyr Asp Thr Thr Ala Gly
            20                  25                  30

Ala Gly Thr Tyr Gly Tyr Val Val Asp Ser Gly Ile Asn Thr Ala His
        35                  40                  45

Thr Asp Phe Gly Gly Arg Ala Ser Leu Gly Tyr Asn Ala Ala Pro Gly
    50                  55                  60

Ala His Thr Asp Thr Leu Gly His Gly Thr His Val Ala Gly Thr Ile
65                  70                  75                  80

Ala Ser Asn Thr Tyr Gly Val Ala Lys Arg Ala Asn Val Ile Ser Val
                85                  90                  95

Lys Val Phe Val Gly Asn Gln Ala Ser Thr Ser Val Ile Leu Asp Gly
            100                 105                 110

Phe Asn Trp Ala Val Asn Asp Ile Thr Ser Lys Asn Arg Ala Ser Arg
```

|       |     |     | 115 |     |     |     | 120 |     |     |     | 125 |     |     |
|-------|-----|-----|-----|-----|-----|-----|-----|-----|-----|-----|-----|-----|-----|

Ser Val Ile Asn Met Ser Leu Gly Gly Pro Ser Ser Gln Thr Trp Ala
    130                 135                 140

Thr Ala Ile Asn Ala Ala Tyr Ser Gln Gly Val Leu Ser Val Val Ala
145                150               155               160

Ala Gly Asn Gly Asp Ser Asn Gly Arg Pro Leu Pro Ala Ser Gly Gln
            165               170               175

Ser Pro Ala Asn Val Pro Asn Ala Ile Thr Val Ala Ala Ala Asp Ser
        180               185               190

Ser Trp Arg Thr Ala Ser Phe Thr Asn Tyr Gly Pro Glu Val Asp Ile
    195                 200               205

Phe Gly Pro Gly Val Asn Ile Gln Ser Thr Trp Tyr Thr Ser Asn Ser
    210                 215               220

Ala Thr Asn Thr Ile Ser Gly Thr Ser Met Ala Cys Pro His Val Ala
225                230               235               240

Gly Leu Ala Leu Tyr Leu Gln Ala Leu Glu Asn Leu Asn Thr Pro Ala
            245               250               255

Ala Val Thr Asn Arg Ile Lys Ser Leu Ala Thr Thr Gly Arg Ile Thr
        260             265               270

Gly Ser Leu Ser Gly Ser Pro Asn Leu Met Ala Phe Asn Gly Ala Thr
    275                 280               285

Ala

<210> SEQ ID NO 19
<211> LENGTH: 870
<212> TYPE: DNA
<213> ORGANISM: Artificial sequence
<220> FEATURE:
<223> OTHER INFORMATION: Description of Artificial Sequence: Synthetic
     polynucleotide
<220> FEATURE:
<223> OTHER INFORMATION: The nucleotide sequence encoding the amino acid
     sequence of the mature form of Fe_RF6318 serine protease variant
     comprising substitutions V208I, A111D, A281L and I185M

<400> SEQUENCE: 19

```
gctctgacca ctcagagcaa cgctccttgg ggtcttgctg ccatctcccg ccgaaccccc        60
ggtggcagca cctacaccta cgacaccact gccggtgccg gtacttacgg ttacgtcgtt       120
gactctggta tcaacaccgc ccacactgac tttggcggcc gtgcttctct cggttacaac       180
gctgctggtg gcgcccacac tgatacccct ggccacggta cccacgttgc tggtaccatt       240
gcctccaaca cctacggtgt tgccaagcgt gccaacgtca tctctgtcaa ggttttcgtc       300
ggtaaccaag cttctacctc tgttatcctt gacggtttca actgggctgt caacgacatc       360
acctccaaga accgtgctag ccgctctgtc atcaacatgt ctctcggtgg tcctctcttct      420
cagacctggg ctactgccat caacgctgcc tacagccaag gtgtcctctc cgttgttgct       480
gccggtaacg gtgattccaa cggtcgtcct ctccccgcct ctggccagtc tcctgccaac       540
gttcccaacg ctatgaccgt tgctgccgcc gactccagct ggcgaactgc ctcttcacc        600
aactacggtc tgaggtcga tatcttcggt cctggtgtca acatccagtc cacctggtac       660
acctccaaca gcgctaccaa caccatcagc ggtacctcca tggcttgccc tcacgttgct       720
ggtcttgctc tctacctcca ggctctcgag aacctcaata ccctgctgc cgtcaccaac       780
cgcatccaagt ctcttgccac taccggccga atcactggca gctcagcgg cagccccaac       840
ctcatggctt tcaacggcgc tactgcttaa                                        870
```

```
<210> SEQ ID NO 20
<211> LENGTH: 289
<212> TYPE: PRT
<213> ORGANISM: Artificial sequence
<220> FEATURE:
<223> OTHER INFORMATION: Description of Artificial Sequence: Synthetic
      polypeptide
<220> FEATURE:
<223> OTHER INFORMATION: The amino acid sequence of the mature form of
      Fe_RF6318 serine protease variant comprising substitutions V208I,
      A111D, A281L and I185M

<400> SEQUENCE: 20
```

Ala Leu Thr Thr Gln Ser Asn Ala Pro Trp Gly Leu Ala Ala Ile Ser
1               5                   10                  15

Arg Arg Thr Pro Gly Gly Ser Thr Tyr Thr Tyr Asp Thr Thr Ala Gly
            20                  25                  30

Ala Gly Thr Tyr Gly Tyr Val Val Asp Ser Gly Ile Asn Thr Ala His
        35                  40                  45

Thr Asp Phe Gly Gly Arg Ala Ser Leu Gly Tyr Asn Ala Ala Gly Gly
    50                  55                  60

Ala His Thr Asp Thr Leu Gly His Gly Thr His Val Ala Gly Thr Ile
65                  70                  75                  80

Ala Ser Asn Thr Tyr Gly Val Ala Lys Arg Ala Asn Val Ile Ser Val
                85                  90                  95

Lys Val Phe Val Gly Asn Gln Ala Ser Thr Ser Val Ile Leu Asp Gly
            100                 105                 110

Phe Asn Trp Ala Val Asn Asp Ile Thr Ser Lys Asn Arg Ala Ser Arg
        115                 120                 125

Ser Val Ile Asn Met Ser Leu Gly Gly Pro Ser Ser Gln Thr Trp Ala
    130                 135                 140

Thr Ala Ile Asn Ala Ala Tyr Ser Gln Gly Val Leu Ser Val Val Ala
145                 150                 155                 160

Ala Gly Asn Gly Asp Ser Asn Gly Arg Pro Leu Pro Ala Ser Gly Gln
                165                 170                 175

Ser Pro Ala Asn Val Pro Asn Ala Met Thr Val Ala Ala Ala Asp Ser
            180                 185                 190

Ser Trp Arg Thr Ala Ser Phe Thr Asn Tyr Gly Pro Glu Val Asp Ile
        195                 200                 205

Phe Gly Pro Gly Val Asn Ile Gln Ser Thr Trp Tyr Thr Ser Asn Ser
    210                 215                 220

Ala Thr Asn Thr Ile Ser Gly Thr Ser Met Ala Cys Pro His Val Ala
225                 230                 235                 240

Gly Leu Ala Leu Tyr Leu Gln Ala Leu Glu Asn Leu Asn Thr Pro Ala
                245                 250                 255

Ala Val Thr Asn Arg Ile Lys Ser Leu Ala Thr Thr Gly Arg Ile Thr
            260                 265                 270

Gly Ser Leu Ser Gly Ser Pro Asn Leu Met Ala Phe Asn Gly Ala Thr
        275                 280                 285

Ala

```
<210> SEQ ID NO 21
<211> LENGTH: 870
<212> TYPE: DNA
<213> ORGANISM: Artificial sequence
<220> FEATURE:
<223> OTHER INFORMATION: Description of Artificial Sequence: Synthetic
      polynucleotide
```

<220> FEATURE:
<223> OTHER INFORMATION: The nucleotide sequence encoding the amino acid sequence of the mature form of Fe_RF6318 serine protease variant comprising substitutions V208I, A111D, A281L and T268R

<400> SEQUENCE: 21

```
gctctgacca ctcagagcaa cgctccttgg ggtcttgctg ccatctcccg ccgaacccc      60
ggtggcagca cctacaccta cgacaccact gccggtgccg gtacttacgg ttacgtcgtt    120
gactctggta tcaacaccgc ccacactgac tttggcggcc gtgcttctct cggttacaac    180
gctgctggtg gcgcccacac tgatacccct ggccacggta cccacgttgc tggtaccatt    240
gcctccaaca cctacggtgt tgccaagcgt gccaacgtca tctctgtcaa ggttttcgtc    300
ggtaaccaag cttctacctc tgttatcctt gacggtttca actgggctgt caacgacatc    360
acctccaaga accgtgctag ccgctctgtc atcaacatgt ctctcggtgg tccctcttct    420
cagacctggg ctactgccat caacgctgcc tacagccaag gtgtcctctc cgttgttgct    480
gccggtaacg tgattccaa cggtcgtcct ctcccccgcct ctggccagtc tcctgccaac    540
gttcccaacg ctatcaccgt tgctgccgcc gactccagct ggcgaactgc ctctttcacc    600
aactacggtc tgaggtcga tatcttcggt cctggtgtca acatccagtc cacctggtac    660
acctccaaca gcgctaccaa caccatcagc ggtacctcca tggcttgccc tcacgttgct    720
ggtcttgctc tctacctcca ggctctcgag aacctcaata cccctgctgc cgtcaccaac    780
cgcatcaagt ctcttgccac tcgaggccgc atcactggca gcctcagcgg cagccccaac    840
ctcatggctt tcaacggcgc tactgcttaa                                      870
```

<210> SEQ ID NO 22
<211> LENGTH: 289
<212> TYPE: PRT
<213> ORGANISM: Artificial sequence
<220> FEATURE:
<223> OTHER INFORMATION: Description of Artificial Sequence: Synthetic polypeptide
<220> FEATURE:
<223> OTHER INFORMATION: The amino acid sequence of the mature form of Fe_RF6318 serine protease variant comprising substitutions V208I, A111D, A281L and T268R

<400> SEQUENCE: 22

```
Ala Leu Thr Thr Gln Ser Asn Ala Pro Trp Gly Leu Ala Ala Ile Ser
 1               5                  10                  15

Arg Arg Thr Pro Gly Gly Ser Thr Tyr Thr Tyr Asp Thr Thr Ala Gly
            20                  25                  30

Ala Gly Thr Tyr Gly Tyr Val Val Asp Ser Gly Ile Asn Thr Ala His
        35                  40                  45

Thr Asp Phe Gly Gly Arg Ala Ser Leu Gly Tyr Asn Ala Ala Gly Gly
    50                  55                  60

Ala His Thr Asp Thr Leu Gly His Gly Thr His Val Ala Gly Thr Ile
65                  70                  75                  80

Ala Ser Asn Thr Tyr Gly Val Ala Lys Arg Ala Asn Val Ile Ser Val
                85                  90                  95

Lys Val Phe Val Gly Asn Gln Ala Ser Thr Ser Val Ile Leu Asp Gly
            100                 105                 110

Phe Asn Trp Ala Val Asn Asp Ile Thr Ser Lys Asn Arg Ala Ser Arg
        115                 120                 125

Ser Val Ile Asn Met Ser Leu Gly Gly Pro Ser Ser Gln Thr Trp Ala
    130                 135                 140
```

Thr Ala Ile Asn Ala Ala Tyr Ser Gln Gly Val Leu Ser Val Val Ala
145                 150                 155                 160

Ala Gly Asn Gly Asp Ser Asn Gly Arg Pro Leu Pro Ala Ser Gly Gln
            165                 170                 175

Ser Pro Ala Asn Val Pro Asn Ala Ile Thr Val Ala Ala Ala Asp Ser
            180                 185                 190

Ser Trp Arg Thr Ala Ser Phe Thr Asn Tyr Gly Pro Glu Val Asp Ile
            195                 200                 205

Phe Gly Pro Gly Val Asn Ile Gln Ser Thr Trp Tyr Thr Ser Asn Ser
210                 215                 220

Ala Thr Asn Thr Ile Ser Gly Thr Ser Met Ala Cys Pro His Val Ala
225                 230                 235                 240

Gly Leu Ala Leu Tyr Leu Gln Ala Leu Glu Asn Leu Asn Thr Pro Ala
                245                 250                 255

Ala Val Thr Asn Arg Ile Lys Ser Leu Ala Thr Arg Gly Arg Ile Thr
            260                 265                 270

Gly Ser Leu Ser Gly Ser Pro Asn Leu Met Ala Phe Asn Gly Ala Thr
            275                 280                 285

Ala

<210> SEQ ID NO 23
<211> LENGTH: 873
<212> TYPE: DNA
<213> ORGANISM: Artificial sequence
<220> FEATURE:
<223> OTHER INFORMATION: Description of Artificial Sequence: Synthetic
      polynucleotide
<220> FEATURE:
<223> OTHER INFORMATION: The nucleotide sequence encoding the amino acid
      sequence of the mature form of Fe_RF6318 serine protease variant
      comprising substitutions V208I, A111D, A281L, Q103A, insertion
      G104

<400> SEQUENCE: 23
gctctgacca ctcagagcaa cgctccttgg ggtcttgctg ccatctcccg ccgaaccccc      60
ggtggcagca cctacaccta cgacaccact gccggtgccg gtacttacgg ttacgtcgtt     120
gactctggta tcaacaccgc ccacactgac tttggcggcc gtgcttctct cggttacaac     180
gctgctggtg gcgcccacac tgataccctt ggccacggta cccacgttgc tggtaccatt     240
gcctccaaca cctacggtgt tgccaagcgt gccaacgtca tctctgtcaa ggttttcgtc     300
ggtaacgccg gcgcttctac ctctgttatc cttgacggtt tcaactgggc tgtcaacgac     360
atcacctcca agaaccgtgc tagccgctct gtcatcaaca tgtctctcgg tggtccctct     420
tctcagacct gggctactgc catcaacgct gcctacagcc aaggtgtcct ctccgttgtt     480
gctgccggta acggtgattc caacggtcgt cctctccccg cctctggcca gtctcctgcc     540
aacgttccca acgctatcac cgttgctgcc gccgactcca gctggcgaac tgcctctttc     600
accaactacg gtcctgaggt cgatatcttc ggtcctggtg tcaacatcca gtccacctgg     660
tacacctcca acagcgctac caacaccatc agcggtacct ccatggcttg ccctcacgtt     720
gctggtcttg ctctctacct ccaggctctc gagaacctca ataccctgc tgccgtcacc     780 aaccgcatca gtctcttgc cactaccggc cgcatcactg gcagcctcag cggcagcccc     840
aacctcatgg ctttcaacgg cgctactgct taa                                  873

<210> SEQ ID NO 24
<211> LENGTH: 290
<212> TYPE: PRT

-continued

<213> ORGANISM: Artificial sequence
<220> FEATURE:
<223> OTHER INFORMATION: Description of Artificial Sequence: Synthetic
      polypeptide
<220> FEATURE:
<223> OTHER INFORMATION: The amino acid sequence of the mature form of
      Fe_RF6318 serine protease variant comprising substitutions V208I,
      A111D, A281L, Q103A, insertion G104

<400> SEQUENCE: 24

Ala Leu Thr Thr Gln Ser Asn Ala Pro Trp Gly Leu Ala Ala Ile Ser
1               5                   10                  15

Arg Arg Thr Pro Gly Gly Ser Thr Tyr Thr Tyr Asp Thr Thr Ala Gly
            20                  25                  30

Ala Gly Thr Tyr Gly Tyr Val Val Asp Ser Gly Ile Asn Thr Ala His
        35                  40                  45

Thr Asp Phe Gly Gly Arg Ala Ser Leu Gly Tyr Asn Ala Ala Gly Gly
    50                  55                  60

Ala His Thr Asp Thr Leu Gly His Gly Thr His Val Ala Gly Thr Ile
65                  70                  75                  80

Ala Ser Asn Thr Tyr Gly Val Ala Lys Arg Ala Asn Val Ile Ser Val
                85                  90                  95

Lys Val Phe Val Gly Asn Ala Gly Ala Ser Thr Ser Val Ile Leu Asp
            100                 105                 110

Gly Phe Asn Trp Ala Val Asn Asp Ile Thr Ser Lys Asn Arg Ala Ser
        115                 120                 125

Arg Ser Val Ile Asn Met Ser Leu Gly Gly Pro Ser Ser Gln Thr Trp
    130                 135                 140

Ala Thr Ala Ile Asn Ala Ala Tyr Ser Gln Gly Val Leu Ser Val Val
145                 150                 155                 160

Ala Ala Gly Asn Gly Asp Ser Asn Gly Arg Pro Leu Pro Ala Ser Gly
                165                 170                 175

Gln Ser Pro Ala Asn Val Pro Asn Ala Ile Thr Val Ala Ala Ala Asp
            180                 185                 190

Ser Ser Trp Arg Thr Ala Ser Phe Thr Asn Tyr Gly Pro Glu Val Asp
        195                 200                 205

Ile Phe Gly Pro Gly Val Asn Ile Gln Ser Thr Trp Tyr Thr Ser Asn
    210                 215                 220

Ser Ala Thr Asn Thr Ile Ser Gly Thr Ser Met Ala Cys Pro His Val
225                 230                 235                 240

Ala Gly Leu Ala Leu Tyr Leu Gln Ala Leu Glu Asn Leu Asn Thr Pro
                245                 250                 255

Ala Ala Val Thr Asn Arg Ile Lys Ser Leu Ala Thr Thr Gly Arg Ile
            260                 265                 270

Thr Gly Ser Leu Ser Gly Ser Pro Asn Leu Met Ala Phe Asn Gly Ala
        275                 280                 285

Thr Ala
290

<210> SEQ ID NO 25
<211> LENGTH: 870
<212> TYPE: DNA
<213> ORGANISM: Artificial sequence
<220> FEATURE:
<223> OTHER INFORMATION: Description of Artificial Sequence: Synthetic
      polynucleotide
<220> FEATURE:
<223> OTHER INFORMATION: The nucleotide sequence encoding the amino acid
      sequence of the mature form of Fe_RF6318 serine protease variant comprising substitutions V208I, A111D, A281L, T3C and T29C

<400> SEQUENCE: 25

```
gctctgtgca ctcagagcaa cgctccttgg ggtcttgctg ccatctcccg ccgaacccccc    60
ggtggcagca cctacaccta cgactgcact gccggtgccg gtacttacgg ttacgtcgtt   120
gactctggta tcaacaccgc ccacactgac tttggcggcc gtgcttctct cggttacaac   180
gctgctggtg gcgcccacac tgataccctt ggccacggta cccacgttgc tggtaccatt   240
gcctccaaca cctacggtgt tgccaagcgt gccaacgtca tctctgtcaa ggttttcgtc   300
ggtaaccaag cttctacctc tgttatcctt gacggtttca ctgggctgt caacgacatc    360
acctccaaga accgtgctag ccgctctgtc atcaacatgt ctctcggtgg tccctcttct   420
cagacctggg ctactgccat caacgctgcc tacagccaag tgtcctctc cgttgttgct    480
gccggtaacg gtgattccaa cggtcgtcct ctccccgcct ctggccagtc tcctgccaac   540
gttcccaacg ctatcaccgt tgctgccgcc gactccagct ggcgaactgc ctctttcacc   600
aactacggtc ctgaggtcga tatcttcggt cctggtgtca catccagtc cacctggtac    660
acctccaaca cgctaccaa caccatcagc ggtacctcca tggcttgccc tcacgttgct   720
ggtcttgctc tctacctcca ggctctcgag aacctcaata cccctgctgc cgtcaccaac   780
cgcatcaagt ctcttgccac taccggccgc atcactggca gcctcagcgg cagccccaac   840
ctcatggctt tcaacggcgc tactgcttaa                                    870
```

<210> SEQ ID NO 26
<211> LENGTH: 289
<212> TYPE: PRT
<213> ORGANISM: Artificial sequence
<220> FEATURE:
<223> OTHER INFORMATION: Description of Artificial Sequence: Synthetic polypeptide
<220> FEATURE:
<223> OTHER INFORMATION: The amino acid sequence of the mature form of Fe_RF6318 serine protease variant comprising substitutions V208I, A111D, A281L, T3C and T29C

<400> SEQUENCE: 26

```
Ala Leu Cys Thr Gln Ser Asn Ala Pro Trp Gly Leu Ala Ala Ile Ser
1               5                   10                  15

Arg Arg Thr Pro Gly Gly Ser Thr Tyr Thr Tyr Asp Cys Thr Ala Gly
            20                  25                  30

Ala Gly Thr Tyr Gly Tyr Val Val Asp Ser Gly Ile Asn Thr Ala His
        35                  40                  45

Thr Asp Phe Gly Gly Arg Ala Ser Leu Gly Tyr Asn Ala Ala Gly Gly
    50                  55                  60

Ala His Thr Asp Thr Leu Gly His Gly Thr His Val Ala Gly Thr Ile
65                  70                  75                  80

Ala Ser Asn Thr Tyr Gly Val Ala Lys Arg Ala Asn Val Ile Ser Val
                85                  90                  95

Lys Val Phe Val Gly Asn Gln Ala Ser Thr Ser Val Ile Leu Asp Gly
            100                 105                 110

Phe Asn Trp Ala Val Asn Asp Ile Thr Ser Lys Asn Arg Ala Ser Arg
        115                 120                 125

Ser Val Ile Asn Met Ser Leu Gly Gly Pro Ser Ser Gln Thr Trp Ala
    130                 135                 140

Thr Ala Ile Asn Ala Ala Tyr Ser Gln Gly Val Leu Ser Val Val Ala
145                 150                 155                 160
```

```
Ala Gly Asn Gly Asp Ser Asn Gly Arg Pro Leu Pro Ala Ser Gly Gln
            165                 170                 175

Ser Pro Ala Asn Val Pro Asn Ala Ile Thr Val Ala Ala Ala Asp Ser
        180                 185                 190

Ser Trp Arg Thr Ala Ser Phe Thr Asn Tyr Gly Pro Glu Val Asp Ile
    195                 200                 205

Phe Gly Pro Gly Val Asn Ile Gln Ser Thr Trp Tyr Thr Ser Asn Ser
    210                 215                 220

Ala Thr Asn Thr Ile Ser Gly Thr Ser Met Ala Cys Pro His Val Ala
225                 230                 235                 240

Gly Leu Ala Leu Tyr Leu Gln Ala Leu Glu Asn Leu Asn Thr Pro Ala
                245                 250                 255

Ala Val Thr Asn Arg Ile Lys Ser Leu Ala Thr Thr Gly Arg Ile Thr
            260                 265                 270

Gly Ser Leu Ser Gly Ser Pro Asn Leu Met Ala Phe Asn Gly Ala Thr
            275                 280                 285

Ala
```

<210> SEQ ID NO 27
<211> LENGTH: 870
<212> TYPE: DNA
<213> ORGANISM: Artificial sequence
<220> FEATURE:
<223> OTHER INFORMATION: Description of Artificial Sequence: Synthetic
      polynucleotide
<220> FEATURE:
<223> OTHER INFORMATION: The nucleotide sequence encoding the amino acid
      sequence of the mature form of Fe_6318 serine protease variant
      comprising substitutions V208I, A111D, A281L, S6R and T24D

<400> SEQUENCE: 27

```
gctctgacca ctcagcgcaa cgctccttgg ggtcttgctg ccatctcccg ccgaaccccc      60
ggtggcagcg actacaccta cgacaccact gccggtgccg gtacttacgg ttacgtcgtt     120
gactctggta tcaacaccgc ccacactgac tttggcggcc gtgcttctct cggttacaac     180
gctgctggtg gcgcccacac tgatacccct ggccacggta cccacgttgc tggtaccatt     240
gcctccaaca cctacggtgt tgccaagcgt gccaacgtca tctctgtcaa ggttttcgtc     300
ggtaaccaag cttctacctc tgttatcctt gacggtttca actgggctgt caacgacatc     360
acctccaaga accgtgctag ccgctctgtc atcaacatgt ctctcggtgg tccctcttct     420
cagacctggg ctactgccat caacgctgcc tacagccaag gtgtcctctc cgttgttgct     480
gccggtaacg tgattccaa cggtcgtcct ctcccccgcct ctggccagtc tcctgccaac     540
gttcccaacg ctatcaccgt tgctgccgcc gactccagct ggcgaactgc ctctttcacc     600
aactacggtc ctgaggtcga tatcttcggt cctggtgtca acatccagtc cacctggtac     660
acctccaaca gcgctaccaa caccatcagc ggtacctcca tggcttgccc tcacgttgct     720
ggtcttgctc tctacctcca ggctctcgag aacctcaata cccctgctgc cgtcaccaac     780
cgcatcaagt ctcttgccac taccggccgc atcactggca gcctcagcgg cagccccaac     840
ctcatggctt tcaacggcgc tactgcttaa                                      870
```

<210> SEQ ID NO 28
<211> LENGTH: 289
<212> TYPE: PRT
<213> ORGANISM: Artificial sequence
<220> FEATURE:
<223> OTHER INFORMATION: Description of Artificial Sequence: Synthetic
      polypeptide <220> FEATURE:
<223> OTHER INFORMATION: The amino acid sequence of the mature form of Fe_RF6318 serine protease variant comprising substitutions V208I, A111D, A281L, S6R and T24D

<400> SEQUENCE: 28

```
Ala Leu Thr Thr Gln Arg Asn Ala Pro Trp Gly Leu Ala Ala Ile Ser
1               5                   10                  15

Arg Arg Thr Pro Gly Gly Ser Asp Tyr Thr Tyr Asp Thr Thr Ala Gly
            20                  25                  30

Ala Gly Thr Tyr Gly Tyr Val Val Asp Ser Gly Ile Asn Thr Ala His
        35                  40                  45

Thr Asp Phe Gly Gly Arg Ala Ser Leu Gly Tyr Asn Ala Ala Gly Gly
    50                  55                  60

Ala His Thr Asp Thr Leu Gly His Gly Thr His Val Ala Gly Thr Ile
65                  70                  75                  80

Ala Ser Asn Thr Tyr Gly Val Ala Lys Arg Ala Asn Val Ile Ser Val
                85                  90                  95

Lys Val Phe Val Gly Asn Gln Ala Ser Thr Ser Val Ile Leu Asp Gly
            100                 105                 110

Phe Asn Trp Ala Val Asn Asp Ile Thr Ser Lys Asn Arg Ala Ser Arg
        115                 120                 125

Ser Val Ile Asn Met Ser Leu Gly Gly Pro Ser Ser Gln Thr Trp Ala
    130                 135                 140

Thr Ala Ile Asn Ala Ala Tyr Ser Gln Gly Val Leu Ser Val Val Ala
145                 150                 155                 160

Ala Gly Asn Gly Asp Ser Asn Gly Arg Pro Leu Pro Ala Ser Gly Gln
                165                 170                 175

Ser Pro Ala Asn Val Pro Asn Ala Ile Thr Val Ala Ala Ala Asp Ser
            180                 185                 190

Ser Trp Arg Thr Ala Ser Phe Thr Asn Tyr Gly Pro Glu Val Asp Ile
        195                 200                 205

Phe Gly Pro Gly Val Asn Ile Gln Ser Thr Trp Tyr Thr Ser Asn Ser
    210                 215                 220

Ala Thr Asn Thr Ile Ser Gly Thr Ser Met Ala Cys Pro His Val Ala
225                 230                 235                 240

Gly Leu Ala Leu Tyr Leu Gln Ala Leu Glu Asn Leu Asn Thr Pro Ala
                245                 250                 255

Ala Val Thr Asn Arg Ile Lys Ser Leu Ala Thr Thr Gly Arg Ile Thr
            260                 265                 270

Gly Ser Leu Ser Gly Ser Pro Asn Leu Met Ala Phe Asn Gly Ala Thr
        275                 280                 285

Ala
```

<210> SEQ ID NO 29
<211> LENGTH: 870
<212> TYPE: DNA
<213> ORGANISM: Artificial sequence
<220> FEATURE:
<223> OTHER INFORMATION: Description of Artificial Sequence: Synthetic polynucleotide
<220> FEATURE:
<223> OTHER INFORMATION: The nucleotide sequence encoding the amino acid sequence of the mature form of Fe_RF6318 serine protease variant comprising substitutions V208I, A111D, A281L and V100D

<400> SEQUENCE: 29

```
gctctgacca ctcagagcaa cgctccttgg ggtcttgctg ccatctcccg ccgaaccccc    60
```

```
ggtggcagca cctacaccta cgacaccact gccggtgccg gtacttacgg ttacgtcgtt    120
gactctggta tcaacaccgc ccacactgac tttggcggcc gtgcttctct cggttacaac    180
gctgctggtg gcgcccacac tgatacccct tggccacggta cccacgttgc tggtaccatt    240
gcctccaaca cctacggtgt tgccaagcgt gccaacgtca tctctgtcaa ggttttcgac    300
ggtaaccaag cttctacctc tgttatcctt gacggtttca actgggctgt caacgacatc    360
acctccaaga accgtgctag ccgctctgtc atcaacatgt ctctcggtgg tccctcttct    420
cagacctggg ctactgccat caacgctgcc tacagccaag gtgtcctctc cgttgttgct    480
gccggtaacg gtgattccaa cggtcgtcct ctccccgcct ctggccagtc tcctgccaac    540
gttcccaacg ctatcaccgt tgctgccgcc gactccagct ggcgaactgc ctctttcacc    600
aactacggtc tgaggtcga tatcttcggt cctggtgtca acatccagtc cacctggtac    660
acctccaaca gcgctaccaa caccatcagc ggtacctcca tggcttgccc tcacgttgct    720
ggtcttgctc tctacctcca ggctctcgag aacctcaata cccctgctgc cgtcaccaac    780
cgcatcaagt ctcttgccac taccggccgc atcactggca gcctcagcgg cagccccaac    840
ctcatggctt tcaacggcgc tactgcttaa                                     870
```

<210> SEQ ID NO 30
<211> LENGTH: 289
<212> TYPE: PRT
<213> ORGANISM: Artificial sequence
<220> FEATURE:
<223> OTHER INFORMATION: Description of Artificial Sequence: Synthetic polypeptide
<220> FEATURE:
<223> OTHER INFORMATION: The amino acid sequence of the mature form of Fe_RF6318 serine protease variant comprising substitutions V208I, A111D, A281L and V100D

<400> SEQUENCE: 30

```
Ala Leu Thr Thr Gln Ser Asn Ala Pro Trp Gly Leu Ala Ala Ile Ser
1               5                   10                  15

Arg Arg Thr Pro Gly Gly Ser Thr Tyr Thr Tyr Asp Thr Thr Ala Gly
            20                  25                  30

Ala Gly Thr Tyr Gly Tyr Val Val Asp Ser Gly Ile Asn Thr Ala His
        35                  40                  45

Thr Asp Phe Gly Gly Arg Ala Ser Leu Gly Tyr Asn Ala Ala Gly Gly
    50                  55                  60

Ala His Thr Asp Thr Leu Gly His Gly Thr His Val Ala Gly Thr Ile
65                  70                  75                  80

Ala Ser Asn Thr Tyr Gly Val Ala Lys Arg Ala Asn Val Ile Ser Val
                85                  90                  95

Lys Val Phe Asp Gly Asn Gln Ala Ser Thr Ser Val Ile Leu Asp Gly
            100                 105                 110

Phe Asn Trp Ala Val Asn Asp Ile Thr Ser Lys Asn Arg Ala Ser Arg
        115                 120                 125

Ser Val Ile Asn Met Ser Leu Gly Gly Pro Ser Ser Gln Thr Trp Ala
    130                 135                 140

Thr Ala Ile Asn Ala Ala Tyr Ser Gln Gly Val Leu Ser Val Val Ala
145                 150                 155                 160

Ala Gly Asn Gly Asp Ser Asn Gly Arg Pro Leu Pro Ala Ser Gly Gln
                165                 170                 175

Ser Pro Ala Asn Val Pro Asn Ala Ile Thr Val Ala Ala Ala Asp Ser
            180                 185                 190
```

```
Ser Trp Arg Thr Ala Ser Phe Thr Asn Tyr Gly Pro Glu Val Asp Ile
        195                 200                 205

Phe Gly Pro Gly Val Asn Ile Gln Ser Thr Trp Tyr Thr Ser Asn Ser
    210                 215                 220

Ala Thr Asn Thr Ile Ser Gly Thr Ser Met Ala Cys Pro His Val Ala
225                 230                 235                 240

Gly Leu Ala Leu Tyr Leu Gln Ala Leu Glu Asn Leu Asn Thr Pro Ala
                245                 250                 255

Ala Val Thr Asn Arg Ile Lys Ser Leu Ala Thr Thr Gly Arg Ile Thr
                260                 265                 270

Gly Ser Leu Ser Gly Ser Pro Asn Leu Met Ala Phe Asn Gly Ala Thr
            275                 280                 285

Ala

<210> SEQ ID NO 31
<211> LENGTH: 870
<212> TYPE: DNA
<213> ORGANISM: Artificial sequence
<220> FEATURE:
<223> OTHER INFORMATION: Description of Artificial Sequence: Synthetic
      polynucleotide
<220> FEATURE:
<223> OTHER INFORMATION: The nucleotide sequence encoding the amino acid
      sequence of the mature form of Fe_RF6318 serine protease variant
      comprising substitutions V208I, A111D, A281L and V100K

<400> SEQUENCE: 31
gctctgacca ctcagagcaa cgctccttgg ggtcttgctg ccatctcccg ccgaaccccc      60
ggtggcagca cctacaccta cgacaccact gccggtgccg gtacttacgg ttacgtcgtt     120
gactctggta tcaacaccgc ccacactgac tttggcggcc gtgcttctct cggttacaac     180
gctgctggtg gcgcccacac tgataccctt ggccacggta cccacgttgc tggtaccatt     240
gcctccaaca cctacggtgt tgccaagcgt gccaacgtca tctctgtcaa ggttttcaag     300
ggtaaccaag cttctaccct tgttatcctt gacggtttca ctgggctgt caacgacatc     360 acctccaaga accgtgctag ccgctctgtc atcaacatgt ctctcggtgg tccctcttct     420
cagacctggg ctactgccat caacgctgcc tacagccaag gtgtcctctc cgttgttgct     480
gccggtaacg gtgattccaa cggtcgtcct ctcccgcct ctggccagtc tcctgccaac     540
gttcccaacg ctatcaccgt tgctgccgcc gactccagct ggcgaactgc ctctttcacc     600
aactacggtc tgaggtcga tatcttcggt cctggtgtca acatccagtc cacctggtac     660
acctccaaca gcgctaccaa caccatcagc ggtacctcca tggcttgccc tcacgttgct     720
ggtcttgctc tctacctcca ggctctcgag aacctcaata cccctgctgc cgtcaccaac     780
cgcatcaagt ctcttgccac taccggccgc atcactggca gcctcagcgg cagccccaac     840
ctcatggctt tcaacggcgc tactgcttaa                                      870

<210> SEQ ID NO 32
<211> LENGTH: 289
<212> TYPE: PRT
<213> ORGANISM: Artificial sequence
<220> FEATURE:
<223> OTHER INFORMATION: Description of Artificial Sequence: Synthetic
      polypeptide
<220> FEATURE:
<223> OTHER INFORMATION: The amino acid sequence of the mature form of
      Fe_RF6318 serine protease variant comprising substitutions V208I,
      A111D, A281L and V100K
```

<400> SEQUENCE: 32

Ala Leu Thr Thr Gln Ser Asn Ala Pro Trp Gly Leu Ala Ala Ile Ser
1               5                   10                  15

Arg Arg Thr Pro Gly Gly Ser Thr Tyr Thr Tyr Asp Thr Thr Ala Gly
            20                  25                  30

Ala Gly Thr Tyr Gly Tyr Val Val Asp Ser Gly Ile Asn Thr Ala His
        35                  40                  45

Thr Asp Phe Gly Gly Arg Ala Ser Leu Gly Tyr Asn Ala Ala Gly Gly
    50                  55                  60

Ala His Thr Asp Thr Leu Gly His Gly Thr His Val Ala Gly Thr Ile
65              70                  75                  80

Ala Ser Asn Thr Tyr Gly Val Ala Lys Arg Ala Asn Val Ile Ser Val
                85                  90                  95

Lys Val Phe Lys Gly Asn Gln Ala Ser Thr Ser Val Ile Leu Asp Gly
            100                 105                 110

Phe Asn Trp Ala Val Asn Asp Ile Thr Ser Lys Asn Arg Ala Ser Arg
        115                 120                 125

Ser Val Ile Asn Met Ser Leu Gly Gly Pro Ser Ser Gln Thr Trp Ala
    130                 135                 140

Thr Ala Ile Asn Ala Ala Tyr Ser Gln Gly Val Leu Ser Val Val Ala
145                 150                 155                 160

Ala Gly Asn Gly Asp Ser Asn Gly Arg Pro Leu Pro Ala Ser Gly Gln
                165                 170                 175

Ser Pro Ala Asn Val Pro Asn Ala Ile Thr Val Ala Ala Ala Asp Ser
            180                 185                 190

Ser Trp Arg Thr Ala Ser Phe Thr Asn Tyr Gly Pro Glu Val Asp Ile
        195                 200                 205

Phe Gly Pro Gly Val Asn Ile Gln Ser Thr Trp Tyr Thr Ser Asn Ser
    210                 215                 220

Ala Thr Asn Thr Ile Ser Gly Thr Ser Met Ala Cys Pro His Val Ala
225                 230                 235                 240

Gly Leu Ala Leu Tyr Leu Gln Ala Leu Glu Asn Leu Asn Thr Pro Ala
                245                 250                 255

Ala Val Thr Asn Arg Ile Lys Ser Leu Ala Thr Thr Gly Arg Ile Thr
            260                 265                 270

Gly Ser Leu Ser Gly Ser Pro Asn Leu Met Ala Phe Asn Gly Ala Thr
        275                 280                 285

Ala

<210> SEQ ID NO 33
<211> LENGTH: 870
<212> TYPE: DNA
<213> ORGANISM: Artificial sequence
<220> FEATURE:
<223> OTHER INFORMATION: Description of Artificial Sequence: Synthetic polynucleotide
<220> FEATURE:
<223> OTHER INFORMATION: The nucleotide sequence encoding the amino acid sequence of the mature form of Fe_RF6318 serine protease variant comprising substitutions V208I, A111D, A281L and T106N

<400> SEQUENCE: 33
gctctgacca ctcagagcaa cgctccttgg ggtcttgctg ccatctcccg ccgaaccccc      60
ggtggcagca cctacaccta cgacaccact gccggtgccg gtacttacgg ttacgtcgtt     120
gactctggta tcaacaccgc ccacactgac tttggcggcc gtgcttctct cggttacaac     180

```
gctgctggtg cgcccacac tgatacccctt ggccacggta cccacgttgc tggtaccatt    240
gcctccaaca cctacggtgt tgccaagcgt gccaacgtca tctctgtcaa ggttttcgtc    300
ggtaaccaag cttctaactc tgttatcctt gacggtttca actgggctgt caacgacatc    360
acctccaaga accgtgctag ccgctctgtc atcaacatgt ctctcggtgg tccctcttct    420
cagacctggg ctactgccat caacgctgcc tacagccaag gtgtcctctc cgttgttgct    480
gccggtaacg gtgattccaa cggtcgtcct ctccccgcct ctggccagtc tcctgccaac    540
gttcccaacg ctatcaccgt tgctgccgcc gactccagct ggcgaactgc ctctttcacc    600
aactacggtc ctgaggtcga tatcttcggt cctggtgtca acatccagtc cacctggtac    660
acctccaaca gcgctaccaa caccatcagc ggtacctcca tggcttgccc tcacgttgct    720
ggtcttgctc tctacctcca ggctctcgag aacctcaata cccctgctgc cgtcaccaac    780
cgcatcaagt ctcttgccac taccggccgc atcactggga gcctcagcgg cagccccaac    840
ctcatggctt tcaacggcgc tactgcttaa                                      870
```

<210> SEQ ID NO 34
<211> LENGTH: 289
<212> TYPE: PRT
<213> ORGANISM: Artificial sequence
<220> FEATURE:
<223> OTHER INFORMATION: Description of Artificial Sequence: Synthetic
       polypeptide
<220> FEATURE:
<223> OTHER INFORMATION: The amino acid sequence of the mature form of
       Fe_RF6318 serine protease variant comprising substitutions V208I,
       A111D, A281L and T106N <400> SEQUENCE: 34

Ala Leu Thr Thr Gln Ser Asn Ala Pro Trp Gly Leu Ala Ala Ile Ser
1               5                   10                  15

Arg Arg Thr Pro Gly Gly Ser Thr Tyr Thr Tyr Asp Thr Thr Ala Gly
            20                  25                  30

Ala Gly Thr Tyr Gly Tyr Val Val Asp Ser Gly Ile Asn Thr Ala His
        35                  40                  45

Thr Asp Phe Gly Gly Arg Ala Ser Leu Gly Tyr Asn Ala Ala Gly Gly
    50                  55                  60

Ala His Thr Asp Thr Leu Gly His Gly Thr His Val Ala Gly Thr Ile
65                  70                  75                  80

Ala Ser Asn Thr Tyr Gly Val Ala Lys Arg Ala Asn Val Ile Ser Val
                85                  90                  95

Lys Val Phe Val Gly Asn Gln Ala Ser Asn Ser Val Ile Leu Asp Gly
            100                 105                 110

Phe Asn Trp Ala Val Asn Asp Ile Thr Ser Lys Asn Arg Ala Ser Arg
        115                 120                 125

Ser Val Ile Asn Met Ser Leu Gly Gly Pro Ser Ser Gln Thr Trp Ala
    130                 135                 140

Thr Ala Ile Asn Ala Ala Tyr Ser Gln Gly Val Leu Ser Val Val Ala
145                 150                 155                 160

Ala Gly Asn Gly Asp Ser Asn Gly Arg Pro Leu Pro Ala Ser Gly Gln
                165                 170                 175

Ser Pro Ala Asn Val Pro Asn Ala Ile Thr Val Ala Ala Ala Asp Ser
            180                 185                 190

Ser Trp Arg Thr Ala Ser Phe Thr Asn Tyr Gly Pro Glu Val Asp Ile
        195                 200                 205

Phe Gly Pro Gly Val Asn Ile Gln Ser Thr Trp Tyr Thr Ser Asn Ser

```
        210                 215                 220
Ala Thr Asn Thr Ile Ser Gly Thr Ser Met Ala Cys Pro His Val Ala
225                 230                 235                 240

Gly Leu Ala Leu Tyr Leu Gln Ala Leu Glu Asn Leu Asn Thr Pro Ala
                245                 250                 255

Ala Val Thr Asn Arg Ile Lys Ser Leu Ala Thr Thr Gly Arg Ile Thr
            260                 265                 270

Gly Ser Leu Ser Gly Ser Pro Asn Leu Met Ala Phe Asn Gly Ala Thr
        275                 280                 285

Ala
```

<210> SEQ ID NO 35
<211> LENGTH: 870
<212> TYPE: DNA
<213> ORGANISM: Artificial sequence
<220> FEATURE:
<223> OTHER INFORMATION: Description of Artificial Sequence: Synthetic polynucleotide
<220> FEATURE:
<223> OTHER INFORMATION: The nucleotide sequence encoding the amino acid sequence of the mature form of Fe_RF6318 serine protease variant comprising substitutions V208I, A111D, A281L, T3C, T29C, S6R and T24D

<400> SEQUENCE: 35

```
gctctgtgca ctcagcgcaa cgctccttgg ggtcttgctg ccatctcccg ccgaaccccc      60
ggtggcagcg actacaccta cgactgcact gccggtgccg gtacttacgg ttacgtcgtt     120
gactctggta tcaacaccgc ccacactgac tttggcggcc gtgcttctct cggttacaac     180
gctgctggtg gcgcccacac tgataccctt ggccacggta cccacgttgc tggtaccatt     240
gcctccaaca cctacggtgt tgccaagcgt gccaacgtca tctctgtcaa ggttttcgtc     300
ggtaaccaag cttctaccct tgttatcctt gacggtttca ctgggctgt caacgacatc     360
acctccaaga accgtgctag ccgctctgtc atcaacatgt ctctcggtgg tccctcttct     420
cagacctggg ctactgccat caacgctgcc tacagccaag gtgtcctctc cgttgttgct     480
gccggtaacg tgattccaa cggtcgtcct ctcccccgcct ctggccagtc tcctgccaac     540
gttcccaacg ctatcaccgt tgctgccgcc gactccagct ggcgaactgc ctctttcacc     600
aactacggtc tgaggtcga tatcttcggt cctggtgtca acatccagtc cacctggtac     660
acctccaaca gcgctaccaa caccatcagc ggtacctcca tggcttgccc tcacgttgct     720
ggtcttgctc tctacctcca ggctctcgag aacctcaata ccctgctgc cgtcaccaac     780
cgcatcaagt ctcttgccac taccggccgc atcactggca gcctcagcgg cagccccaac     840
ctcatggctt tcaacggcgc tactgcttaa                                      870
```

<210> SEQ ID NO 36
<211> LENGTH: 289
<212> TYPE: PRT
<213> ORGANISM: Artificial sequence
<220> FEATURE:
<223> OTHER INFORMATION: Description of Artificial Sequence: Synthetic polypeptide
<220> FEATURE:
<223> OTHER INFORMATION: The amino acid sequence of the mature form of Fe_RF6318 serine protease variant comprising substitutions V208I, A111D, A281L, T3C, T29C, S6R and T24D

<400> SEQUENCE: 36

```
Ala Leu Cys Thr Gln Arg Asn Ala Pro Trp Gly Leu Ala Ala Ile Ser
1               5                   10                  15
```

Arg Arg Thr Pro Gly Gly Ser Asp Tyr Thr Tyr Asp Cys Thr Ala Gly
            20                  25                  30

Ala Gly Thr Tyr Gly Tyr Val Val Asp Ser Gly Ile Asn Thr Ala His
        35                  40                  45

Thr Asp Phe Gly Gly Arg Ala Ser Leu Gly Tyr Asn Ala Ala Gly Gly
 50                  55                  60

Ala His Thr Asp Thr Leu Gly His Gly Thr His Val Ala Gly Thr Ile
 65                  70                  75                  80

Ala Ser Asn Thr Tyr Gly Val Ala Lys Arg Ala Asn Val Ile Ser Val
                85                  90                  95

Lys Val Phe Val Gly Asn Gln Ala Ser Thr Ser Val Ile Leu Asp Gly
            100                 105                 110

Phe Asn Trp Ala Val Asn Asp Ile Thr Ser Lys Asn Arg Ala Ser Arg
            115                 120                 125

Ser Val Ile Asn Met Ser Leu Gly Gly Pro Ser Ser Gln Thr Trp Ala
        130                 135                 140

Thr Ala Ile Asn Ala Ala Tyr Ser Gln Gly Val Leu Ser Val Val Ala
145                 150                 155                 160

Ala Gly Asn Gly Asp Ser Asn Gly Arg Pro Leu Pro Ala Ser Gly Gln
                165                 170                 175

Ser Pro Ala Asn Val Pro Asn Ala Ile Thr Val Ala Ala Ala Asp Ser
            180                 185                 190

Ser Trp Arg Thr Ala Ser Phe Thr Asn Tyr Gly Pro Glu Val Asp Ile
        195                 200                 205

Phe Gly Pro Gly Val Asn Ile Gln Ser Thr Trp Tyr Thr Ser Asn Ser
210                 215                 220

Ala Thr Asn Thr Ile Ser Gly Thr Ser Met Ala Cys Pro His Val Ala
225                 230                 235                 240

Gly Leu Ala Leu Tyr Leu Gln Ala Leu Glu Asn Leu Asn Thr Pro Ala
                245                 250                 255

Ala Val Thr Asn Arg Ile Lys Ser Leu Ala Thr Thr Gly Arg Ile Thr
            260                 265                 270

Gly Ser Leu Ser Gly Ser Pro Asn Leu Met Ala Phe Asn Gly Ala Thr
        275                 280                 285

Ala

<210> SEQ ID NO 37
<211> LENGTH: 870
<212> TYPE: DNA
<213> ORGANISM: Artificial sequence
<220> FEATURE:
<223> OTHER INFORMATION: Description of Artificial Sequence: Synthetic
      polynucleotide
<220> FEATURE:
<223> OTHER INFORMATION: The nucleotide sequence encoding the amino acid
      sequence of the mature form of Fe_RF6318 serine protease variant
      comprising substitutions V208I, A111D, A281L, I185M and G210A

<400> SEQUENCE: 37
gctctgacca ctcagagcaa cgctccttgg ggtcttgctg ccatctcccg ccgaaccccc      60
ggtggcagca cctacaccta cgacaccact gccggtgccg gtacttacgg ttacgtcgtt     120
gactctggta tcaacaccgc ccacactgac tttggcggcc gtgcttctct cggttacaac     180
gctgctggtg gcgcccacac tgataccctt ggccacggta cccacgttgc tggtaccatt     240
gcctccaaca cctacggtgt tgccaagcgt gccaacgtca tctctgtcaa ggttttcgtc     300

```
ggtaaccaag cttctacctc tgttatcctt gacggtttca actgggctgt caacgacatc    360
acctccaaga accgtgctag ccgctctgtc atcaacatgt ctctcggtgg tccctcttct    420
cagacctggg ctactgccat caacgctgcc tacagccaag gtgtcctctc cgttgttgct    480
gccggtaacg gtgattccaa cggtcgtcct ctccccgcct ctggccagtc tcctgccaac    540
gttcccaacg ctatgaccgt tgctgccgcc gactccagct ggcgaactgc ctctttcacc    600
aactacggtc ctgaggtcga tatcttcgcc cctggtgtca acatccagtc cacctggtac    660
acctccaaca gcgctaccaa caccatcagc ggtacctcca tggcttgccc tcacgttgct    720
ggtcttgctc tctacctcca ggctctcgag aacctcaata ccctgctgc cgtcaccaac    780
cgcatcaagt ctcttgccac taccggccgc atcactggag cctcagcgg cagccccaac    840
ctcatggctt tcaacggcgc tactgcttaa                                     870
```

<210> SEQ ID NO 38
<211> LENGTH: 289
<212> TYPE: PRT
<213> ORGANISM: Artificial sequence
<220> FEATURE:
<223> OTHER INFORMATION: Description of Artificial Sequence: Synthetic
      polypeptide
<220> FEATURE:
<223> OTHER INFORMATION: The amino acid sequence of the mature form of
      Fe_RF6318 serine protease variant comprising substitutions V208I,
      A111D, A281L, I185M and G210A

<400> SEQUENCE: 38

```
Ala Leu Thr Thr Gln Ser Asn Ala Pro Trp Gly Leu Ala Ala Ile Ser
1               5                   10                  15

Arg Arg Thr Pro Gly Gly Ser Thr Tyr Thr Tyr Asp Thr Thr Ala Gly
            20                  25                  30

Ala Gly Thr Tyr Gly Tyr Val Val Asp Ser Gly Ile Asn Thr Ala His
        35                  40                  45

Thr Asp Phe Gly Gly Arg Ala Ser Leu Gly Tyr Asn Ala Ala Gly Gly
    50                  55                  60

Ala His Thr Asp Thr Leu Gly His Gly Thr His Val Ala Gly Thr Ile
65                  70                  75                  80

Ala Ser Asn Thr Tyr Gly Val Ala Lys Arg Ala Asn Val Ile Ser Val
                85                  90                  95

Lys Val Phe Val Gly Asn Gln Ala Ser Thr Ser Val Ile Leu Asp Gly
            100                 105                 110

Phe Asn Trp Ala Val Asn Asp Ile Thr Ser Lys Asn Arg Ala Ser Arg
        115                 120                 125

Ser Val Ile Asn Met Ser Leu Gly Gly Pro Ser Ser Gln Thr Trp Ala
    130                 135                 140

Thr Ala Ile Asn Ala Ala Tyr Ser Gln Gly Val Leu Ser Val Val Ala
145                 150                 155                 160

Ala Gly Asn Gly Asp Ser Asn Gly Arg Pro Leu Pro Ala Ser Gly Gln
                165                 170                 175

Ser Pro Ala Asn Val Pro Asn Ala Met Thr Val Ala Ala Ala Asp Ser
            180                 185                 190

Ser Trp Arg Thr Ala Ser Phe Thr Asn Tyr Gly Pro Glu Val Asp Ile
        195                 200                 205

Phe Ala Pro Gly Val Asn Ile Gln Ser Thr Trp Tyr Thr Ser Asn Ser
    210                 215                 220

Ala Thr Asn Thr Ile Ser Gly Thr Ser Met Ala Cys Pro His Val Ala
225                 230                 235                 240
```

```
Gly Leu Ala Leu Tyr Leu Gln Ala Leu Glu Asn Leu Asn Thr Pro Ala
                245                 250                 255

Ala Val Thr Asn Arg Ile Lys Ser Leu Ala Thr Thr Gly Arg Ile Thr
            260                 265                 270

Gly Ser Leu Ser Gly Ser Pro Asn Leu Met Ala Phe Asn Gly Ala Thr
        275                 280                 285

Ala

<210> SEQ ID NO 39
<211> LENGTH: 870
<212> TYPE: DNA
<213> ORGANISM: Artificial sequence
<220> FEATURE:
<223> OTHER INFORMATION: Description of Artificial Sequence: Synthetic
      polynucleotide
<220> FEATURE:
<223> OTHER INFORMATION: The nucleotide sequence encoding the amino acid
      sequence of the mature form of Fe_RF6318 serine protease variant
      comprising substitutions V208I, A111D, A281L and V100Q

<400> SEQUENCE: 39
gctctgacca ctcagagcaa cgctccttgg ggtcttgctg ccatctcccg ccgaaccccc       60
ggtggcagca cctacaccta cgacaccact gccggtgccg gtacttacgg ttacgtcgtt      120
gactctggta tcaacaccgc ccacactgac tttggcggcc gtgcttctct cggttacaac      180
gctgctggtg gcgcccacac tgatacccct tggccacggta cccacgttgc tggtaccatt     240
gcctccaaca cctacggtgt tgccaagcgt gccaacgtca tctctgtcaa ggttttccag      300
ggtaaccaag cttctacctc tgttatcctt gacggtttca ctgggctgt caacgacatc       360 acctccaaga accgtgctag ccgctctgtc atcaacatgt ctctcggtgg tccctcttct      420
cagacctggg ctactgccat caacgctgcc tacagccaag gtgtcctctc cgttgttgct     480
gccggtaacg gtgattccaa cggtcgtcct ctccccgcct ctggccagtc tcctgccaac     540
gttcccaacg ctatcaccgt tgctgccgcc gactccagct ggcgaactgc ctctttcacc     600
aactacggtc tgaggtcga tatcttcggt cctggtgtca acatccagtc cacctggtac     660
acctccaaca gcgctaccaa caccatcagc ggtacctcca tggcttgccc tcacgttgct    720
ggtcttgctc tctacctcca ggctctcgag aacctcaata ccctgctgc cgtcaccaac     780 cgcatcaagt ctcttgccac taccggccgc atcactggca gcctcagcgg cagccccaac    840
ctcatggctt caacggcgc tactgcttaa                                      870

<210> SEQ ID NO 40
<211> LENGTH: 289
<212> TYPE: PRT
<213> ORGANISM: Artificial sequence
<220> FEATURE:
<223> OTHER INFORMATION: Description of Artificial Sequence: Synthetic
      polypeptide
<220> FEATURE:
<223> OTHER INFORMATION: The amino acid sequence of the mature form of
      Fe_RF6318 serine protease variant comprising substitutions V208I,
      A111D, A281L and V100Q

<400> SEQUENCE: 40

Ala Leu Thr Thr Gln Ser Asn Ala Pro Trp Gly Leu Ala Ala Ile Ser
1               5                   10                  15

Arg Arg Thr Pro Gly Gly Ser Thr Tyr Thr Tyr Asp Thr Thr Ala Gly
            20                  25                  30

Ala Gly Thr Tyr Gly Tyr Val Val Asp Ser Gly Ile Asn Thr Ala His
```

```
                 35                  40                  45
Thr Asp Phe Gly Gly Arg Ala Ser Leu Gly Tyr Asn Ala Ala Gly Gly
 50                  55                  60
Ala His Thr Asp Thr Leu Gly His Gly Thr His Val Ala Gly Thr Ile
 65                  70                  75                  80
Ala Ser Asn Thr Tyr Gly Val Ala Lys Arg Ala Asn Val Ile Ser Val
                 85                  90                  95
Lys Val Phe Gln Gly Asn Gln Ala Ser Thr Ser Val Ile Leu Asp Gly
                100                 105                 110
Phe Asn Trp Ala Val Asn Asp Ile Thr Ser Lys Asn Arg Ala Ser Arg
            115                 120                 125
Ser Val Ile Asn Met Ser Leu Gly Gly Pro Ser Ser Gln Thr Trp Ala
130                 135                 140
Thr Ala Ile Asn Ala Ala Tyr Ser Gln Gly Val Leu Ser Val Val Ala
145                 150                 155                 160
Ala Gly Asn Gly Asp Ser Asn Gly Arg Pro Leu Pro Ala Ser Gly Gln
                165                 170                 175
Ser Pro Ala Asn Val Pro Asn Ala Ile Thr Val Ala Ala Ala Asp Ser
            180                 185                 190
Ser Trp Arg Thr Ala Ser Phe Thr Asn Tyr Gly Pro Glu Val Asp Ile
        195                 200                 205
Phe Gly Pro Gly Val Asn Ile Gln Ser Thr Trp Tyr Thr Ser Asn Ser
210                 215                 220
Ala Thr Asn Thr Ile Ser Gly Thr Ser Met Ala Cys Pro His Val Ala
225                 230                 235                 240
Gly Leu Ala Leu Tyr Leu Gln Ala Leu Glu Asn Leu Asn Thr Pro Ala
                245                 250                 255
Ala Val Thr Asn Arg Ile Lys Ser Leu Ala Thr Thr Gly Arg Ile Thr
            260                 265                 270
Gly Ser Leu Ser Gly Ser Pro Asn Leu Met Ala Phe Asn Gly Ala Thr
        275                 280                 285
Ala
```

<210> SEQ ID NO 41
<211> LENGTH: 870
<212> TYPE: DNA
<213> ORGANISM: Artificial sequence
<220> FEATURE:
<223> OTHER INFORMATION: Description of Artificial Sequence: Synthetic
      polynucleotide
<220> FEATURE:
<223> OTHER INFORMATION: The nucleotide sequence encoding the amino acid
      sequence of the mature form of Fe_RF6318 serine protease variant
      comprising substitutions V208I, A111D, A281L and K123R

<400> SEQUENCE: 41

```
gctctgacca ctcagagcaa cgctccttgg ggtcttgctg ccatctcccg ccgaaccccc    60
ggtggcagca cctacaccta cgacaccact gccggtgccg gtacttacgg ttacgtcgtt   120
gactctggta tcaacaccgc ccacactgac tttggcggcc gtgcttctct cggttacaac   180
gctgctggtg gcgcccacac tgatacccct tggccacggta cccacgttgc tggtaccatt   240
gcctccaaca cctacggtgt tgccaagcgt gccaacgtca tctctgtcaa ggttttcgtc   300
ggtaaccaag cttctacctc tgttatcctt gacggtttca actgggctgt caacgacatc   360
acctcccgca accgtgctag ccgctctgtc atcaacatgt ctctcggtgg tccctcttct   420
cagacctggg ctactgccat caacgctgcc tacagccaag gtgtcctctc cgttgttgct   480
```

-continued

```
gccggtaacg gtgattccaa cggtcgtcct ctccccgcct ctggccagtc tcctgccaac    540
gttcccaacg ctatcaccgt tgctgccgcc gactccagct ggcgaactgc ctctttcacc    600
aactacggtc ctgaggtcga tatcttcggt cctggtgtca acatccagtc cacctggtac    660
acctccaaca gcgctaccaa caccatcagc ggtacctcca tggcttgccc tcacgttgct    720
ggtcttgctc tctacctcca ggctctcgag aacctcaata ccctgctgc cgtcaccaac    780 cgcatcaagt ctcttgccac taccggccgc atcactggca gcctcagcgg cagccccaac    840
ctcatggctt tcaacggcgc tactgcttaa                                    870
```

<210> SEQ ID NO 42
<211> LENGTH: 289
<212> TYPE: PRT
<213> ORGANISM: Artificial sequence
<220> FEATURE:
<223> OTHER INFORMATION: Description of Artificial Sequence: Synthetic polypeptide
<220> FEATURE:
<223> OTHER INFORMATION: The amino acid sequence of the mature form of Fe_RF6318 serine protease variant comprising substitutions V208I, A111D, A281L and K123R

<400> SEQUENCE: 42

```
Ala Leu Thr Thr Gln Ser Asn Ala Pro Trp Gly Leu Ala Ala Ile Ser
1               5                   10                  15

Arg Arg Thr Pro Gly Gly Ser Thr Tyr Thr Tyr Asp Thr Thr Ala Gly
                20                  25                  30

Ala Gly Thr Tyr Gly Tyr Val Val Asp Ser Gly Ile Asn Thr Ala His
            35                  40                  45

Thr Asp Phe Gly Gly Arg Ala Ser Leu Gly Tyr Asn Ala Ala Gly Gly
        50                  55                  60

Ala His Thr Asp Thr Leu Gly His Gly Thr His Val Ala Gly Thr Ile
65                  70                  75                  80

Ala Ser Asn Thr Tyr Gly Val Ala Lys Arg Ala Asn Val Ile Ser Val
                85                  90                  95

Lys Val Phe Val Gly Asn Gln Ala Ser Thr Ser Val Ile Leu Asp Gly
            100                 105                 110

Phe Asn Trp Ala Val Asn Asp Ile Thr Ser Arg Asn Arg Ala Ser Arg
        115                 120                 125

Ser Val Ile Asn Met Ser Leu Gly Gly Pro Ser Ser Gln Thr Trp Ala
    130                 135                 140

Thr Ala Ile Asn Ala Ala Tyr Ser Gln Gly Val Leu Ser Val Val Ala
145                 150                 155                 160

Ala Gly Asn Gly Asp Ser Asn Gly Arg Pro Leu Pro Ala Ser Gly Gln
                165                 170                 175

Ser Pro Ala Asn Val Pro Asn Ala Ile Thr Val Ala Ala Ala Asp Ser
            180                 185                 190

Ser Trp Arg Thr Ala Ser Phe Thr Asn Tyr Gly Pro Glu Val Asp Ile
        195                 200                 205

Phe Gly Pro Gly Val Asn Ile Gln Ser Thr Trp Tyr Thr Ser Asn Ser
    210                 215                 220

Ala Thr Asn Thr Ile Ser Gly Thr Ser Met Ala Cys Pro His Val Ala
225                 230                 235                 240

Gly Leu Ala Leu Tyr Leu Gln Ala Leu Glu Asn Leu Asn Thr Pro Ala
                245                 250                 255

Ala Val Thr Asn Arg Ile Lys Ser Leu Ala Thr Thr Gly Arg Ile Thr
```

```
                  260                 265                 270
Gly Ser Leu Ser Gly Ser Pro Asn Leu Met Ala Phe Asn Gly Ala Thr
        275                 280                 285
Ala
```

<210> SEQ ID NO 43
<211> LENGTH: 870
<212> TYPE: DNA
<213> ORGANISM: Artificial sequence
<220> FEATURE:
<223> OTHER INFORMATION: Description of Artificial Sequence: Synthetic
      polynucleotide
<220> FEATURE:
<223> OTHER INFORMATION: The nucleotide sequence encoding the amino acid
      sequence of the mature form of Fe_RF6318 serine protease variant
      comprising substitutions V208I, A111D, A281L and S157T

<400> SEQUENCE: 43

```
gctctgacca ctcagagcaa cgctccttgg ggtcttgctg ccatctcccg ccgaaccccc    60
ggtggcagca cctacaccta cgacaccact gccggtgccg gtacttacgg ttacgtcgtt   120
gactctggta tcaacaccgc ccacactgac tttggcggcc gtgcttctct cggttacaac   180
gctgctggtg gcgccacac tgataccctt ggccacggta cccacgttgc tggtaccatt   240
gcctccaaca cctacggtgt tgccaagcgt gccaacgtca tctctgtcaa ggttttcgtc   300
ggtaaccaag cttctacctc tgttatcctt gacggtttca ctgggctgt caacgacatc   360
acctccaaga accgtgctag ccgctctgtc atcaacatgt ctctcggtgg tccctcttct   420
cagacctggg ctactgccat caacgctgcc tacagccaag gtgtcctcac cgttgttgct   480
gccggtaacg gtgattccaa cggtcgtcct ctccccgcct ctggccagtc tcctgccaac   540
gttcccaacg ctatcaccgt tgctgccgcc gactccagct ggcgaactgc ctctttcacc   600
aactacggtc tgaggtcga tatcttcggt cctggtgtca acatccagtc cacctggtac   660
acctccaaca cgctaccaa caccatcagc ggtacctcca tggcttgccc tcacgttgct   720
ggtcttgctc tctacctcca ggctctcgag aacctcaata cccctgctgc cgtcaccaac   780
cgcatcaagt tcttgccac taccggccgc atcactggca gcctcagcgg cagccccaac   840
ctcatggctt tcaacggcgc tactgcttaa                                    870
```

<210> SEQ ID NO 44
<211> LENGTH: 289
<212> TYPE: PRT
<213> ORGANISM: Artificial sequence
<220> FEATURE:
<223> OTHER INFORMATION: Description of Artificial Sequence: Synthetic
      polypeptide
<220> FEATURE:
<223> OTHER INFORMATION: The amino acid sequence of the mature form of
      Fe_RF6318 serine protease variant comprising substitutions V208I,
      A111D, A281L and S157T

<400> SEQUENCE: 44

```
Ala Leu Thr Thr Gln Ser Asn Ala Pro Trp Gly Leu Ala Ala Ile Ser
1               5                   10                  15
Arg Arg Thr Pro Gly Gly Ser Thr Tyr Thr Tyr Asp Thr Thr Ala Gly
            20                  25                  30
Ala Gly Thr Tyr Gly Tyr Val Val Asp Ser Gly Ile Asn Thr Ala His
        35                  40                  45
Thr Asp Phe Gly Gly Arg Ala Ser Leu Gly Tyr Asn Ala Ala Gly Gly
    50                  55                  60
```

| Ala | His | Thr | Asp | Thr | Leu | Gly | His | Gly | Thr | His | Val | Ala | Gly | Thr | Ile |
|---|---|---|---|---|---|---|---|---|---|---|---|---|---|---|---|
| 65 | | | | 70 | | | | | 75 | | | | | 80 | |

Ala Ser Asn Thr Tyr Gly Val Ala Lys Arg Ala Asn Val Ile Ser Val
              85                  90                  95

Lys Val Phe Val Gly Asn Gln Ala Ser Thr Ser Val Ile Leu Asp Gly
                100                 105                 110

Phe Asn Trp Ala Val Asn Asp Ile Thr Ser Lys Asn Arg Ala Ser Arg
            115                 120                 125

Ser Val Ile Asn Met Ser Leu Gly Gly Pro Ser Ser Gln Thr Trp Ala
        130                 135                 140

Thr Ala Ile Asn Ala Ala Tyr Ser Gln Gly Val Leu Thr Val Val Ala
145                 150                 155                 160

Ala Gly Asn Gly Asp Ser Asn Gly Arg Pro Leu Pro Ala Ser Gly Gln
                165                 170                 175

Ser Pro Ala Asn Val Pro Asn Ala Ile Thr Val Ala Ala Ala Asp Ser
                180                 185                 190

Ser Trp Arg Thr Ala Ser Phe Thr Asn Tyr Gly Pro Glu Val Asp Ile
        195                 200                 205

Phe Gly Pro Gly Val Asn Ile Gln Ser Thr Trp Tyr Thr Ser Asn Ser
210                 215                 220

Ala Thr Asn Thr Ile Ser Gly Thr Ser Met Ala Cys Pro His Val Ala
225                 230                 235                 240

Gly Leu Ala Leu Tyr Leu Gln Ala Leu Glu Asn Leu Asn Thr Pro Ala
                245                 250                 255

Ala Val Thr Asn Arg Ile Lys Ser Leu Ala Thr Thr Gly Arg Ile Thr
            260                 265                 270

Gly Ser Leu Ser Gly Ser Pro Asn Leu Met Ala Phe Asn Gly Ala Thr
        275                 280                 285

Ala

<210> SEQ ID NO 45
<211> LENGTH: 870
<212> TYPE: DNA
<213> ORGANISM: Artificial sequence
<220> FEATURE:
<223> OTHER INFORMATION: Description of Artificial Sequence: Synthetic polynucleotide
<220> FEATURE:
<223> OTHER INFORMATION: The nucleotide sequence encoding the amino acid sequence of the mature form of Fe_RF6318 serine protease variant comprising substitutions V208I, A111D, A281L and G175S

<400> SEQUENCE: 45

```
gctctgacca ctcagagcaa cgctccttgg ggtcttgctg ccatctcccg ccgaaccccc      60
ggtggcagca cctacaccta cgacaccact gccggtgccg gtacttacgg ttacgtcgtt     120
gactctggta tcaacaccgc ccacactgac tttggcggcc gtgcttctct cggttacaac     180
gctgctggtg cgcccacac tgatacccct ggccacggta cccacgttgc tggtaccatt     240
gcctccaaca cctacggtgt tgccaagcgt gccaacgtca tctctgtcaa ggttttcgtc     300
ggtaaccaag cttctacctc tgttatcctt gacggtttca actgggctgt caacgacatc     360
acctccaaga accgtgctag ccgctctgtc atcaacatgt ctctcggtgg tccctcttct     420
cagacctggg ctactgccat caacgctgcc tacagccaag gtgtcctctc cgttgttgct     480
gccggtaacg gtgattccaa cggtcgtcct ctccccgcct cttccagtc tcctgccaac     540
gttcccaacg ctatcaccgt tgctgccgcc gactccagct ggcgaactgc ctcctttcacc    600
```

```
aactacggtc ctgaggtcga tatcttcggt cctggtgtca acatccagtc cacctggtac    660
acctccaaca gcgctaccaa caccatcagc ggtacctcca tggcttgccc tcacgttgct    720
ggtcttgctc tctacctcca ggctctcgag aacctcaata ccctgctgc cgtcaccaac    780 cgcatcaagt tccttgccac taccggccgc atcactggca gcctcagcgg cagccccaac    840
ctcatggctt tcaacggcgc tactgcttaa                                      870
```

<210> SEQ ID NO 46
<211> LENGTH: 289
<212> TYPE: PRT
<213> ORGANISM: Artificial sequence
<220> FEATURE:
<223> OTHER INFORMATION: Description of Artificial Sequence: Synthetic polypeptide
<220> FEATURE:
<223> OTHER INFORMATION: The amino acid sequence of the mature form of Fe_RF6318 serine protease variant comprising substitutions V208I, A111D, A281L and G175S

<400> SEQUENCE: 46

```
Ala Leu Thr Thr Gln Ser Asn Ala Pro Trp Gly Leu Ala Ala Ile Ser
1               5                   10                  15

Arg Arg Thr Pro Gly Gly Ser Thr Tyr Thr Tyr Asp Thr Thr Ala Gly
            20                  25                  30

Ala Gly Thr Tyr Gly Tyr Val Val Asp Ser Gly Ile Asn Thr Ala His
        35                  40                  45

Thr Asp Phe Gly Gly Arg Ala Ser Leu Gly Tyr Asn Ala Ala Gly Gly
    50                  55                  60

Ala His Thr Asp Thr Leu Gly His Gly Thr His Val Ala Gly Thr Ile
65                  70                  75                  80

Ala Ser Asn Thr Tyr Gly Val Ala Lys Arg Ala Asn Val Ile Ser Val
                85                  90                  95

Lys Val Phe Val Gly Asn Gln Ala Ser Thr Ser Val Ile Leu Asp Gly
            100                 105                 110

Phe Asn Trp Ala Val Asn Asp Ile Thr Ser Lys Asn Arg Ala Ser Arg
        115                 120                 125

Ser Val Ile Asn Met Ser Leu Gly Gly Pro Ser Ser Gln Thr Trp Ala
    130                 135                 140

Thr Ala Ile Asn Ala Ala Tyr Ser Gln Gly Val Leu Ser Val Val Ala
145                 150                 155                 160

Ala Gly Asn Gly Asp Ser Asn Gly Arg Pro Leu Pro Ala Ser Ser Gln
                165                 170                 175

Ser Pro Ala Asn Val Pro Asn Ala Ile Thr Val Ala Ala Ala Asp Ser
            180                 185                 190

Ser Trp Arg Thr Ala Ser Phe Thr Asn Tyr Gly Pro Glu Val Asp Ile
        195                 200                 205

Phe Gly Pro Gly Val Asn Ile Gln Ser Thr Trp Tyr Thr Ser Asn Ser
    210                 215                 220

Ala Thr Asn Thr Ile Ser Gly Thr Ser Met Ala Cys Pro His Val Ala
225                 230                 235                 240

Gly Leu Ala Leu Tyr Leu Gln Ala Leu Glu Asn Leu Asn Thr Pro Ala
                245                 250                 255

Ala Val Thr Asn Arg Ile Lys Ser Leu Ala Thr Thr Gly Arg Ile Thr
            260                 265                 270

Gly Ser Leu Ser Gly Ser Pro Asn Leu Met Ala Phe Asn Gly Ala Thr
        275                 280                 285
```

Ala

<210> SEQ ID NO 47
<211> LENGTH: 870
<212> TYPE: DNA
<213> ORGANISM: Artificial sequence
<220> FEATURE:
<223> OTHER INFORMATION: Description of Artificial Sequence: Synthetic polynucleotide
<220> FEATURE:
<223> OTHER INFORMATION: The nucleotide sequence encoding the amino acid sequence of the mature form of Fe_RF6318 serine protease variant comprising substitutions V208I, A111D, A281L and Q176T

<400> SEQUENCE: 47

```
gctctgacca ctcagagcaa cgctccttgg ggtcttgctg ccatctcccg ccgaaccccc      60
ggtggcagca cctacaccta cgacaccact gccggtgccg gtacttacgg ttacgtcgtt     120
gactctggta tcaacaccgc ccacactgac tttggcggcc gtgcttctct cggttacaac     180
gctgctggtg gcgcccacac tgatacccct ggccacggta cccacgttgc tggtaccatt     240
gcctccaaca cctacggtgt tgccaagcgt gccaacgtca tctctgtcaa ggttttcgtc     300
ggtaaccaag cttctacctc tgttatcctt gacggtttca actgggctgt caacgacatc     360
acctccaaga accgtgctag ccgctctgtc atcaacatgt ctctcggtgg tccctcttct     420
cagacctggg ctactgccat caacgctgcc tacagccaag tgtcctctc cgttgttgct     480
gccggtaacg gtgattccaa cggtcgtcct ctccccgcct ctggcacctc tcctgccaac     540
gttcccaacg ctatcaccgt tgctgccgcc gactccagct ggcgaactgc ctctttcacc     600
aactacggtc tgaggtcga tatcttcggt cctggtgtca catccagtc cacctggtac      660
acctccaaca gcgctaccaa caccatcagc ggtacctcca tggcttgccc tcacgttgct     720
ggtcttgctc tctacctcca ggctctcgag aacctcaata cccctgctgc cgtcaccaac     780
cgcatcaagt ctcttgccac taccggccgc atcactggca gcctcagcgg cagccccaac     840
ctcatggctt tcaacggcgc tactgcttaa                                     870
```

<210> SEQ ID NO 48
<211> LENGTH: 289
<212> TYPE: PRT
<213> ORGANISM: Artificial sequence
<220> FEATURE:
<223> OTHER INFORMATION: Description of Artificial Sequence: Synthetic polypeptide
<220> FEATURE:
<223> OTHER INFORMATION: The amino acid sequence of the mature form of Fe_RF6318 serine protease variant comprising substitutions V208I, A111D, A281L and Q176T

<400> SEQUENCE: 48

```
Ala Leu Thr Thr Gln Ser Asn Ala Pro Trp Gly Leu Ala Ala Ile Ser
 1               5                  10                  15

Arg Arg Thr Pro Gly Gly Ser Thr Tyr Thr Tyr Asp Thr Thr Ala Gly
                20                  25                  30

Ala Gly Thr Tyr Gly Tyr Val Val Asp Ser Gly Ile Asn Thr Ala His
            35                  40                  45

Thr Asp Phe Gly Gly Arg Ala Ser Leu Gly Tyr Asn Ala Ala Gly Gly
        50                  55                  60

Ala His Thr Asp Thr Leu Gly His Gly Thr His Val Ala Gly Thr Ile
 65                 70                  75                  80

Ala Ser Asn Thr Tyr Gly Val Ala Lys Arg Ala Asn Val Ile Ser Val
                85                  90                  95
```

Lys Val Phe Val Gly Asn Gln Ala Ser Thr Ser Val Ile Leu Asp Gly
            100                 105                 110

Phe Asn Trp Ala Val Asn Asp Ile Thr Ser Lys Asn Arg Ala Ser Arg
        115                 120                 125

Ser Val Ile Asn Met Ser Leu Gly Gly Pro Ser Gln Thr Trp Ala
        130                 135                 140

Thr Ala Ile Asn Ala Ala Tyr Ser Gln Gly Val Leu Ser Val Val Ala
145                 150                 155                 160

Ala Gly Asn Gly Asp Ser Asn Gly Arg Pro Leu Pro Ala Ser Gly Thr
                165                 170                 175

Ser Pro Ala Asn Val Pro Asn Ala Ile Thr Val Ala Ala Ala Asp Ser
            180                 185                 190

Ser Trp Arg Thr Ala Ser Phe Thr Asn Tyr Gly Pro Glu Val Asp Ile
        195                 200                 205

Phe Gly Pro Gly Val Asn Ile Gln Ser Thr Trp Tyr Thr Ser Asn Ser
        210                 215                 220

Ala Thr Asn Thr Ile Ser Gly Thr Ser Met Ala Cys Pro His Val Ala
225                 230                 235                 240

Gly Leu Ala Leu Tyr Leu Gln Ala Leu Glu Asn Leu Asn Thr Pro Ala
                245                 250                 255

Ala Val Thr Asn Arg Ile Lys Ser Leu Ala Thr Thr Gly Arg Ile Thr
            260                 265                 270

Gly Ser Leu Ser Gly Ser Pro Asn Leu Met Ala Phe Asn Gly Ala Thr
        275                 280                 285

Ala

<210> SEQ ID NO 49
<211> LENGTH: 870
<212> TYPE: DNA
<213> ORGANISM: Artificial sequence
<220> FEATURE:
<223> OTHER INFORMATION: Description of Artificial Sequence: Synthetic
      polynucleotide
<220> FEATURE:
<223> OTHER INFORMATION: The nucleotide sequence encoding the amino acid
      sequence of the mature form of Fe_RF6318 serine protease variant
      comprising substitutions V208I, A111D, A281L and C236T

<400> SEQUENCE: 49
gctctgacca ctcagagcaa cgctccttgg ggtcttgctg ccatctcccg ccgaaccccc      60
ggtggcagca cctacaccta cgacaccact gccggtgccg gtacttacgg ttacgtcgtt     120
gactctggta tcaacaccgc ccacactgac tttggcggcc gtgcttctct cggttacaac     180
gctgctggtg cgcccacac tgataccctt ggccacggta cccacgttgc tggtaccatt      240
gcctccaaca cctacggtgt tgccaagcgt gccaacgtca tctctgtcaa ggttttcgtc     300
ggtaaccaag cttctacctc tgttatcctt gacggtttca ctgggctgt caacgacatc     360 acctccaaga accgtgctag ccgctctgtc atcaacatgt ctctcggtgg tccctcttct     420
cagacctggg ctactgccat caacgctgcc tacagccaag gtgtcctctc cgttgttgct     480
gccggtaacg gtgattccaa cggtcgtcct ctccccgcct ctggccagtc tcctgccaac     540
gttcccaacg ctatcaccgt tgctgccgcc gactccagct ggcgaactgc ctctttcacc     600
aactacggtc ctgaggtcga tatcttcggt cctggtgtca acatccagtc cacctggtac     660
acctccaaca gcgctaccaa caccatcagc ggtacctcca tggctacccc tcacgttgct     720
ggtcttgctc tctacctcca ggctctcgag aacctcaata cccctgctgc cgtcaccaac     780

```
cgcatcaagt ctcttgccac taccggccgc atcactggca gcctcagcgg cagccccaac    840
ctcatggctt tcaacggcgc tactgcttaa                                     870
```

<210> SEQ ID NO 50
<211> LENGTH: 289
<212> TYPE: PRT
<213> ORGANISM: Artificial sequence
<220> FEATURE:
<223> OTHER INFORMATION: Description of Artificial Sequence: Synthetic polypeptide
<220> FEATURE:
<223> OTHER INFORMATION: The amino acid sequence of the mature form of Fe_RF6318 serine protease variant comprising substitutions V208I, A111D, A281L and C236T

<400> SEQUENCE: 50

```
Ala Leu Thr Thr Gln Ser Asn Ala Pro Trp Gly Leu Ala Ala Ile Ser
  1               5                  10                  15

Arg Arg Thr Pro Gly Gly Ser Thr Tyr Thr Tyr Asp Thr Thr Ala Gly
             20                  25                  30

Ala Gly Thr Tyr Gly Tyr Val Val Asp Ser Gly Ile Asn Thr Ala His
         35                  40                  45

Thr Asp Phe Gly Gly Arg Ala Ser Leu Gly Tyr Asn Ala Ala Gly Gly
     50                  55                  60

Ala His Thr Asp Thr Leu Gly His Gly Thr His Val Ala Gly Thr Ile
 65                  70                  75                  80

Ala Ser Asn Thr Tyr Gly Val Ala Lys Arg Ala Asn Val Ile Ser Val
                 85                  90                  95

Lys Val Phe Val Gly Asn Gln Ala Ser Thr Ser Val Ile Leu Asp Gly
            100                 105                 110

Phe Asn Trp Ala Val Asn Asp Ile Thr Ser Lys Asn Arg Ala Ser Arg
        115                 120                 125

Ser Val Ile Asn Met Ser Leu Gly Gly Pro Ser Ser Gln Thr Trp Ala
    130                 135                 140

Thr Ala Ile Asn Ala Ala Tyr Ser Gln Gly Val Leu Ser Val Val Ala
145                 150                 155                 160

Ala Gly Asn Gly Asp Ser Asn Gly Arg Pro Leu Pro Ala Ser Gly Gln
                165                 170                 175

Ser Pro Ala Asn Val Pro Asn Ala Ile Thr Val Ala Ala Ala Asp Ser
            180                 185                 190

Ser Trp Arg Thr Ala Ser Phe Thr Asn Tyr Gly Pro Glu Val Asp Ile
        195                 200                 205

Phe Gly Pro Gly Val Asn Ile Gln Ser Thr Trp Tyr Thr Ser Asn Ser
    210                 215                 220

Ala Thr Asn Thr Ile Ser Gly Thr Ser Met Ala Thr Pro His Val Ala
225                 230                 235                 240

Gly Leu Ala Leu Tyr Leu Gln Ala Leu Glu Asn Leu Asn Thr Pro Ala
                245                 250                 255

Ala Val Thr Asn Arg Ile Lys Ser Leu Ala Thr Thr Gly Arg Ile Thr
            260                 265                 270

Gly Ser Leu Ser Gly Ser Pro Asn Leu Met Ala Phe Asn Gly Ala Thr
        275                 280                 285

Ala
```

<210> SEQ ID NO 51
<211> LENGTH: 1239

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1236)

<400> SEQUENCE: 51 atg act agc ttc cgc cgt atc gct ctt ggc ctt gca gct ctg ctg ccc        48
Met Thr Ser Phe Arg Arg Ile Ala Leu Gly Leu Ala Ala Leu Leu Pro
1               5                   10                  15 gca gtc ctc gcc gct ccc acc gag aag cga cag gag ctc act gcc gcg        96
Ala Val Leu Ala Ala Pro Thr Glu Lys Arg Gln Glu Leu Thr Ala Ala
                20                  25                  30 cct gac aag tac atc atc acc ctc aag ccc gag gct gct gag gcc aag       144
Pro Asp Lys Tyr Ile Ile Thr Leu Lys Pro Glu Ala Ala Glu Ala Lys
            35                  40                  45 gtc gag gct cac atg gcc tgg gtt acc gac gtc cac cgc cgc agc ctc       192
Val Glu Ala His Met Ala Trp Val Thr Asp Val His Arg Arg Ser Leu
        50                  55                  60 ggc aag cgt gac act tcc ggt gtt gag aag aag ttc aac atc agc agc       240
Gly Lys Arg Asp Thr Ser Gly Val Glu Lys Lys Phe Asn Ile Ser Ser
65                  70                  75                  80 tgg aac gcc tac tct ggc gag ttc gac gat gct acc att gct gag atc       288
Trp Asn Ala Tyr Ser Gly Glu Phe Asp Asp Ala Thr Ile Ala Glu Ile
                85                  90                  95 aag aag agc ccc gag gtt gcc ttc gtc gag ccc gac tac att gtc acc       336
Lys Lys Ser Pro Glu Val Ala Phe Val Glu Pro Asp Tyr Ile Val Thr
                100                 105                 110 ctc gac tac aag gtt gag cct ctc tct gac cgt gct ctg acc act cag       384
Leu Asp Tyr Lys Val Glu Pro Leu Ser Asp Arg Ala Leu Thr Thr Gln
            115                 120                 125 agc aac gct cct tgg ggt ctt gct gcc atc tcc cgc cga acc ccc ggt       432
Ser Asn Ala Pro Trp Gly Leu Ala Ala Ile Ser Arg Arg Thr Pro Gly
        130                 135                 140 ggc agc acc tac acc tac gac acc act gcc ggt gcc ggt act tac ggt       480
Gly Ser Thr Tyr Thr Tyr Asp Thr Thr Ala Gly Ala Gly Thr Tyr Gly
145                 150                 155                 160 tac gtc gtt gac tct ggt atc aac acc gcc cac act gac ttt ggc ggc       528
Tyr Val Val Asp Ser Gly Ile Asn Thr Ala His Thr Asp Phe Gly Gly
                165                 170                 175 cgt gct tct ctc ggt tac aac gct gct ggt ggc gcc cac act gat acc       576
Arg Ala Ser Leu Gly Tyr Asn Ala Ala Gly Gly Ala His Thr Asp Thr
                180                 185                 190 ctt ggc cac ggt acc cac gtt gct ggt acc att gcc tcc aac acc tac       624
Leu Gly His Gly Thr His Val Ala Gly Thr Ile Ala Ser Asn Thr Tyr
            195                 200                 205 ggt gtt gcc aag cgt gcc aac gtc atc tct gtc aag gtt ttc gtc ggt       672
Gly Val Ala Lys Arg Ala Asn Val Ile Ser Val Lys Val Phe Val Gly
        210                 215                 220 aac caa gct tct acc tct gtt atc ctt gct ggt ttc aac tgg gct gtc       720
Asn Gln Ala Ser Thr Ser Val Ile Leu Ala Gly Phe Asn Trp Ala Val
225                 230                 235                 240 aac gac atc acc tcc aag aac cgt gct agc cgc tct gtc atc aac atg       768
Asn Asp Ile Thr Ser Lys Asn Arg Ala Ser Arg Ser Val Ile Asn Met
                245                 250                 255 tct ctc ggt ggt ccc tct tct cag acc tgg gct act gcc atc aac gct       816
Ser Leu Gly Gly Pro Ser Ser Gln Thr Trp Ala Thr Ala Ile Asn Ala
                260                 265                 270
```

```
gcc tac agc caa ggt gtc ctc tcc gtt gtt gct gcc ggt aac ggt gat      864
Ala Tyr Ser Gln Gly Val Leu Ser Val Val Ala Ala Gly Asn Gly Asp
        275                 280                 285 tcc aac ggt cgt cct ctc ccc gcc tct ggc cag tct cct gcc aac gtt      912
Ser Asn Gly Arg Pro Leu Pro Ala Ser Gly Gln Ser Pro Ala Asn Val
    290                 295                 300 ccc aac gct atc acc gtt gct gcc gcc gac tcc agc tgg cga act gcc      960
Pro Asn Ala Ile Thr Val Ala Ala Ala Asp Ser Ser Trp Arg Thr Ala
305                 310                 315                 320 tct ttc acc aac tac ggt cct gag gtc gat gtc ttc ggt cct ggt gtc     1008
Ser Phe Thr Asn Tyr Gly Pro Glu Val Asp Val Phe Gly Pro Gly Val
                325                 330                 335 aac atc cag tcc acc tgg tac acc tcc aac agc gct acc aac acc atc     1056
Asn Ile Gln Ser Thr Trp Tyr Thr Ser Asn Ser Ala Thr Asn Thr Ile
            340                 345                 350 agc ggt acc tcc atg gct tgc cct cac gtt gct ggt ctt gct ctc tac     1104
Ser Gly Thr Ser Met Ala Cys Pro His Val Ala Gly Leu Ala Leu Tyr
        355                 360                 365 ctc cag gct ctc gag aac ctc aat acc cct gct gcc gtc acc aac cgc     1152
Leu Gln Ala Leu Glu Asn Leu Asn Thr Pro Ala Ala Val Thr Asn Arg
370                 375                 380 atc aag tct ctt gcc act acc ggc cgc atc act ggc agc ctc agc ggc     1200
Ile Lys Ser Leu Ala Thr Thr Gly Arg Ile Thr Gly Ser Leu Ser Gly
385                 390                 395                 400 agc ccc aac gcc atg gct ttc aac ggc gct act gct taa                 1239
Ser Pro Asn Ala Met Ala Phe Asn Gly Ala Thr Ala
                405                 410

<210> SEQ ID NO 52
<211> LENGTH: 412
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Thr Ser Phe Arg Arg Ile Ala Leu Gly Leu Ala Ala Leu Leu Pro
1               5                   10                  15

Ala Val Leu Ala Ala Pro Thr Glu Lys Arg Gln Glu Leu Thr Ala Ala
            20                  25                  30

Pro Asp Lys Tyr Ile Ile Thr Leu Lys Pro Glu Ala Ala Glu Ala Lys
        35                  40                  45

Val Glu Ala His Met Ala Trp Val Thr Asp Val His Arg Arg Ser Leu
    50                  55                  60

Gly Lys Arg Asp Thr Ser Gly Val Glu Lys Lys Phe Asn Ile Ser Ser
65                  70                  75                  80

Trp Asn Ala Tyr Ser Gly Glu Phe Asp Asp Ala Thr Ile Ala Glu Ile
                85                  90                  95

Lys Lys Ser Pro Glu Val Ala Phe Val Glu Pro Asp Tyr Ile Val Thr
            100                 105                 110

Leu Asp Tyr Lys Val Glu Pro Leu Ser Asp Arg Ala Leu Thr Thr Gln
        115                 120                 125

Ser Asn Ala Pro Trp Gly Leu Ala Ala Ile Ser Arg Arg Thr Pro Gly
    130                 135                 140

Gly Ser Thr Tyr Thr Tyr Asp Thr Ala Gly Ala Gly Thr Tyr Gly
145                 150                 155                 160

Tyr Val Val Asp Ser Gly Ile Asn Thr Ala His Thr Asp Phe Gly Gly
                165                 170                 175
```

Arg Ala Ser Leu Gly Tyr Asn Ala Ala Gly Gly Ala His Thr Asp Thr
                180                 185                 190

Leu Gly His Gly Thr His Val Ala Gly Thr Ile Ala Ser Asn Thr Tyr
            195                 200                 205

Gly Val Ala Lys Arg Ala Asn Val Ile Ser Val Lys Val Phe Val Gly
        210                 215                 220

Asn Gln Ala Ser Thr Ser Val Ile Leu Ala Gly Phe Asn Trp Ala Val
225                 230                 235                 240

Asn Asp Ile Thr Ser Lys Asn Arg Ala Ser Arg Ser Val Ile Asn Met
                245                 250                 255

Ser Leu Gly Gly Pro Ser Ser Gln Thr Trp Ala Thr Ala Ile Asn Ala
            260                 265                 270

Ala Tyr Ser Gln Gly Val Leu Ser Val Val Ala Gly Asn Gly Asp
        275                 280                 285

Ser Asn Gly Arg Pro Leu Pro Ala Ser Gly Gln Ser Pro Ala Asn Val
    290                 295                 300

Pro Asn Ala Ile Thr Val Ala Ala Ala Asp Ser Ser Trp Arg Thr Ala
305                 310                 315                 320

Ser Phe Thr Asn Tyr Gly Pro Glu Val Asp Val Phe Gly Pro Gly Val
                325                 330                 335

Asn Ile Gln Ser Thr Trp Tyr Thr Ser Asn Ser Ala Thr Asn Thr Ile
            340                 345                 350

Ser Gly Thr Ser Met Ala Cys Pro His Val Ala Gly Leu Ala Leu Tyr
        355                 360                 365

Leu Gln Ala Leu Glu Asn Leu Asn Thr Pro Ala Ala Val Thr Asn Arg
    370                 375                 380

Ile Lys Ser Leu Ala Thr Thr Gly Arg Ile Thr Gly Ser Leu Ser Gly
385                 390                 395                 400

Ser Pro Asn Ala Met Ala Phe Asn Gly Ala Thr Ala
                405                 410

<210> SEQ ID NO 53
<211> LENGTH: 1285
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
ccgcggactg cgcatcatga ctagcttccg ccgtatcgct cttggccttg cagctctgct      60
gcccgcagtc ctcgccgctc ccaccgagaa gcgacaggag ctcactgccg cgcctgacaa     120
gtacatcatc accctcaagc ccgaggctgc tgaggcaaag gtcgaggctc acatggcctg     180
ggttaccgac gtccaccgcc gcagcctcgg caagcgtgac acttccggtg ttgagaagaa     240
gttcaacatc agcagctgga acgcctactc tggcgagttc gacgatgcta ccattgctga     300
gatcaagaag agccccgagg ttgccttcgt cgagcccgac tacattgtca ccctcgacta     360
caaggttgag cctctctctg accgtgctct gaccactcag agcaacgctc cttggggtct     420
tgctgccatc tcccgccgaa cccccggtgg cagcacctac acctacgaca ccactgccgg     480
tgccggtact tacggttacg tcgttgactc tggtatcaac accgcccaca ctgactttgg     540
cggccgtgct tctctcggtt acaacgctgc tggtggcgcc cacactgata cccttggcca     600
cggtacccac gttgctggta ccattgcctc caacacctac ggtgttgcca agcgtgccaa     660

-continued

```
cgtcatctct gtcaaggttt tcgtcggtaa ccaagcttct acctctgtta tccttgctgg      720
tttcaactgg gctgtcaacg acatcacctc caagaaccgt gctagccgct ctgtcatcaa      780
catgtctctc ggtggtccct cttctcagac ctgggctact gccatcaacg ctgcctacag      840
ccaaggtgtc ctctccgttg ttgctgccgg taacggtgat ccaacggtc gtcctctccc       900 cgcctctggc cagtctcctg ccaacgttcc caacgctatc accgttgctg ccgccgactc      960
cagctggcga actgcctctt tcaccaacta cggtcctgag gtcgatgtct cggtcctgg     1020 tgtcaacatc cagtccacct ggtacacctc caacagcgct accaacacca tcagcggtac    1080
ctccatggct tgccctcacg ttgctggtct tgctctctac ctccaggctc tcgagaacct    1140 caataccccct gctgccgtca ccaaccgcat caagtctctt gccactaccg gccgcatcac   1200
tggcagcctc agcggcagcc ccaacgccat ggctttcaac ggcgctactg cttaaagctc    1260
cgtggcgaaa gcctgacgca ccggt                                          1285
```

<210> SEQ ID NO 54
<211> LENGTH: 1239
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(1236)

<400> SEQUENCE: 54

```
atg act agc ttc cgc cgt atc gct ctt ggc ctt gca gct ctg ctg ccc     48
Met Thr Ser Phe Arg Arg Ile Ala Leu Gly Leu Ala Ala Leu Leu Pro
1               5                   10                  15 gca gtc ctc gcc gct ccc acc gag aag cga cag gag ctc act gcc gcg    96
Ala Val Leu Ala Ala Pro Thr Glu Lys Arg Gln Glu Leu Thr Ala Ala
                20                  25                  30 cct gac aag tac atc atc acc ctc aag ccc gag gct gct gag gcc aag   144
Pro Asp Lys Tyr Ile Ile Thr Leu Lys Pro Glu Ala Ala Glu Ala Lys
            35                  40                  45 gtc gag gct cac atg gcc tgg gtt acc gac gtc cac cgc cgc agc ctc   192
Val Glu Ala His Met Ala Trp Val Thr Asp Val His Arg Arg Ser Leu
        50                  55                  60 ggc aag cgt gac act tcc ggt gtt gag aag aag ttc aac atc agc agc   240
Gly Lys Arg Asp Thr Ser Gly Val Glu Lys Lys Phe Asn Ile Ser Ser
65                  70                  75                  80 tgg aac gcc tac tct ggc gag ttc gac gat gct acc att gct gag atc   288
Trp Asn Ala Tyr Ser Gly Glu Phe Asp Asp Ala Thr Ile Ala Glu Ile
                85                  90                  95 aag aag agc ccc gag gtt gcc ttc gtc gag ccc gac tac att gtc acc   336
Lys Lys Ser Pro Glu Val Ala Phe Val Glu Pro Asp Tyr Ile Val Thr
            100                 105                 110 ctc gac tac aag gtt gag cct ctc tct gac cgt gct ctg acc act cag   384
Leu Asp Tyr Lys Val Glu Pro Leu Ser Asp Arg Ala Leu Thr Thr Gln
        115                 120                 125 agc aac gct cct tgg ggt ctt gct gcc atc tcc cgc cga acc ccc ggt   432
Ser Asn Ala Pro Trp Gly Leu Ala Ala Ile Ser Arg Arg Thr Pro Gly
    130                 135                 140 ggc agc acc tac acc tac gac acc act gcc ggt gcc ggt act tac ggt   480
Gly Ser Thr Tyr Thr Tyr Asp Thr Thr Ala Gly Ala Gly Thr Tyr Gly
145                 150                 155                 160 tac gtc gtt gac tct ggt atc aac acc gcc cac act gac ttt ggc ggc   528
Tyr Val Val Asp Ser Gly Ile Asn Thr Ala His Thr Asp Phe Gly Gly
                165                 170                 175
```

```
cgt gct tct ctc ggt tac aac gct gct ggt ggc gcc cac act gat acc     576
Arg Ala Ser Leu Gly Tyr Asn Ala Ala Gly Gly Ala His Thr Asp Thr
            180                 185                 190 ctt ggc cac ggt acc cac gtt gct ggt acc att gcc tcc aac acc tac     624
Leu Gly His Gly Thr His Val Ala Gly Thr Ile Ala Ser Asn Thr Tyr
        195                 200                 205 ggt gtt gcc aag cgt gcc aac gtc atc tct gtc aag gtt ttc gtc ggt     672
Gly Val Ala Lys Arg Ala Asn Val Ile Ser Val Lys Val Phe Val Gly
    210                 215                 220 aac caa gct tct acc tct gtt atc ctt gac ggt ttc aac tgg gct gtc     720
Asn Gln Ala Ser Thr Ser Val Ile Leu Asp Gly Phe Asn Trp Ala Val
225                 230                 235                 240 aac gac atc acc tcc aag aac cgt gct agc cgc tct gtc atc aac atg     768
Asn Asp Ile Thr Ser Lys Asn Arg Ala Ser Arg Ser Val Ile Asn Met
                245                 250                 255 tct ctc ggt ggt ccc tct tct cag acc tgg gct act gcc atc aac gct     816
Ser Leu Gly Gly Pro Ser Ser Gln Thr Trp Ala Thr Ala Ile Asn Ala
            260                 265                 270 gcc tac agc caa ggt gtc ctc tcc gtt gtt gct gcc ggt aac ggt gat     864
Ala Tyr Ser Gln Gly Val Leu Ser Val Val Ala Ala Gly Asn Gly Asp
        275                 280                 285 tcc aac ggt cgt cct ctc ccc gcc tct ggc cag tct cct gcc aac gtt     912
Ser Asn Gly Arg Pro Leu Pro Ala Ser Gly Gln Ser Pro Ala Asn Val
    290                 295                 300 ccc aac gct atc acc gtt gct gcc gcc gac tcc agc tgg cga act gcc     960
Pro Asn Ala Ile Thr Val Ala Ala Ala Asp Ser Ser Trp Arg Thr Ala
305                 310                 315                 320 tct ttc acc aac tac ggt cct gag gtc gat atc ttc ggt cct ggt gtc    1008
Ser Phe Thr Asn Tyr Gly Pro Glu Val Asp Ile Phe Gly Pro Gly Val
                325                 330                 335 aac atc cag tcc acc tgg tac acc tcc aac agc gct acc aac acc atc    1056
Asn Ile Gln Ser Thr Trp Tyr Thr Ser Asn Ser Ala Thr Asn Thr Ile
            340                 345                 350 agc ggt acc tcc atg gct tgc cct cac gtt gct ggt ctt gct ctc tac    1104
Ser Gly Thr Ser Met Ala Cys Pro His Val Ala Gly Leu Ala Leu Tyr
        355                 360                 365 ctc cag gct ctc gag aac ctc aat acc cct gct gcc gtc acc aac cgc    1152
Leu Gln Ala Leu Glu Asn Leu Asn Thr Pro Ala Ala Val Thr Asn Arg
    370                 375                 380 atc aag tct ctt gcc act acc ggc cgc atc act ggc agc ctc agc ggc    1200
Ile Lys Ser Leu Ala Thr Thr Gly Arg Ile Thr Gly Ser Leu Ser Gly
385                 390                 395                 400 agc ccc aac ctc atg gct ttc aac ggc gct act gct taa                1239
Ser Pro Asn Leu Met Ala Phe Asn Gly Ala Thr Ala
                405                 410

<210> SEQ ID NO 55
<211> LENGTH: 412
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Thr Ser Phe Arg Arg Ile Ala Leu Gly Leu Ala Ala Leu Leu Pro
1               5                   10                  15

Ala Val Leu Ala Ala Pro Thr Glu Lys Arg Gln Glu Leu Thr Ala Ala
            20                  25                  30
```

-continued

```
Pro Asp Lys Tyr Ile Ile Thr Leu Lys Pro Glu Ala Ala Glu Ala Lys
        35                  40                  45
Val Glu Ala His Met Ala Trp Val Thr Asp Val His Arg Arg Ser Leu
    50                  55                  60
Gly Lys Arg Asp Thr Ser Gly Val Glu Lys Lys Phe Asn Ile Ser Ser
65                  70                  75                  80
Trp Asn Ala Tyr Ser Gly Glu Phe Asp Asp Ala Thr Ile Ala Glu Ile
                85                  90                  95
Lys Lys Ser Pro Glu Val Ala Phe Val Glu Pro Asp Tyr Ile Val Thr
            100                 105                 110
Leu Asp Tyr Lys Val Glu Pro Leu Ser Asp Arg Ala Leu Thr Thr Gln
            115                 120                 125
Ser Asn Ala Pro Trp Gly Leu Ala Ala Ile Ser Arg Arg Thr Pro Gly
        130                 135                 140
Gly Ser Thr Tyr Thr Tyr Asp Thr Thr Ala Gly Ala Gly Thr Tyr Gly
145                 150                 155                 160
Tyr Val Val Asp Ser Gly Ile Asn Thr Ala His Thr Asp Phe Gly Gly
                165                 170                 175
Arg Ala Ser Leu Gly Tyr Asn Ala Ala Gly Gly Ala His Thr Asp Thr
            180                 185                 190
Leu Gly His Gly Thr His Val Ala Gly Thr Ile Ala Ser Asn Thr Tyr
        195                 200                 205
Gly Val Ala Lys Arg Ala Asn Val Ile Ser Val Lys Val Phe Val Gly
    210                 215                 220
Asn Gln Ala Ser Thr Ser Val Ile Leu Asp Gly Phe Asn Trp Ala Val
225                 230                 235                 240
Asn Asp Ile Thr Ser Lys Asn Arg Ala Ser Arg Ser Val Ile Asn Met
                245                 250                 255
Ser Leu Gly Gly Pro Ser Ser Gln Thr Trp Ala Thr Ala Ile Asn Ala
            260                 265                 270
Ala Tyr Ser Gln Gly Val Leu Ser Val Val Ala Ala Gly Asn Gly Asp
        275                 280                 285
Ser Asn Gly Arg Pro Leu Pro Ala Ser Gly Gln Ser Pro Ala Asn Val
    290                 295                 300
Pro Asn Ala Ile Thr Val Ala Ala Ala Asp Ser Ser Trp Arg Thr Ala
305                 310                 315                 320
Ser Phe Thr Asn Tyr Gly Pro Glu Val Asp Ile Phe Gly Pro Gly Val
                325                 330                 335
Asn Ile Gln Ser Thr Trp Tyr Thr Ser Asn Ser Ala Thr Asn Thr Ile
            340                 345                 350
Ser Gly Thr Ser Met Ala Cys Pro His Val Ala Gly Leu Ala Leu Tyr
        355                 360                 365
Leu Gln Ala Leu Glu Asn Leu Asn Thr Pro Ala Ala Val Thr Asn Arg
    370                 375                 380
Ile Lys Ser Leu Ala Thr Thr Gly Arg Ile Thr Gly Ser Leu Ser Gly
385                 390                 395                 400
Ser Pro Asn Leu Met Ala Phe Asn Gly Ala Thr Ala
                405                 410
```

VARIANTS OF FUNGAL SERINE PROTEASE

CROSS-REFERENCE TO RELATED APPLICATIONS

This application claims the benefit of U.S. Provisional Application No. 61/456,055, filed Oct. 29, 2010, as well as Finnish Application No. 20106135, filed Oct. 29, 2010. The contents of each of the foregoing applications are hereby incorporated by reference in their entireties.

SEQUENCE LISTING

The instant application contains a Sequence Listing which has been submitted electronically in ASCII format and is hereby incorporated by reference in its entirety. The ASCII copy, created on Nov. 20, 2013, is named 30836-0005001_SL.txt and is 129,064 bytes in size.

FIELD OF THE INVENTION

The present invention relates to fungal serine protease variants useful in various applications, particularly in laundry and dish-washing detergents. The invention relates also to a nucleic acid molecule encoding said protease variant, a recombinant vector, a host cell for producing said protease variant, an enzyme composition comprising said protease variant as well as a process for preparing such composition. This invention further relates to various uses of said protease variant or compositions comprising said protease variant.

BACKGROUND

Microbial proteases are among the most important hydrolytic enzymes and find applications in various industrial sectors, such as detergents, food, leather, pharmaceuticals, diagnostics, waste management and silver recovery. Microbial extracellular proteases account for a major part, more than one third, of the total worldwide industrial enzyme sales (Chemy and Fidantsef, 2003). Approximately 90% of the commercial proteases are detergent enzymes (Gupta et al., 2002). The commercial detergent preparations currently in use comprise the naturally occurring alkaline serine proteases (EC 3.4.21) of the subtilisin family or subtilisins, originating from *Bacillus* species, or are recombinant protease preparations thereof (Maurer, 2004).

Examples of commercial proteases are such as subtilisin Carlsberg (Alcalase®), subtilisin 309 (Savinase®), Subtilisin 147 (Esperase®), Kannase®, EverlaseD, Ovozyme®, and the cold-wash protease Polarzyme® (Novozymes A/S, DK); Purafect®, Purafect® Ox, Purafect® Prime and Properase® (Genencor Int., Inc., USA); and the BLAP S and X series (Henkel, Del.).

Several alkaline serine proteases and genes encoding these enzymes have also been isolated from eukaryotic organisms, including yeast and filamentous fungi. U.S. Pat. No. 3,652,399 and EP 519229 (Takeda Chemical Industries, Ltd., JP) disclose an alkaline protease from the genus *Fusarium* (asexual state, teleomorph) or *Gibberella*, (sexual state, anamorph) particularly from *Fusarium* sp. S-19-5 (ATCC 20192, IFO 8884), *F. oxysporum* f. sp. *lini* (IFO 5880) or *G. saubinetti* (ATCC 20193, IFO6608), useful in the formulation of detergent and other cleanser compositions. WO 88/03946 and WO 89/04361 (Novo Industri A/S, DK) disclose an enzymatic detergent additive and a detergent composition comprising a protease and a lipase, wherein the fungal protease is derived from *Fusarium*, particularly *F. oxysporum* or *F. solani*. WO1994025583 (NovoNordisk A/S, DK) discloses an active trypsin-like protease enzyme derivable from a *Fusarium* species, in particular a strain of *F. oxysporum* (DSM 2672), and the DNA sequence encoding the same. The amino acid sequence of a novel protease deriving from *Fusarium* sp. BLB (FERM BP-10493) is disclosed in WO 2006101140 (SODX Co. Ltd, Nakamura). Use of *F. equiseti* and other fungi in reducing organic matter in waste waters is disclosed in the EP 1464626 patent application (Biovitis S.A., FR). The amino acid and nucleotide sequences of the serine proteases from *F. equiseti* and *F. acuminatum* have been disclosed in FI20095497 and FI20095499, respectively (AB Enzymes Oy, FI). The amino acid and nucleotide sequences of the serine protease derived from several *Trichoderma* species have been disclosed e.g. in WO2008045148A (Catalyst Biosciences, Inc., U.S.A.), WO96/018722A (Centro de Investigacion y de Estudios Avanzados del I.P.N., MX) and WO98/020116A (Novo Nordisk A/S, DK). Also, alkaline proteases from fungal species such as *Tritirachium* and *Conidiobolus* have been reported (reviewed in Anwar and Saleemuddin, 1998).

Different methods have been used for improving the stability of the industrial serine proteases. WO 92/03529 (NovoNordisk A/S, DK) discloses detergent compositions comprising a reversible protease inhibitor of the peptide or protein type. In one preferred embodiment the protease is a subtilisin, preferably derived from *Bacillus* and the inhibitor is a subtilisin inhibitor of family III, VI or VII. The liquid detergent compositions comprising proteases often include protease inhibitors such as boric acid with or without polyols to inhibit the autocatalytic activity of proteases. One of such inhibitors is 4-formyl phenyl boronic acid (4-FPBA) disclosed in US0120649 (Novozymes A/S, DK). EP0352244A2 (NovoNordisk A/S, DK) discloses improvement of stability of *Bacillus* derived enzymes using amphoteric compounds, such as surfactants.

Variants of the natural serine proteases with improved catalytic efficiency and/or better stability towards temperature, oxidizing agents and different washing conditions have been developed through site-directed and/or random mutagenesis. Most of the work has been carried out with *Bacillus* derived subtilisins. Replacement of one or more amino acid residues of *B. amyloliquefaciens* subtilisin is disclosed in WO98/55634 and WO99/20727 (Procter & Gamble Co., Genencor Int., Inc., U.S.A.) and in WO99/20770, US20090011489A and EP1025241B2 (Genencor Int., Inc., U.S.A.). Protease variants of *B. lentus* subtilisin with improved wash performance are disclosed in WO2003/062381 and EP1523553B1 (Genencor Int., Inc., U.S.A.). The substitutions of R170S-A1R, R170S-G61R, R170S-N216R or R170S-0100R do not change the net electrostatic charge of the variant when compared to the precurcor protease. Multiply-substituted variants of *B. lentus* protease with altered net charge, resulting in improved efficacy at low, medium or high detergent concentrations is disclosed in EP 1612271 A2 (Genencor Int., Inc. U.S.A.).

EP2138574A2 (Novozymes A/S, DK) discloses subtilase variants including insertion, substitution or deletion of an amino acid in one or more positions of the amino acid sequence of subtilisin BPN'. US2009/0203111A1 (Novozymes A/S, DK) discloses JP170 and BPN' variants having altered properties and methods for their production. *Bacillus* sp. subtilisin variant useful in dishwashing detergent is disclosed in US20100152088A (Danisco US, Inc., U.S.A.).

Variants of fungal serine proteases have been prepared for trypsin-like proteases. WO95/030743A1 (NovoNordisk A/S, DK) discloses variants of a trypsin-like *Fusarium* protease, in which a naturally occurring amino acid residue (other than proline) is substituted with a proline residue at one or more positions which positions are not located in regions in which the protease is characterized by possessing alpha-helical or beta-sheet structure. The variants have improved proteolytic stability and are less susceptible to oxidation as compared to the parent protease. EP1546318B (Novozymes Inc., U.S.A.) discloses trypsin variants of *Fusarium oxysporum* comprising substitutions, insertions or deletions of one or more amino acids of the precursor protease.

Despite the fact that numerous patent publications, reviews and articles have been published, in which serine proteases from various microorganisms, for example, the low temperature alkaline proteases from actinomycete (*Nocardiopsis dassonvillei*) and fungal (*Paecilomyces marquandii*) microorganisms are disclosed, e.g. in EP 0290567 and EP 0290569 (Novo Nordisk A/S, DK), there is still a great need for alternative serine proteases, which are suitable for and effective in modifying, degrading and removing proteinaceous materials of different stains, particularly in low or moderate temperature ranges and which are stable in the presence of detergents with highly varying properties. Due to autocatalytic property of serine proteases, the stability during storage is also very important.

It is also desirable that the serine protease can be produced in high amounts, and can be cost-effectively down-stream processed, by easy separation from fermentation broth and mycelia.

SUMMARY OF THE INVENTION

The present invention provides serine protease variants of the Fe_RF6318 serine protease originating from the filamentous fungus *Fusarium equiseti* RF6318 deposited at Centraalbureau voor Schimmelcultures on 7 Apr. 2006 under accession number CBS 119568. The wild-type Fe_RF6318 serine protease has broad substrate specificity, is active at broad pH ranges and has a broad temperature optimum, i.e. functions both at low and moderate temperatures, as disclosed in the patent application FI20095497 (AB Enzymes Oy, FI), filed on 30 Apr. 2009. Particularly, the present invention provides Fe_RF6318 variants, which have improved thermal stability and are more stable in varying detergent compositions compared to the native precursor protease. The Fe_RF6318 variants have similar or improved wash performance compared to the parent wild-type Fe_RF6318 protease. The Fe_RF6318 variants of the invention are capable of removing proteinaceous material, including stains in washing laundry and dishes, at lower temperatures than the present commercial enzyme preparations, thereby saving energy. The Fe_RF6318 variant proteases can be produced in high-yielding fungal hosts and their down-stream processing, e.g. separation of fermentation broth and mycelia is easy to perform.

The present invention relates to a Fe_RF6318 serine protease variant polypeptides, which have serine protease activity and comprise an amino acid sequence having substitution of valine at position 208 of the parent Fe_RF6318 serine protease with an amino acid other than valine, wherein the position of the substitution corresponds to the amino acid sequence of the mature Fe_RF6318 enzyme as defined in SEQ ID NO:2. Preferably, the Fe_RF6318 variants comprise the substitution V208I relative to the parent mature Fe_RF6318 serine protease.

The Fe_RF6318 variants of the invention comprise a substitution which results in improved thermal stability as well as improved stability in detergents and has retained or improved wash performance compared to the parent mature Fe_RF6318 serine protease of SEQ ID NO:2.

Preferably, the Fe_RF6318 variant, in addition to the substitution of valine at position 208 of the parent Fe_RF6318 serine protease, comprises one or more amino acid changes, which are selected from the group consisting of a substitution, insertion, and deletion. The preferred changes are selected from the group consisting of an amino acid substitution at position 3, 6, 7, 8, 14, 17, 18, 22, 24, 25, 28, 29, 33, 34, 36, 37, 46, 47, 52, 56, 61, 63, 65, 69, 76, 77, 83, 88, 91, 100, 103, 106, 111, 113, 114, 121, 123, 138, 144, 151, 153, 155, 157, 158, 164, 167, 169, 173, 174, 175, 176, 185, 196, 205, 206, 210, 214, 216, 230, 234, 236, 239, 247, 248, 249, 252, 256, 260, 268, 281, 282, 283, 284, 286, 287 or 288; a deletion of asparagine at position 167; a deletion of alanine at position 65 and histidine at position 66; and an amino acid insertion at position 104, wherein the amino acid positions correspond to the amino acid sequence of the mature Fe_RF6318 serine protease of SEQ ID NO:2.

More preferably, according to increase in thermostability, the changes include, in addition to the substitution of valine at position 208 of the parent Fe_RF6318 serine protease, one or more amino acid changes selected from the group consisting of an amino acid substitution at position 3, 6, 14, 24, 29, 33, 34, 47, 52, 61, 63, 65, 83, 91, 100, 103, 106, 111, 121, 144, 153, 157, 158, 164, 175, 176, 185, 210, 234, 236, 256, 268 or 281, and an amino acid insertion at position 104.

Even more preferably, according to increase in thermostability, the changes include, in addition to the substitution of valine at position 208 of the parent Fe_RF6318 serine protease, one or more amino acid changes selected from the group consisting of an amino acid substitution at position 3, 6, 24, 29, 33, 47, 100, 103, 106, 111, 185, 210, 268 or 281, and an amino acid insertion at position 104.

Most preferably, according to increase in thermostability, the Fe_RF6318 variant of the invention comprises an amino acid sequence having the substitution V208I (SEQ ID NO:6), V208I-A111D (SEQ ID NO:8), V208I-A281L (SEQ ID NO:10), V208I-A111D-A281L (SEQ ID NO:12), V208I-A111D-A281L-A33E (SEQ ID NO:14), V208I-A111D-A281L-A47E (SEQ ID NO:16), V208I-A111D-A281L-I185M (SEQ ID NO:20), V208I-A111D-A281L-T268R (SEQ ID NO:22), V208I-A111D-A281L-Q103A-ins.G104 (SEQ ID NO:24), V208I-A111D-A281L-T3C-T29C (SEQ ID NO:26), V208I-A111D-A281L-S6R-T24D (SEQ ID NO:28), V208I-A111D-A281L-V100D (SEQ ID NO:30), V208I-A111D-A281L-T106N (SEQ ID NO:34), V208I-A111D-A281L-T3C-T29C-S6R-T24D (SEQ ID NO:36) or V208I-A111D-A281L-I185M-G210A (SEQ ID NO:38) relative to the parent Fe_RF6318 serine protease, wherein the amino acid positions correspond to the amino acid sequence of the mature Fe_RF6318 serine protease defined in SEQ ID NO:2.

More preferably, according to stability in detergent, the changes include, in addition to the substitution of valine at position 208 of the parent Fe_RF6318 serine protease, one or more amino acid substitutions at position 3, 6, 24, 29, 33, 37, 47, 61, 63, 65, 83, 100, 111, 123, 157, 175, 176, 185, 210, 234, 236, 247, 268, 281.

Even more preferably, according to stability in detergent, the changes include, in addition to the substitution of valine at position 208 of the parent Fe_RF6318 serine protease, one or more amino acid substitutions at position 3, 6, 24, 29, 33, 47, 63, 100, 111, 123, 157, 175, 176, 185, 210, 236, 268, 281.

Most preferably, according to the increase in detergent stability, the Fe_RF6318 variant of the invention comprises an amino acid sequence having the substitution V208I (SEQ ID NO:6), V208I-A111D (SEQ ID NO:8), V208I-A281L (SEQ ID NO:10), V208I-A111D-A281L (SEQ ID NO:12), V208I-A111D-A281L-A33E (SEQ ID NO:14), V208I-A111D-A281L-A47E (SEQ ID NO:16), V208I-A111D-A281L-G63P (SEQ ID NO:18), V208I-A111D-A281L-I185M (SEQ ID NO:20), V208I-A111D-A281L-T268R (SEQ ID NO:22), V208I-A111D-A281L-T3C-T29C (SEQ ID NO:26), V208I-A111D-A281L-V100K (SEQ ID NO:32), V208I-A111D-A281L-T3C-T29C-S6R-T24D (SEQ ID NO:36), V208I-A111D-A281L-I185M-G210A (SEQ ID NO:38), V208I-A111D-A281L-V100Q (SEQ ID NO:40), V208I-A111D-A281L-K123R (SEQ ID NO:42), V208I-A111D-A281L-S157T (SEQ ID NO:44), V208I-A111D-A281L-G175S (SEQ ID NO:46), V208I-A111D-A281L-Q176T (SEQ ID NO:48) or V208I-A111D-A281L-C236T (SEQ ID NO:50) relative to the parent Fe_RF6318 serine protease, wherein the amino acid positions correspond to the amino acid sequence of the mature Fe_RF6318 serine protease defined in SEQ ID NO:2.

The Fe_RF6318 serine protease variant of the invention is encoded by an isolated polynucleotide sequence which encodes the polypeptide comprising the amino acid sequence of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, and SEQ ID NO:50.

The present invention relates also, to an isolated nucleic acid molecule comprising a nucleotide sequence which encodes the Fe_RF6318 serine protease variant, which has serine protease activity and comprises an amino acid sequence having substitution of valine at position 208 of the mature Fe_RF6318 serine protease with an amino acid other than valine, wherein the position of the substitution corresponds to the amino acid sequence of the mature Fe_RF6318 enzyme as defined in SEQ ID NO:2.

Preferably, the nucleic acid molecule of the invention comprises a nucleotide sequence which encodes a Fe_RF6318 variant which, in addition to the substitution of valine at position 208 of the Fe_RF6318 serine protease, comprises one or more amino acid changes, which are selected from the group consisting of a substitution, insertion and deletion. The preferred changes include, in addition to the substitution of valine at position 208 of the parent Fe_RF6318 serine protease, one or more amino acid changes selected from the group consisting of an amino acid substitution at position, 3, 6, 7, 8, 14, 17, 18, 22, 24, 25, 28, 29, 33, 34, 36, 37, 46, 47, 52, 56, 61, 63, 65, 69, 76, 77, 83, 88, 91, 100, 103, 106, 111, 113, 114, 121, 123, 138, 144, 151, 153, 155, 157, 158, 164, 167, 169, 173, 174, 175, 176, 185, 196, 205, 206, 210, 214, 216, 230, 234, 236, 239, 247, 248, 249, 252, 256, 260, 268, 281, 282, 283, 284, 286, 287 or 288, a deletion of asparagine at position 167, deletion of alanine at position 65 and histidine at position 66, and an amino acid insertion at position 104, wherein the amino acid positions correspond to the amino acid sequence of the mature Fe_RF6318 serine protease of SEQ ID NO:2.

According to a most preferred embodiment of the invention the isolated nucleic acid molecule comprises the nucleotide sequence defined in SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, and SEQ ID NO:49.

The invention further relates to recombinant expression vectors comprising the nucleotide sequences of the invention operably linked to regulatory sequences capable of directing expression of the gene encoding the Fe_RF6318 serine protease variant of the invention in a suitable host, such as a filamentous fungus. Suitable hosts include heterologous hosts, preferably microbial hosts of the genus Trichoderma, Aspergillus, Fusarium, Humicola, Chrysosporium, Neurospora, Rhizopus, Penicillium and Mortiriella. Preferably said enzyme is produced in Trichoderma or Aspergillus, most preferably in T. reesei.

The invention relates also to a host cell comprising the recombinant expression vector as described above. Preferred host cells include the microbial hosts, such as filamentous fungi of a genus Trichoderma, Aspergillus, Fusarium, Humicola, Chrysosporium, Neurospora, Rhizopus, Penicillium and Mortiriella. Preferably said host is Trichoderma or Aspergillus, most preferably T. reesei.

The present invention relates to a process of producing a variant polypeptides having serine protease activity, said process comprising the steps of culturing the host cell of the invention and recovering the variant polypeptide.

The invention further relates to a process for obtaining an enzyme preparation, which comprises the serine protease variant of the invention. The process comprises the steps of culturing a host cell of the invention and either recovering the variant polypeptide from the cells or separating the cells from the culture medium and obtaining the supernatant.

The invention relates to an enzyme preparation, which comprises the Fe_RF6318 variant polypeptide of the invention.

The enzyme preparation of the invention may further comprise other enzymes selected from the group of protease, amylase, cellulase, lipase, xylanase, mannanase, cutinase, pectinase or oxidase with or without a mediator as well as suitable additives selected from the group of stabilizers, buffers, surfactants, bleaching agents, mediators, anti-corrosion agents, builders, antiredeposition agents, optical brighteners, dyes, pigments, caustics, abrasives and preservatives, etc.

The spent culture medium of the production host can be used as such, or the host cells may be removed, and/or it may be concentrated, filtrated or fractionated. It may also be dried. The enzyme preparation of the invention may be in the form of liquid, powder or granulate.

The invention further relates to a detergent composition comprising the Fe_RF6318 serine protease variant of the invention.

Also within the invention is the Fe_RF6318 serine protease variant or the enzyme preparation comprising said variant for use in detergents, in treating fibers, in treating wool, in treating hair, in treating leather, in treating food or feed, or in any application involving modification, degradation or removal of proteinaceous material. Particularly, the enzyme or enzyme preparation is useful as a detergent additive in detergent liquids and detergent powders.

BRIEF DESCRIPTION OF DRAWINGS

FIGS. 1A and B show the nucleotide sequence of *Fusarium equiseti* RF6318 Fe prtS8A cDNA (SEQ ID NO:51) used for constructing the mutant proteases and the deduced amino acid sequence (SEQ ID NO: 52). The putative signal peptide, analyzed by SignalP V3.0 program is in lower case letters and underlined. The pro sequence and the deduced amino acids of the pro sequence are in lower case letters. The mature nucleotide and the deduced amino acid sequences are in capital letters (the N-terminal sequence has been previously determined from the purified wild type Fe_RF6318 protein; FI20095497). The stop codon is shown by an asterisk below the sequence.

FIGS. 2A and B show the nucleotide sequence of a synthetic construction including the *Fusarium equiseti* RF6318 Fe prtS8A wild type cDNA sequence (SEQ ID NO: 53), fused at its 5'-end to a partial cbh1 promoter (from SacII site, marked and underlined) and at its 3'-end to the cbh1 terminator sequence (to AgeI site, marked and underlined). Analogous synthetic constructions were ordered for each mutant protease cDNA and were used for construction of the expression cassettes. 'pcbh1, partial cbh1 promoter; tcbh1' partial cbh1 terminator.

FIGS. 8A and 8B show the nucleotide sequence (SEQ ID NO: 54) and the deduced amino acid sequence (SEQ ID NO: 55) of the m26 mutant protease cDNA used as a starting sequence for the "D-series" mutant proteases. The putative signal peptide, analyzed by SignalP V3.0 program is in lower case letters and underlined. The pro sequence and the deduced amino acids of the pro sequence are in lower case letters. The mature nucleotide and the deduced amino acid sequences are in capital letters. The stop codon is shown by an asterisk below the sequence. The mutated codons and modified amino acids compared to the wild type sequence (FIG. 1) are boxed.

SEQUENCE LISTING

Figure 3:
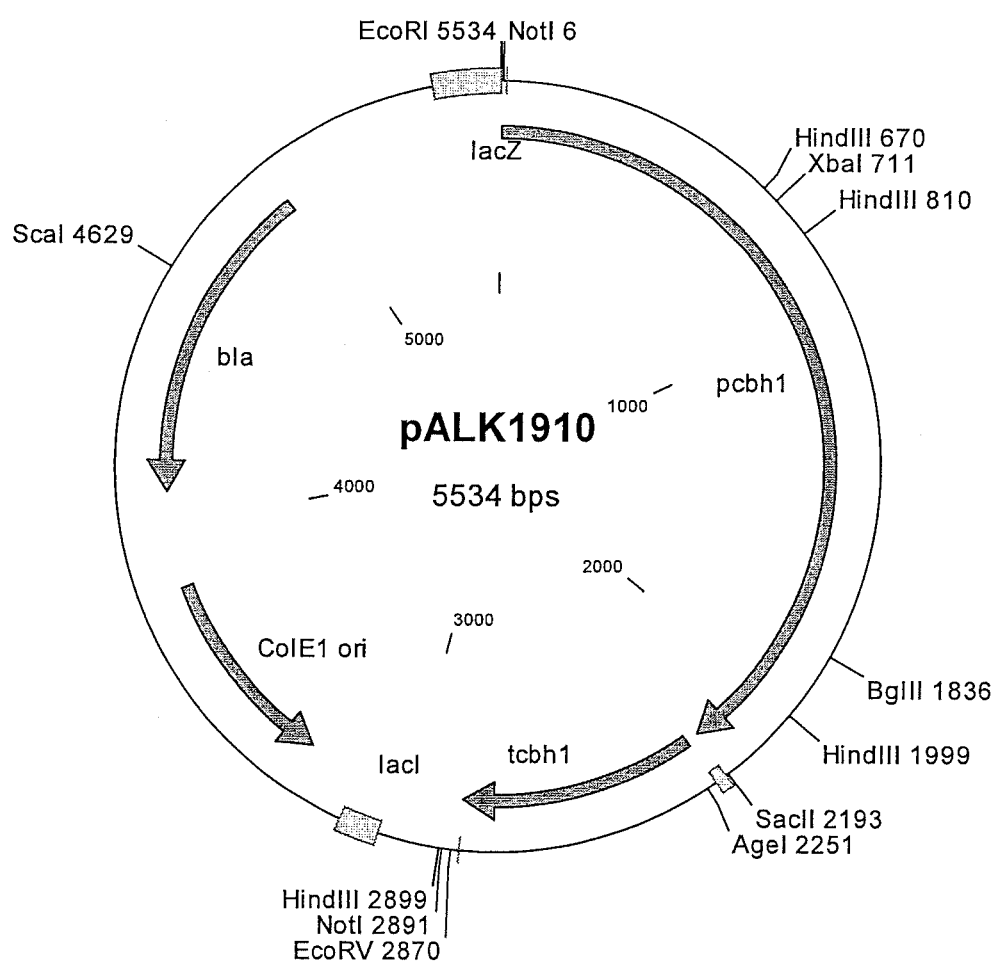
FIG. 3 shows the plasmid map of pALK1910 used as a backbone for constructing the cassettes for m1-m14 mutant protease production. The DNA fragments encoding the mutant proteases (cDNAs with 5' partial cbh1 promoter and 3' partial cbh1 terminator, see FIG. 2) and cleaved with SacII and AgeI were ligated into SacII and AgeI cleaved pALK1910. For the m1-m14 expression cassettes, the amdS marker gene was then ligated to the EcoRV site of the constructed plasmids. Only the relevant restriction sites are shown. pcbh1, cbh1 promoter; tcbh1, cbh1 terminator.

SEQ ID NO:1 The nucleotide sequence encoding the amino acid sequence of the mature form of *Fusarium equiseti* RF6318 (Fe_RF6318) protease.

SEQ ID NO:2 The amino acid sequence of the mature form of *Fusarium equiseti* RF6318 (Fe_RF6318) protease.

SEQ ID NO:3 The nucleotide sequence encoding the amino acid sequence of the mature form of *Fusarium acuminatum* RF7182 protease.

SEQ ID NO:4 The amino acid sequence of the mature form of *Fusarium acuminatum* RF7182 protease.

SEQ ID NO:5 The nucleotide sequence encoding the amino acid sequence of the mature form of Fe_RF6318 serine protease variant comprising substitution V208I.

SEQ ID NO:6 The amino acid sequence of the mature form of Fe_RF6318 swine protease variant comprising substitution V208I.

SEQ ID NO:7 The nucleotide sequence encoding the amino acid sequence of the mature form of Fe_RF6318 serine protease variant comprising substitutions V208I and A111D.

SEQ ID NO:8 The amino acid sequence of the mature form of Fe_RF6318 serine protease variant comprising substitutions V208I and A111D.

SEQ ID NO:9 The nucleotide sequence encoding the amino acid sequence of the mature form of Fe_RF6318 serine protease variant comprising substitutions V208I and A281L.

SEQ ID NO:10 The amino acid sequence of the mature form of Fe_RF6318 serine protease variant comprising substitutions V208I and A281L.

SEQ ID NO:11 The nucleotide sequence encoding the amino acid sequence of the mature form of Fe_RF6318 serine protease variant comprising substitutions V208I, A111D and A281L.

SEQ ID NO:12 The amino acid sequence of the mature form of Fe_RF6318 serine protease variant comprising substitutions V208I, A111D and A281L.

SEQ ID NO:13 The nucleotide sequence encoding the amino acid sequence of the mature form of Fe_RF6318 serine protease variant comprising substitutions V208I, A111D, A281L and A33E.

SEQ ID NO:14 The amino acid sequence of the mature form of Fe_RF6318 serine protease variant comprising substitutions V208I, A111D, A281L and A33E.

SEQ ID NO:15 The nucleotide sequence encoding the amino acid sequence of the mature form of Fe_RF6318 serine protease variant comprising substitutions V208I, A111D, A281L and A47E.

SEQ ID NO:16 The amino acid sequence of the mature form of Fe_RF6318 serine protease variant comprising substitutions V208I, A111D, A281L and A47E.

SEQ ID NO:17 The nucleotide sequence encoding the amino acid sequence of the mature form of Fe_RF6318 serine protease variant comprising substitutions V208I, A111 D, A281L and G63P.

SEQ ID NO:18 The amino acid sequence of the mature form of Fe_RF6318 serine protease variant comprising substitutions V208I, A111D, A281L and G63P.

SEQ ID NO:19 The nucleotide sequence encoding the amino acid sequence of the mature form of Fe_RF6318 serine protease variant comprising substitutions V208I, A111D, A281L and I185M.

SEQ ID NO:20 The amino acid sequence of the mature form of Fe_RF6318 serine protease variant comprising substitutions V208I, A111D, A281L and I185M.

SEQ ID NO:21 The nucleotide sequence encoding the amino acid sequence of the mature form of Fe_RF6318 serine protease variant comprising substitutions V208I, A111D, A281L and T268R.

SEQ ID NO:22 The amino acid sequence of the mature form of Fe_RF6318 serine protease variant comprising substitutions V208I, A111D, A281L and T268R.

SEQ ID NO:23 The nucleotide sequence encoding the amino acid sequence of the mature form of Fe_RF6318 serine protease variant comprising substitutions V208I, A111D, A281L, Q103A, insertion G104.

SEQ ID NO:24 The amino acid sequence of the mature form of Fe_RF6318 serine protease variant comprising substitutions V208I, A111D, A281L, Q103A, insertion G104.

SEQ ID NO:25 The nucleotide sequence encoding the amino acid sequence of the mature form of Fe_RF6318 serine protease variant comprising substitutions V208I, A111D, A281L, T3C and T29C.

SEQ ID NO:26 The amino acid sequence of the mature form of Fe_RF6318 serine protease variant comprising substitutions V208I, A111D, A281L, T3C and T29C.

SEQ ID NO:27 The nucleotide sequence encoding the amino acid sequence of the mature form of Fe_RF6318 serine protease variant comprising substitutions V208I, A111D, A281L, S6R and T24D.

SEQ ID NO:28 The amino acid sequence of the mature form of Fe_RF6318 serine protease variant comprising substitutions V208I, A111D, A281L, S6R and T24D.

SEQ ID NO:29 The nucleotide sequence encoding the amino acid sequence of the mature form of Fe_RF6318 serine protease variant comprising substitutions V208I, A111D, A281L and V100D.

SEQ ID NO:30 The amino acid sequence of the mature form of Fe_RF6318 serine protease variant comprising substitutions V208I, A111D, A281L and V100D.

SEQ ID NO:31 The nucleotide sequence encoding the amino acid sequence of the mature form of Fe_RF6318 serine protease variant comprising substitutions V208I, A111D, A281L and V100K.

SEQ ID NO:32 The amino acid sequence of the mature form of Fe_RF6318 serine protease variant comprising substitutions V208I, A111D, A281L and V100K.

SEQ ID NO:33 The nucleotide sequence encoding the amino acid sequence of the mature form of Fe_RF6318 serine protease variant comprising substitutions V208I, A111D, A281L and T106N.

SEQ ID NO:34 The amino acid sequence of the mature form of Fe_RF6318 serine protease variant comprising substitutions V208I, A111D, A281L and T106N.

SEQ ID NO:35 The nucleotide sequence encoding the amino acid sequence of the mature form of Fe_RF6318 serine protease variant comprising substitutions V208I, A111D, A281L, T3C, T29C, S6R and T24D.

SEQ ID NO:36 The amino acid sequence of the mature form of Fe_RF6318 serine protease variant comprising substitutions V208I, A111D, A281L, T3C, T29C, S6R and T24D.

SEQ ID NO:37 The nucleotide sequence encoding the amino acid sequence of the mature form of Fe_RF6318 serine protease variant comprising substitutions V208I, A111D, A281L, I185M and G210A.

SEQ ID NO:38 The amino acid sequence of the mature form of Fe_RF6318 serine protease variant comprising substitutions V208I, A111D, A281L, I185M and G210A.

SEQ ID NO:39 The nucleotide sequence encoding the amino acid sequence of the mature form of Fe_RF6318 serine protease variant comprising substitutions V208I, A111D, A281L and V100Q.

SEQ ID NO:40 The amino acid sequence of the mature form of Fe_RF6318 serine protease variant comprising substitutions V208I, A111D, A281L and V100Q.

SEQ ID NO:41 The nucleotide sequence encoding the amino acid sequence of the mature form of Fe_RF6318 serine protease variant comprising substitutions V208I, A111D, A281L and K123R.

SEQ ID NO:42 The amino acid sequence of the mature form of Fe_RF6318 serine protease variant comprising substitutions V208I, A111D, A281L and K123R.

SEQ ID NO:43 The nucleotide sequence encoding the amino acid sequence of the mature form of Fe_RF6318 serine protease variant comprising substitutions V208I, A111D, A281L and S157T.

SEQ ID NO:44 The amino acid sequence of the mature form of Fe_RF6318 serine protease variant comprising substitutions V208I, A111D, A281L and S157T.

SEQ ID NO:45 The nucleotide sequence encoding the amino acid sequence of the mature form of Fe_RF6318 serine protease variant comprising substitutions V208I, A111D, A281L and G175S.

SEQ ID NO:46 The amino acid sequence of the mature form of Fe_RF6318 serine protease variant comprising substitutions V208I, A111D, A281L and G175S.

SEQ ID NO:47 The nucleotide sequence encoding the amino acid sequence of the mature form of Fe_RF6318 serine protease variant comprising substitutions V208I, A111D, A281L and Q176T.

SEQ ID NO:48 The amino acid sequence of the mature form of Fe_RF6318 serine protease variant comprising substitutions V208I, A111D, A281L and Q176T.

SEQ ID NO:49 The nucleotide sequence encoding the amino acid sequence of the mature form of Fe_RF6318 serine protease variant comprising substitutions V208I, A111D, A281L and C236T.

SEQ ID NO:50 The amino acid sequence of the mature form of Fe_RF6318 serine protease variant comprising substitutions V208I, A111D, A281L and C236T.

DETAILED DESCRIPTION OF THE INVENTION

The present invention provides variants of a fungal Fe_RF6318 serine protease deriving from *Fusarium equiseti* RF6318, deposited at Centraalbureau voor Schimmelcultures on 7 Apr. 2006 under accession number CBS119568. The Fe_RF6318 wild-type protease shows broad substrate specificity, is stable at high pH ranges and has a broad temperature optimum, i.e. good performance both at low and moderate temperatures as disclosed in the patent application FI20095497, filed on 30 Apr. 2009. The variant enzymes are ideal for detergent applications, withstanding oxidizing and chelating agents and being effective at low enzyme levels in detergent solutions. Particularly, the variants of the Fe_RF6318 serine protease have improved thermal stability and they stand varying detergents better than the native Fe_RF6318 serine protease having the naturally occurring amino acid sequence. Thus, the present invention provides alternative serine proteases for use in detergent and other applications. The Fe_RF6318 serine protease variants can be produced in high-yielding fungal hosts and their downstream processing, e.g. separation of fermentation broth and mycelia is easy to perform.

By "serine protease" or "serine endopeptidase" or "serine endoproteinase" is in connection to this invention meant an enzyme classified as EC 3.4.21 by the Nomenclature of the International Union of Biochemistry and Molecular Biology. Based on their structural similarities, serine proteases have been grouped into at least six clans (SA, SB, SC, SE, SF and SG; S denoting serine protease), which have been further subgrouped into families with similar amino acid sequences and three-dimensional structures (see, for example the Serine protease home page at the Department of Biochemistry and Molecular Biophysics, Washington University of Medicine, St. Louis, Mo., USA). These protein hydrolyzing or degrading enzymes are characterized by the presence of a nucleophilic serine group in their active site, and the proteases of clan SA and clan SB are also distinguished by having essential aspartate and histidine residues, which along with the serine, form a catalytic triad.

The major clans of serine proteases include the "chymotrypsin-like", including chymotrypsin, trypsin and elastase (clan SA) and "subtilisin-like" (clan SB) proteases. The characterized "subtilisin-like serine proteases" or "subtilases" of clan SB (EC 3.4.21.62), represented by various *Bacillus*, like

*B. amyloliquifaciens, B. licheniformis* and *B. subtilis* (Rao et al., 1998), are specific for aromatic or hydrophobic residues, such as tyrosine, phenylalanine and leucine. The enzymes target different regions of the polypeptide chain, based upon the side chains of the amino acid residues surrounding the site of cleavage.

By the term "serine protease activity" as used in the invention is meant hydrolytic activity on protein containing substrates, e.g. casein, hemoglobin, keratin and BSA. The methods for analyzing proteolytic activity are well-known in the literature and are referred e.g. in Gupta et al. (2002) and Maurer and Gabler (2005).

Proteases can be classified using group specific inhibitors. The diverse group of "serine protease inhibitors" includes synthetic chemical inhibitors and natural proteinaceous inhibitors. Thus, the serine protease activity can be determined in an assay based on cleavage of a specific substrate or in an assay using any protein containing substrate with or without a specific inhibitor of serine proteases under suitable conditions.

The serine proteases are synthesized as inactive "zymogenic precursors" or "zymogens" in the form of a preproenzyme, which are activated by removal of the signal sequence (secretion signal peptide or prepeptide) and the prosequence (propeptide) to yield an active mature form of the enzyme (Chen and Inouye, 2008). This activation process involves action of proteases and may result from limited self-digestive or autocatalytic processing of the serine protease, e.g. during posttranslational phases of the production or in the spent culture medium or during the storage of the culture medium or enzyme preparation. Activation of the proenzyme may also be achieved by adding a proteolytic enzyme capable of converting the inactive proenzyme into active mature enzyme into the culture medium during or after cultivation of the host organism. The shortening of the enzyme can also be achieved e.g. by truncating the gene encoding the polypeptide prior to transforming it to the production host. The "prepro-form" of the Fe_RF6318 serine protease in the present invention means an enzyme comprising the pre- and propeptides. The "pro-form" means an enzyme, which comprises the propeptide but lacks the prepeptide (signal sequence).

The term "mature" means the form of the serine protease enzyme which after removal of the signal sequence (prepeptide) and propeptide comprises the essential amino acids for enzymatic or catalytic activity. In filamentous fungi it is the native form secreted into the culture medium.

The largest group of commercial serine proteases are "alkaline serine proteases", which means that the enzymes are active and stable at pH 9 to pH 11 or even at pH 10 to 12.5 (Shimogaki et al., 1991) and have isoelectric point around pH 9. Determination of the optimal pH of the catalytic activity can be carried out in a suitable buffer at different pH values by following the activity on a protein substrate. The detergent proteases perform best when the pH value of the detergent solution in which it works is approximately the same as the pI value for the enzyme. pI can be determined by isoelectric focusing on an immobilized pH gradient gel composed of polyacrylamide, starch or agarose or by estimating the pI from the amino acid sequence, for example by using the pI/MW tool at ExPASy server (Gasteiger et al., 2003).

The molecular masses of mature alkaline serine proteases range between 15 and 35 kDa, typically from about 25 to 30 kDa. The molecular mass of the serine protease can be determined by mass spectrometry or on SDS-PAGE according to Laemmli (1970). The molecular mass can also be predicted from the amino acid sequence of the enzyme.

The temperature optima of most natural serine proteases are around 60° C. (Rao et al., 1998). The temperature optimum of serine protease can be determined in a suitable buffer at different temperatures by using casein as a substrate as described in Example 1a or by using other substrates and buffer systems described in the literature (Gupta et al., 2002).

The parent Fe_RF6318 protease is a subtilisin-like serine protease belonging to clan SB, family 8 of serine proteases. The mature wild-type Fe_RF6318 serine protease has a molecular weight of ca. 29 kDa, an optimal temperature of approximately 60° C. at pH 9 using 15 min reaction time and casein as a substrate, a pH optimum at approximately pH 10 at 50° C. using 15 min reaction time and casein as a substrate. The wild-type Fe_RF6318 serine protease has a good performance in the presence of detergents with highly varying properties, at broad, i.e. from low to moderate temperature ranges. The wild-type Fe_RF6318 serine protease, depending on the washing conditions and auxiliary ingredients and additives in detergents, is useful particularly in temperatures at or below 50° C. as disclosed in FI20095497 (AB Enzymes Oy, FI).

From the properties described above it can be concluded that the wild-type Fe_RF6318 serine protease is capable of satisfying the greatly varying demands of detergent customers and detergent industry and is well suited to the requirements of future regulations and customer habits, e.g. to the need for lower washing temperatures.

To improve the performance of the Fe_RF6318 serine protease in varying industrial applications, such as in detergents, the properties of the native enzyme may be further optimized. These properties include improvement of the storage stability, e.g. by decreasing the autoproteolytic activity of the enzyme. Other properties to be optimized include the stability in the presence or absence of detergent, pH stability, oxidative stability or resistance against bleaching agents and substrate specificity. It is self-evident that e.g. in laundry and dish washing compositions the wash performance of the modified protease may not be impaired in comparison to the parent or precursor protease enzyme. In other words the enzyme variants have similar or even improved wash performance or stain removal property compared to the parent serine protease.

Based on information derived from the crystal structures and sequence similarity comparisons between homologous proteins, variants with improved stability and/or improved performance may be designed.

A variant with improved stability may be obtained e.g. by substitution with proline, introduction of a disulfide bond, altering a hydrogen bond contact, altering charge distribution, introduction of a salt bridge, introduction of metal binding sites, filling an internal structural cavity with one or more amino acids with bulkier side groups (in e.g. regions which are structurally mobile), substitution of histidine residues with other amino acids, removal of a deamidation site, or by helix capping. Stability of the protein may be improved also by substitution of at least one amino acid with cysteine residue or insertion of one or more cysteine residues which create at least one disulfide bridge.

The change in the amino acid sequence may be obtained by constructing a modified nucleotide sequence or DNA sequence by using genetic engineering. As a result a modified nucleotide sequence is obtained, which encodes the variant or mutant polypeptide of the invention. The methods for modifying the nucleotide sequences include e.g. site-directed and random mutagenesis. For site-directed mutagenesis, a method based on protein structure, a good understanding of the structure-function relationship would be beneficial. In the absence of such deep understanding, methods based on random mutagenesis may be used. For example, as disclosed in Sambrook and Russell (2001) oligonucleotide-directed mutagenesis for changing the base sequence of a segment of the coding DNA may be used to test the role of particular residues in the structure, catalytic activity, and ligand-binding capacity of a protein. In the absence of a three-dimensional structure, this type of proteing engineering relies on educated guesses concerning the structure of the protein and contribution of individual residues to protein stability and function.

WO 97/07206 discloses a method for preparing polypeptide variants by shuffling different nucleotide sequences of homologous DNA sequences by in vivo recombination.

The variant or mutant serine proteases of the present invention were designed basing on sequence comparison of the *Fusarium equiseti* RF6318 and *F. acuminatum* RF7182 protease (Fe_RF6318 and FaRF7182, respectively) amino acid sequences (SEQ ID NO:2 and SEQ ID NO:4, respectively) and their three-dimensional structures. Isolation of the Fe_RF6318 and Fa_RF7182 serine proteases and their amino acid and nucleotide sequences are disclosed in patent applications FI20095497 and FI20095499 (AB Enzymes Oy, FI), both filed on 30 Apr. 2009. Also sequences of other serine proteases of the subtilisin clan were used in comparisons. The modifications of Fe_RF6318 serine protease aimed on increasing the stability of the wild type Fe_RF6318 protease e.g. by reducing flexibility of the protein structure.

The term "variant" or "mutant" polypeptide in the present invention means a change in the amino acid sequence of the parent or precursor Fe_RF6318 enzyme having the amino acid sequence of the wild-type enzyme. The change may be a substitution of a naturally-occurring amino acid with any of the nineteen other naturally occurring L-amino acids, or a deletion or insertion of a naturally-occurring amino acid at the specific amino acid position. Instead of using the full name of the amino acid, also the three letter or one letter codes for amino acids are used as identified in the literature, e.g. in the standard molecular biology handbooks, such as Sambrook and Russell (2001).

Altogether 94 mutant proteases, named as m1-m26 and D1-D68 were designed (Table 1).

TABLE 1

The mutant proteases m1-m26 and D1-D68. The mutant protease code, modifications made on the amino acid and nucleotide sequences (codons) of the parent/naturally-occurring wild type protease polypeptide or protease cDNA and the codes for the expression plasmids are shown. The modified native amino acid, its position in the mature protease sequence and the amino acid replacing the native amino acid in the mutated protease are shown. For the cDNA and amino acid sequences of the mature wild type Fe_RF6318 protease, see SEQ ID NO: 1 and SEQ ID NO: 2, respectively. For, example the code R17H means that the arginine at position 17 of SEQ ID NO: 2 was substituted with histidine. The code ΔA65ΔH66 means that the alanine at position 65 and the histidine at position 66 of SEQ ID NO: 2 were deleted, the deletions resulting in renumbering all the subsequent amino acids. The code ins. G104 means that glycine was inserted at position 104 of SEQ ID NO: 2, the insertion resulting in renumbering of all the subsequent amino acids.

| Mutant code | Modification (amino acid sequence) | Modification (cDNA sequence) | Expression cassette Code | SEQ ID NO: (aa seq) |
|---|---|---|---|---|
| Wild type | No | No | pALK2764 | |
| m1 | R17H | CGC→CAC | pALK2765 | |
| m2 | Y25L | TAC→CTC | pALK2766 | |
| m3 | D28R | GAC→CGC | pALK2767 | |
| m4 | D28Y | GAC→TAC | pALK2768 | |
| m5 | ΔA65ΔH66 | ΔGCC, ΔCAC | pALK2740 | |
| m6 | T69N | ACC→AAC | pALK2741 | |
| m7 | A77S | GCT→AGC | pALK2742 | |
| m8 | A111D | GCT→GAC | pALK2743 | |
| m9 | N167L | AAC→CTC | pALK2744 | |
| m10 | R169N | CGT→AAC | pALK2745 | |
| m11 | E205G | GAG→GGC | pALK2746 | |
| m12 | Q216P | CAG→CCC | pALK2747 | |
| m13 | M282V | ATG→GTC | pALK2748 | |
| m14 | R17H, R169N | CGC→CAC, CGT→AAC | pALK2749 | |
| m15 | T46I | ACC→ATC | pALK2885 | |
| m16 | A88S | GCC→AGC | pALK2886 | |
| m17 | A173V | GCC→GTC | pALK2887 | |
| m18 | V208I | GTC→ATC | pALK2888 | 6 |

TABLE 1-continued

The mutant proteases m1-m26 and D1-D68. The mutant protease code, modifications made on the amino acid and nucleotide sequences (codons) of the parent/ naturally-occurring wild type protease polypeptide or protease cDNA and the codes for the expression plasmids are shown. The modified native amino acid, its position in the mature protease sequence and the amino acid replacing the native amino acid in the mutated protease are shown. For the cDNA and amino acid sequences of the mature wild type Fe_RF6318 protease, see SEQ ID NO: 1 and SEQ ID NO: 2, respectively. For, example the code R17H means that the arginine at position 17 of SEQ ID NO: 2 was substituted with histidine. The code ΔA65ΔH66 means that the alanine at position 65 and the histidine at position 66 of SEQ ID NO: 2 were deleted, the deletions resulting in renumbering all the subsequent amino acids. The code ins. G104 means that glycine was inserted at position 104 of SEQ ID NO: 2, the insertion resulting in renumbering of all the subsequent amino acids.

| Mutant code | Modification (amino acid sequence) | Modification (cDNA sequence) | Expression cassette Code | SEQ ID NO: (aa seq) |
|---|---|---|---|---|
| m19 | V239L | GTT→CTC | pALK2889 | |
| m20 | A248V | GCT→GTC | pALK2890 | |
| m21 | A281L | GCC→CTC | pALK2891 | |
| m22 | A111D, T46I, A88S, A173V, V208I, V239L, A248V, A281L | GCT→GAC, ACC→ATC, GCC→AGC, GCC→GTC, GTC→ATC, GTT→CTC, GCT→GTC, GCC→CTC | pALK2892 | |
| m23 | R17H, R18K, G22S, F284Y, A287N, T288G | CGC→CAC, CGA→AAG, GGC→AGC, TTC→TAC, GCT→AAC, ACT→GGC | pALK2893 | |
| m24 | A111D, V208I | GCT→GAC, GTC→ATC | pALK2897 | 8 |
| m25 | V208I, A281L | GTC→ATC, GCC→CTC | pALK2898 | 10 |
| m26 | A111D, V208I, A281L | GCT→GAC, GTC→ATC, GCC→CTC | pALK2899 | 12 |
| D1 | A111D, V208I, A281L, N7R | GCT→GAC, GTC→ATC, GCC→CTC, AAC→CGC | pALK3051 | |
| D2 | A111D, V208I, A281L, A33E | GCT→GAC, GTC→ATC, GCC→CTC, GCC→GAG | pALK3052 | 14 |
| D3 | A111D, V208I, A281L, A47E | GCT→GAC, GTC→ATC, GCC→CTC, GCC→GAG | pALK3053 | 16 |
| D4 | A111D, V208I, A281L, S56R | GCT→GAC, GTC→ATC, GCC→CTC, TCT→CGC | pALK3054 | |
| D5 | A111D, V208I, A281L, A61P | GCT→GAC, GTC→ATC, GCC→CTC, GCT→CCC | pALK3055 | |
| D6 | A111D, V208I, A281L, G63P | GCT→GAC, GTC→ATC, GCC→CTC, GGT→CCC | pALK3056 | 18 |
| D7 | A111D, V208I, A281L, V76A | GCT→GAC, GTC→ATC, GCC→CTC, GTT→GCC | pALK3057 | |
| D8 | A111D, V208I, A281L, N83D | GCT→GAC, GTC→ATC, GCC→CTC, AAC→GAC | pALK3058 | |
| D9 | A111D, V208I, A281L, N114R | GCT→GAC, GTC→ATC, GCC→CTC, AAC→CGC | pALK3059 | |
| D10 | A111D, V208I, A281L, V155I | GCT→GAC, GTC→ATC, GCC→CTC, GTC→ATC | pALK3060 | |
| D11 | A111D, V208I, A281L, V158I | GCT→GAC, GTC→ATC, GCC→CTC, GTT→ATC | pALK3061 | |
| D12 | A111D, V208I, A281L, G164A | GCT→GAC, GTC→ATC, GCC→CTC, GGT→GCC | pALK3062 | |
| D13 | A111D, V208I, A281L, I185M | GCT→GAC, GTC→ATC, GCC→CTC, ATC→ATG | pALK3063 | 20 |
| D14 | A111D, V208I, A281L, T196R | GCT→GAC, GTC→ATC, GCC→CTC, ACT→CGC | pALK3064 | |

TABLE 1-continued

The mutant proteases m1-m26 and D1-D68. The mutant protease code,
modifications made on the amino acid and nucleotide sequences (codons) of the parent/
naturally-occurring wild type protease polypeptide or protease cDNA and the codes for
the expression plasmids are shown. The modified native amino acid, its position in the
mature protease sequence and the amino acid replacing the native amino acid in the mutated
protease are shown. For the cDNA and amino acid sequences of the mature wild type
Fe_RF6318 protease, see SEQ ID NO: 1 and SEQ ID NO: 2, respectively. For, example the
code R17H means that the arginine at position 17 of SEQ ID NO: 2 was substituted with
histidine. The code ΔA65ΔH66 means that the alanine at position 65 and the histidine at
position 66 of SEQ ID NO: 2 were deleted, the deletions resulting in renumbering all the
subsequent amino acids. The code ins. G104 means that glycine was inserted at position 104
of SEQ ID NO: 2, the insertion resulting in renumbering of all the subsequent amino acids.

| Mutant code | Modification (amino acid sequence) | Modification (cDNA sequence) | Expression cassette Code | SEQ ID NO: (aa seq) |
|---|---|---|---|---|
| D15 | A111D, V208I, A281L, V206L | GCT→GAC, GTC→ATC, GCC→CTC, GTC→CTC | pALK3065 | |
| D16 | A111D, V208I, A281L, M234S | GCT→GAC, GTC→ATC, GCC→CTC, ATG→AGC | pALK3066 | |
| D17 | A111D, V208I, A281L, Q247L | GCT→GAC, GTC→ATC, GCC→CTC, CAG→CTC | pALK3067 | |
| D18 | A111D, V208I, A281L, N260R | GCT→GAC, GTC→ATC, GCC→CTC, AAC→CGC | pALK3068 | |
| D19 | A111D, V208I, A281L, T268R | GCT→GAC, GTC→ATC, GCC→CTC, ACC→CGA | pALK3069 | 22 |
| D20 | A111D, V208I, A281L, ΔN167 | GCT→GAC, GTC→ATC, GCC→CTC, ΔAAC | pALK3070 | |
| D21 | A111D, V208I, A281L, Q103A, ins. G104 | GCT→GAC, GTC→ATC, GCC→CTC, CAA→GCC, ins. GGC | pALK3071 | 24 |
| D22 | A111D, V208I, A281L, T3C, T29C | GCT→GAC, GTC→ATC, GCC→CTC, ACC→TGC, ACC→TGC | pALK3072 | 26 |
| D23 | A111D, V208I, A281L, S6R, T24D | GCT→GAC, GTC→ATC, GCC→CTC, AGC→CGC, ACC→GAC | pALK3073 | 28 |
| D24 | A111D, V208I, A281L, T121D, Q153R | GCT→GAC, GTC→ATC, GCC→CTC, ACC→GAC, CAA→CGA | pALK3074 | |
| D25 | A111D, V208I, A281L, S174R, E205D | GCT→GAC, GTC→ATC, GCC→CTC, TCT→CGA, GAG→GAC | pALK3075 | |
| D26 | A111D, V208I, A281L, N214D, S230R | GCT→GAC, GTC→ATC, GCC→CTC, AAC→GAC, AGC→CGA | pALK3076 | |
| D27 | A111D, V208I, A281L, Y151F, G286S, A283V, A287T | GCT→GAC, GTC→ATC, GCC→CTC, TAC→TTC, GCT→GTC, GGC→AGC, GCT→ACC | pALK3077 | |
| D28 | A111D, V208I, A281L, A33E, N83D, N114R, T196R, N260R | GCT→GAC, GTC→ATC, GCC→CTC, GCC→GAG, AAC→GAC, AAC→CGC, ACT→CGC, AAC→CGC | pALK3078 | |
| D29 | A111D, V208I, A281L, V155I, V158I, I185M, V206L, G210A, A283V | GCT→GAC, GTC→ATC, GCC→CTC, GTC→ATC, GTT→ATC, ATC→ATG, GTC→CTC, GGT→GCC, GCT→GTC | pALK3079 | |
| D30 | A111D, V208I, A281L, S6R, T24D, T121D, Q153R, S174R, E205D, A33E, T196R | GCT→GAC, GTC→ATC, GCC→CTC, AGC→CGC, ACC→GAC, ACC→GAC, CAA→CGA, TCT→CGA, GAG→GAC, GCC→GAG, ACT→CGC | pALK3080 | |

TABLE 1-continued

The mutant proteases m1-m26 and D1-D68. The mutant protease code, modifications made on the amino acid and nucleotide sequences (codons) of the parent/naturally-occurring wild type protease polypeptide or protease cDNA and the codes for the expression plasmids are shown. The modified native amino acid, its position in the mature protease sequence and the amino acid replacing the native amino acid in the mutated protease are shown. For the cDNA and amino acid sequences of the mature wild type Fe_RF6318 protease, see SEQ ID NO: 1 and SEQ ID NO: 2, respectively. For, example the code R17H means that the arginine at position 17 of SEQ ID NO: 2 was substituted with histidine. The code ΔA65ΔH66 means that the alanine at position 65 and the histidine at position 66 of SEQ ID NO: 2 were deleted, the deletions resulting in renumbering all the subsequent amino acids. The code ins. G104 means that glycine was inserted at position 104 of SEQ ID NO: 2, the insertion resulting in renumbering of all the subsequent amino acids.

| Mutant code | Modification (amino acid sequence) | Modification (cDNA sequence) | Expression cassette Code | SEQ ID NO: (aa seq) |
|---|---|---|---|---|
| D31 | A111D, V208I, A281L, A8V | GCT→GAC, GTC→ATC, GCC→CTC, GCT→GTC | pALK3101 | |
| D32 | A111D, V208I, A281L, G34S | GCT→GAC, GTC→ATC, GCC→CTC, GGT→AGC | pALK3102 | |
| D33 | A111D, V208I, A281L, G34N | GCT→GAC, GTC→ATC, GCC→CTC, GGT→AAC | pALK3103 | |
| D34 | A111D, V208I, A281L, Y36D | GCT→GAC, GTC→ATC, GCC→CTC, TAC→GAC | pALK3104 | |
| D35 | A111D, V208I, A281L, G52E | GCT→GAC, GTC→ATC, GCC→CTC, GGC→GAG | pALK3105 | |
| D36 | A111D, V208I, A281L, A91T | GCT→GAC, GTC→ATC, GCC→CTC, GCC→ACC | pALK3106 | |
| D37 | A111D, V208I, A281L, V100T | GCT→GAC, GTC→ATC, GCC→CTC, GTC→ACG | pALK3107 | |
| D38 | A111D, V208I, A281L, V100D | GCT→GAC, GTC→ATC, GCC→CTC, GTC→GAC | pALK3108 | 30 |
| D39 | A111D, V208I, A281L, V100K | GCT→GAC, GTC→ATC, GCC→CTC, GTC→AAG | pALK3109 | 32 |
| D40 | A111D, V208I, A281L, T106A | GCT→GAC, GTC→ATC, GCC→CTC, ACG→GCC | pALK3110 | |
| D41 | A111D, V208I, A281L, T106N | GCT→GAC, GTC→ATC, GCC→CTC, ACC→AAC | pALK3111 | 34 |
| D42 | A111D, V208I, A281L, P138D | GCT→GAC, GTC→ATC, GCC→CTC, CCC→GAC | pALK3112 | |
| D43 | A111D, V208I, A281L, P138K | GCT→GAC, GTC→ATC, GCC→CTC, CCC→AAG | pALK3113 | |
| D44 | A111D, V208I, A281L, A144N | GCT→GAC, GTC→ATC, GCC→CTC, GCT→AAC | pALK3114 | |
| D45 | A111D, V208I, A281L, A144T | GCT→GAC, GTC→ATC, GCC→CTC, GCT→ACC | pALK3115 | |
| D46 | A111D, V208I, A281L, E205N | GCT→GAC, GTC→ATC, GCC→CTC, GAG→AAC | pALK3116 | |
| D47 | A111D, V208I, A281L, E205R | GCT→GAC, GTC→ATC, GCC→CTC, GAG→CGC | pALK3117 | |
| D48 | A111D, V208I, A281L, L249T | GCT→GAC, GTC→ATC, GCC→CTC, CTC→ACC | pALK3118 | |
| D49 | A111D, V208I, A281L, L252T | GCT→GAC, GTC→ATC, GCC→CTC, CTC→ACC | pALK3119 | |
| D50 | A111D, V208I, A281L, L252A | GCT→GAC, GTC→ATC, GCC→CTC, CTC→GCC | pALK3120 | |
| D51 | A111D, V208I, A281L, A256S | GCT→GAC, GTC→ATC, GCC→CTC, GCT→AGC | pALK3121 | |

TABLE 1-continued

The mutant proteases m1-m26 and D1-D68. The mutant protease code, modifications made on the amino acid and nucleotide sequences (codons) of the parent/ naturally-occurring wild type protease polypeptide or protease cDNA and the codes for the expression plasmids are shown. The modified native amino acid, its position in the mature protease sequence and the amino acid replacing the native amino acid in the mutated protease are shown. For the cDNA and amino acid sequences of the mature wild type Fe_RF6318 protease, see SEQ ID NO: 1 and SEQ ID NO: 2, respectively. For, example the code R17H means that the arginine at position 17 of SEQ ID NO: 2 was substituted with histidine. The code ΔA65ΔH66 means that the alanine at position 65 and the histidine at position 66 of SEQ ID NO: 2 were deleted, the deletions resulting in renumbering all the subsequent amino acids. The code ins. G104 means that glycine was inserted at position 104 of SEQ ID NO: 2, the insertion resulting in renumbering of all the subsequent amino acids.

| Mutant code | Modification (amino acid sequence) | Modification (cDNA sequence) | Expression cassette Code | SEQ ID NO: (aa seq) |
|---|---|---|---|---|
| D52 | A111D, V208I, A281L, Q247L, L249T | GCT→GAC, GTC→ATC, GCC→CTC, CAG→CTC; CTC→ACC | pALK3122 | |
| D53 | A111D, V208I, A281L, T3C, T29C, S6R, T24D | GCT→GAC, GTC→ATC, GCC→CTC, ACC→TGC; ACC→TGC; AGC→CGC; ACC→GAC | pALK3123 | 36 |
| D54 | A111D, V208I, A281L, I185C, T259C | GCT→GAC, GTC→ATC, GCC→CTC, ATC→TGC; ACC→TGC | pALK3124 | |
| D55 | A111D, V208I, A281L, G210A, I185M | GCT→GAC, GTC→ATC, GCC→CTC, GGT→GCC; ATC→ATG | pALK3125 | 38 |
| D56 | A111D, V208I, A281L, A33E, A47E, N83D | GCT→GAC, GTC→ATC, GCC→CTC, GCC→GAG; GCC→GAG; AAC→GAC | pALK3126 | |
| D57 | A111D, V208I, A281L, A14T | GCT→GAC, GTC→ATC, GCC→CTC, GCC→ACC | pALK3127 | |
| D58 | A111D, V208I, A281L, G22S | GCT→GAC, GTC→ATC, GCC→CTC, GGC→TCC | pALK3128 | |
| D59 | A111D, V208I, A281L, G37A | GCT→GAC, GTC→ATC, GCC→CTC, GGT→GCC | pALK3129 | |
| D60 | A111D, V208I, A281L, A65D | GCT→GAC, GTC→ATC, GCC→CTC, GCC→GAC | pALK3130 | |
| D61 | A111D, V208I, A281L, V100Q | GCT→GAC, GTC→ATC, GCC→CTC, GTC→CAG | pALK3131 | 40 |
| D62 | A111D, V208I, A281L, F113Y | GCT→GAC, GTC→ATC, GCC→CTC, TTC→TAC | pALK3132 | |
| D63 | A111D, V208I, A281L, K123R | GCT→GAC, GTC→ATC, GCC→CTC, AAG→CGC | pALK3133 | 42 |
| D64 | A111D, V208I, A281L, S157T | GCT→GAC, GTC→ATC, GCC→CTC, TCC→SACC | pALK3134 | 44 |
| D65 | A111D, V208I, A281L, G175S | GCT→GAC, GTC→ATC, GCC→CTC, GGC→TCC | pALK3135 | 46 |
| D66 | A111D, V208I, A281L, Q176T | GCT-GAC, GTC→ATC, GCC→CTC, CAG→ACC | pALK3136 | 48 |
| D67 | A111D, V208I, A281L, C236T | GCT→GAC, GTC→ATC, GCC→CTC, TGC→ACC | pALK3137 | 50 |
| D68 | A111D, V208I, A281L, A287N | GCT→GAC, GTC→ATC, GCC→CTC, GCT→AAC | pALK3138 | |

The expression cassettes harboring the corresponding modified nucleotide sequences were synthesized as described in Examples 3, 6, 9 and 16. The codons for the amino acids were chosen to be such that are generally used in *T. reesei* cellulase and xylanase genes (Bergquist et al., 2002) and that did not create any additional SacII, AgeI or NotI restriction sites into the nucleotide sequence. The *T. reesei* host was transformed with the expression cassettes and the transformants were screened for protease activity on haemoglobin plates as described in Example 4. The transformants showing the strongest intensities of dark brown color around the growing mycelia were chosen for shake flask cultivations in a lactose-based cellulase-inducing medium. The protease activity from the culture supernatants was determined according to the method disclosed in Example 1a and the thermal stability according to the method of Example 1b. The protease variants showing the best stability in these preliminary assays were produced in larger amounts by cultivating the corresponding T. reesei transformants in laboratory scale bioreactors in a cellulase-inducing complex medium. The spent culture media of the shake flask and/or fermentor cultivations were used for determination of the thermal stability (Examples 1b, 8, 11 and 17), stain removal performance (Examples 12, 14 and 17) and detergent stability (Examples 13, 15 and 17).

The expression "improved thermal stability" or "improved thermostability" means that after incubating the culture supernatants comprising the protease variant of the invention at different temperatures for definitive time intervals, the residual protease activity measured from the culture supernatant is better than the residual activity of the parent wild-type Fe_RF6318 protease incubated in corresponding conditions. The thermal stability may be determined using shake flask or fermentation supernatant as an enzyme source as described in Example 1b. Alternatively a purified enzyme may be used. The residual activity of the sample is measured and calculated following e.g. the assay described in Example 1a or any other assay determining protease activity described in the literature (Gupta et al., 2002).

By the term "stain removal performance" in connection to the present invention is meant that the enzyme or enzyme variant is capable of hydrolyzing or removing proteinaceous stains, in particular the insoluble substances or material on the substrate. Typically, the wash performance in varying conditions and exposed to varying treatments is measured as "stain removal efficiency" or "stain removal effect" or "degree of cleaning property", meaning a visible and measurable increase of lightness or change in colour of the stained material, e.g. in artificially soiled swatches or test cloths. Lightness or change in colour values can be measured, for example by measuring the colour as reflectance values with a spectrophotometer using L*a*b* colour space coordinates as described in Examples 12, 14 and 17. Fading or removal of proteinaceous stain indicating of the protease performance (stain removal efficiency) is calculated for example as ΔL*, which means lightness value L* of enzyme treated fabric minus lightness value L* of fabric treated with buffer or washing liquor without enzyme (enzyme blank or control). The presence of detergent may improve the performance of the enzyme in removing the stains.

By the term "improved wash performance" is meant that the performance of the serine protease variant of the invention is better or remarkably better than the performance of the parent or precursor serine protease, which does not include amino acid changes, i.e. an enzyme corresponding to the native serine protease obtainable from the wild-type F. equiseti RF6318 strain. The parent amino acid sequence of the serine protease may also be produced by a recombinant strain expressing and secreting said unmodified serine protease.

The expression "detergent" is used to mean substance or material intended to assist cleaning or having cleaning properties. The term "detergency" indicates presence or degree of cleaning property. The degree of cleaning property can be tested on different proteinaceous or protein containing substrate materials or stains or stain mixtures bound to solid, water-insoluble carrier, such as textile fibers or glass. Typical proteinaceous material includes blood, milk, ink, egg, grass and sauces. For testing purposes mixtures of proteinaceous stains are commercially available. The function of the detergent enzyme is to degrade and remove the protein-containing stains. Test results depend on the type of stain, the composition of the detergent and the nature and status of textiles used in the washing test (Maurer, 2004).

In the present invention the term "detergent stability" means that the enzyme or enzyme variant sufficiently retains its activity in detergent solution, during storage and/or washing. Therefore it is efficient in degrading or removing proteinaceous stains or material in the presence of a detergent such as the Liquid Base detergent for colored fabric (see Table 7 of Example 12), the Ecolabel Reference Detergent, light duty (wfk Testgewebe GmbH) or the Commercial liquid detergent as described in Table 8 of Example 13. The stability may be assayed by determining the residual activity e.g. after one or several days incubation (at 37° C.) in the presence of a detergent. The residual protease activity may be determined using the method described in Example 1a or any other method disclosed in the literature (Gupta et al. 2002).

The expression "V208I" means a replacement of a valine (V) at position 208 with an isoleucine (I). For sequence numbering, the amino acid sequence of Fe_RF6318 serine protease is numbered according to the mature sequence shown in SEQ ID NO:2. Similarly, e.g. the expression "A111D" means that the alanine (A) at position 111 of the mature Fe_RF6318 serine protease of SEQ ID NO:2 is substituted with an aspartic acid (D).

Figure 6:
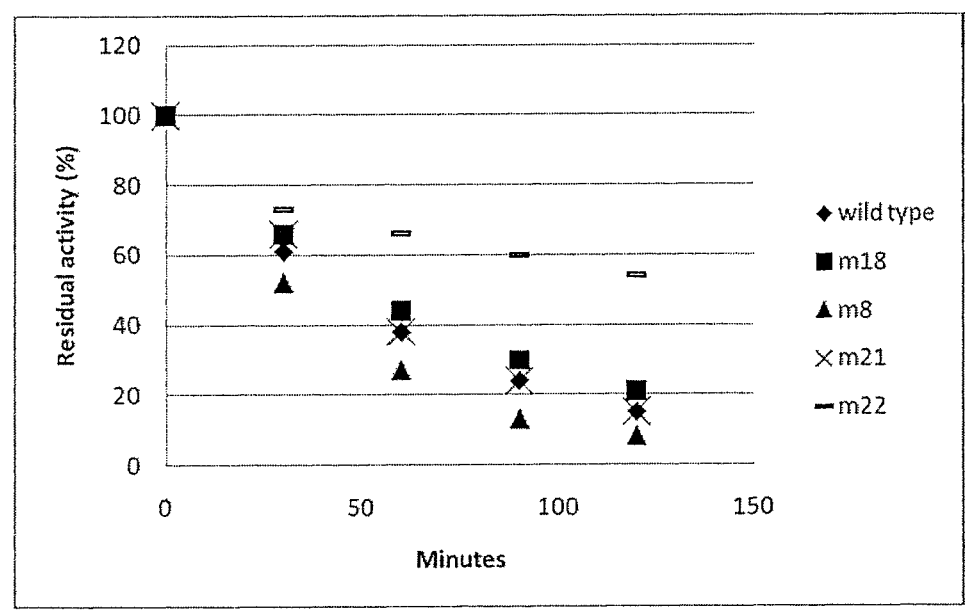
FIG. 6 shows the thermal stability of m-series mutant proteases determined from fermentation culture supernatants in 20 mM Tris buffer, pH 8.5. Enzyme samples were incubated at 45° C. for 120 minutes and the residual activity was analyzed at definite intervals.

The spent culture supernatants of the protease variants m7 (comprising the amino acid substitution A77S), m8 (A111D), m18 (V208I), and m21 (A281L) showed better thermal stability than the parent wild-type Fe_RF6318 protease. The multiply substituted variant m22 (A111D, T46I, A88S, A173V, A208I, A239L, A248V and A281L) was clearly more stable than the parent wild-type protease (Example 5). The thermal stability assays performed with the fermentor culture supernatants confirmed that the protease variants m18 and m21 containing single amino acid substitutions were among the ones that seemed to be the most stable in the assays (FIG. 6). Also, they showed good performance in the preliminary stain removal tests.

Figure 7:
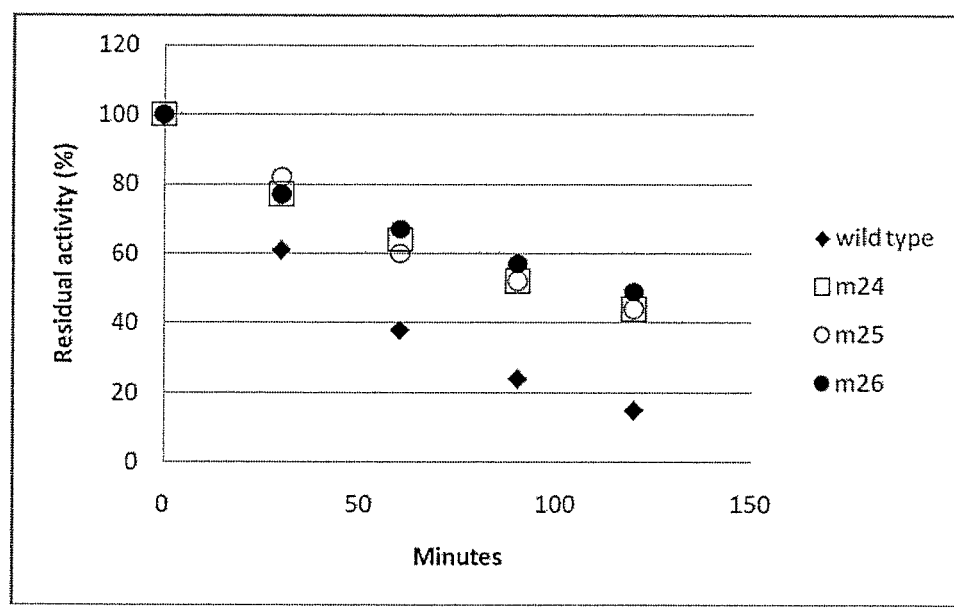
FIG. 7 shows the thermal stability of mutant proteases m24, m25 and m26 determined from fermentation culture supernatants in 20 mM Tris buffer, pH 8.5. Enzyme samples were incubated at 45° C. for 100 minutes and the residual activity was analyzed at definite intervals. Wild type protease Fe_RF6318 was used for comparison.

Three new mutant genes m24 (encoding the amino acid change A111D, V208I), m25 (V208I, A281L) and m26 (A111D, V208I, A281L) were designed and constructed as described in Example 6. The thermal stability assays performed with the fermentor culture supernatants showed that the protease variants m24, m25 and m26 comprising two or three amino acid substitutions had better stability than the parent wild-type Fe_RF6318 protease. Also, the protease variants had better stability compared to the m8, m18 and m21 protease variants having only single mutations (FIG. 7).

The m26 variant was chosen as a background molecule for designing new protease variants of the D-series. The expression cassettes encoding the designed variant were transformed to T. reesei and the transformants were screened as described in Example 7.

Figure 9:
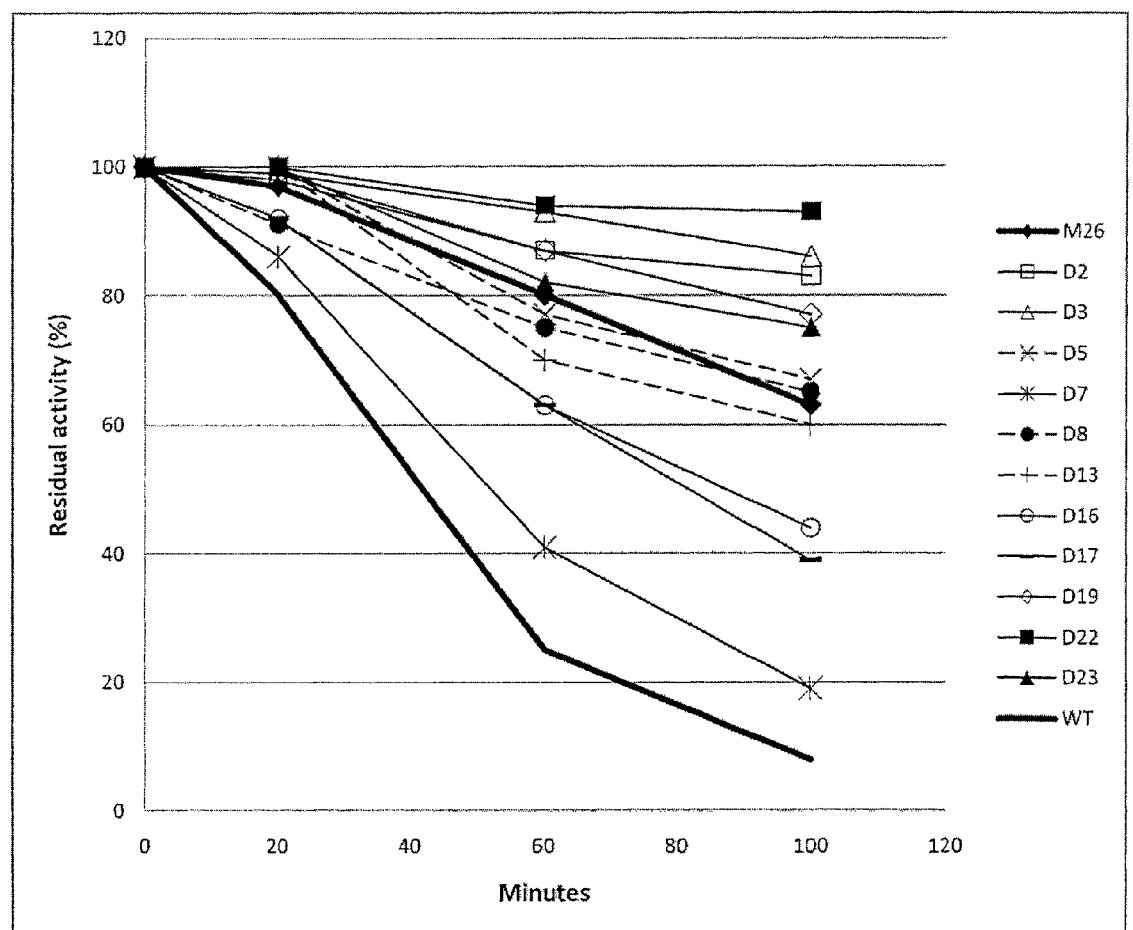
FIG. 9 shows the thermal stability of chosen D-series mutants. The stabilities were determined from fermentation culture supernatants in 20 mM Tris buffer, pH 8.5. Enzyme samples were incubated at 45° C. for 100 minutes and the residual activity was analyzed at definite intervals. The m26 mutant protease was used for comparison.

The thermostability of mutant proteases D2 (A111D, A208I, A2818L, A33E), D3 (A111D, V208I, A281L, A47E), D19 (A111D, V208I, A281L, T268R), D22 (A111D, V208I, A281L, T3C, T29C) and D23 (A111D, V208I, A281L, S6R, T24D) was better than that of the mutant protease m26 comprising three amino acid substitutions (A111D, V208I, A281L), as shown in FIG. 9. Mutant proteases D5 (A111D, V298I, A281L, A61P), D8 (A111D, V298I, N83D) and D13 (A111D, V208I, A281L, I185M) had approximately equal thermal stability as m26 mutant protease. Mutant proteases D7 (A111D, V208I, A281L, V76A), D16 (A111D, V208I, A281L, M234S) and D17 (A111D, V208I, A281L, Q247L) had lower thermal stability than m26 mutant protease but the stability was better than the stability of wild type Fe_RF6318 protease. The D38 (A111D, V208I, A281L, V100D), D41 (A111D, V208I, A281L, T106N), D53 (A111D, V208I, A281L, T3C, T29C, S6R, T24D) and D55 (A111D, V208I, A281L, I185M, G210A) mutant proteases show clearly better thermal stability than m26, as shown in Example 17 (Table 10).

Figure 10A:
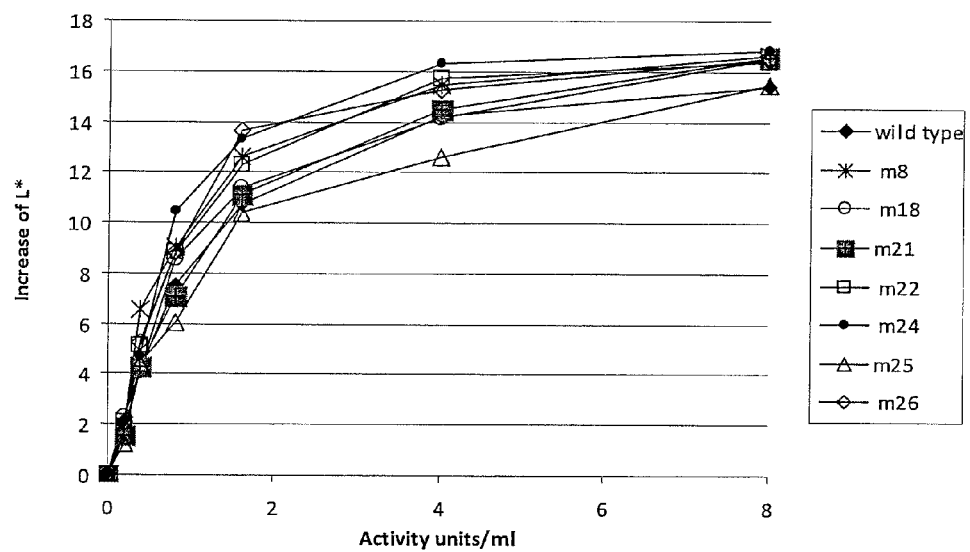
FIG. 10A describes the stain removal performance of selected mutant proteases from m-series with blood/milk/ink stain (Art.117, EMPA) at 30° C., approx. pH 7.4, 60 mM in the presence of Liquid Base detergent for colored fabrics with concentration of 5 g/l. Wild type protease Fe_RF6318 was used for comparison.
Figure 10B:
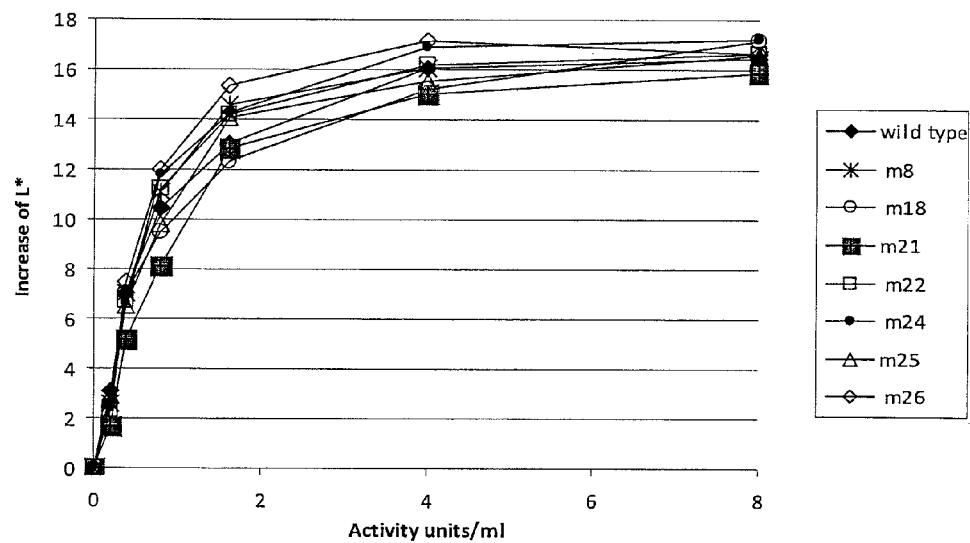
FIG. 10B describes the stain removal performance of selected mutant proteases from m-series with blood/milk/ink stain (Art.117, EMPA) at 45° C., approx. pH 7.4, 60 min in the presence of Liquid Base detergent for colored fabrics with concentration of 5 g/l. Wild type protease was used for comparison.

The stain removal performance of the mutant proteases of m-series showing the best thermal stability and the parent Fe_RF6318 protease produced in *T. reesei* were tested for their ability to remove blood/milk/ink standard stain at 30° C. and 45° C. in the presence of Liquid Base detergent for colored fabrics at a concentration of 5 g/l (pH approx. 7.4). As shown in Example 12 with the stabilized fermentation culture supernatants comprising the serine protease variants m8 (A111D), m18 (V208I), m21 (A281L), m22 (A111D, T46I, A88S, A173V, V208I, V239L, A248V, A281L), m24 (A111D, V208I), m25 (V208I, A281L), and m26 (A111D, V208I, A281L) of the invention, the mutations have not affected harmfully on the stain removal performance compared to the parent Fe_RF6318 protease (FIGS. 10A and 10B). The mutant proteases showed similar wash performance as the parent Fe_RF6318 protease also when tested in the presence of another liquid detergent, Ecolabel Reference Detergent, and with detergent powders, like ECE reference detergent 77 without optical brightener (Art. 601, EMPA) and ECE reference detergent 98 without phosphate (Art. 600, EMPA).

Figure 14A:
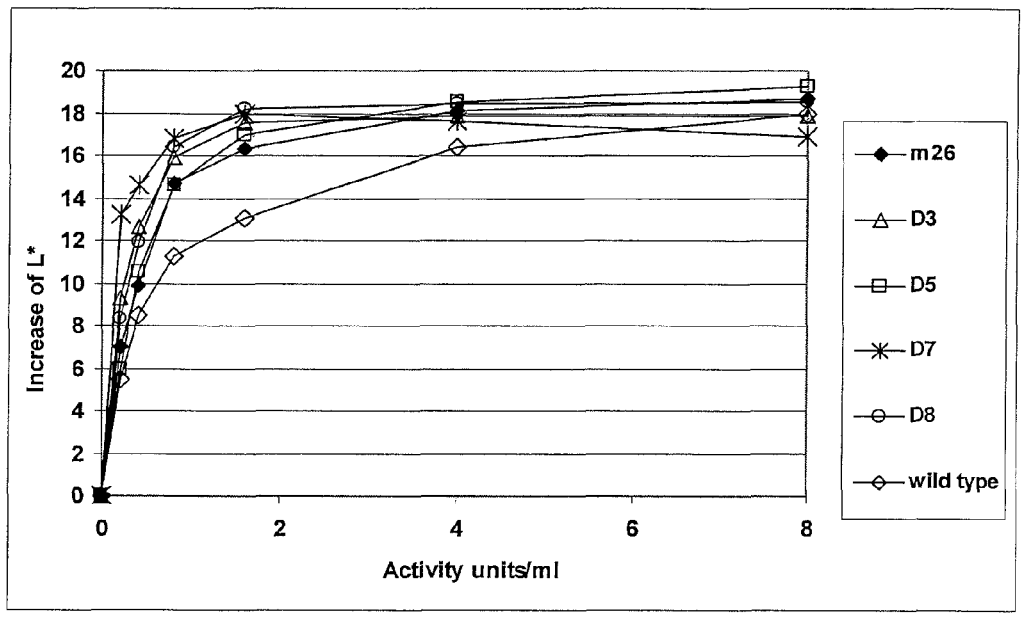
FIG. 14A describes the stain removal performance of mutant proteases from D-series (D3, D5, D7 and D8) with blood/milk/ink stain (Art.117, EMPA) at 30° C., approx. pH 7.8, 60 min in the presence of Commercial liquid detergent with concentration of 5 g/l. Mutant protease m26 and wild type protease were used for comparison.
Figure 14B:
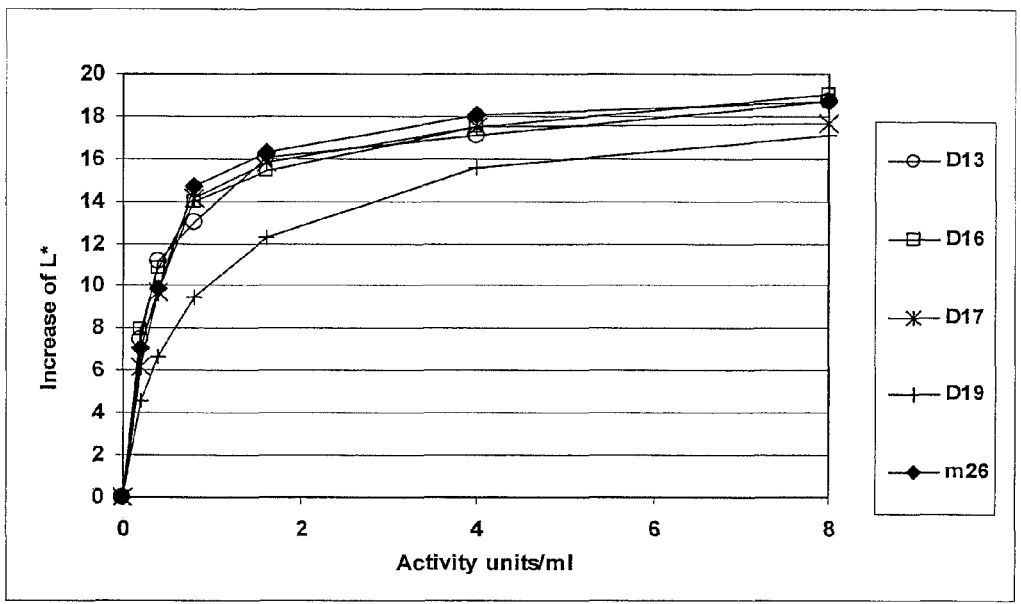
FIG. 14B describes the stain removal performance of mutant proteases from D-series (D13, D16, D17 and D18) with blood/milk/ink stain (Art.117, EMPA) at 30° C., approx. pH 7.8, 60 min in the presence of Commercial liquid detergent with concentration of 5 g/l. Mutant protease m26 was used for comparison.
Figure 15A:
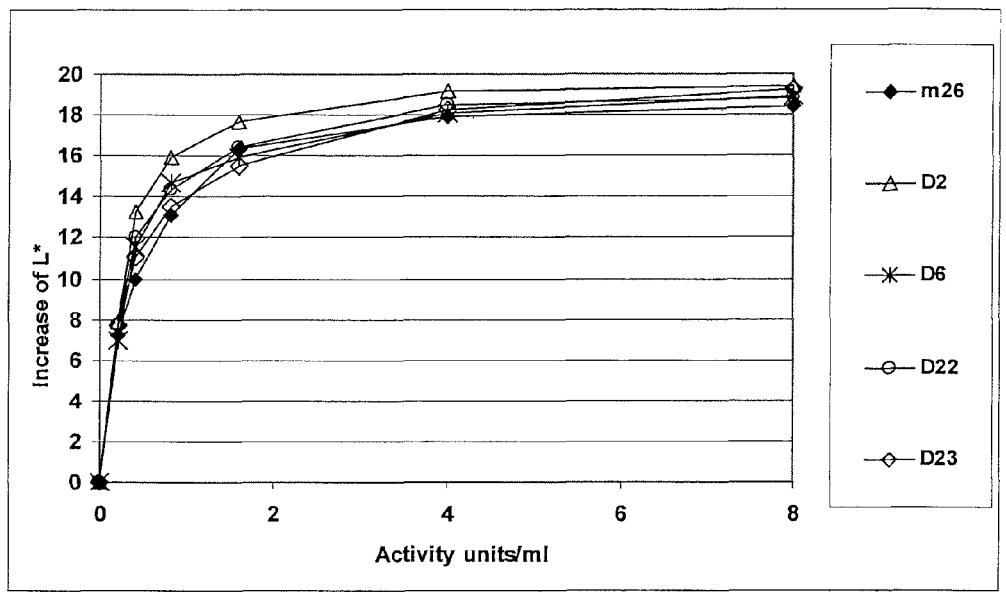
FIG. 15A describes the stain removal performance of mutants from D-series (D2, D6, D22 and D23) with blood/milk/ink stain (Art.117, EMPA) at 30° C., approx. pH 7.8, 60 min in the presence of Commercial liquid detergent with concentration of 5 g/l. Mutant protease m26 was used for comparison.

The stain removal performance of the mutant proteases of D-series showing the best thermal stability (Example 11) and the parent Fe_RF6318 protease produced in *T. reesei*, as described in Example 10, were tested for their ability to remove blood/milk/ink standard stain at 30° C. and 50° C. in the presence of Commercial liquid detergent at a concentration of 5 g/l (pH approx. 7.8). As shown in Example 14 the stabilized culture supernatants comprising the serine protease variants D2 (A111D, V208I, A281L, A33E), D3 (A111D, V208I, A281L, A47E), D5 (A111D, V208I, A281L, A61P), D6 (A111D, V208I, A281L, G63P), D7 (A111D, V208I, A281L, V76A), D8 (A111D, V208I, A281L, N83D), D13 (A111D, V208I, A281L, I185M), D16 (A111D, V208I, A281L, M234S), D17 (A111D, V208I, A281L, Q247L), D18 (A111D, V208I, A281L, N260R), D22 (A111D, V208I, A281L, T3C, T29C), and D23 (A111D, V208I, A281L, S6R, T24D) of the invention had better performance at 30° C. than the parent Fe_RF6318 protease and similar or better performance than the m26 variant comprising three amino acid substitutions (FIGS. 14A, 14B and 15A). The D19 (A111D, V208I, A281L, T268R) variant had similar performance compared to the parent Fe_RF6318 protease.

Figure 14C:
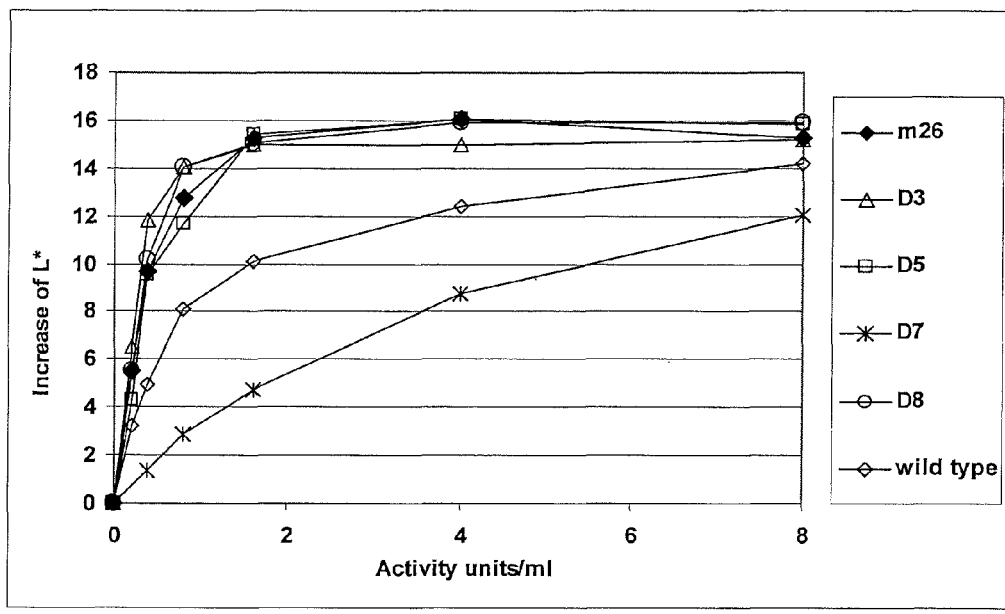
FIG. 14C describes the stain removal performance of mutant proteases from D-series (D3, D5, D7 and D8) with blood/milk/ink stain (Art.117, EMPA) at 50° C., approx. pH 7.8 60 min in the presence of Commercial liquid detergent with concentration of 5 g/l. Mutant protease m26 and wild type were used for comparison.
Figure 14D:
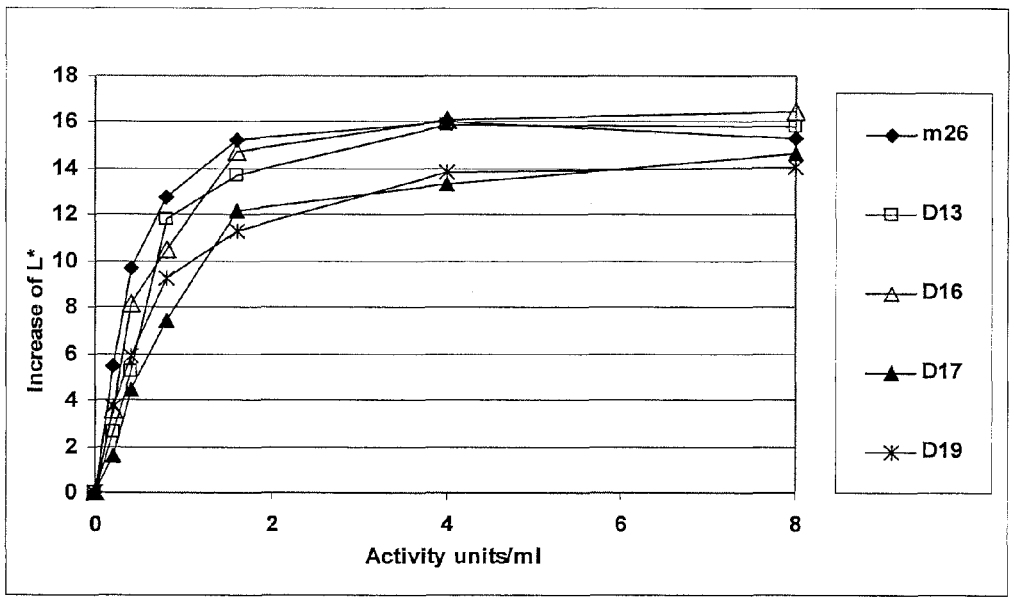
FIG. 14D describes the stain removal performance of mutants from D-series (D13, D16, D17 and D18) with blood/milk/ink stain (Art.117, EMPA) at 50° C., approx. pH 7.8 60 min in the presence of Commercial liquid detergent with concentration of 5 g/l. Mutant protease m26 was used for comparison.
Figure 15B:
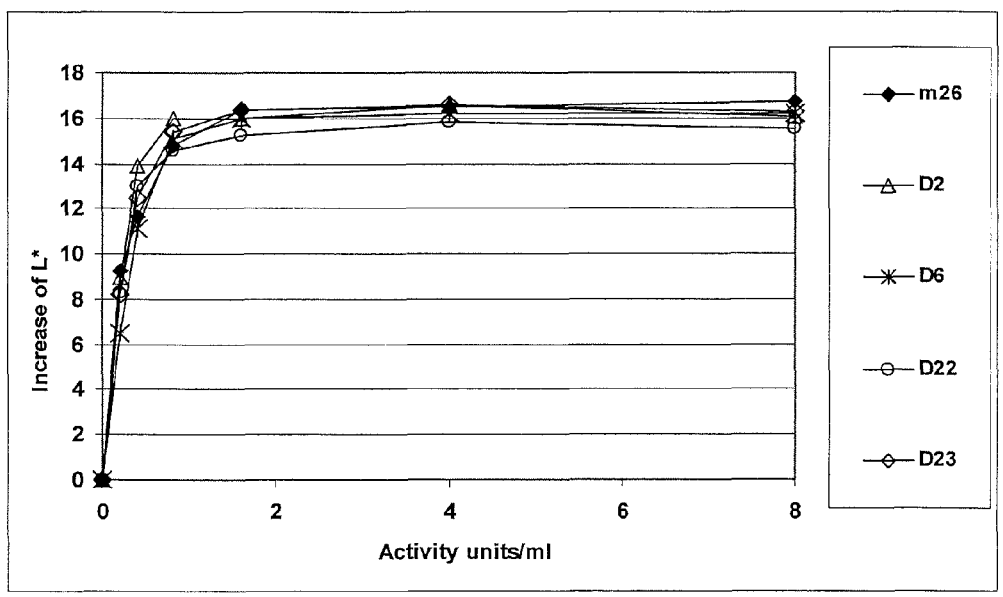
FIG. 15B describes the stain removal performance of mutants from D-series (D2, D6, D22 and D23) with blood/milk/ink stain (Art.117, EMPA) at 50° C., approx. pH 7.8, 60 min in the presence of Commercial liquid detergent with concentration of 5 g/l. Mutant protease m26 was used for comparison.

At 50° C. the variants D2, D3, D5, D6, D8, D13, D16, D22, and D23 had relatively similar stain removal performance compared to the m26 variant comprising three amino acid substitutions (FIGS. 14C, 14D and 15B). The D17 and D19 variants were slightly better in removing the blood/milk/ink standard stain than the parent Fe_RF6318 protease.

The performance of all tested D31-D68 mutant proteases, except D39, to remove blood/milk/ink standard stain in the presence of Commercial liquid detergent at 30° C., was similar or better compared to m26 protease. The ability of D35 (A111D, V208I, A281L, G52E), D37 (A111D, V208I, A281L, V100T), D38 (A111D, V208I, A281L, V100D) and D44 (A111D, V208I, A281L, A144N) mutant proteases was shown to be especially good compared to m26 (Example 17).

Figure 12A:
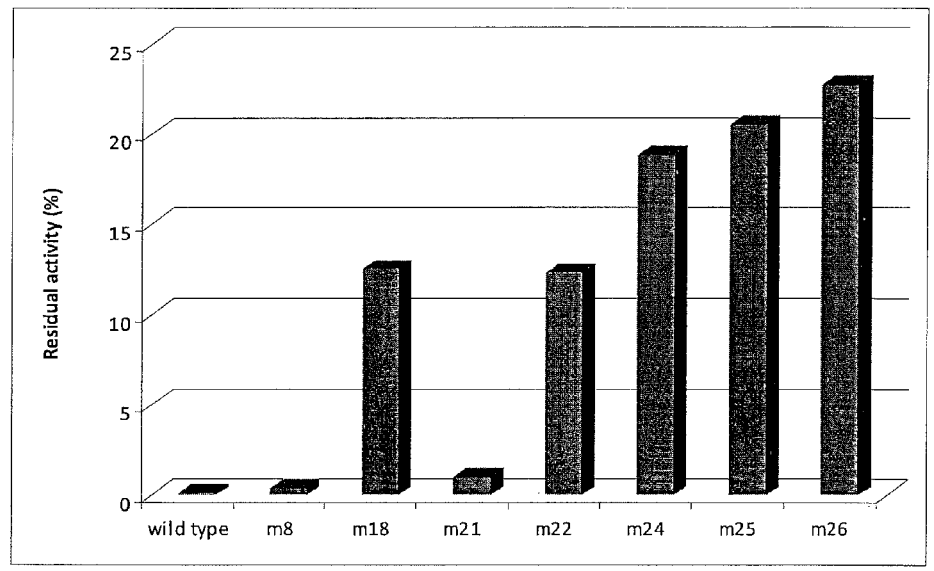
FIG. 12A shows the stability of selected mutant proteases from m-series and wild type in Ecolabel Reference Detergent (Mk Testgewebe GmbH) incubated at 37° C. for 18 hours (pH approx. 7.2).
Figure 12B:
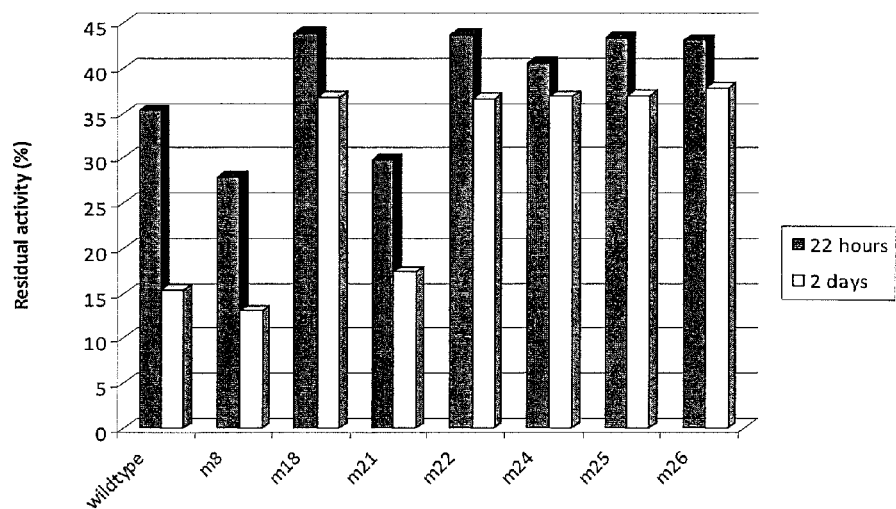
FIG. 12B shows the stability of selected mutant proteases from m-series and wild type protease in Commercial liquid detergent incubated at 37° C., pH approx 8.2, for 22 hours and two days (approx. 44 hours).
Figure 13A:
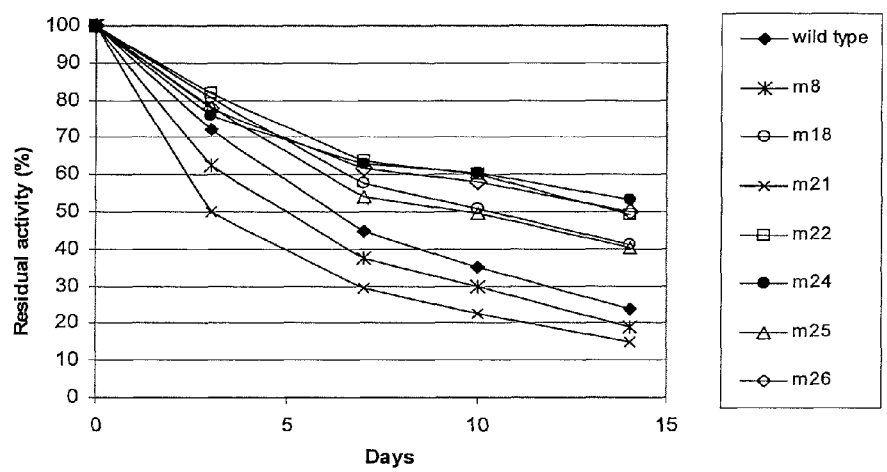
FIG. 13A shows the stability of selected mutant proteases from m-series in Ecolabel Reference Detergent (wfk Testgewebe GmbH) with 2% sodium tetraborate decahydrate and 17% propylene glycol incubated at 37° (pH approx. 6.5). Wild type protease was used for comparison.

The serine protease variants of the present invention had improved stability in the presence of various liquid detergents, as shown in Examples 13 and 15. Stability of the m18 (V208I), m22 (A111D, T46I, A88S, A173V, V208I, V239L, A248V, A281L), m24 (A111D, V208I), m25 (V208I, A281L), and m26 (A111D, V208I, a281L) variants was considerably improved compared to the parent Fe_RF6318 serine protease in Ecolabel Reference Detergent and in Commercial liquid detergent (FIGS. 12-13).

Figure 16A:
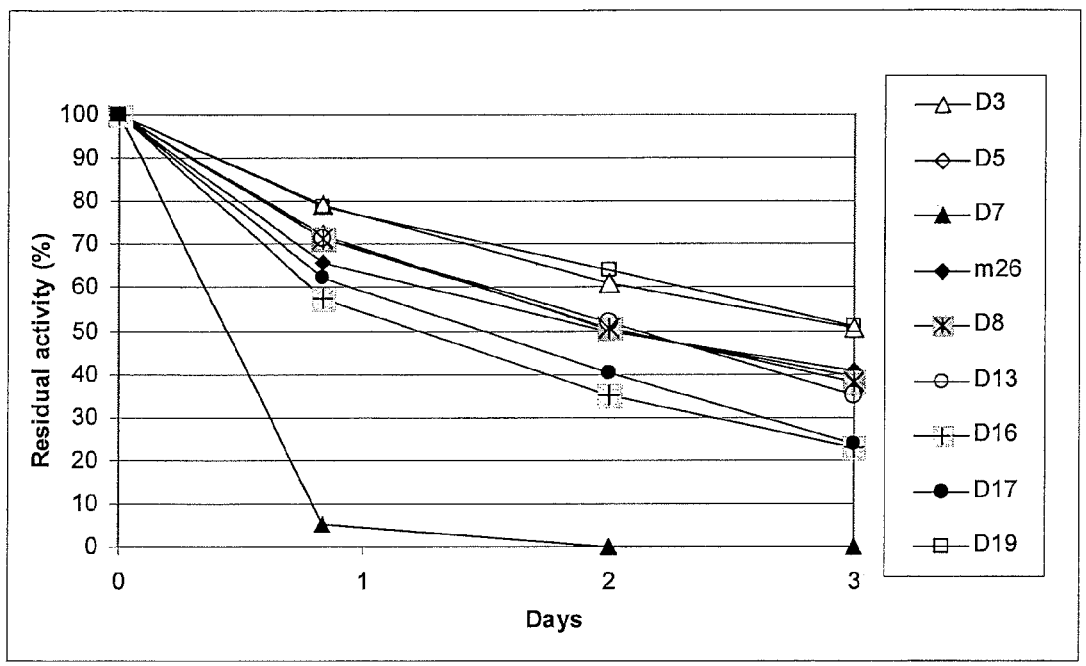
FIG. 16A shows the stability of mutants of D-series (D3, D5, D7, D8, D13, D16, D17 and D19) in Commercial liquid detergent incubated at 37° C., pH approx. 8.2. Mutant protease m26 was used for comparison.

Stability of mutants D2 (A111D, V208I, A281L, A33E), D3 (A111D, V208I, A281L, A47E), D6 (A111D, V208I, A281L, G63P), D19 (A111D, V208I, A281L, T268R) and D22 (A111D, T46I, A88S, A173V, V208I, V239L, A248V, A281L) was better compared to m26 and mutants D5 (A111D, V208I, A281L, A61P), D8 (A111D, V208I, A281L, N83D), D13 (A111D, V208I, A281L, I185M) and D23 (A111D, V208I, A281L, S6R, T24D) had similar stability in Commercial liquid detergent (FIGS. 16A and B). The stability of mutants D16 (A111D, V208I, A281L, M234S), D17 (A111D, V208I, A281L, Q247L) and especially D7 (A111D, V208I, A281L, V76A) was lower compared to m26. However, the mutants D16 and D17 were more stable than the wild type (FIG. 12B) in previous test.

Figure 13B:
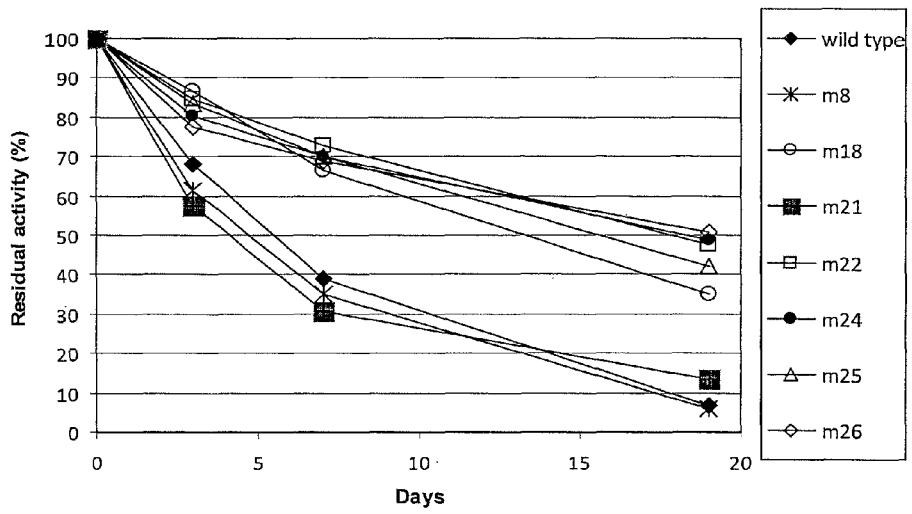
FIG. 13B shows the stability of selected mutant proteases from m-series in Commercial liquid detergent with 2% sodium tetraborate decahydrate and 17% propylene glycol incubated at 37° C. and pH approx. 7.5. Wild type protease was used for comparison.
Figure 17A:
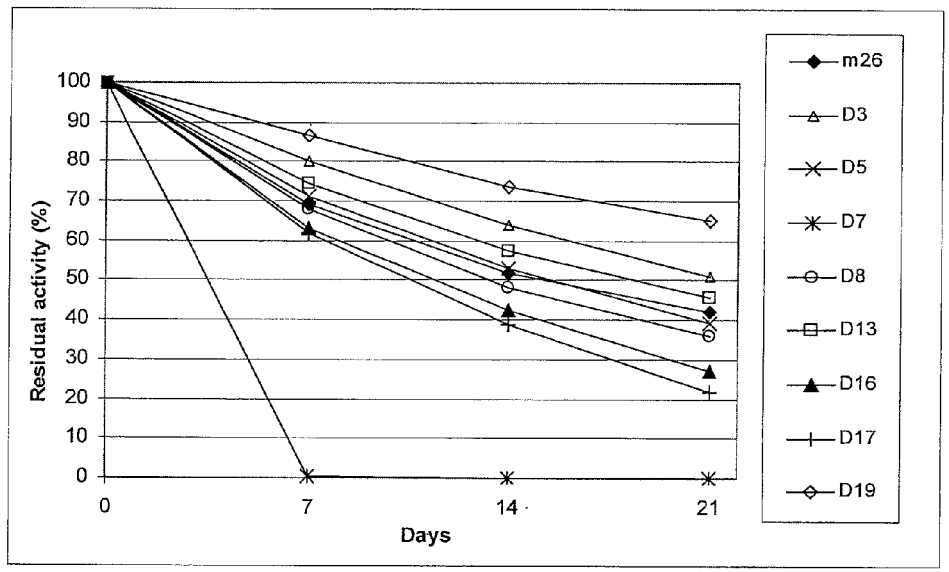
FIG. 17A shows the stability of mutants from D-series (D3, D5, D7, D8, D13, D16, D17 and D19) in Commercial liquid detergent with 2% sodium tetraborate decahydrate and 17% propylene glycol incubated at 37° C., pH approx. 7.5. Mutant protease m26 was used for comparison.

In Commercial liquid detergent with added sodium tetraborate decahydrate and propylene glycol (FIGS. 17A and B), stability of mutants D2 (A111D, V208I, A281L, A33E), D3 (A111D, V208I, A281L, A47E), D6 (A111D, V208I, A281L, G63P), D13 (A111D, V208I, A281L, I185M), D22 (A111D, T46I, A88S, A173V, V208I, V239L, A248V, A281L) and especially D19 (A111D, V208I, A281L, T268R), was better compared to m26 and mutant D5 (A111D, V298I, A281L, A61P) had relatively similar stability The stability of mutants D8 (A111D, V208I, A281L, N83D), D16 (A111D, V208I, A281L, M234S), D17 (A111D, V208I, A281L, Q247L), D23 (A111D, V208I, A281L, S6R, T24D) and especially D7 (A111D, V208I, A281L, V76A) was lower compared to m26. However, all the D-series mutants having lower stability compared to m26, except D7 were more stable than the wild type (FIG. 13B).

Figure 18:
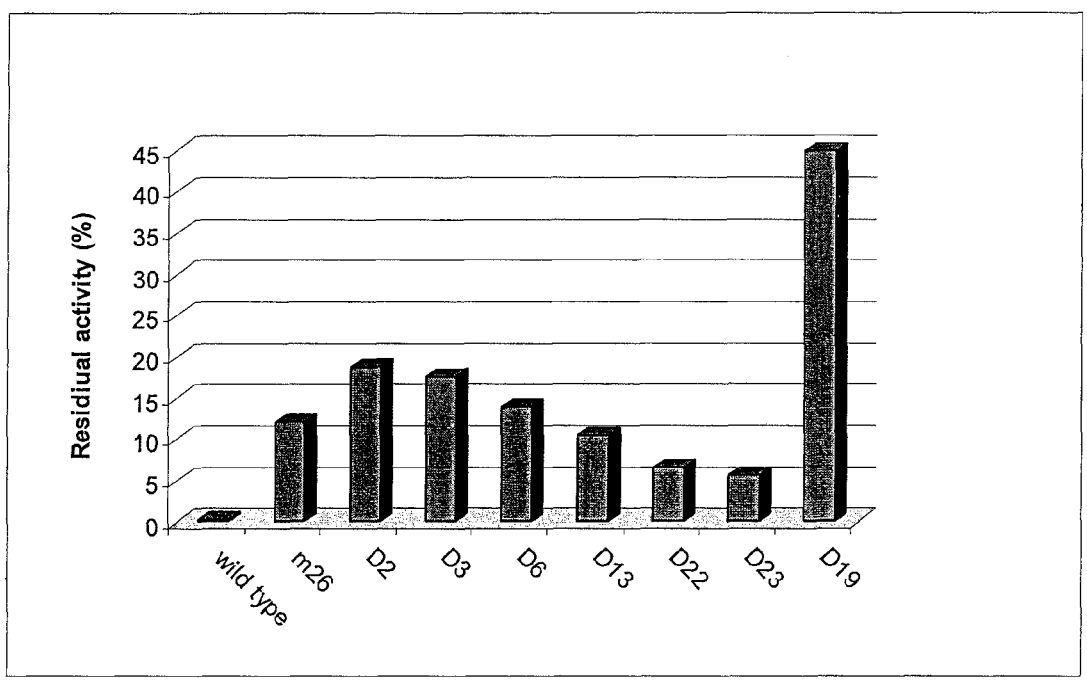
FIG. 18 shows stability of mutant of D-series in Ecolabel Reference Detergent incubated at 37° C. pH approx. 7.2 for 20 hours. Mutant protease m26 and wild type protease were used for comparison.

All mutant D-series proteases tested showed considerably improved stability in Ecolabel Reference Detergent compared to wild type (Example 15, FIG. 18 and Example 17, Table 10). From D1-D30 serie of mutant proteases D2 (A111D, V208I, A281L, A33E), D3 (A111D, V208I, A281L, A47E), D6 (A111D, V208I, A281L, G63P) and especially D19 (A111D, V208I, A281L, T268R) had also better stability than m26. From D31-D68 serie of mutant proteases D39 (A111D, V208I, A281L V100K), D53 (A111D, V208I, A281L, T3C, T29C, S6R, T24D), D55 (A111D, V208I, A281L, I185M, G210A), D61 (A111D, V208I, A281L, V100Q), D63 (A111D, V208I, A281L, K123R), D64 (A111D, V208I, A281L, S157T), D65 (A111D, V208I, A281L, G175S), D66 (A111D, V208I, A281L, Q176T) and D67 (A111D, V208I, A281L, C236T) showed especially good stability in Ecolabel Reference Detergent compared to m26.

The results show that mutant proteases were constructed that have improved stability and also similar or even better stain removal performance compared to the wild type protease. According to a preferred embodiment the Fe_RF6318 serine protease variant of the invention is a polypeptide, which has serine protease activity and comprises an amino acid sequence having a substitution of valine at position 208 of the parent wild type Fe_RF6318 serine protease with an amino acid other than valine, wherein the position of the substitution corresponds to the amino acid sequence of the mature Fe_RF6318 enzyme as defined in SEQ ID NO:2.

Preferably, the serine protease variant of the invention comprises a substitution which results in improved thermal stability and/or improved stability in liquid detergents and has retained or improved wash performance in liquid and powdered detergents compared to the parent mature Fe_RF6318 serine protease of SEQ ID NO:2.

Further, the serine protease variant of the invention has good performance in the presence of detergent, i.e. is capable of degrading or removing proteinaceous stains or material in the presence of detergent at low to moderate temperature ranges, such as from 30° C. to 50° C. Specifically the protease variant of the invention has similar or better wash performance than the parent wild-type Fe_RF6318 protease.

Preferably, the serine protease variant has serine protease activity and comprises an amino acid sequence having substitution of valine at position 208 of the parent Fe_RF6318 serine protease with an amino acid selected from the group of isoleucine, leucine and methionine, wherein the position of the substitution corresponds to the amino acid sequence of the mature Fe_RF6318 enzyme as defined in SEQ ID NO:2. The substitutions with isoleucine, leucine and methionine change rigidity of the polypeptide.

Thus, one preferred embodiment of the invention is a Fe_RF6318 variant, which has serine protease activity and comprises an amino acid sequence having substitution of valine at position 208 of the parent Fe_RF6318 serine protease with an amino acid isoleucine (V208I), with an amino acid leucine (V208L) or with an amino acid methionine (V208M), wherein the position of the substitution corresponds to the amino acid sequence of the mature Fe_RF6318 enzyme as defined in SEQ ID NO:2.

Preferably, the serine protease variant of the invention comprises an amino acid sequence having the substitution V208I relative to the parent mature Fe_RF6318 serine protease, wherein the position of the substitution corresponds to the amino acid sequence of the mature Fe_RF6318 enzyme as defined in SEQ ID NO:2.

Another preferred embodiment of the invention is a serine protease variant which has serine protease activity and, in addition to the substitution of valine at position 208 of the parent Fe_RF6318 serine protease, comprises one or more amino acid changes, which are selected from the group consisting of a substitution, insertion and deletion.

The term "substitution" in the present invention means replacement of one or more amino acids in the naturally-occurring amino-acid sequence of a protein or polypeptide with another amino acid. If a functionally equivalent amino acid is substituted, the protein may retain wild-type activity. Substitution may also diminish or eliminate protein function or modify the wild-type activity. Substitutions are indicated by the term corresponding to "V208I" which means that valine at position 208 of the parent Fe_RF6318 is substituted with isoleucine, wherein the amino acid position corresponds to the amino acid sequence of the mature Fe_RF6318 serine protease of SEQ ID NO:2.

Insertion of one or more amino acids to the wild-type amino acid sequence may result in an enzyme which is more resistant to the action of other proteases, including also autocatalysis. The present invention provides stabilization of the Fe_RF6318 serine protease by insertion of glycine at position 104 of the parent Fe_RF6318 serine protease. The insertion is indicated by the term "G104".

Stabilization may be improved also by introducing one or more cysteines into the amino acid sequence, thus creating additional disulphide bonds and stabilizing the three-dimensional structure of the protein. The invention provides e.g. variants which include one additional cysteine bridge between cysteines at positions 3 and 29 of the parent Fe_RF6318 protease, indicated by the term "T3C-T29C". Stability of the three-dimensional structure may also be improved by insertion of additional salt bridges between the amino acids. The present invention provides e.g. variants which include a salt bridge between arginine at position 6 and aspartic acid at position 24 of the parent Fe_RF6318 protease, indicated by the term "S6R-T24D".

Deletion of a naturally-occurring amino acid is indicated by the symbol "Δ". Thus, the term "ΔN167" means that the asparagine at position 167 of the parent Fe_RF6318 protease is deleted. Similarly, the terms "ΔA65" and "ΔH66" mean that the alanine at position 65 and histidine at position 66 of the parent Fe_RF6318 protease are deleted.

In one preferred embodiment of the invention the serine protease variant comprises, in addition to the substitution of valine at position 208 of the parent Fe_RF6318 serine protease, one or more amino acid changes selected from the group consisting of an amino acid substitution at position 3, 6, 7, 8, 14, 17, 18, 22, 24, 25, 28, 29, 33, 34, 36, 37, 46, 47, 52, 56, 61, 63, 65, 69, 76, 77, 83, 88, 91, 100, 103, 106, 111, 113, 114, 121, 123, 138, 144, 151, 153, 155, 157, 158, 164, 167, 169, 173, 174, 175, 176, 185, 196, 205, 206, 210, 214, 216, 230, 234, 236, 239, 247, 248, 249, 252, 256, 260, 268, 281, 282, 283, 284, 286, 287 or 288 of the parent Fe_RF6318 serine protease, a deletion of asparagine at position 167 of the parent Fe_RF6318 serine protease, a deletion of alanine at position 65 and histidine at position 66 of the parent Fe_RF6318 serine protease, and an amino acid insertion at position 104 of the parent Fe_RF6318 serine protease, wherein the amino acid positions correspond to the amino acid sequence of the mature Fe_RF6318 serine protease of SEQ ID NO:2.

In another preferred embodiment of the invention, according to increase in thermostability, the serine protease variant comprises, in addition to the substitution of valine at position 208 of the parent Fe_RF6318 serine protease, one or more amino acid changes selected from the group consisting of an amino acid substitution at position 3, 6, 14, 24, 29, 33, 34, 47, 52, 61, 63, 65, 83, 91, 100, 103, 106, 111, 121, 144, 153, 157, 158, 164, 175, 176, 185, 210, 234, 236, 256, 268 or 281 of the parent Fe_RF6318 serine protease, and an amino acid insertion at position 104 of the parent Fe_RF6318 serine protease, wherein the amino acid positions correspond to the amino acid sequence of the mature Fe_RF6318 serine protease of SEQ ID NO:2.

In another preferred embodiment of the invention, according to increase in thermostability, the serine protease variant comprises, in addition to the substitution of valine at position 208 of the mature Fe_RF6318 serine protease, one or more amino acid changes selected from the group consisting of an amino acid substitution at position 3, 6, 24, 29, 33, 47, 100, 103, 106, 111, 185, 210, 268 or 281 of the parent Fe_RF6318 serine protease, and an amino acid insertion at position 104 of the parent Fe_RF6318 serine protease, wherein the amino acid positions correspond to the amino acid sequence of the mature Fe_RF6318 serine protease of SEQ ID NO:2.

In the most preferred embodiment of the invention, according to increase in thermostability, the serine protease variant comprises an amino acid sequence having the substitution V208I (SEQ ID NO:6), V208I-A111D (SEQ ID NO:8), V208I-A281L (SEQ ID NO:10), V208I-A111D-A281L (SEQ ID NO:12), V208I-A111D-A281L-A33E (SEQ ID NO:14), V208I-A111D-A281L-A47E (SEQ ID NO:16), V208I-A111D-A281L-I185M (SEQ ID NO:20), V208I-A111D-A281L-T268R (SEQ ID NO:22), V208I-A111D-A281L-Q103A-ins.G104 (SEQ ID NO:24), V208I-A111D-

A281L-T3C-T29C SEQ ID NO:26), V208I-A111D-A281L-S6R-T24D (SEQ ID NO:28), V208I-A111D-A281L-V100D (SEQ ID NO:30), V208I-A111D-A281L-T106N (SEQ ID NO: 34), V208I-A111D-A281L-T3C-T29C-S6R-T24D (SEQ ID NO:36) or V208I-A111D-A281L-I185M-G210A (SEQ ID NO:38) relative to the parent Fe_RF6318 serine protease, wherein the amino acid positions correspond to the amino acid sequence of the mature Fe_RF6318 serine protease defined in SEQ ID NO:2.

In another preferred embodiment of the invention, according to stability in detergent, the serine protease variant comprises, in addition to the substitution of valine at position 208 of the parent Fe_RF6318 serine protease, one or more amino acid substitutions at position 3, 6, 24, 29, 33, 37, 47, 61, 63, 65, 83, 100, 111, 123, 157, 175, 176, 185, 210, 234, 236, 247, 268 or 281 of the parent Fe_RF6318 serine protease, wherein the amino acid positions correspond to the amino acid sequence of the mature Fe_RF6318 serine protease of SEQ ID NO:2.

In another preferred embodiment of the invention, according to stability in detergent, the serine protease variant comprises, in addition to the substitution of valine at position 208 of the parent Fe_RF6318 serine protease, one or more amino acid substitutions at position 3, 6, 24, 29, 33, 47, 63, 100, 111, 123, 157, 175, 176, 185, 210, 236, 268 or 281 of the parent Fe_RF6318 serine protease, wherein the amino acid positions correspond to the amino acid sequence of the mature Fe_RF6318 serine protease of SEQ ID NO:2.

In the most preferred embodiment of the invention, according to stability in detergent, the serine protease variant comprises an amino acid sequence having a substitution V208I (SEQ ID NO:6), V208I-A111D (SEQ ID NO:8), V208I-A281L (SEQ ID NO:10), V208I-A111D-A281L (SEQ ID NO:12), V208I-A111D-A281L-A33E (SEQ ID NO:14), V208I-A111D-A281L-A47E (SEQ ID NO:16), V208I-A111D-A281L-G63P (SEQ ID NO:18), V208I-A111D-A281L-I185M (SEQ ID NO:20), V208I-A111D-A281L-T268R (SEQ ID NO:22), V208I-A111D-A281L-T3C-T29C (SEQ ID NO:26), V208I-A111D-A281L-V100K (SEQ ID NO:32), V208I-A111D-A281L-T3C-T29C-S6R-T24D (SEQ ID NO:36), V208I-A111D-A281L-I185M-G210A (SEQ ID NO:38), V208I-A111D-A281L-V100Q (SEQ ID NO:40), V208I-A111D-A281L-K123R (SEQ ID NO:42), V208I-A111D-A281L-S157T (SEQ ID NO:44), V208I-A111D-A281L-G175S (SEQ ID NO:46), V208I-A111D-A281L-Q176T (SEQ ID NO:48) or V208I-A111D-A281L-C236T (SEQ ID NO:50) relative to the parent Fe_RF6318 serine protease, wherein the amino acid positions correspond to the amino acid sequence of the mature Fe_RF6318 serine protease defined in SEQ ID NO:2.

According to the most preferred embodiment of the invention the serine protease variant polypeptide is encoded by an isolated polynucleotide sequence which encodes the polypeptide comprising the amino acid sequence of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, and SEQ ID NO:50.

Thus, within the scope of the invention is the polypeptide encoded by the nucleic acid molecule, which includes the nucleotide sequence comprising the "coding sequence" for the enzyme. The expression "coding sequence" means the nucleotide sequence which initiates from the translation start codon (ATG) and stops at the translation stop codon (TAA, TAG or TGA). The translated full-length polypeptide starts usually with methionine and comprises intron regions. Thus, within the scope of the invention are the serine protease variants which comprise the mature form of the Fe_RF6318 enzyme, as well as the pro-form and prepro-form of the enzyme. The prepro-form is the preferred construction since this facilitates the expression, secretion and maturation of the serine protease variants.

The present invention relates also to an isolated nucleic acid molecule comprising a nucleotide sequence encoding the fungal serine protease (Fe_RF6318) variant according to the invention.

Thus, according to a preferred embodiment of the invention the isolated nucleic acid molecule comprises a nucleotide sequence encoding the Fe_RF6318 serine protease variant, which has serine protease activity and comprises an amino acid sequence having substitution of valine at position 208 of the parent Fe_RF6318 serine protease with an amino acid other than valine, wherein the position of the substitution corresponds to the amino acid sequence of the mature Fe_RF6318 enzyme as defined in SEQ ID NO:2.

Preferably, the isolated nucleic acid molecule comprises a nucleotide sequence encoding a fungal serine protease (Fe_RF6318) variant which carries a substitution resulting in improved thermal stability and/or improved stability in detergents when compared to the parent mature Fe_RF6318 serine protease of SEQ ID NO:2. The variant has retained or improved wash performance in liquid or powdered detergents compared to the parent mature Fe_RF6318 serine protease of SEQ ID NO:2. Thus, the fungal serine protease variant of the invention has good performance in the presence of detergent, i.e. is capable of degrading or removing proteinaceous stains or material in the presence of detergent at low to moderate temperature ranges, such as from 30° C. to 50° C.

One preferred embodiment of the invention is an isolated nucleic acid molecule which comprises a nucleotide sequence encoding a serine protease variant, which has serine protease activity and comprises an amino acid sequence having substitution of valine at position 208 of the parent Fe_RF6318 serine protease with an amino acid selected from the group of isoleucine, leucine and methionine wherein the position of the substitution corresponds to the amino acid sequence of the mature Fe_RF6318 enzyme as defined in SEQ ID NO:2. The substitutions with isoleucine, leucine and methionine change the rigidity of the polypeptide.

Thus, one preferred embodiment of the invention is an isolated nucleic acid molecule comprising a nucleotide sequence encoding a serine protease variant, which has serine protease activity and comprises an amino acid sequence having substitution of valine at position 208 of the parent Fe_RF6318 serine protease with an amino acid isoleucine (V208I), with an amino acid leucine (V208L), or with an amino acid methionine (V208M), wherein the position of the substitution corresponds to the amino acid sequence of the mature Fe_RF6318 enzyme as defined in SEQ ID NO:2.

Preferably, the encoded serine protease variant of the invention comprises an amino acid sequence having the substitution V208I relative to the parent mature Fe_RF6318 serine protease, wherein the position of the substitution corresponds to the amino acid sequence of the mature Fe_RF6318 enzyme as defined in SEQ ID NO:2.

Another preferred embodiment of the invention is an isolated nucleic acid molecule which comprises a nucleotide sequence encoding a serine protease variant, which has serine protease activity and, in addition to the substitution of valine at position 208 of the parent Fe_RF6318 serine protease, comprises one or more amino acid changes, which are selected from the group consisting of a substitution, insertion, deletion or insertion.

In one preferred embodiment of the invention the isolated nucleic acid molecule comprises a nucleotide sequence which encodes a serine protease variant comprising, in addition to the substitution of valine at position 208 of the parent Fe_RF6318 serine protease, one or more amino acid changes selected from the group consisting of an amino acid substitution at position 3, 6, 7, 8, 14, 17, 18, 22, 24, 25, 28, 29, 33, 34, 36, 37, 46, 47, 52, 56, 61, 63, 65, 69, 76, 77, 83, 88, 91, 100, 103, 106, 111, 113, 114, 121, 123, 138, 144, 151, 153, 155, 157, 158, 164, 167, 169, 173, 174, 175, 176, 185, 196, 205, 206, 210, 214, 216, 230, 234, 236, 239, 247, 248, 249, 252, 256, 260, 268, 281, 282, 283, 284, 286, 287 or 288 of the parent Fe_RF6318 serine protease, a deletion of asparagine at position 167 of the parent Fe_RF6318 serine protease, a deletion of alanine at position 65 and histidine at position 66 of the parent. Fe_RF6318 serine protease, and an amino acid insertion at position 104 of the parent Fe_RF6318 serine protease, wherein the amino acid positions correspond to the amino acid sequence of the mature Fe_RF6318 serine protease of SEQ ID NO:2.

In another preferred embodiment of the invention, according to increase in thermostability, the isolated nucleic acid molecule comprises a nucleotide sequence, which encodes a serine protease variant comprising, in addition to the substitution of valine at position 208 of the parent Fe_RF6318 serine protease, one or more amino acid changes selected from the group consisting of an amino acid substitution at position 3, 6, 14, 24, 29, 33, 34, 47, 52, 61, 63, 65, 83, 91, 100, 103, 106, 111, 121, 144, 153, 157, 158, 164, 175, 176, 185, 210, 234, 236, 256, 268 or 281 of the parent Fe_RF6318 serine protease, and an amino acid insertion at position 104 of the parent Fe_RF6318 serine protease, wherein the amino acid positions correspond to the amino acid sequence of the mature Fe_RF6318 serine protease of SEQ ID NO:2.

In another preferred embodiment of the invention, according to increase in thermostability, the isolated nucleic acid molecule comprises a nucleotide sequence which encodes a serine protease variant comprising, in addition to the substitution of valine at position 208 of the parent Fe_RF6318 serine protease, one or more amino acid changes selected from the group consisting of an amino acid substitution at position 3, 6, 24, 29, 33, 47, 100, 103, 106, 111, 185, 210, 268 or 281 of the parent Fe_RF6318 serine protease, and an amino acid insertion at position 104 of the parent Fe_RF6318 serine protease, wherein the amino acid positions correspond to the amino acid sequence of the mature Fe_RF6318 serine protease of SEQ ID NO:2.

In the most preferred embodiment of the invention, according to increase in thermostability, the encoded serine protease variant comprises an amino acid sequence having substitution V208I, V208I-A111D, V208I-A281L, V208I-A111D-A281L, V208I-A111D-A281L-A33E, V208I-A111D-A281L-A47E, V208I-A111D-A281L-I185M, V208I-A111D-A281L-T268R, V208I-A111D-A281L-Q103A-ins.G104, V208I-A111D-A281L-T3C-T29C, V208I-A111D-A281L-S6R-T24D, V208I-A111D-A281L-V100D, V208I-A111D-A281L-T106N, V208I-A111D-A281L-T3C-T29C-S6R-T24D or V208I-A111D-A281L-I185M-G210A relative to the parent Fe_RF6318 serine protease, wherein the amino acid positions correspond to the amino acid sequence of the mature Fe_RF6318 serine protease defined in SEQ ID NO:2.

In another preferred embodiment of the invention, according to stability in detergent, the isolated nucleic acid molecule comprises a nucleotide sequence which encodes a serine protease variant comprising, in addition to substitution of valine at position 208 of the parent Fe_RF6318 serine protease, one or more amino acid substitutions at position 3, 6, 24, 29, 33, 37, 47, 61, 63, 65, 83, 100, 111, 123, 157, 175, 176, 185, 210, 234, 236, 247, 268, 281 of the parent Fe_RF6318 serine protease, wherein the amino acid positions correspond to the amino acid sequence of the mature Fe_RF6318 serine protease of SEQ ID NO:2.

In another preferred embodiment of the invention, according to stability in detergent, the encoded serine protease variant comprises, in addition to the substitution of valine at position 208 of the parent Fe_RF6318 serine protease, one or more amino acid substitutions at position 3, 6, 24, 29, 33, 47, 63, 100, 111, 123, 157, 175, 176, 185, 210, 236, 268, 281 of the parent Fe_RF6318 serine protease, wherein the amino acid positions correspond to the amino acid sequence of the mature Fe_RF6318 serine protease of SEQ ID NO:2.

In the most preferred embodiment of the invention, according to stability in detergent, the encoded serine protease variant comprises an amino acid sequence having the substitution V208I, V208I-A111D, V208I-A281L, V208I-A111D-A281L, V208I-A111D-A281L-A33E, V208I-A111D-A281L-A47E, V208I-A111D-A281L-G63P, V208I-A111D-A281L-I185M, V208I-A111D-A281L-T268R, V208I-A111D-A281L-T3C-T29C, V208I-A111D-A281L-V100K, V208I-A111D-A281L-T3C-T29C-S6R-T24D, V208I-A111D-A281L-I185M-G210A, V208I-A111D-A281L-V100Q, V208I-A111D-A281L-K123R, V208I-A111D-A281L-S157T, V208I-A111D-A281L-G175S, V208I-A111D-A281L-Q176T or V208I-A111D-A281L-C236T relative to the parent Fe_RF6318 serine protease, wherein the amino acid positions correspond to the amino acid sequence of the mature Fe_RF6318 serine protease defined in SEQ ID NO:2.

According to the most preferred embodiment of the invention the isolated nucleic acid molecule comprises the nucleotide sequence defined in SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, and SEQ ID NO:49.

The nucleic acid molecule of the invention may be RNA or DNA, wherein the DNA may constitute of the genomic DNA or cDNA.

Standard molecular biology methods can be used in construction of the polynucleotide sequence encoding the fungal serine protease variant of the invention, including isolation of genomic and plasmid DNA, digestion of DNA to produce DNA fragments, sequencing, *E. coli* transformations etc. The basic methods are described in the standard molecular biology handbooks, e.g. Sambrook and Russell, 2001.

Constructions of the Fe prtS8A mutant genes encoding the Fe_RF6318 polypeptide variants of the invention are described in Examples 3, 6, 9 and 16. Briefly, the synthetic cDNAs encoding the wild type Fe_RF6318 protease and the protease variants of the invention were ordered from GenScript Corporation (NJ, U.S.A.). The inserts from the GenScript plasmids were isolated from agarose gel after SacII-AgeI digestion and ligated to pALK1919 or pALK2777 vector backbone. The expression cassettes contained the cDNAs encoding the full-length wild-type Fe_RF6318 serine protease or the protease variants of the invention. The cassettes contained also the *T. reesei* cbh1 (cel7A) promoter and terminator regions and the amdS marker gene (Hynes et al.

Figure 5A:
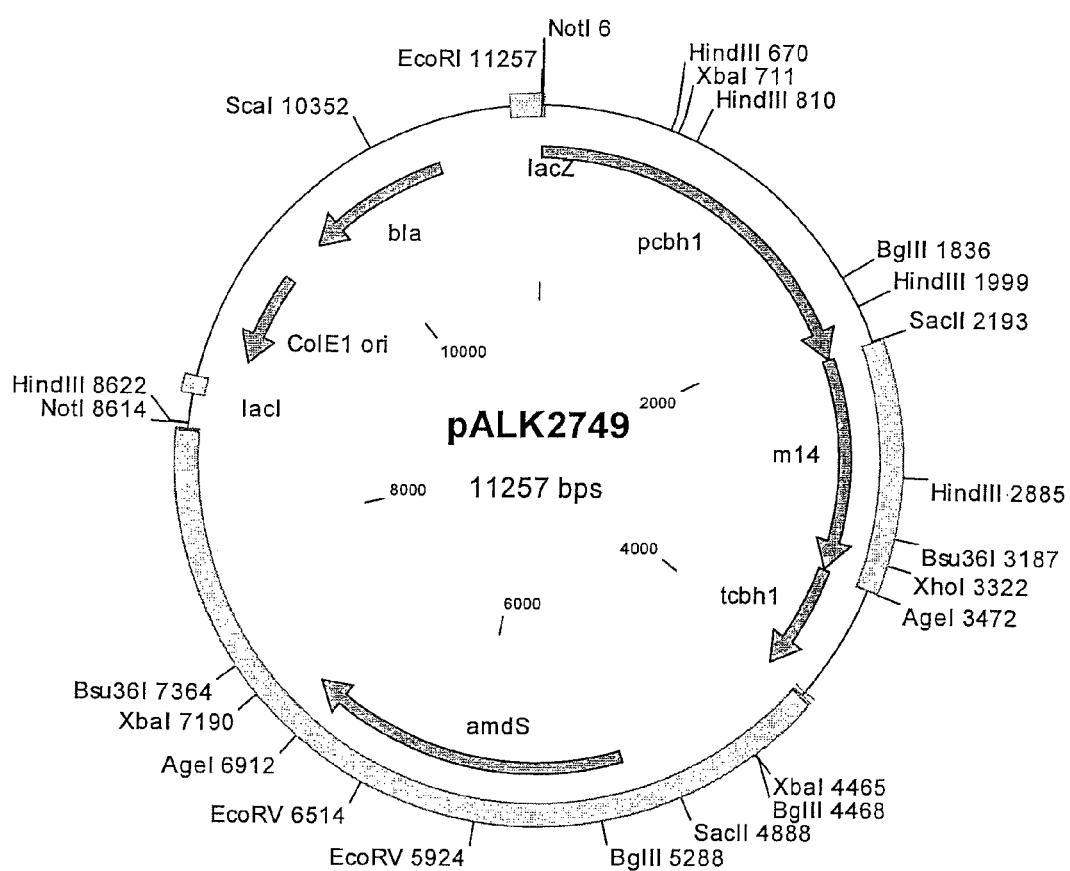
FIG. 5A shows the map of pALK2749 including the m14 expression cassette as an example of a plasmid constructed for mutant protease expression in *T. reesei*, basing on ligation of the mutant gene to pALK1910. The corresponding plasmids including the cassettes for m1-m13 production are listed in Table 2. Only the relevant restriction sites are shown. pcbh1, cbh1 promoter; tcbh1, cbh1 terminator; m14, Fe prtS8A mutant protease gene (cDNA) m14; amdS, amdS marker gene.
Figure 5B:
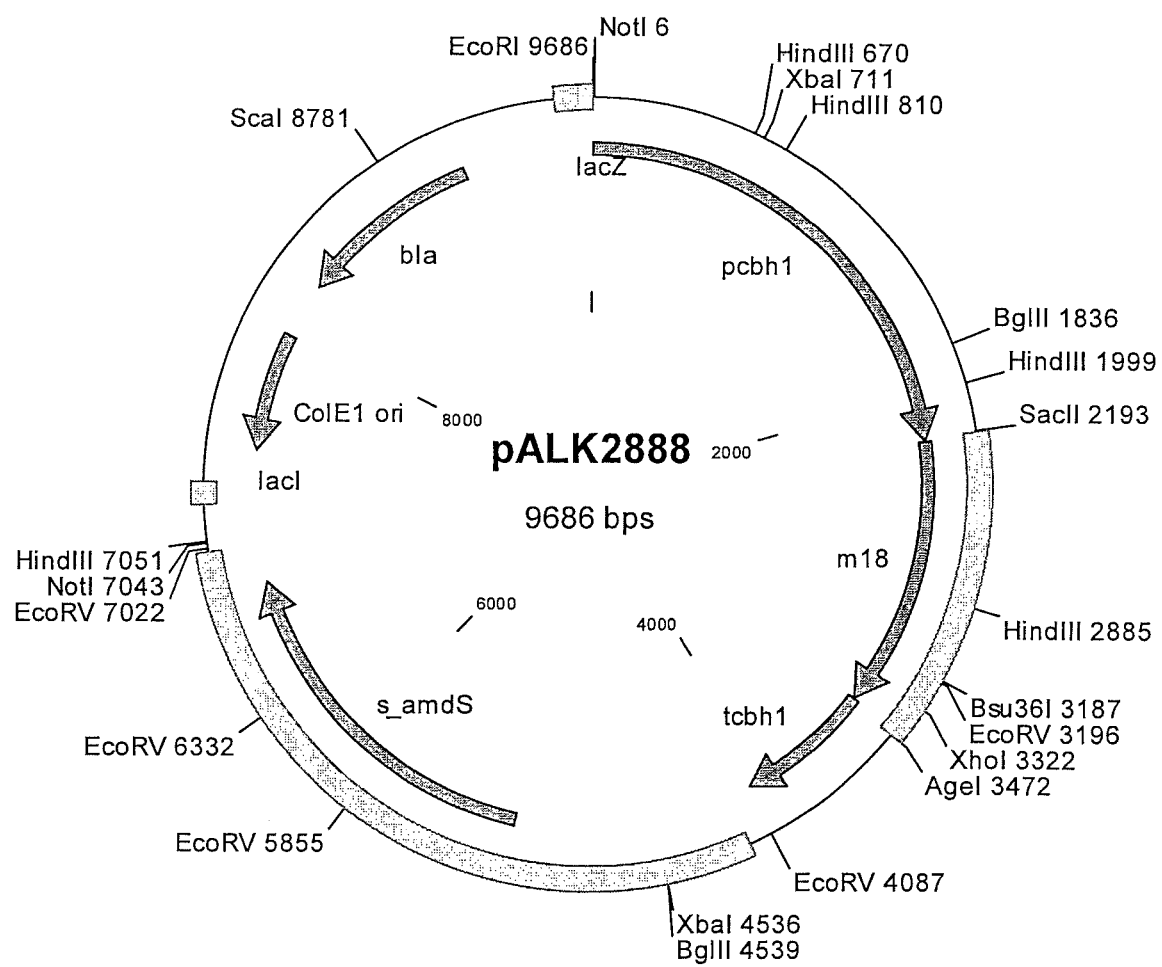
FIG. 5B shows the map of pALK2888 including the m18 expression cassette as an example of a plasmid constructed for mutant protease expression in *T. reesei*, basing on ligation of the mutant gene to pALK2777. The corresponding plasmids including the cassettes for m15-m17 and m19-m23 mutant protease production are listed in Table 2, those for m24-m26 production in Table 4, for D1-D30 production in Table 5 and for D31-D68 production in Table 9. Only the relevant restriction sites are shown. pcbh1, cbh1 promoter; tcbh1, cbh1 terminator; m18, Fe prtS8A mutant protease gene III18 (cDNA); s_amdS, synthetic amdS marker gene (cDNA).

1983) for selecting the transformants. The sequences of the gene fusions and the mutations in the cDNA sequences were confirmed from the genetic constructions by sequencing. Examples of the plasmid constructions carrying the mutant protease expression cassette are provided in FIG. 5.

The nucleic acid molecule of the invention may also be an analogue of the nucleotide sequence characterized above. For example, due to degeneracy of the nucleotide sequence. The "degeneracy" means analogues of the nucleotide sequence, which differ in one or more nucleotides or codons, but which encode the Fe_RF6318 protease variant of the invention.

The present invention relates also to a recombinant expression vector or recombinant expression construct, which can be used to propagate or express the nucleic acid sequence encoding the chosen swine protease variant in a suitable prokaryotic or eukaryotic host. The recombinant expression vector comprises a nucleotide sequence encoding the serine protease variant of the invention operably linked to regulatory sequences which facilitate or direct expression and preferably, secretion of a sequence encoding the serine protease variant of the invention in a suitable host, such as promoters, enhancers, terminators (including transcription and translation termination signals) and signal sequences operably linked the polynucleotide sequence encoding said serine protease variant. The expression vector may further comprise marker genes for selection of the transformant strains or the selection marker may be introduced to the host in another vector construct by co-transformation. Said regulatory sequences may be homologous or heterologous to the production organism or they may originate from the organism, from which the gene encoding the serine protease is isolated.

Examples of promoters for expressing the serine protease variant of the invention in filamentous fungal hosts are the promoters of *A. oryzae* TAKA amylase, alkaline protease ALP and triose phosphate isomerase, *Rhizopus miehei* lipase, *Aspergillus niger* or *A. awamori* glucoamylase (glaA), *Fusarium oxysporum* trypsin-like protease, *Chrysosporium lucknowense* cellobiohydrolase 1 promoter, *Trichoderma reesei* cellobiohydrolase I (Cel7A) etc.

In yeast, for example promoters of *S. cerevisiae* enolase (ENO-1), galactokinase (GAL1), alcohol dehydrogenase (ADH2) and 3-phosphoglycerate kinase can be used to provide expression.

Examples of promoter sequences for directing the transcription of the serine protease variant of the invention in a bacterial host are the promoter of lac operon of *Escherichia coli*, the *Streptomyces coelicolor* agarase dagA promoter, the promoter of the *B. licheniformis* alpha-amylase gene (amyL), the promoter of the *B. stearothermophilus* maltogenic amylase gene (amyM), the promoters of the *B. sublitis* xylA and xylB genes, etc.

Suitable terminators include those of the above mentioned genes or any other characterized terminator sequences.

Suitable transformation or selection markers include those which complement a defect in the host, for example the dal genes from *B. subtilis* or *B. licheniformis* or *Aspergillus* amdS and niaD. The selection may be based also on a marker conferring antibiotic resistance, such as ampicillin, kanamycin, chloramphenicol, tetracycline, phleomycin or hygromycin resistance.

Extracellular secretion of the serine protease variant of the invention is preferable. Thus, the recombinant vector comprises sequences facilitating secretion in the selected host. The signal sequence of the serine protease of the invention or the presequence or prepeptide may be included in the recombinant expression vector or the natural signal sequence may be replaced with another signal sequence capable of facilitating secretion in the selected host. Thus, the chosen signal sequence may be homologous or heterologous to the expression host.

Examples of suitable signal sequences are those of the fungal or yeast organisms, e.g. signal sequences from well expressed genes. Such signal sequences are well known from the literature.

The recombinant vector may further comprise sequences facilitating integration of the vector into the host chromosomal DNA to obtain stable expression.

The Fe_RF6318 protease variant of the invention was expressed with its own signal sequence from the *T. reesei* cbh1 (cel7A) promoter as described in Examples 3, 6, 9 and 16. The expression constructs used to transform the *T. reesei* host included also cbh1 terminator and amdS marker for selecting the transformants from the untrasformed cells.

The present invention relates also to host cells comprising the recombinant expression vector as described above. Suitable hosts for production of the fungal serine protease variant are homologous or heterologous hosts, such as the microbial hosts including bacteria, yeasts and fungi. Production systems in plant or mammalian cells are also possible.

Filamentous fungi, such *Trichoderma, Aspergillus, Fusarium, Humicola, Chrysosporium, Neurospora, Rhizopus, Penicillium* and *Mortiriella*, are preferred production hosts due to the ease of down-stream processing and recovery of the enzyme product. Suitable expression and production host systems are for example the production system developed for the filamentous fungus host *Trichoderma reesei* (EP 244234), or *Aspergillus* production systems, such as *A. oryzae* or *A. niger* (WO 9708325, U.S. Pat. No. 5,843,745, U.S. Pat. No. 5,770,418), *A. awamori, A. sojae* and *A. japonicus*-type strains, or the production system developed for *Fusarium*, such as *F. oxysporum* (Malardier et al., 1989) or *F. venenatum*, and for *Neurospora crassa, Rhizopus miehei, Mortiriella alpinis, H. lanuginosa* or *H. insolens* or for *Chrysosporium lucknowense* (U.S. Pat. No. 6,573,086). Suitable production systems developed for yeasts are systems developed for *Saccharomyces, Schizosaccharomyces* or *Pichia pastoris*. Suitable production systems developed for bacteria are a production system developed for *Bacillus*, for example for *B. subtilis, B. licheniformis, B. amyloliquefaciens*, for *E. coli*, or for the actinomycete *Streptomyces*.

Preferably the serine protease variant of the invention is produced in a filamentous fungal host of the genus *Trichoderma* or *Aspergillus*, such as *T. reesei*, or *A. niger, A oryzae, A. sojae, A. awamori* or *A. japonicus*-type strains. According the most preferred embodiment of the invention the fungal serine protease (Fe_RF6318) variant is produced in *T. reesei*.

The production host cell may be homologous or heterologous to the serine protease variant of the invention. The host may be free of homogenous proteases due to removal of proteases either by inactivation or removal of one or more host proteases, e.g. by deletion of the gene(s) encoding such homogenous or homologous proteases.

The serine protease enzyme variant of the invention derives from a filamentous fungi belonging to a genus *Fusarium*. Fungal alkaline proteases are advantageous to the bacterial proteases due to the ease of down-stream processing to produce a microbe-free enzyme or enzyme composition. Mycelium can be easily removed through filtration techniques prior to the purification of the enzyme.

The present invention relates also to a process for producing a polypeptide having serine protease activity, said process comprising the steps of culturing the natural or recombinant host cell carrying the recombinant expression vector for a serine protease variant of the invention under suitable conditions and optionally isolating said variant enzyme. The production medium may be a medium suitable for growing the host organism and containing inducers for efficient expression. Suitable media are well-known from the literature.

The invention further relates to a process for obtaining an enzyme preparation comprising a variant polypeptide, which has serine protease activity, said process comprising the steps of culturing a host cell carrying the expression vector of the invention and either recovering the variant polypeptide from the cells or separating the cells from the culture medium and obtaining the supernatant having serine protease activity.

The produced variant enzymes can be purified by using conventional methods of enzyme chemistry, such as salt preparation, ultrafiltration, ion exchange chromatography, affinity chromatography, gel filtration and hydrophobic interaction chromatography. Purification can be monitored by protein determination, enzyme activity assays and by SDS polyacrylamide gel electrophoresis. The enzyme activity and stability of the purified enzyme at various temperature and pH values as well as the molecular mass and the isoelectric point can be determined.

Naturally, it is possible to separate the enzyme of the present invention by using other known purification methods instead, or in addition to the methods described herein.

The present invention relates also to an enzyme preparation, which comprises the serine protease variant characterized above. Within the invention is an enzyme preparation which comprises the fungal serine protease variant of the invention, obtained by culturing a host cell, which carries the recombinant expression vector of the invention.

Said enzyme preparation may further comprise different types of enzymes in addition to the serine protease variant of this invention, for example another protease, an amylase, a lipase, a cellulase, cutinase, a pectinase, a mannanase, a xylanase and/or an oxidase such as a laccase or peroxidase with or without a mediator. These enzymes are expected to enhance the performance of the serine protease variants of the invention by removing the carbohydrates and oils or fats present in the material to be handled. Said enzymes may be natural or recombinant enzymes produced by the host strain or may be added to the culture supernatant after the production process.

Said enzyme preparation may further comprise a suitable additive selected from the group of surfactants or surface active agent, buffers, anti-corrosion agents, stabilizers, bleaching agents, mediators, builders, caustics, abrasives and preservatives, optical brighteners, antiredeposition agents, dyes, pigments, perfumes, etc.

Surfactants are useful in emulsifying grease and wetting surfaces. The surfactant may be a non-ionic including semipolar and/or anionic and/or cationic and/or zwitterionic.

Buffers may be added to the enzyme preparation to modify pH or affect performance or stability of other ingredients.

Suitable stabilizers include polyols such as propylene glycol or glycerol, a sugar or sugar alcohol, lactic acid, boric acid, or boric or boronic acid derivatives, peptides, lyotropic salts, etc.

Bleaching agent is used to oxidize and degrade organic compounds. Examples of suitable chemical bleaching systems are $H_2O_2$ sources, such as perborate or percarbonate with or without peracid-forming bleach activators such as tetraacetylethylenediamine, or alternatively peroxyacids, e.g. amide, imide or sulfone type. Chemical oxidizers may be replaced partially or completely by using oxidizing enzymes, such as laccases or peroxidases. Many laccases do not function effectively in the absence of mediators.

Builders or complexing agents include substances, such as zeolite, diphosphate, triphosphate, carbonate, citrate, etc. The enzyme preparation may further comprise one or more polymers, such as carboxymethylcellulose, poly(ethylene glycol), poly(vinyl alcohol), poly(vinylpyrrolidone), etc. Also, softeners, caustics, preservatives for preventing spoilage of other ingredients, abrasives and substances modifying the foaming and viscosity properties can be added.

According to one preferred embodiment of the invention said enzyme preparation is in the form of liquid, powder or granulate.

The Fe_RF6318 serine protease variant of the present invention may like other proteases, particularly alkaline proteases be used in the detergent, protein, brewing, meat, photographic, leather, dairy and pharmaceutical industries (Kalisz, 1988; Rao et al., 1998). For example, it may be used as an alternative to chemicals to convert fibrous protein waste (e.g. horn, feather, nails and hair) to useful biomass, protein concentrate or amino acids (Anwar and Saleemuddin, 1998). The use of fungal serine protease variant of the present invention may like other enzymes prove successful in improving leather quality and in reducing environmental pollution and saving energy and it may like alkaline proteases be useful in synthesis of peptides and resolution of the mixture of D,L-amino acids. The fungal serine protease variants of the present invention may find use in pharmaceutical industry and may also like other alkaline proteases be applicable in removal of blood on surgical equipments and cleaning contact lenses or dentures. Like alkaline protease from *Conidiobolus coronatus*, the serine protease variant of the present invention may be used for replacing trypsin in animal cell cultures. The protease variants of the invention can also be used in cleaning of membranes and destruction of biofilms. In baking the protease variants can be used e.g. in destruction of the gluten network and in other food applications in hydrolysis of food proteins, e.g proteins in milk. They can also be used e.g. in treating yeast, rendering (extracting more protein from animal bones), creating new flavours, reducing bitterness, changing emulsifying properties, generating bioactive peptides and reducing allergenicity of proteins. The substrates include animal, plant and microbial proteins.

The present invention relates to the use of the serine protease variant or the enzyme preparation comprising said variant for detergents, treating textile fibers, for treating wool, for treating hair, for treating leather, for treating feed or food, or for any application involving modification, degradation or removal of proteinaceous material.

One preferred embodiment of the invention is therefore the use of the serine protease variant as characterized above as a detergent additive useful for laundry detergent and dish wash compositions, including automatic dish washing compositions.

The serine protease of the present invention degrades various kinds of proteinaceous stains under conditions of neutral and alkaline pH and even in the presence of liquid or powdered detergents with different compositions (as shown in Examples 12 and 14).

One preferred embodiment of the invention is a detergent composition comprising the Fe_RF6318 variant protease as an ingredient. The detergent composition may also comprise the enzyme composition of the invention. The serine protease variant of the invention was shown to have an improved stability in different liquid detergents. Thus, its stability against the destabilizing agents present in the detergent compositions such as surfactants, complexing agents or bleaching agents is better than the stability of the wild-type Fe_RF6318 serine protease.

The "detergent composition" includes an effective amount of a serine protease variant, which has serine protease activity and comprises an amino acid sequence having a substitution of valine at position 208 of the parent Fe_RF6318 polypeptide with an amino acid other than valine, and one or more amino acid changes selected from the group consisting of a substitution at position 3, 6, 7, 8, 14, 17, 18, 22, 24, 25, 28, 29, 33, 34, 36, 37, 46, 47, 52, 56, 61, 63, 65, 69, 76, 77, 83, 88, 91, 100, 103, 106, 111, 113, 114, 121, 123, 138, 144, 151, 153, 155, 157, 158, 164, 167, 169, 173, 174, 175, 176, 185, 196, 205, 206, 210, 214, 216, 230, 234, 236, 239, 247, 248, 249, 252, 256, 260, 268, 281, 282, 283, 284, 286, 287 or 288 of the parent Fe_RF6318 serine protease, a deletion of asparagine at position 167 of the parent Fe_RF6318 serine protease, a deletion of alanine at position 65 and histidine at position 66 of the parent Fe_RF6318 serine protease, and an amino acid insertion at position 104 of the parent Fe_RF6318 serine protease, wherein the position of the substitution corresponds to the amino acid sequence of the mature Fe_RF6318 enzyme as defined in SEQ ID NO:2.

The term "effective amount" of a serine protease refers to the quantity of the protease enzyme necessary to achieve the enzymatic activity in the specific detergent composition. Preferably the detergent composition of the invention comprises from about 0.0001% to about 10% by weight of the detergent composition of a protease variant of the invention, more preferably from 0.001% to about 1%, more preferably from 0.001% to about 0.1%.

According to the experimental results provided below serine protease variants were constructed which have improved thermal stability compared to the parent Fe_RF6318 serine protease. The variants have also improved stability in the presence of different liquid detergents. Similar effects may be observed in any detergent composition wherein the serine protease variant of the invention is an ingredient. The disclosed serine protease variants have similar or even better stain removal performance than the parent Fe_RF6318 serine protease. The protease variant of the invention or the enzyme preparation comprising said variant may be formulated for use in a hand or machine laundry or may be formulated for use in household hard surface cleaning or preferably in hand or machine dishwashing operations.

EXAMPLE 1 a. Protease Activity Assay

Protease activity was measured using casein as substrate. Rate of casein degradation by a protease was measured by monitoring the release of acid-soluble peptide fragments as a function of time. Acid-soluble peptides were quantified spectrophotometrically. The result was expressed as 1 µg of tyrosine per min per ml (or g).

First all reagent solutions needed in the assay were prepared in deionized water, Milli-Q or equivalent as follows.
(STW) Synthetic Tap Water:
  The following stock solutions were prepared:
  (A) 5.8 g $CaCl_2 \times 2$ $H_2O$/200 ml $H_2O$
  (B) 2.8 g $MgCl_2 \times 6$ $H_2O$/200 ml $H_2O$
  (C) 4.2 g $NaHCO_3$/200 ml $H_2O$
  10 ml of these solutions were added in the given order to 300 ml of $H_2O$ with stirring, then made up to 1 liter with $H_2O$. The resulting solution was called as synthetic tap water.

Tris Solution, 0.3 M in Synthetic Tap Water:
  36.3 g of Trizma base (SIGMA T-1503) was dissolved in synthetic tap water and made up to 1 liter.
Casein Solution:
  6 g of Casein Hammarstein grade (Cat. No. 101289 (MP Biomedicals, LCC, US) was added to 350 ml synthetic tap water and dissolved with magnetic stirring for 10 min. 50 ml of Tris solution was added and the solution was stirred for another 10 min. Then, the solution was heated up to 70° C. After that the temperature was let to decrease or cooled to 50° C. and the pH was adjusted to 8.5 with 0.1M NaOH. Stirring was continued until room temperature was reached. The solution was made up to 500 ml with synthetic tap water. The substrate solution was stored for maximum of 3 days in refrigerator or stored as frozen.
110 mM Trichloroacetic Acid Reagent (Reaction Stop Solution):
  18 g of TCA (Merck 807) was dissolved in $H_2O$ and made up to 1 liter.
0.5 M $Na_2CO_3$:
  53 g of $Na_2CO_3$ was dissolved in $H_2O$ and made up to 1 liter.
Folin Solution:
  25 ml of 2N Folin-Ciocalteu's phenol reagent (SIGMA, F 9252) was diluted up to 100 ml with $H_2O$.
Sample Dilution Buffer:
  The sample was diluted in 50 mM Tris-HCl buffer pH 8.5.
  The most suitable dilution will yield an absorbance of 0.4-0.8 in the reaction.
Assay:
  The assay was started by temperating 2.5 ml of substrate solution in test tubes for 5 min at 50° C. After that 0.5 ml of diluted enzyme solution was added, mixed with vortex mixer and the reaction was conducted at 50° C. for exactly 30 min. The enzyme blank was prepared like the sample but the reaction stop solution (110 mM TCA) was added in test tube before the sample. After the reaction 2.5 ml of stop solution was added in tubes (not for blank), the contents were mixed and allowed to stand for 30 minutes at room temperature. Tubes were centrifuged 4000 rpm for 10 minutes (Hettich Rotanta 460). One ml of clear supernatant was mixed with 2.5 ml 0.5 M $Na_2CO_3$ and 0.5 ml diluted Folin reagent. After waiting for 10 min (colour development) the absorbance of the mixture (colour) was measured at 660 nm against an enzyme blank. The activity was read from standard curve and the result was multiplied by the dilution factor. At least two parallel samples were used in each measurement.
Standard:
  A stock solution of tyrosine was prepared by dissolving 100 mg of tyrosine (Merck 8371) in 0.2 M HCl and made the volume up to 500 ml. The following dilutions were made from the stock solution in 0.2 M HCl:

| Dilution | Tyrosine concentration (µg/ml) |
| --- | --- |
| 1:1 | 200 |
| 3:4 | 150 |
| 1:2 | 100 |
| 1:3 | 66.7 |
| 1:4 | 50 |

-continued

| Dilution | Tyrosine concentration (µg/ml) |
|---|---|
| 1:6 | 33.3 |
| 1:8 | 25 |
| 1:12 | 16.7 |

Duplicate assays of each standard dilution were made. 1 ml of each standard dilution was mixed with 2.5 ml 0.5 M Na$_2$CO$_3$ and 0.5 ml of diluted Folin reagent in test tubes. After waiting for 10 min (colour development) the absorbance of the mixture (colour) was measured at 660 nm against an reagent blank. The reagent blank was prepared by adding 0.2 M HCl instead of standard dilution. The corresponding enzyme activity was obtained by dividing tyrosine concentration (µg/ml) by the time of hydrolysis, 30 min.

b. Analysis of Thermal Stability of Proteases

The thermal stability of proteases (protease mutants) was determined using shake flask culture or fermentation supernatant as an enzyme source. Culture supernatants were diluted in 20 mM Tris buffer (Trizma base) pH 8.5. Samples were incubated in test tubes at 40° C., 45° C. or 50° C. in a water bath, for definite time intervals (0-140 min) before residual activity of samples was measured and calculated following standard assay procedure described in Example 1a except that the reaction temperature in the analysis was 40° C., 45° C. or 50° C.

EXAMPLE 2

Isolation of DNA and Molecular Biology Methods Used

Standard molecular biology methods were used in the isolation and enzyme treatments of DNA (e.g. isolation of plasmid DNA, digestion of DNA to produce DNA fragments, ligations), in *E. coli* transformations, sequencing etc. The basic methods used were either as described by the enzyme, reagent or kit manufacturer or as described in the standard molecular biology handbooks, e.g. Sambrook and Russell (2001). Isolation of genomic DNA from *T. reesei* strains was done as described in detail by Raeder and Broda (1985). The oligonucleotides used for sequencing were ordered from Sigma-Aldrich.

EXAMPLE 3

Figure 4:
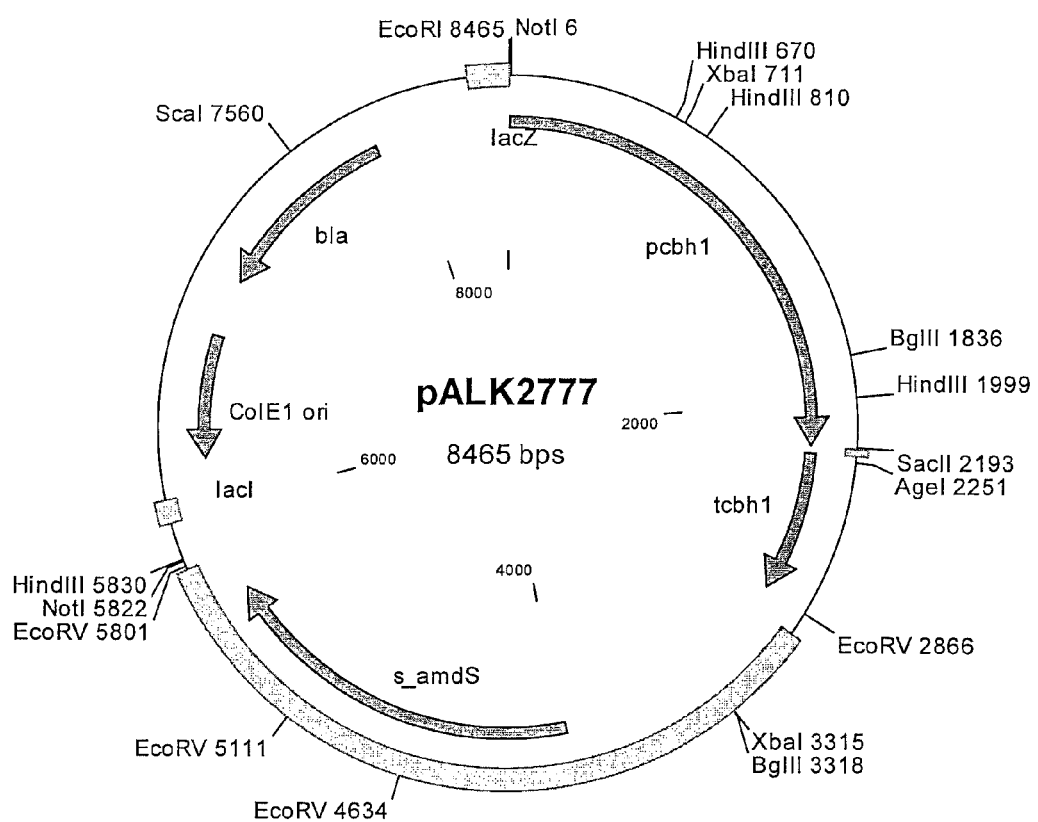
FIG. 4 shows the map of pALK2777 used as a backbone for constructing the cassettes for m15-m26 and D1-D68 mutant protease expression. The DNA fragments encoding the mutant proteases (cDNAs with 5' partial cbh1 promoter and 3' partial cbh1 terminator, see FIG. 2) and cleaved with SacII and AgeI were ligated into SacII-AgeI cleaved pALK2777. This plasmid includes a synthetic amdS marker gene for transformant screening. Only the relevant restriction sites are shown. pcbh1, cbh1 promoter; tcbh1, cbh1 terminator; s_amdS, synthetic amdS marker gene (cDNA).

Design of the m-Series Mutant Proteases m1-m23 and Construction of their Expression Cassettes Mutant proteases were designed basing on sequence comparison of the *Fusarium equiseti* RF6318 (Fe_RF6318) and *F. acuminatum* RF7182 (Fa_RF7182) protease amino acid sequences (SEQ ID NO:2/FI20095497 and SEQ ID NO:14/FI20095499, respectively) and protease structures. The mature amino acid sequences of above *Fusarium* proteases are included as SEQ ID NO:2 and SEQ ID NO:4 in this application. The modifications aimed on increasing the stability of the wild type Fe_RF6318 protease e.g. by reducing the flexibility of the protein structure. First, altogether 23 mutant proteases named as m1-m23 were designed. For construction of the expression cassettes, synthetic genes encoding the wild type Fe_RF6318 protease and mutant proteases were ordered from GenScript Corporation (NJ, US). The mutations were designed and made on the wild type Fe prtS8A cDNA sequence (the cDNA sequence encoding the full-length protease is shown in FIG. 1 and the cDNA sequence encoding the mature polypeptide is included as SEQ ID NO:1). The codons for the amino acids were chosen to be such that are generally used in *T. reesei* cellulase and xylanase genes (Bergquist et al., 2002) and that did not create any additional SacII, AgeI or NotI sites into the sequence. The codes for the mutant proteases designed and the modifications made are listed in Table 2. In addition to the protease cDNA sequence, the synthetic genes ordered included at their 5'-end a partial *Trichoderma reesei* cbh1 (cel7A) promoter sequence from SacII site (position −16 from ATG) to position −1 and in their 3'-end the partial cbh1-terminator sequence to AgeI site (the partial terminator includes 30 nucleotides after the STOP codon). One example of such a synthetic construction (includes the wild type Fe prtS8A cDNA) is shown in FIG. 2. The above additional 5'- and 3'-sequences enabled exact fusions of the synthetic protease cDNAs to the *T. reesei* cbh1 promoter and terminator in the expression cassettes pALK1910 and pALK2777 (FIGS. 3 and 4, respectively). The cbh1 sequences can be found e.g. from JGI's *T. reesei* genome sequence v2.0 (gene ID 123989).

The synthetic gene constructions were, at GenScript, ligated to pUC57 vector (EcoRV site). For construction of the protease expression cassettes, the inserts from the GenScript plasmids were isolated from agarose gel after SacII-AgeI digestion. The inserts including the m1-m14 protease cDNAs were ligated to pALK1910 (FIG. 3) and those including the m15-m23 proteases to pALK2777 (FIG. 4) plasmid digested with SacII and AgeI. Then, the amdS marker (wild type *Aspergillus* gene with its native promoter and terminator; the 4470 bp EcoRI-SpeI fragment from p3SR2; Hynes et al., 1983) was ligated to the EcoRV site of the plasmids basing on pALK1910 backbone. The pALK2777 plasmid already contains a synthetic amdS marker gene and thus the expression plasmids that were constructed using this backbone were ready after the above one-step ligation of the insert to SacII-AgeI digested plasmid. The synthetic amdS in pALK2777 contains a shortened terminator (to XbaI site) compared to the native amdS in pALK1910. Also, the introns of the native amdS gene have been removed and chosen restriction sites from the amdS promoter and gene have been modified to ease the construction and isolation of the expression cassettes. However, the amino acid sequence encoded by the synthetic amdS gene is identical to that encoded by the wild type amdS gene.

The sequences of the gene fusions and the mutations in the cDNA sequences were confirmed from the genetic constructions by sequencing.

The final expression cassettes contain the Fe prtS8A wild type cDNA or mutant protease cDNA (with the protease gene's own signal and pro sequences) were fused to the *T. reesei* cbh1 promoter and terminator (exact fusions) and the amdS marker gene (either native or synthetic, see above) following the cbh1 terminator region. For examples of the plasmids including mutant protease expression cassettes, see FIG. 5.

TABLE 2

The mutant proteases m1-m23. The mutant protease code, modifications made on the amino acid and nucleotide sequences (codons) of the wild type protease/protease cDNA and the codes for the expression plasmids are shown. The modified native amino acid, its position in the mature protease sequence (SEQ ID NO:2) and the amino acid replacing the native amino acid in the mutated protease are shown.

| Mutant code | Modification (amino acid sequence) | Modification (cDNA sequence) | Expression cassette Code |
|---|---|---|---|
| Wild type | No | No | pALK2764 |
| m1 | R17H | CGC→CAC | pALK2765 |
| m2 | Y25L | TAC→CTC | pALK2766 |
| m3 | D28R | GAC→CGC | pALK2767 |
| m4 | D28Y | GAC→TAC | pALK2768 |
| m5 | ΔA65ΔH66 | ΔGCC, ΔCAC | pALK2740 |
| m6 | T69N | ACC→AAC | pALK2741 |
| m7 | A77S | GCT→AGC | pALK2742 |
| m8 | A111D | GCT→GAC | pALK2743 |
| m9 | N167L | AAC→CTC | pALK2744 |
| m10 | R169N | CGT→AAC | pALK2745 |
| m11 | E205G | GAG→GGC | pALK2746 |
| m12 | Q216P | CAG→CCC | pALK2747 |
| m13 | M282V | ATG→GTC | pALK2748 |
| m14 | R17H, R169N (m1, m10) | CGC→CAC, CGT→AAC | pALK2749 |
| m15 | T46I | ACC→ATC | pALK2885 |
| m16 | A88S | GCC→AGC | pALK2886 |
| m17 | A173V | GCC→GTC | pALK2887 |
| m18 | V208I | GTC→ATC | pALK2888 |
| m19 | V239L | GTT→CTC | pALK2889 |
| m20 | A248V | GCT→GTC | pALK2890 |
| m21 | A281L | GCC→CTC | pALK2891 |
| m22 | m8, m15-m21 combined (altogether 8 mutations) | as in m8 and m15-m21 | pALK2892 |
| m23 | R17H (m1), R18K, G22S, F284Y, A287N, T288G | CGC→CAC, CGA→AAG, GGC→AGC, TTC→TAC, GCT→AAC, ACT→GGC | pALK2893 |

EXAMPLE 4

Production of the m-Series Mutant Proteases m1-m23 in *Trichoderma reesei*

The expression cassettes were isolated from the vector backbones from agarose gel after NotI digestion and were used for transforming *T. reesei* protoplasts. The host strain used in the transformations did not produce any of the four major *T. reesei* cellulases (CBHI, CBHII, EGI, EGII). The transformations were performed as in Pennilä et al. (1987) with the modifications described in Karhunen et al. (1993). The transformants producing the highest protease activities were screened by streaking spores from the transformant colonies on haemoglobin test plates. The isolates showing strongest intensity of dark brown color around the growing mycelia were chosen for further cultivations. The haemoglobin plates contained (per 1 liter): 15 g $KH_2PO_4$, 5 g $(NH_4)_2SO_4$, 20 g lactose, 10 ml of trace element stock solution, 20 g haemoglobin (BD BBL Bovine, freeze-dried, REF212392), 10 ml Triton X-100 (10% stock solution) and 10 g Bacto agar. The pH of the plates was adjusted to 7 by KOH prior to autoclaving. After autoclaving (121° C., 15 min) and cooling of the media to about 50° C., 2.4 ml 1M $MgSO_4 \times 7H_2O$ and 5.4 ml 1M $CaCl_2 \times 2 H_2O$ (per liter) were added. The trace element stock solution contained (per liter): 0.5 g $FeSO_4 \times 7H_2O$, 0.156 g $MnSO_4 \times H_2O$, 0.14 g $ZnSO_4 \times 7H_2O$ and 0.49 g $CoCl_2 \times 6H_2O$.

The chosen transformants from each transformation were purified on selection plates through single conidia and sporulated on PD slants prior to their cultivations in liquid medium.

From the PD slants the transformants were inoculated to shake flasks containing 50 ml of complex lactose-based cellulase inducing medium (Joutsjoki et al., 1993) buffered with 5% $KH_2PO_4$ at pH 6.0. The protease production of the transformants was analyzed from the culture supernatants after growing them for 5 to 7 days at 30° C., 250 rpm. The culture supernatants were analysed by running samples on SDS-PAGE gels and by determining the protease activity against casein, as described in Example 1a. In SDS-PAGE gels, a major protein band of about 29 kDa corresponding to the mass of recombinant Fe_RF6318 protease was detected from most of the spent culture supernatants. Also, most of the transformants produced clearly increased protease activity compared to host.

The integration of the expression cassettes into the fungal genomes was confirmed from the chosen transformants by using Southern blot analysis in which several genomic digests were included. A protease expression cassette was used as a probe in the analysis.

The properties of the mutant proteases were analysed from the culture supernatants as described in Example 5. The mutant proteases showing the best stability in the assays were produced in larger amounts by cultivating the corresponding *T. reesei* transformants in laboratory scale bioreactors. Cellulase inducing complex medium was used in the cultivations. The spent culture medium obtained from the fermentor cultivations was used for more detailed characterization of the mutant proteases, thermal stability tests (Example 5), stain removal performance (Example 12) and detergent stability tests (Example 13).

EXAMPLE 5

Characterisation of the m1-m23 Series Mutant Proteases

The thermal stability of protease mutants were determined as described in Example 1b using culture supernatants from shake flask cultivations as enzyme source (Example 4). The data obtained from the tests is shown on Table 3. The data indicated that the mutant proteases m7, m8, m18 and m21 showed better thermal stability than the wild type enzyme (wt). The multiply substituted protease variant m22 was clearly more stable than the wild type protease.

Table 3. Stability of the mutant proteases. Results are a summary from the thermal stability tests performed at 40 and 45° C. The shake flask culture supernatants were used in the assays. The symbol "−" indicates that the stability of the mutant protease is lower compared to the wild type enzyme, those marked with "0" show similar stability as the wild type enzyme, "+" show better stability and "++" clearly better stability than the wild type enzyme. ND, not determined.

| Mutant code (see Table 2) | Stability compared to wild type Fe_RF6318 |
| --- | --- |
| m1 | − |
| m2 | − |
| m3 | − |
| m4 | 0 |
| m5 | ND |
| m6 | 0 |
| m7 | + |
| m8 | + |

-continued

| Mutant code (see Table 2) | Stability compared to wild type Fe_RF6318 |
| --- | --- |
| m9 | 0 |
| m10 | 0 |
| m11 | − |
| m12 | − |
| m13 | ND |
| m14 | ND |
| m15 | − |
| m16 | − |
| m17 | − |
| m18 | + |
| m19 | − |
| m20 | − |
| m21 | + |
| m22 | ++ |
| m23 | − |

Transformants that according to data obtained from the shake flask culture supernatants produced mutant proteases with improved properties were cultivated in laboratory scale bioreactors (Example 4) to obtain more material for further analysis. The temperature stabilities of the mutant proteases were analysed from the fermentation culture supernatants as described in Example 1b. The temperature stability curves of m8, m18, m21 and m22 mutant proteases compared to that of the wild type protease are shown in FIG. 6.

The data indicates that mutant proteases m18 and m21 have equal or better thermal stability than the wild type protease. The multiply substituted protease variant m22 is clearly more stable than the wild type protease. The thermal stability of m8 protease in fermentation sample was lower compared to wild type protease. This was contrary to previous results obtained from the analysis of shake flask samples.

EXAMPLE 6

Combination of the Chosen m-Series Mutations into One Molecule, Construction of Mutant Proteases m24-m26

According to the results obtained for the m1-m23 mutant proteins (analysis of the shake flask culture supernatants, Table 3), m8, m18 and m21 including single mutations were among the ones that seemed to be the most stable in the assays (Example 5). Also, they showed good performance in the preliminary stain removal tests (not shown).

Thus, three new mutant genes m24, m25 and m26 were designed and constructed that included two (m24 and m25) or three (m26) of the m-series mutations combined into one molecule. The m24 mutant gene (cDNA) contained m8 and m18 mutations, m25 contained the m18 and m21 mutations and m26 contained the m8, m18 and m21 mutations (see Tables 2 and 4).

The m8 and m18 mutations were combined into one molecule (m24) by using the protease gene's internal Bsu36I site in the construction. The Bsu36I is located between the m8 and m18 mutation sites (position 979-985 in FIG. 1; see also FIG. 5 for the position of Bsu36I site) and is a single cutter in the GenScript pUC57 based plasmids including the synthetic protease genes. The GenScript plasmid with m18 mutant cDNA (mutation at 3' side from the Bsu36I site) was cleaved with Bsu36I and EcoRI (at the linker). The DNA fragment with the pUC57 vector (from EcoRI site in the linker) and the end of the synthetic gene construction (from the Bsu36I site) was isolated from agarose gel and used as a vector in the ligation. The insert for the ligation was isolated from the GenScript plasmid including the m8 mutant cDNA by EcoRI-Bsu36I digestion. The insert contained the pUC57 linker from EcoRI and the beginning of synthetic gene to the Bsu36I site. As a result, a pUC57 based plasmid was obtained with the m24 mutant protease cDNA as an insert (with the partial cbh1 promoter and terminator sequences at the 5'- and 3'-ends, respectively).

The m18 and m21 mutations were combined into one molecule (m25) by using the internal XhoI site in the construction. The XhoI is located between the m18 and m21 mutation sites (position 1114-1119 in FIG. 1; see also FIG. 5 for position of the XhoI site) and is, like Bsu36I, a single cutter for the GenScript pUC57 based plasmids with the synthetic genes. The GenScript plasmid with m21 mutant cDNA (mutation at 3' side from the XhoI site) was cleaved with XhoI and EcoRI (at the linker). The DNA fragment with the pUC57 vector (from EcoRI site in the linker) and the end of the synthetic gene construction (from the XhoI site) was isolated from agarose gel and used as a vector in the ligation. The EcoRI-XhoI insert for the ligation (pUC57 linker from EcoRI and beginning of the synthetic gene to the XhoI site) was isolated from the GenScript plasmid including the m18 mutation. The resulting pUC57 based plasmid contained the m25 mutant cDNA as an insert (with the partial cbh1 promoter and terminator sequences at the 5'- and 3'-ends, respectively).

The m8, m18 and m21 mutations were combined into one molecule (m26) by combining the end of the m25 synthetic gene (including m18 and m21 mutations) and the beginning of the m8 gene with each other, by using the Bsu36I site in the construction as described above.

The sequences of the fusions and mutations in the cDNA sequences were confirmed by sequencing.

For construction of the mutant protease expression cassettes, the m24, m25 and m26 inserts were isolated from the pUC57 vectors from agarose gels after SacII and AgeI digestion and ligated to pALK2777 (FIG. 4) cleaved with SacII and AgeI (like m15-m23 in Example 3).

The culture supernatants obtained from the shake flask cultivations were analysed by running samples on SDS-PAGE gels and by determining the protease activity against casein, as described in Example 1a. In SDS-PAGE gels, a major protein band of about 29 kDa corresponding to the mass of recombinant Fe_RF6318 protease was detected from the spent culture supernatants. Also, the transformants produced clearly increased protease activities compared to host.

The integration of the expression cassette into the fungal genomes was confirmed from chosen transformants by using Southern blot analysis in which several genomic digests were included. A protease expression cassette was used as a probe in the analysis.

The transformants producing the best protease activities in the shake flask cultivations were cultivated in laboratory scale fermentors (as in Example 4). The properties of the mutant proteases were analysed from the spent culture supernatants as described in Example 1b, Example 12 and Example 13.

EXAMPLE 8

Characterisation of the m24-m26 Mutant Proteases

The thermal stability of the m24, m25 and m26 protease mutants was determined as described in Example 1b using the culture supernatants from fermentor cultivations as an enzyme source (Example 7). The results obtained are shown in FIG. 7. The data obtained indicates that the stability of protease mutants m24 (combining the m8 and m18 mutations), m25 (combining the m18 and m21 mutations) and m26 (combining the m8, m18 and m21 mutations) had clearly better stability than the wild type protease. Also, these mutant proteases had better stability compared to the m8, m18 and m21 protease mutants having single mutations (FIG. 6).

TABLE 4

The mutant proteases m24-m26. The mutant protease code, modifications made on the amino acid and nucleotide sequences (codons) compared to the wild type protease/gene and the codes for the expression plasmids are shown. The modified native amino acid, its position in the mature protease sequence (SEQ ID NO: 2) and the amino acid replacing the native amino acid after mutation are shown.

| Mutant code | Modification (amino acid sequence) | Modification (cDNA sequence) | Expression cassette code |
|---|---|---|---|
| m24 | A111D, V208I (m8 and m18 combined) | GCT→GAC, GTC→ATC | pALK2897 |
| m25 | V208I, A281L (m18 and m21 combined) | GTC→ATC, GCC→CTC | pALK2898 |
| m26 | A111D, V208I, A281L (m8, m18 and m21 combined) | GCT→GAC, GTC→ATC, GCC→CTC | pALK2899 |

EXAMPLE 7

Production of the m-Series Mutant Proteases in *Trichoderma reesei*

The Nod expression cassettes were isolated from the plasmids pALK2897-pALK2899 and transformed into *T. reesei* as described in Example 4. The purification, screening and cultivations of the *T. reesei* transformants was performed as described in Example 4.

EXAMPLE 9

Design of the D1-D30 Mutant Proteases and Construction of their Expression Cassettes New mutations were designed to further improve the stability of protease. The m26 protease was chosen as a background molecule as m26 had, in the previous tests (Example 8) shown better thermal stability compared to the wild type protease.

The mutant proteases designed and the modifications made to the m26 protease cDNA sequence are listed in Table 5. For the mutations already included in m26, see Table 4. The m26 nucleotide (cDNA) sequence encoding the mature protease amino acid sequence and mature protein sequence are included as SEQ ID NO:11 and SEQ ID NO:12, respectively. The m26 cDNA sequence encoding the full-length m26 protease amino acid sequence is included in FIG. 8. The synthetic genes were ordered from GenScript as described in Example 3. The D-series mutant genes (with the 5'- and 3'-additional cbh1 promoter and terminator sequences, see FIG. 2) were isolated from the pUC57 backbone by SacII-AgeI digestion as described in Example 3. The inserts were ligated to pALK2777, digested with SacII and AgeI as described in Example 3.

TABLE 5

The mutant proteases D1-D30. The mutant protease code, modifications made on the amino acid and nucleotide sequences (codons) of the m26 mutant protease and the codes for the expression plasmids are shown. The modified native amino acid, its position in the mature m26 protease sequence (SEQ ID NO: 12) and the amino acid replacing the native amino acid after mutation are shown. The cDNA encoding the mature m26 amino acid sequence and mature m26 amino acid sequences are included as SEQ ID NO: 11 and SEQ ID NO: 12, respectively.

|     | Modification (amino acid sequence) | Modification (cDNA sequence) | Expression cassette code |
|-----|-----|-----|-----|
| D1  | N7R | AAC→CGC | pALK3051 |
| D2  | A33E | GCC→GAG | pALK3052 |
| D3  | A47E | GCC→GAG | pALK3053 |
| D4  | S56R | TCT→CGC | pALK3054 |
| D5  | A61P | GCT→CCC | pALK3055 |
| D6  | G63P | GGT→CCC | pALK3056 |
| D7  | V76A | GTT→GCC | pALK3057 |
| D8  | N83D | AAC→GAC | pALK3058 |
| D9  | N114R | AAC→CGC | pALK3059 |
| D10 | V155I | GTC→ATC | pALK3060 |
| D11 | V158I | GTT→ATC | pALK3061 |
| D12 | G164A | GGT→GCC | pALK3062 |
| D13 | I185M | ATC→ATG | pALK3063 |
| D14 | T196R | ACT→CGC | pALK3064 |
| D15 | V206L | GTC→CTC | pALK3065 |
| D16 | M234S | ATG→AGC | pALK3066 |
| D17 | Q247L | CAG→CTC | pALK3067 |
| D18 | N260R | AAC→CGC | pALK3068 |
| D19 | T268R | ACC→CGA | pALK3069 |
| D20 | ΔN167 | ΔAAC | pALK3070 |
| D21 | Q103A, ins. G104 | CAA→GCC, ins. GGC | pALK3071 |
| D22 | T3C, T29C | ACC→TGC, ACC→TGC | pALK3072 |
| D23 | S6R, T24D | AGC→CGC, ACC→GAC | pALK3073 |
| D24 | T121D, Q153R | ACC→GAC, CAA→CGA | pALK3074 |
| D25 | S174R, E205D | TCT→CGA, GAG→GAC | pALK3075 |
| D26 | N214D, S230R | AAC→GAC, AGC→CGA | pALK3076 |
| D27 | Y151F, G286S, A283V, A287T | TAC→TTC, GCT→GTC, GGC→AGC, GCT→ACC | pALK3077 |

TABLE 5-continued

The mutant proteases D1-D30. The mutant protease code, modifications made on the amino acid and nucleotide sequences (codons) of the m26 mutant protease and the codes for the expression plasmids are shown. The modified native amino acid, its position in the mature m26 protease sequence (SEQ ID NO: 12) and the amino acid replacing the native amino acid after mutation are shown. The cDNA encoding the mature m26 amino acid sequence and mature m26 amino acid sequences are included as SEQ ID NO: 11 and SEQ ID NO: 12, respectively.

| | Modification (amino acid sequence) | Modification (cDNA sequence) | Expression cassette code |
|---|---|---|---|
| D28 | A33E, N83D, N114R T196R, N260R (D2, D8, D9, D14, D18 combined) | As in D2, D8, D9, D14, D18 | pALK3078 |
| D29 | V155I, V158I, I185M, V206L G210A, A283V | As in D10, D11, D13, D15 and GGT→GCC, GCT→GTC | pALK3079 |
| D30 | S6R, T24D, T121D, Q153R, S174R, E205D, A33E, T196R | AGC→CGC, ACC→GAC, ACC→GAC, CAA→CGA, TCT→CGA, GAG→GAC and as in D2, D14 | pALK3080 |

EXAMPLE 10

Production of the Mutant Proteases in *Trichoderma reesei* (D-Series of Mutants)

The NotI expression cassettes were isolated from the plasmids and transformed into *T. reesei* as described in Example 4. The screening and cultivation of the *T. reesei* transformants (in shake flasks and in fermentors) was performed as described in Example 4.

The properties of the mutant proteases were analysed from the culture supernatants as described in Example 5. The mutant proteases showing the best thermal stability in these assays and good performance in the preliminary stain removal tests (not shown) were produced in larger amounts by cultivating the corresponding *T. reesei* transformants in laboratory scale bioreactors as described in Example 4. The spent culture medium obtained from the fermentor cultivations was used for more detailed characterization of the mutant proteases, thermal stability tests (Example 11), stain removal performance (Example 14) and detergent stability tests (Example 15).

EXAMPLE 11

Characterisation of the D-Series Mutant Proteases

The thermal stability of protease mutants was determined as described in Example 1b using culture supernatants from shake flask and fermentor cultivations as enzyme sources (Example 10).

The thermal stability of D mutants was compared to m26, which is the background molecule for the D series of mutants. A summary of the results obtained from the shake flask culture supernatants is shown in Table 6. The data indicates that the thermal stability of mutant proteases D2, D3, D13, D19, D21, D22 and D23 was better than that of m26 protease.

Table 6. Stability of the D1-D30 mutant proteases. Results are a summary from the thermal stability tests performed at 45° C. The shake flask culture supernatants were used in the assays. The symbol "−" indicates that the stability of the mutant protease is lower compared to the wild type recombinant enzyme, those marked with "0" show similar stability as the wild type enzyme, and "+" show better stability than the wild type enzyme. The mutants with "++" has similar stability as m26 mutant protease and those with "+++" symbol show better stability than m26. ND, not determined.

| Mutant code (see Table 2) | Stability compared to Fe_RF6318 and m26 |
|---|---|
| D1 | + |
| D2 | +++ |
| D3 | +++ |
| D4 | + |
| D5 | ++ |
| D6 | ++ |
| D7 | + |
| D8 | ++ |
| D9 | 0 |
| D10 | + |
| D11 | ++ |
| D12 | ++ |
| D13 | +++ |
| D14 | 0 |
| D15 | − |
| D16 | ++ |
| D17 | + |
| D18 | + |
| D19 | +++ |
| D20 | + |
| D21 | +++ |
| D22 | +++ |
| D23 | +++ |
| D24 | ++ |
| D25 | + |
| D26 | ND |
| D27 | ND |
| D28 | ND |
| D29 | 0 |
| D30 | 0 |

The thermal stabilities of mutant proteases were determined in more detail from the fermentation culture supernatants. Transformants producing the mutant protease D21 were not cultivated in bioreactors because the specific activity of D21 was decreased compared to the wild type enzyme. The results of a selection of mutant proteases are shown in FIG. 9.

The results obtained indicate that mutant proteases D2, D3, D19, D22 and D23 had better thermal stability than mutant protease m26. Mutant proteases D5, D8 and D13 had approximately equal thermal stability as m26 mutant protease. Mutant proteases D7, D16 and D17 had lower thermal stability than m26 mutant protease but the stability was better than the stability of wt protease.

EXAMPLE 12

Stain Removal Performance of Mutants of m-Series with Liquid Detergents

Mutant proteases of m-series showing the best thermal stability (Examples 5 and 8) and wild type protease produced in *Trichoderma*, as described in Examples 4 and 7, were chosen for application tests. Fermentation culture supernatants were first stabilized with 50% propylen glycol and were then tested for their ability to remove blood/milk/ink standard stain at 30° C. and 45° C. in the presence of Liquid Base detergent for colored fabrics (Table 7), at concentration of 5 g/l. Standard stain, artificially soiled test cloth Art.117 (blood/milk/ink, polyester+cotton, EMPA Testmaterialen AG, Switzerland) was used as test material. Each enzyme preparation was dosed 0, 0.2, 0.4, 0.8, 1.6, 4, and 8 activity units (µmol tyrosine/min) per ml wash liquor. Activity was measured as described in Example 1a.

An amount of 5 g of Liquid base detergent was dissolved in 1 liter of tap water (dH<4), mixed well with magnetic stirrer and tempered to 30° C. and 45°. The pH in the wash liquor was approx. 7.4. The stain fabric was first cut in to 1.5 cm×1.5 cm swatches and the pieces were made rounder by cutting the corners. Pieces were placed in wells of microtiter plates (Nunc 150200). Into each well having a diameter of 2 cm, 1.5 ml wash liquor containing detergent and enzyme dilution in water (below 60 µl) was added on top of the fabric. The plates with samples were in incubated in Infors Ecotron incubator shaker at 30° C. and 45° C. for 60 min with 130 rpm. After that the swatches were carefully rinsed under running water (appr. at washing temperature) and dried overnight at indoor air, on a grid, protected against daylight.

TABLE 7

Composition of Liquid Base detergent for colored fabric.

| Ingredient | % |
|---|---|
| NaLES (sodium lauryl ether sulphate) | 4.9 |
| Nonionic C12-15 7EO (ethylene oxide) | 15 |
| Na-Soap (Palm Kernel FA) | 4.4 |
| Coco Glucoside | 1 |
| <Total Surfactant> | <25.30> |
| Polyol (Glycerin) | 5 |
| Phosphonate (32%) (ThermPhos) | 2 |
| PVP-Sokalan HP 53 (BASF) | 1 |
| Sokalan PA 15 (BASF) | 1.56 |
| Sorez-100 (ISP) | 0.4 |
| Water up to 100% | |

The stain removal effect was evaluated by measuring the colour as reflectance values with Minolta CM 2500 spectrophotometer using L*a*b* colour space coordinates (illuminant) D65/2°. The colour from both sides of the swatches was measured after the treatment. Each value was the average of at least 2 parallel fabric samples measured from both side of the fabric. Fading of blood/milk/ink stain, indicating the protease performance (stain removal efficiency), was calculated as ΔL*, which means lightness value L* of enzyme treated fabric minus lightness value L* of fabric treated with washing liquor without enzyme (enzyme blank, control).

The results obtained with mutants m8, m18, m21, m22, m24, m25 and m26 are shown in FIGS. 10A and 10B. The mutations have not affected harmfully on the stain removal performance.

Some mutants of m-series were tested at 30° C. also with another liquid detergent Ecolabel Reference Detergent, light duty (Ch. Nr. 196-391, wfk Testgewebe GmbH) and detergent powders, like ECE reference detergent 77 without optical brightener (Art. 601, EMPA) and ECE reference detergent 98 without phosphate (Art. 600, EMPA) at concentrations 3.3 g/l and/or 5 g/l. The tested mutant protease preparations showed similar performance compared to wild type protease preparation.

EXAMPLE 13

Stability of Mutants of m-Series in Liquid Detergents

Stability of mutants m8, m18, m21, m22, m24, m25 and m26 at 37° C. was tested in liquid detergents mentioned in Example 12, Liquid Base detergent for colored fabric and Ecolabel Reference detergent, and in addition to these Commercial liquid detergent (both without enzymes) described in Table 8.

TABLE 8

Composition of Commercial liquid detergent.

| Ingredient | % |
|---|---|
| Anionic surfactants | 15-30 |
| Nonionic surfactants, soap | 5-15 |
| Phosphonate, polycarboxylate | 5 |
| Optical brighteners and perfumes | |
| pH 8.2-8.6 | |

Two types of test systems were used:
A) 0.4 g enzyme preparation (containing 50% propylene glycol) and 9.6 g of detergent solution were mixed well in Sarstedt's test tubes (13 ml).
B) 0.4 g enzyme preparation (containing 50% propylene glycol) and 2.5 g of solution containing 8% sodium tetraborate decahydrate and 8 mM $CaCl_2$ (pH adjusted to 6 with HCl) in distilled water, 1.5 g propylene glycol and 5.6 g of detergent solution were mixed well in Sarsted's test tubes (13 ml). This solution contains 17% of propylene glycol and 2% sodium tetraborate decahydrate as stabilizing agents.

In both cases 0.2% of Proxel LV was added as preservative in detergent before mixing it with other components. The pH values of the samples prepared in Liquid Base detergent using recipe A, were approx. 8.2, and using recipe B approx. 7. pHs of the samples prepared in Ecolabel Reference Detergent were approx. 7.2 and 6.5 and in Commercial liquid detergent approx. 8.2 and 7.5, respectively. Test tubes were incubated at 37° C. and the protease activity was measured at certain intervals according to the method described in Example 1a.

Figure 11A:
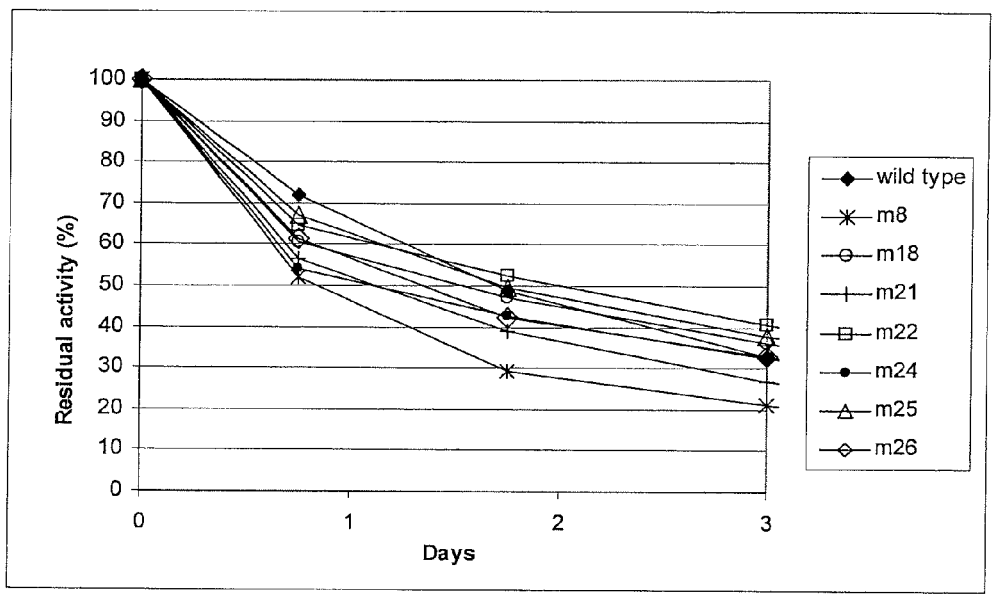
FIG. 11A shows the stability of selected mutant proteases from m-series and wild type protease in Liquid Base detergent for colored fabrics at 37° C. (pH approx. 8.2).
Figure 11B:
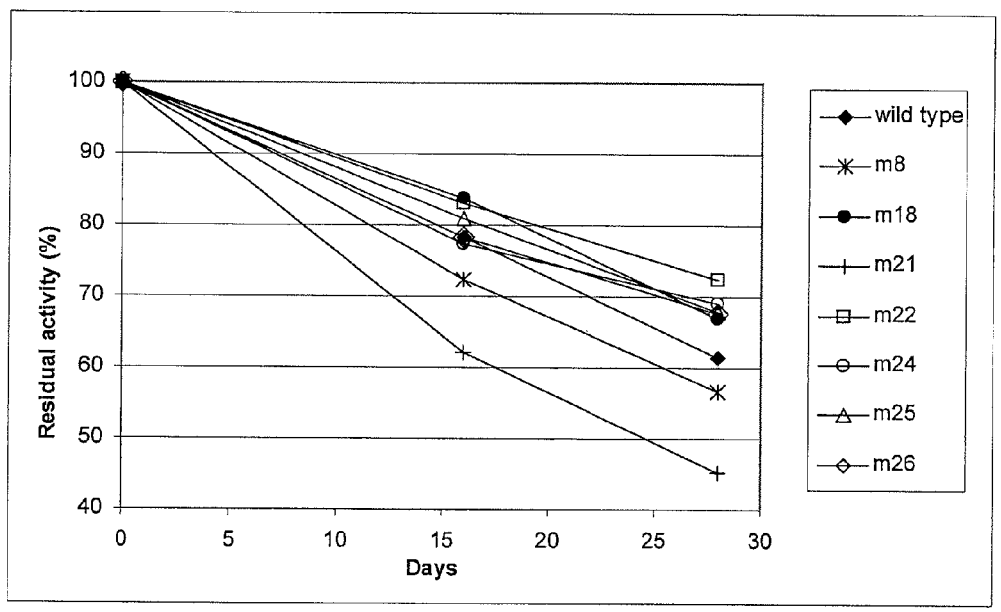
FIG. 11B shows the stability of selected mutant proteases from m-series in Liquid Base detergent for colored fabrics with 2% sodium tetraborate decahydrate and 17% propylene glycol incubated at 37° C. (pH approx. 7).

Results of detergent stability tests are shown in FIGS. 11-13. In Liquid Base detergent (FIG. 11) the stability of mutants, except m8 and m21 was similar or slightly improved compared to the wild type protease. The stability of m-series mutants, except m8 and m21, was considerably improved in Ecolabel (FIG. 12) and Commercial liquid detergents (FIG. 13). The results show that mutant proteases were constructed that have improved stability compared and also have similar or even better stain removal performance compared to the wild type protease.

EXAMPLE 14

Stain Removal Performance of Mutants of D-Series with Liquid Detergents

Based on thermal stability tests (Example 11) and preliminary stain removal tests at 30° C. made with shake flask supernatants of mutant proteases of D-series produced in *Trichoderma*, as described in Examples 10, the transformants producing the best mutant protease candidates were cultivated in laboratory scale bioreactors. Fermentation culture supernatants containing the mutant proteases were stabilized with 50% propylen glycol and were then tested for their ability to remove blood/milk/ink standard stain at 30° C. and 50° C. in the presence of liquid detergent at concentration of 5 g/l. Wild type and mutant m26 used as background molecule for D-series mutants, were used for comparison. The testing method and dosing was similar to Example 12, except that the Commercial liquid detergent, described in Example 13, was used. Also the colour of the swatches after treatment was measured with Minolta CM 2500 spectrophotometer using L*a*b* colour space coordinates and stain removal effect calculated as ΔL* as described in Example 12.

The results are shown in FIGS. 14 and 15. In stain removal tests at 30° C. (FIGS. 14A, 14B and 15A) all mutant proteases, except D19, had better performance than wild type and similar or better performance compared to m26. D19 had similar performance compared to wild type. At 50° C. (FIGS. 14C, 14D and 15B) only mutant D7 had weaker performance than wild type. Mutants D17 and D19 were slightly better than the wild type and mutant proteases D2, D3, D5, D6, D8, D13, D16, D22 and D23 had relatively similar stain removal performance compared to m26.

EXAMPLE 15

Stability of Mutants of D-Series in Liquid Detergents

Stability of D-series mutant proteases in fermentation culture supernatants (containing 50% propylen glycol) was tested at 37° C. for 20 hours in Commercial liquid detergent and using similar test systems as described Example 13. Mutant m26 used as background molecule for mutations in D-series and having improved stability and stain removal effect compared to wild type was used as reference. The stability of the best performing mutants from Example 14 and most stable mutants in Commercial liquid detergent were tested also with Ecolabel Reference Detergent, light duty (wfk Testgewebe GmbH)

Figure 16B:
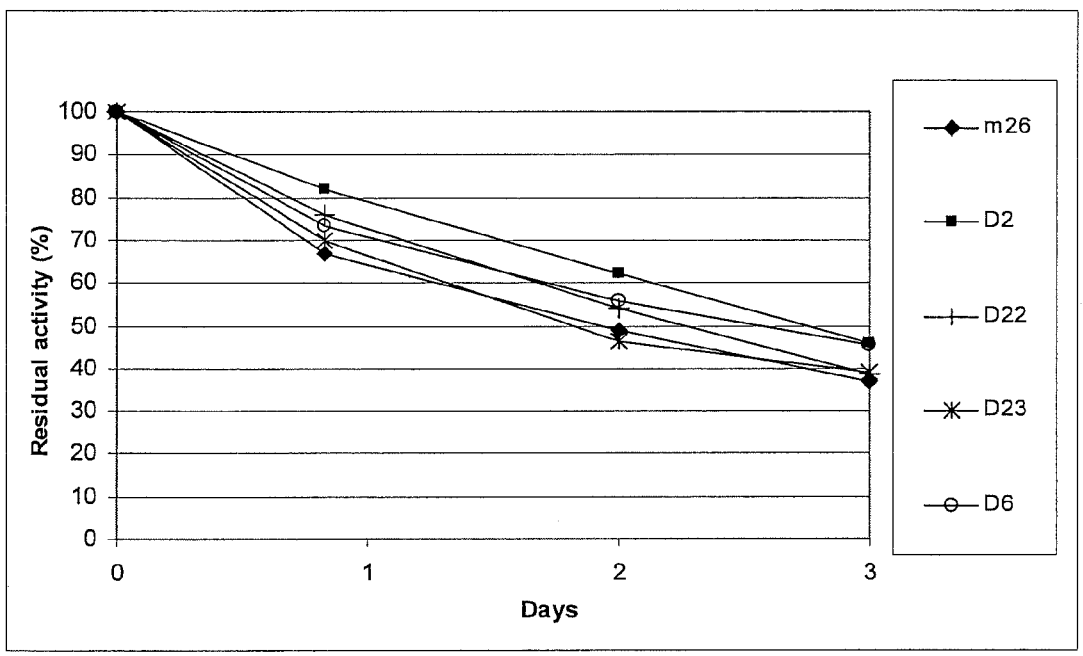
FIG. 16B shows the stability of mutants of D-series (D2, D6, D22, and D23) in Commercial liquid detergent incubated at 37° C., pH approx. 8.2. Mutant protease m26 was used for comparison.
Figure 17B:
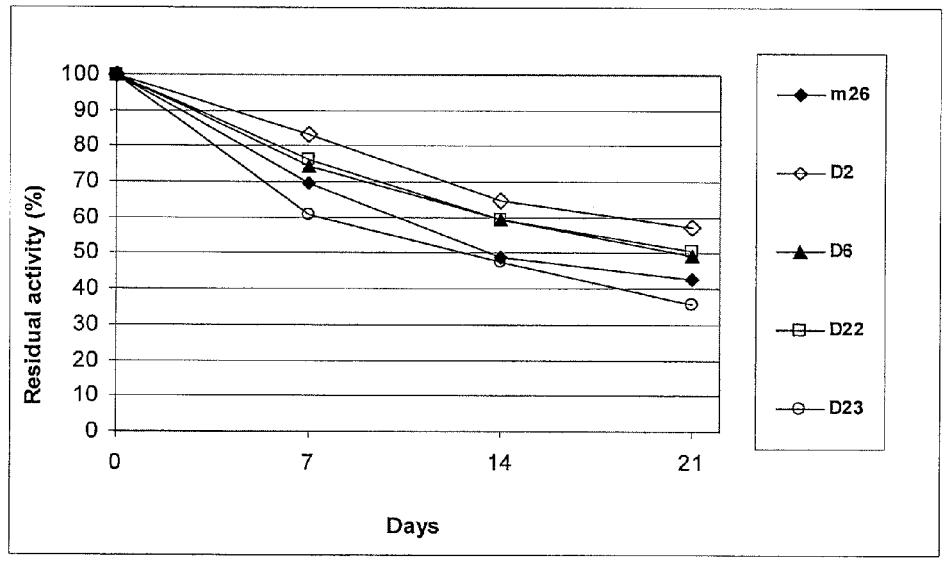
FIG. 17B shows stability of mutants from D-series (D2, D6, D22 and D23) in Commercial liquid detergent with 2% sodium tetraborate decahydrate and 17% propylene glycol incubated at 37° C., pH approx. 7.5. Mutant protease m26 was used for comparison.

Results of detergent stability tests in Commercial liquid detergent are shown in FIGS. 16-17. Stability of mutants D2, D3, D6, D19 and D22 was better compared to m26. The mutants D5, D8, D13 and D23 had similar stability as m26 in Commercial liquid detergent containing no stabilizers (FIGS. 16A and B). The stability of mutants D16, D17 and especially D7 was lower compared to m26 (FIG. 16A). However, D16 and D17 were more stable than the wild type (FIG. 12B) in the previous test.

In detergent test system which contains sodium tetraborate decahydrate and propylene glycol, the stability of mutants D2, D3, D6, D13, D22 and especially D19, was better compared to m26 (FIG. 17). The stability of mutants D8, D16, D17, D23 and especially D7 was lower compared to m26. However all the mutants having lower stability compared to m26, except D7, were more stable than the wild type (FIG. 13B) in previous tests.

All the mutant proteases tested showed considerably improved stability in Ecolabel Reference detergent compared to wild type (FIG. 18). Mutant proteases D2, D3, D6 and especially D19 had also better stability than m26.

The results show that mutant proteases were constructed that have improved stability compared and also have similar or even better stain removal performance compared to the wild type protease.

EXAMPLE 16

Design of D31-D68 Mutant Proteases, Construction of their Expression Cassettes and Production of Mutant Proteases in *T. Reesei*

Additional mutations were designed to improve the stability of protease. The m26 protease was chosen as a background molecule, as in Example 9.

The mutant proteases designed and the modifications made to the m26 protease cDNA sequence are listed in Table 9. For the mutations already included in m26, see Table 4. The full-length m26 nucleotide (cDNA) and protein sequences are included as SEQ ID NO:11 and SEQ ID NO:12, respectively. The cDNA sequence encoding the full-length m26 protease is shown in FIG. 8. The synthetic genes were ordered from GenScript as described in Example 3. The D-series mutant genes (with the 5'- and 3'-additional cbh1 promoter and terminator sequences, see FIG. 2) were isolated from the pUC57 backbone by SacII-AgeI digestion as described in Example 3. The inserts were ligated to pALK2777, digested with SacII and AgeI as described in Example 3.

TABLE 9

The mutant proteases D31-D68. The mutant protease code, modifications made on the amino acid and nucleotide sequences (codons) of the m26 mutant protease and the codes for the expression plasmids are shown. The modified native amino acid, its position in the mature m26 protease sequence (SEQ ID NO: 12) and the amino acid replacing the native amino acid after mutation are shown. The cDNA encoding the mature m26 amino acid sequence and m26 mature amino acid sequences are included as SEQ ID NO: 11 and SEQ ID NO: 12, respectively.

|  | Modification (amino acid sequence) | Modification (cDNA sequence) | Expression cassette code |
|---|---|---|---|
| D31 | A8V | GCT→GTC | pALK3101 |
| D32 | G34S | GGT→AGC | pALK3102 |

TABLE 9-continued

The mutant proteases D31-D68. The mutant protease code, modifications made on the amino acid and nucleotide sequences (codons) of the m26 mutant protease and the codes for the expression plasmids are shown. The modified native amino acid, its position in the mature m26 protease sequence (SEQ ID NO: 12) and the amino acid replacing the native amino acid after mutation are shown. The cDNA encoding the mature m26 amino acid sequence and m26 mature amino acid sequences are included as SEQ ID NO: 11 and SEQ ID NO: 12, respectively.

|     | Modification (amino acid sequence) | Modification (cDNA sequence) | Expression cassette code |
|-----|-----------------------------------|------------------------------|--------------------------|
| D33 | G34N | GGT→AAC | pALK3103 |
| D34 | Y36D | TAC→GAC | pALK3104 |
| D35 | G52E | GGC→GAG | pALK3105 |
| D36 | A91T | GCC→ACC | pALK3106 |
| D37 | V100T | GTC→ACG | pALK3107 |
| D38 | V100D | GTC→GAC | pALK3108 |
| D39 | V100K | GTC→AAG | pALK3109 |
| D40 | T106A | ACC→GCC | pALK3110 |
| D41 | T106N | ACC→AAC | pALK3111 |
| D42 | P138D | CCC→GAC | pALK3112 |
| D43 | P138K | CCC→AAG | pALK3113 |
| D44 | A144N | GCT→AAC | pALK3114 |
| D45 | A144T | GCT→ACC | pALK3115 |
| D46 | E205N | GAG→AAC | pALK3116 |
| D47 | E205R | GAG→CGC | pALK3117 |
| D48 | L249T | CTC→ACC | pALK3118 |
| D49 | L252T | CTC→ACC | pALK3119 |
| D50 | L252A | CTC→GCC | pALK3120 |
| D51 | A256S | GCT→AGC | pALK3121 |
| D52 | Q247L, L249T | CAG→CTC; CTC→ACC | pALK3122 |
| D53 | T3C, T29C, S6R, T24D | ACC→TGC; ACC→TGC; AGC→CGC; ACC→GAC | pALK3123 |
| D54 | I185C, T259C | ATC→TGC; ACC→TGC | pALK3124 |
| D55 | G210A, I185M | GGT→GCC; ATC→ATG | pALK3125 |
| D56 | A33E, A47E, N83D | GCC→GAG; GCC→GAG; AAC→GAC | pALK3126 |
| D57 | A14T | GCC→ACC | pALK3127 |
| D58 | G22S | GGC→TCC | pALK3128 |
| D59 | G37A | GGT→GCC | pALK3129 |
| D60 | A65D | GCC→GAC | pALK3130 |
| D61 | V100Q | GTC→CAG | pALK3131 |
| D62 | F113Y | TTC→TAC | pALK3132 |
| D63 | K123R | AAG→CGC | pALK3133 |
| D64 | S157T | TCC→ACC | pALK3134 |
| D65 | G175S | GGC→TCC | pALK3135 |

TABLE 9-continued

The mutant proteases D31-D68. The mutant protease code, modifications made on the amino acid and nucleotide sequences (codons) of the m26 mutant protease and the codes for the expression plasmids are shown. The modified native amino acid, its position in the mature m26 protease sequence (SEQ ID NO: 12) and the amino acid replacing the native amino acid after mutation are shown. The cDNA encoding the mature m26 amino acid sequence and m26 mature amino acid sequences are included as SEQ ID NO: 11 and SEQ ID NO: 12, respectively.

|     | Modification (amino acid sequence) | Modification (cDNA sequence) | Expression cassette code |
|-----|------------------------------------|------------------------------|--------------------------|
| D66 | Q176T                              | CAG→ACC                      | pALK3136                 |
| D67 | C236T                              | TGC→ACC                      | pALK3137                 |
| D68 | A287N                              | GCT→AAC                      | pALK3138                 |

The NotI expression cassettes were isolated from the plasmids and transformed into *T. reesei* as described in Example 4. The screening and cultivation of the *T. reesei* transformants (in shake flasks and in fermentors) was performed as described in Example 4.

The properties of the mutant proteases were analysed from the culture supernatants as described in Example 5. The mutant proteases showing the best thermal stability in these assays and good performance in the preliminary stain removal tests (not shown) were produced in larger amounts by cultivating the corresponding *T. reesei* transformants in laboratory scale bioreactors as described in Example 4. The spent culture medium obtained from the shake flask and fermentor cultivations was used for characterization of the mutant proteases, thermal stability tests, stain removal performance and detergent stability tests (Example 17).

EXAMPLE 17

Stain Removal Performance and Stability of Mutants of DII-Series (D32-D68) in Liquid Detergents Selected DII-series mutant proteases (shake flask and fermentation cultivation supernatants), produced in *Trichoderma* as described in Example 16, were tested for their thermostability, wash performance and detergent stability. The results obtained with the mutant proteases were compared to those obtained with the wild type protease and mutant protease m26.

The thermal stability of the mutant proteases at 45° C. in pH 8.5 buffer was tested as described in Example 1 (b). Especially, D38, D41, D53 and D55 show clearly better thermal stability than m26.

The ability of proteases to remove blood/milk/ink standard stain in the presence of Commercial liquid detergent was tested at 30° C. using similar test system as described in Examples 12 and 14. The wash performance of all the mutant proteases (Commercial detergent, 30° C., 60 min), except D39, was similar or better compared to m26 protease. Especially good result was obtained with D35, D37, D38 and D44.

Fermentation culture supernatants were tested for their stability in Commercial liquid detergent and Ecolabel Reference detergent at 37° C. using test system A as described in Example 13, except that the incubation time in Ecolabel tests was 15.5 hours at 37° C. All the mutant proteases showed better stability than the wild type protease in Commercial liquid detergent (not shown) and in Ecolabel Reference Detergent. D39, D53, D55, D61, D63, D64, D65, D66 and D67 showed especially good stability in Ecolabel Reference Detergent compared to m26. The summary of results of thermostability and stability in Ecolabel Reference Detergent are shown in Table 10.

TABLE 10

Summary of the stability tests of selected DII series mutant proteases.

| Mutant protease | Thermal stability | Stability in Ecolabel (residual activity at 37° C., 15.5 h) |
|-----------------|-------------------|-------------------------------------------------------------|
| D32             | ++                | ND                                                          |
| D33             | ++                | ND                                                          |
| D35             | ++                | ND                                                          |
| D36             | ++                | ND                                                          |
| D37             | ++                | ND                                                          |
| D38             | +++               | ND                                                          |
| D39             | ++                | +++                                                         |
| D41             | +++               | ND                                                          |
| D42             | +                 | ND                                                          |
| D44             | ++                | ND                                                          |
| D51             | ++                | ND                                                          |
| D53             | +++               | +++                                                         |
| D55             | +++               | +++                                                         |
| D57             | ++                | +                                                           |
| D59             | +                 | ++                                                          |
| D60             | ++                | ++                                                          |
| D61             | ++                | +++                                                         |
| D62             | +                 | +                                                           |
| D63             | +                 | +++                                                         |
| D64             | ++                | +++                                                         |
| D65             | ++                | +++                                                         |
| D66             | ++                | +++                                                         |
| D67             | ++                | +++                                                         |

Those marked with "+" show better stability than the wild type enzyme.
The mutants with "++" have similar stability as the m26 mutant protease and those with "+++" symbol show better stability than m26.
ND, not determined.

REFERENCES

Anwar, A and M Saleemuddin. 1998. Alkaline proteases: A review. Bioresource Technology 64:175-183.

Bergquist P., Te'o. V., Gibbs, M., Cziferszky, A., de Faria F. P., Azevedo, M., and Nevalainen, H. 2002. Expression of xylanase enzymes from thermophilic microorganisms in fungal hosts. Extremophiles 6: 177-184.

Chen, Y- J, and M Inouye, 2008. The intramolecular chaperone-mediated protein folding. Curr. Opin. Struct. Biol. 18: 765-770.

Chemy, J. R., and Fidantsef, A. L. 2003. Directed evolution of industrial enzymes: an update. Curr. Opin. Biotechnol. 14: 438-443.

Gupta, R, Q K Beg, S Khan and B Chauhan. 2002. An overview on fermentation, downstream processing and properties of microbial alkaline protease. Appl. Microbiol. Biotechnol. 60: 381-395.

Hynes, M. J., Corrick, C. M. and King, J. A. 1983. Isolation of genomic clones containing the amdS gene of *Aspergillus nidulans* and their use in the analysis of structural and regulatory mutations. Mol. Cell. Biol. 3: 1430-143

Joutsjoki, V V, T K Torkkeli, and K M H Nevalainen. 1993. Transformation of *Trichoderma reesei* with the *Hormoconis resinae* glucoamylase P (gamP) gene: production of a heterologous glucoamylase by *Trichoderma reesei*. Curr. Genet. 24:223-228.

Kalisz, H M. 1988. Microbial proteinases. Adv. Biochem. Eng. Biotechnol. 36:1-65.

Karhunen T, A Mäntylä, K M H Nevalainen, and P L Suominen. 1993. High frequency one-step gene replacement in *Trichoderma reesei*. I. Endoglucanase I overproduction. Mol. Gen. Genet. 241:515-522.

Laemmli, U K. 1970. Cleavage of structural proteins during the assembly of the head of bacteriophage T4. Nature 227: 680-685.

Malardier L, M J Daboussi, J Julien, F Roussel, C Scazzocchio and Y Brygoo. 1989. Cloning of the nitrate reductase gene (niaD) of *Aspergillus nidulans* and its use for transformation of *Fusarium oxysporum*. Gene 78:147-156.

Maurer, K- H.2010. Enzymes, Detergent. Encyclopedia of Industrial Biotechnology: Bioprocess, Bioseparation, and Cell Technology, (ed. M. C. Flickinger, John Wiley & Sons, Inc.), pp. 1-17.

Maurer K H and M Gabler. 2005. Handbook of Detergents, Part C. (eds. H Waldhoff and R Spilker. Marcel Dekker. New York, pp. 471-486.

Maurer, K- H. 2004. Detergent proteases. Cuff. Opin. Biotechnol. 15: 330-334.

Penttilä M, H Nevalainen, M Ratto, E Salminen, and J. Knowles. 1987. A versatile transformation system for the cellulolytic filamentous fungus *Trichoderma reesei*. Gene 61:155-164.

Raeder U and P Broda. 1985. Rapid preparation of DNA from filamentous fungi. Lett. Appl. Microbiol. 1:17-20.

Rao, M B, A M Tanksale, M S Ghatge and V V Deshpande. 1998. Molecular and biotechnological aspects of microbial proteases. Microbiol. Mol. Biol. Rev. 62:597-635.

Sambrook J and D W Russell. 2001. Molecular cloning, a laboratory manual. Cold Spring Harbor Laboratory, New York, US.

---

The invention claimed is:

1. An isolated polypeptide variant of the *Fusarium equiseti* Fe_RF6318 serine protease, the polypeptide variant comprising the amino acid sequence set forth in SEQ ID NO:2 with a substitution at position 208 in SEQ ID NO:2 of an amino acid other than valine, and optionally further comprising one or more mutations selected from the group consisting of:
  (a) a substitution of one or more amino acid residues at positions 3, 6, 7, 8, 14, 17, 18, 22, 24, 25, 28, 29, 33, 34, 36, 37, 46, 47, 52, 56, 61, 63, 65, 69, 76, 77, 83, 88, 91, 100, 103, 106, 111, 113, 114, 121, 123, 138, 144, 151, 153, 155, 157, 158, 164, 167, 169, 173, 174, 175, 176, 185, 196, 205, 206, 210, 214, 216, 230, 234, 236, 239, 247, 248, 249, 252, 256, 260, 268, 281, 282, 283, 284, 286, 287, or 288 of SEQ ID NO:2 with an amino acid other than the amino acid occurring at those positions in SEQ ID NO:2;
(b) a deletion of alanine at position 65 of SEQ ID NO:2;
(c) a deletion of histidine at position 66 of SEQ ID NO:2;
(d) a deletion of asparagine at position 167 of SEQ ID NO:2; and
(e) an amino acid insertion after position 103 of SEQ ID NO:2,
wherein the polypeptide variant:
(i) has hydrolytic activity on a substrate selected from the group consisting of casein, hemoglobin, keratin, and BSA, and
(ii) has improved thermal or detergent stability compared to a polypeptide having the amino acid sequence set forth in SEQ ID NO:2.

2. The polypeptide variant of claim 1, wherein the amino acid at position 208 in SEQ ID NO:2 is isoleucine, leucine, or methionine.

3. The polypeptide variant of claim 2, wherein the amino acid at position 208 in SEQ ID NO:2 is isoleucine.

4. The polypeptide variant of claim 1, wherein if the polypeptide variant further comprises one or more mutations, the polypeptide variant has a total of two, three, four, five, six, seven, eight, nine, ten, or eleven mutations in SEQ ID NO:2.

5. The polypeptide variant of claim 4, wherein the polypeptide variant has a total of five mutations in SEQ ID NO:2.

6. The polypeptide variant of claim 5, wherein the five mutations are amino acid substitutions.

7. The polypeptide variant of claim 1, wherein if the polypeptide variant further comprises one or more mutations, the one or more mutations are selected from the group consisting of: an amino acid substitution at position 3, 6, 14, 24, 29, 33, 34, 47, 52, 61, 63, 65, 83, 91, 100, 103, 106, 111, 121, 144, 153, 157, 158, 164, 175, 176, 185, 210, 234, 236, 256, 268, or 281 of SEQ ID NO:2 with an amino acid other than the amino acid occurring at those positions in SEQ ID NO:2, and an amino acid insertion after position 103 of SEQ ID NO:2.

8. The polypeptide variant of claim 1, wherein if the polypeptide variant further comprises one or more mutations, the one or more mutations are selected from the group consisting of: an amino acid substitution at position 3, 6, 24, 29, 33, 47, 100, 103, 106, 111, 185, 210, 268, or 281 of SEQ ID NO:2 with an amino acid other than the amino acid occurring at those positions in SEQ ID NO:2, and an amino acid insertion after position 103 of SEQ ID NO:2.

9. The polypeptide variant of claim 1, wherein if the polypeptide variant further comprises one or more mutations, the one or more mutations are selected from the group consisting of an amino acid substitution at position 3, 6, 24, 29, 33, 37, 47, 61, 63, 65, 83, 100, 111, 123, 157, 175, 176, 185, 210, 234, 236, 247, 268, and 281 of SEQ ID NO:2 with an amino acid other than the amino acid occurring at those positions in SEQ ID NO:2.

10. The polypeptide variant of claim 1, wherein if the polypeptide variant further comprises one or more mutations, the one or more mutations are selected from the group consisting of an amino acid substitution at position 3, 6, 24, 29, 33, 47, 63, 100, 111, 123, 157, 175, 176, 185, 210, 236, 268 and 281 of SEQ ID NO:2 with an amino acid other than the amino acid occurring at those positions in SEQ ID NO:2.

11. The polypeptide variant of claim 1, wherein the polypeptide variant comprises the amino acid sequence set forth in SEQ ID NO: 2 with a substitution selected from the group consisting of V208I, V208I-A111D, V208I-A281L, V208I-A111D-A281L, V208I-A111D-A281L-A33E, V208I-A111D-A281L-A47E, V208I-A111D-A281L-G63P, V208I-A111D-A281L-I185M, V208I-A111D-A281L-T268R, V208I-A111D-A281L-T3C-T29C, V208I-A111D-A281L-V100K, V208I-A111D-A281L-T3C-T29C-S6R-T24D, V208I-A111D-A281L-I185M-G210A, V208I-A111D-A281L-V100Q, V208I-A111D-A281L-K123R, V208I-A111D-A281L-5157T, V208I-A111D-A281L-G175S, V208I-A111D-A281L-Q176T, and V208I-A111D-A281L-C236T in SEQ ID NO:2, wherein the positions of the amino acid substitutions are numbered in reference to the positions in SEQ ID NO:2.

12. The polypeptide variant of claim 1, wherein the polypeptide variant comprises the amino acid sequence set forth in SEQ ID NO:2 with the following amino acid substitutions: V208I-A111D-A281L-I185M-G210A, wherein the positions of the amino acid substitutions are numbered in reference to the positions in SEQ ID NO:2.

13. The polypeptide variant of claim 1, wherein the polypeptide variant comprises an amino acid sequence selected from the group consisting of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, and SEQ ID NO:50.

14. An enzyme preparation comprising the polypeptide variant of claim 1.

15. The enzyme preparation of claim 14, wherein the preparation comprises at least one further enzyme selected from the group consisting of a protease, an amylase, a cellulase, a lipase, a xylanase, a mannanase, a cutinase, a pectinase, and an oxidase with or without a mediator.

16. The enzyme preparation of claim 14, wherein the preparation comprises an additive selected from the group consisting of a stabilizer, a buffer, a surfactant, a builder, a bleaching agent, a mediator, an anti-corrosion agent, an antiredeposition agent, a caustic, an abrasive, an optical brightener, a dye, a pigment, and a preservative.

17. The enzyme preparation of claim 14, wherein the enzyme preparation is in the form of a liquid, a powder, or a granulate.

18. A detergent composition comprising the polypeptide variant of claim 1.

19. The detergent composition of claim 18, wherein the detergent composition is a powder.

20. The detergent composition of claim 18, wherein the detergent composition is a liquid.

21. The detergent composition of claim 18, wherein the detergent composition is a laundry detergent.

22. The detergent composition of claim 18, wherein the detergent composition is a dish washing detergent.

23. A detergent composition comprising the enzyme preparation of claim 14.

24. The detergent composition of claim 23, wherein the detergent composition is a powder.

25. The detergent composition of claim 23, wherein the detergent composition is a liquid.

26. The detergent composition of claim 23, wherein the detergent composition is a laundry detergent.

27. The detergent composition of claim 23, wherein the detergent composition is a dish washing detergent.

28. A method of degrading or removing proteinaceous material from a substance selected from the group consisting of a textile, glass, wool, hair, leather, food, and feed, the method comprising contacting the substance with the polypeptide variant of claim 1.

29. The method of claim 28, wherein the proteinaceous material is a blood stain, a milk stain, an ink stain, an egg stain, a grass stain, or a sauce stain.

30. The method of claim 28, wherein the substance is further contacted with a detergent.

31. A method of degrading or removing proteinaceous material from a substance selected from the group consisting of a textile, wool, hair, leather, food, and feed, the method comprising contacting the substance with the enzyme preparation of claim 14.

* * * * *

UNITED STATES PATENT AND TRADEMARK OFFICE
CERTIFICATE OF CORRECTION

PATENT NO. : 8,945,900 B2
APPLICATION NO. : 13/283891
DATED : February 3, 2015
INVENTOR(S) : Kari Juntunen et al.

It is certified that error appears in the above-identified patent and that said Letters Patent is hereby corrected as shown below:

On the Title Page,

On page 2, column 2 (Other Publications), line 53, delete "*Hypoxrea*" and insert -- *Hypocrea* --;

On page 3, column 1 (Other Publications), line 43, delete "celluloytic" and insert -- cellulolytic --;

In the Specification,

In column 1, line 40, delete "(Chemy" and insert -- (Cherry --;

In column 1, line 62, delete "IFO6608)," and insert -- IFO 6608), --;

In column 2, line 50, delete "-0100R," and insert -- -G100R, --;

In column 2, line 52, delete "precurcor" and insert -- precursor --;

In column 6, line 11, delete "*Mortiriella*." and insert -- *Mortierella*. --;

In column 6, line 19, delete "*Mortiriella*." and insert -- *Mortierella*. --;

In column 7, line 55, delete "III18" and insert -- m18 --;

In column 15, line 6, delete "proteing" and insert -- protein --;

In column 17 (TABLE 1-Continued), line 19 (approx.), delete "AII1D," and insert -- A111D, --;

In column 17 (TABLE 1-Continued), line 24 (approx.), delete "AII1D," and insert -- A111D, --;

In column 17 (TABLE 1-Continued), line 25 (approx.), delete "V2081," and insert -- V208I, --;

In column 19 (TABLE 1-Continued), line 55 (approx.), delete "1185M," and insert -- I185M, --;

In column 23 (TABLE 1-Continued), line 27 (approx.), delete "1185M" and insert -- I185M --;

In column 23 (TABLE 1-Continued), line 47 (approx.), delete "AII1D," and insert -- A111D, --;

In column 36, line 16, delete "untrasformed" and insert -- untransformed --;

In column 36, line 25, delete "*Mortiriella*," and insert -- *Mortierella*, --;

In column 36, line 36, delete "*Mortiriella*" and insert -- *Mortierella* --;

In column 53, line 18, delete "propylen" and insert -- propylene --;

Signed and Sealed this
Second Day of June, 2015

Michelle K. Lee
*Director of the United States Patent and Trademark Office*

CERTIFICATE OF CORRECTION (continued)
U.S. Pat. No. 8,945,900 B2

In column 55, line 17, delete "propylen" and insert -- propylene --;

In column 55, line 45, delete "propylen" and insert -- propylene --;

In column 61, line 1, delete "Chemy," and insert -- Cherry --;

In the Claims,

In column 145, line 64, in claim 1, delete "An isolated polypeptide" and insert -- A polypeptide --;

In column 148, line 10, in claim 11, delete "-5157T," and insert -- -S157T, --.